US007638134B2

(12) United States Patent
Panicali et al.

(10) Patent No.: US 7,638,134 B2
(45) Date of Patent: Dec. 29, 2009

(54) INSERTION SITES IN FOWLPOX VECTORS

(75) Inventors: Dennis L. Panicali, Acton, MA (US); Gail P. Mazzara, Winchester, MA (US); Linda R. Gritz, Somerville, MA (US); Patricia Greenhalgh, Bedford, MA (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/543,944

(22) PCT Filed: Feb. 20, 2004

(86) PCT No.: PCT/US2004/005077

§ 371 (c)(1), (2), (4) Date: Aug. 30, 2005

(87) PCT Pub. No.: WO2005/048957

PCT Pub. Date: Jun. 2, 2005

(65) Prior Publication Data

US 2006/0159706 A1 Jul. 20, 2006

Related U.S. Application Data

(60) Provisional application No. 60/448,591, filed on Feb. 20, 2003.

(51) Int. Cl.
*A61K 39/285* (2006.01)
*A61K 39/38* (2006.01)
*A61K 39/12* (2006.01)
*A61K 39/165* (2006.01)

(52) U.S. Cl. .............. 424/232.1; 424/184.1; 424/199.1; 424/204.1

(58) Field of Classification Search ....................... None
See application file for complete search history.

(56) References Cited

U.S. PATENT DOCUMENTS

| | | | | |
|---|---|---|---|---|
| 5,185,146 A | | 2/1993 | Altenburger | |
| 5,364,773 A | | 11/1994 | Paoletti et al. | |
| 5,445,953 A | * | 8/1995 | Dorner et al. | 435/457 |
| 5,656,465 A | | 8/1997 | Panicali et al. | |
| 6,440,422 B1 | | 8/2002 | Sutter et al. | |

FOREIGN PATENT DOCUMENTS

| | | | |
|---|---|---|---|
| EP | 0 538 496 | A1 | 4/1993 |
| WO | WO 99/63062 | A1 | 12/1999 |
| WO | WO 03/097845 | A1 | 11/2003 |
| WO | WO 2004/098534 | A2 | 11/2004 |

OTHER PUBLICATIONS

Johnston et al., Current Concepts: An HIV Vaccine-Evolving Concepts, 2007, New England Journal Of Medicine, vol. 356, No. 20, pp. 2073-2081.*
Afonso, C.L. et al.; *Journal of Virology*, 74(8):3815-3831 (Apr. 2000).
Antoine, G. et al.; *Virology*; 244:365-396 (1998).
Cooney et al., *Lancet* 337:567-72 (1991).
Damaso et al., *Virology* 277:439-49 (2000).
Goebel, Scott J. et al.; *Virology*, 179:247-266 (1990).
Graham et al., *J. Infect. Dis.* 166:244-52 (1992).
Kari, Irvine R et al.; *Journal of the National Cancer Institute*; 89(21):1595-1601 (Nov. 5, 1997).
Kieny et al., *Nature*312:163-6 (1984).
Mayr et al., *Zentralb. Bakteriol.* 167:375-90 (1978).
Meyer et al., *J. Gen. Virol.* 72:1031-8 (1991).
Smith et al., *Nature* 302: 490-5 (1983).
Smith et al., *Proc. Natl. Acad. Sci. USA* 80:7155-9 (1983).
Vilsmeier, Bernd, *Berliner und Münchener Tierärztliche Wochenschrift* 112(9):329-333 (Sep. 1999), English Abstract only.
Zagury et al., *Nature* 326:249-50 (1987).
Serpinskii et al., "Design of Orthopoxvirus Recombinant Variants by Foreign Gene Insertion into an Intergene Region of Viral Genome," *Mol. Biol.*, 30 (5), Part 1, 626-633 (1996).

* cited by examiner

*Primary Examiner*—Gary B Nickol
*Assistant Examiner*—Benjamin P Blumel
(74) *Attorney, Agent, or Firm*—Leydig, Voit & Mayer, Ltd.

(57) ABSTRACT

The present invention provides novel insertion sites for introducing DNA into pox vectors.

13 Claims, 1 Drawing Sheet

PANVAC-F Plasmids pT1154 and pT8150

SEQUENCE LISTING

```
<160> NUMBER OF SEQ ID NOS: 3

<210> SEQ ID NO 1
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 1

ggtaccggta ccatggaagg ggaaggggtt c                                31


<210> SEQ ID NO 2
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 2

cttggttcat ggtgacactg agctcgagct c                                31


<210> SEQ ID NO 3
<211> LENGTH: 288539
<212> TYPE: DNA
<213> ORGANISM: Fowlpox Virus

<400> SEQUENCE: 3

tgttaaggtg taaaataccc cctattaaaa tatatattat tgttttaata aaaaaaaacc    60

atacggtttt acataaaata atactatatc taatttcctt ccggaaaata ttttataaag   120

ctacccaacg ttagcgaaaa actttttat cgagagctcg agttatagaa aaagttttta   180

tcgagatttc gaaaagcttt tttatcgaga gctcgagtta tagaaaaact ttttatcgag   240

agctcgagtt atagaaaaac ttttttatcg agagctcgag ttatagaaaa agtttttatc   300
```

-continued

```
gagatttcga aaagcttttt tatcgagagc tcgagttata gaaaaacttt tttatcgaga    360
gctcgagtta tagaaaaact tttttatcga gatttcgaaa agctttttta tcgagagctc    420
gagttataga aaaacttttt tatcgagagc tcgagttata gaaaaacttt tttatcgaga    480
gctcgagtta tagaaaaact tttttatcga gagctcgagt tatagaaaaa gtttttatcg    540
agatttcgaa aagctttttt atcgagagct cgagttatag aaaaactttt tatcgagagc    600
tcgagttata gaaaaacttt tttatcgaga gctcgagtta tagaaaaagt tttttatcgag    660
atttcgaaaa gcttttttat cgagagctcg agttatagaa aaactttttt atcgagagct    720
cgagttatag aaaaactttt tatcgagagc tcgagatttc gaaaagcttt tttatcgaga    780
gctcgagtta tagaaaaact ttttatcgag agctcgagtt atagaaaaac tttttatcg    840
agagctcgag ttatagaaaa agtttttatc gagatttcga aaagcttttt tatcgagagc    900
tcgagttata gaaaaagttt tttatcgaga gctcgagtta tagaaaaagt ttttatcgag    960
atttcgaaaa acttttttat cgagagctcg agttatagaa aaactttttt atcgagagct   1020
cgagttatag aaaaactttt ttatcgagag ctcgagttat agaaaaagtt tttatcgaga   1080
tttcgaaaag ctttttatc gagagctcga gttatagaaa aactttttta tcgagagctc   1140
gagttataga aaaacttttt tatcgagagc tcgagttata gaaaaacttt tttatcgaga   1200
gctcgaatgt tagaaaaact tttttatcga gagctcgagt tatagaaaaa gtttttatcg   1260
agatttcgaa aagctttttt atcgagagct cgagttatag aaaaagtttt tatcgagatt   1320
tcgaaaagct tttttatcga gagctcgagt tatagaaaaa gtttttatc gagagctcga   1380
gttatagaaa aagtttttat cgagatttcg aaaaactttt ttatcgagag ctcgagttat   1440
agaaaaactt ttttatcgag agctcgagtt atagaaaaac tttttatcg agagctcgag   1500
ttatagaaaa agtttttatc gagatttcga aaagcttttt tatcgagagc tcgagttata   1560
gaaaaacttt tttatcgaga gctcgagtta tagaaaaact tttttatcga gagctcgagt   1620
tatagaaaaa ctttttatc gagagctcga gttatagaaa aactttttta tcgagagctc   1680
gagttataga aaaacttttt tatcgagagc tcgagttata gaaaaacttt tttatcgaga   1740
gctcgagtta tagaaaaact tttttatcga gagctcgagt tatagaaaaa ctttttatc   1800
gagagctcga gttatagaaa aactttatc acgagattaa aatcttcgtt ggtataataa   1860
aataaaaata tttttattcg tattgattat aaaaagaact ttgcgtggta ggataactat   1920
tatcggtttt tttacatacc agatatcttc ttaccgagca cggagacgtt aatacttttg   1980
gcacttcaga cacgctactt ctagttccgt aagcacactc gttcacggga tcaaaagtcg   2040
aagcggccgc gcggttgtcc acccagaaac gtgagtgatc gtttcccgtc caaatatttt   2100
taagggcttt catttcttct tctgacttac ctatcatgtc agagcctaac ttctcacact   2160
tctggatgcc ttgtctgaat cccacttttt caccggtcga taagaggcag attccgttat   2220
gacttatcca gtcacgagga caatgaataa ccagattatc tctatatgta gtcgcaatag   2280
aggaggacgt agtgatagct gtagtggtat cttccagaaa agaatcccgt ttgcaatcgc   2340
gtactgcgac gaagagagcc gcgaacagac aggacgttat cactacgcta gttaaacaca   2400
gacaagtaat tggtaaaata taccttcgc tattatcgcg caggaacttc attttttctt   2460
tgtaatattc tattggataa ttcattttca tgctagttat atttatgtat tatttattta   2520
ccaaaagaaa tagatcttac ttattaagca gatatgcata aataaaagat ataattgtca   2580
tcggatatcg ggtaaaagtt aaccgtttga tcgtttatta atatcttgaa taactttgtt   2640
agacagtatc tacataatac gtgctaaaat ataatcatat gaattcatca attaatgcct   2700
```

-continued

```
attatgatgt agtctctgcg cataggtatg atttgaagtt gagagatatt tttagcatac   2760
gctatacatg tgaaaccagg accgttacgt caattagtag tttttgacca ttctttatat   2820
catagaattt ggttttccta tgttcggtga tcgcggatgc gaataacggt cgctgttgcc   2880
cccggttcac gcgtatataa taagttaaga cttagagatg cagtggtata acaagacgga   2940
gtcgtctcat tcctctttat ttcttcggcc gaacaaaatc tattatcgat actacgtaca   3000
ctatcgaaga tattagcgtt taccgggcgt ggttggtgtt cacggtatcg gatttaaggc   3060
tctaggatac tagttgtgtt ctttcgatac catatgacgt gccttacaga actaacgctt   3120
gaaaatcaaa cgatattata accgtgtagg agtaaatact tacttccgaa tggttttata   3180
caatctgtta ttaatattaa gagtaagatt tacattttcc ttcgcgcgcg caccgacgac   3240
acccctactc acccgcgtca gttactaacg aaacttgata ctcgccgggg ctctagaata   3300
caaaatgcgc acggacgctc gtataaactc gcgcattttt atttgaagtt aaatcgagac   3360
gccgatatga tcgtagagaa aatagcagcg tggttattgt atccgctatg ccttctacga   3420
tgtttcctct gtaactcggt aaggcccgcc acttgcaaat gcgtccactg tctcttgtat   3480
cccttcgaag tatgttgcga atgcatgagc gagacgttag actctctgga acacagttgt   3540
tgttactgtt gcgtgcttcc tctattgatt atcagagagt tctggagacg cgtgatatta   3600
cctactctaa aagcgacttg cgactgtatt aggctaccgt gcgttctcac cagaagattc   3660
tgtaaaagaa ccatctgccc gttagctaaa tcttggtgtc gttgtttctg ttgcccttgc   3720
gaggttttct tgaggtgtct cctctttcct tgcatgatgt tgagaagaat gcatagaggc   3780
agactgaccg gagtaagaga accgggagcg tttagagatt caagagatcc cgccagacgg   3840
ggaacctggg tcaacgactg gtgcgaagat ctctgcgtat ggatatggtc tccgtgttgt   3900
tacgtcaaga gatgtattcg cacgatgtgc gacaccttca ctaaaaaaat tttctactgg   3960
ttcatcgccc ccgcaggatc gccgagaatg cccgaggaac cttctccgct atcgagaaag   4020
gtcttttcgt cgtgaagcat cgcgacgtgt agatgaaaga gattggacgc caaaaggtat   4080
acgctcgtat tattacgaat cgcgctcgtc gtcgtgcctc gaagatgata aagagaacgc   4140
gagtaaggaa atacaagata aaaacaaact gtcgattcta cgtaatacga tttctaaaac   4200
ggcgtctacc gcaatctttt tcatcagagt aagggatagg ttaagattct taaggacctt   4260
tatcaaaact atcggagaaa aactttacgc taaagccgct ctcatgctct ttcacagact   4320
ggtgacctat aggcttccta tcgttaggga tatagtcccg ttttattacg cgaggaaaaa   4380
tttttggagg ttcgcttttc tatatctcat gaagaaagtc gctgttcgtc ctactaaaaa   4440
ctaatgctaa aaaaaaatct atcgttaata aattaaaagt tatcgggttt tgaatattat   4500
taatctatgc atacgaaacc gtacgtcgcg ttacacgggg agaatccgaa cgtttttcccg   4560
tccgtatagg cacacttacc cacttctggt ttcttgtcat ccccttatcca caaactctgt   4620
cccataccga atttgcttat gaatttcatg tctttttcat tgtctattag actacgtcta   4680
gctaacgtac ccatgggaaa cgttatcaaa cacgtagtcg acgcttcgct gtaagttttt   4740
ttgtgatgca ttttatctaa tcggtttacc cagatacact tattgttgta agaggtgtac   4800
ggtcctctgc aatttagaga gttagcgcaa tccaacatta acaacatcgc tatcaagatt   4860
aatgatttca ttttgataca cggatcaatt ttaatagtct atagagatat accccaccaa   4920
tagttacgcg attaattttc aattatacat aataaaaatc tagaggagtt accatgtgat   4980
tctctgtcga cgacgttacc tcgttagttt tattaattct tctttaagtt ctgacgacgg   5040
ttatatacca aaacagcttt tacttttcgt aagacgataa ttacgttata aaagattaag   5100
```

-continued

```
aaattttatt tttactaaag tatcatgaat aatgacacga tatttacttt gttttattgt   5160
aaaaataaaa aatatgttcg tggggagggg ggaaggagga gagggaagac gggtatcctt   5220
ttattccatc caataaacca ccgtgttata ggaactagtg cacatcagtg ttataaaaca   5280
cgaagaatcg gtttcaaact ctacgcagtt gcccctcgtc acgtatccac tatccgctgt   5340
gggagatccc actcggctca ccgagtagat aagttctcct tctccttcca aaaagtagat   5400
tttcactgta tcgccggcag cggcgcatag gtatctggcc ctacagaatt ccatattcct   5460
gatagctcgc gcgacgaagc ctccgtcgcc cgtgtgatca ttttcataat tcaagggatc   5520
cgacgcggct gccaagacct ttatacccga ctcttgttct actggacgaa cgcggagatt   5580
taaagccatg gctgacgtat agtcgaggac gccctcggta ataaattgat tatattttca   5640
gttttaaaaa attaatttat atgtactcaa tatccttata tagaattatt ttatctcttc   5700
tgatatacgt taggtagatg ccgttcaaat aataaaatat ctgatgacgt ttttatgcgc   5760
gtgttacgtt attataatag ataatagaaa taaacgttaa aataataatt aattatcttt   5820
tcagttgtta aatatattct agttttataa gcgttattca tatataaaaa atataaaaac   5880
taaatcgtat ttattatgat gctacggcgg tcatttaaca aatttacgcg atggagttca   5940
gttgtacggg aactaataac cagttggccg ttcacagatt tacagaaacg cgttttacat   6000
ctttcaaaaa agaactttta gttaatttag gaataagtga cttaaatgat ataaaaaaca   6060
tatgcgagga ttctaaaata ttctttccgg aaaagagaac ggagctctta agtattaaag   6120
atcgtaaatc taaacaaata gttttcgaaa actccctaaa cgatgacttg cttaaaaaat   6180
tacacgcctt gatctatgat gaattaagta cggtagtaga ttccgttacc gtagagaata   6240
ccgttacatt gattatgtat gaaaaaggag attactttgc caggcataga gattttagta   6300
ccgtcttttc taaaaacata atatgcgttc acctgcttct atatttggaa caaccagaaa   6360
cgggaggtga aacggttata tatatcgata ataatacgtc agtgaaatta aaaacagatc   6420
atctatttga taaaactata gaacatgaaa gtattaccgt tgaaagcggt agaaaatgcg   6480
tggcgttatt cgatgtctta ctagaaaaaa agttatccgc gtcaacaaac gtaataggta   6540
gcatagaata cttaggtaaa aaaataaatt tatatgacag agaaaatgat cttcagttgt   6600
gttattgtga tatggtaata gaaagaatga cagaagataa agaatatagc ctaggaatga   6660
tatctgatag atcaggtaga tgtataaaat ctcatcataa cggtagtatt gttagatacc   6720
gtaaagaaga atatggatct ttcgatgctc tatgtatata taacatgaat gaagtggatg   6780
aaatttggac tggtgataag aaacatatta tatggtctac tattgataaa aaaacaggaa   6840
cgtcttttat acctatagat cctgtacttt acgaaaagtt aaaagctatt tcttctaaag   6900
agcataaaga atacaaagat ttgagagggt tttgtaatag cagaacggag tatatttgtt   6960
gttcggtatc taagtactat ttcgacttac ctacaaaaac agatttaata cacgaggtga   7020
ttaattctat cgattatgat actaagtcag tgggtacacc cgactggtat actctgccta   7080
tagaagttaa acaaactatc ctaggtaata tgtcttacga agagttattt aatatagtaa   7140
gaggtaatat agctcttgaa gaagacaatg aatatggctg tgattaacat taatggtaat   7200
acttttctaa aaactaatct caagtattgt ttacaagcga ctgaagtaat agttttagca   7260
aaataatacc tttactgtta gttctacaat cgaaattatg ctgtaacatg aggtaaggat   7320
atatttatta atacgttaca tctttcgaaa gactttgatc gtagtataat attatacatc   7380
tgctctactt attatacata agaaaatttg tattttattt agtgcgctga taaatcgtgt   7440
ttaaagtata caacggacgt ctatttccaa aaaatctgcg cgtgttaacg gattaaaatc   7500
```

-continued

```
tacatgaaaa tatctcttaa actttatttc tacgtataac aaacaacaga ctgattttat   7560
atattacgaa taactatttt cttaggtttt ttatatagat gctatacagt gtttttacgc   7620
gtatatacaa aatacggaaa aataataaaa cagaaatgat tctggcaata tacgaccgca   7680
atgcctatat tgttaaaaaa acaggtatcg gaagtatctt gttacgcgat aacggtacta   7740
ggaatactat gcttaatatt atttacgata ctagtagtcg taacatgcaa atggtattac   7800
gcgtttccgt actttagcaa ggtatgtcct gatgagtgga taggatataa tagtaaatgc   7860
tactacttta ctatcaatga aactaattgg aatgatagca aaaaactatg cgatgttatg   7920
gattcttcat tgataaggtt cgataacata gaaactctaa atttcgtgtc gcgatacggt   7980
aagggtagtt actggataga cataaatcaa aatagaaaaa ttccgggtat taatttctca   8040
ctatattatg aacaaggcgt taatgatatt tgtctattat ttgacacgag taacattatc   8100
gaaatgtctt gtatatttca cgaaagaacg atatgtgtta aagaagatag atacacccat   8160
tggtataccg aatacatgcg ttagatttac tacctctttt ttatacaata gtattttgta   8220
cgttcttgta aacagaaaat ccgtatagtt tatattttta atcaaagtaa taacgaatat   8280
ctcgatgtca cgtataaacg cagattctag atattaaatt ctcaacgtac gtcatttgca   8340
ttccctgaga tgatactttg ctattttatt ataccgtagt ctatacaacc actacaaagt   8400
taaacgaagt aaaattattg attcgttgtt attatttcag cacagtagta ctcgctatct   8460
tcgtttaaat ctaataacac gccctttgaa acatttttgt gctagataat aatacgttat   8520
tattacacta acctgtattt cttctaatct ttaaggtgtg ctaacgatat atcacgggat   8580
taaaaggtta ttagtagtcg tataacaaca taataatagc acatctgtat atttatatac   8640
ctctcgagta cataaaaata atatgttttg ataaaacgta aatcaataag tgtataaggt   8700
attatttctt ttaatgaaga aataggacgt aatgtctaaa tcagatttat attcccgaaa   8760
atatttttct tagatgtata tgttagttaa attacgtgat tatattataa gttatctgct   8820
tactttaaca ttatatagta attatatact aaccgatctt aacacttccg tacaaagagg   8880
tatgcccgca tctgcgagat attgtgattt tcgtatttag atatgtgaat atagttatct   8940
actaacgcga ctttcctcca atttacaaag ctctaaggaa aaaaaataaa ataatactac   9000
cacgttcctc ttttaagagt taactattta ctcggaggta tcggtataca tacaattcta   9060
tataatttag ttaatcgctt tttacgcgca taagtctacg tataatgtct ttgtttaagt   9120
aactatccct ggaatattcc taaaaatagc ggaatttttg tttgtacgtc ggctactagg   9180
aacatgaaag gtacgttcgc ttttacgata ggaattttct ttattccgtc tgtagtgcat   9240
gattcggtaa cactagctgc ttcagttccg tattcatcta cttttatcac agatttttgc   9300
ctgatattac ctatcctcaa agtttttgta tcggatatac ctactaattc acctgacttg   9360
aatagatcat tacatcccat atggattagc gcgtctttca agtctacgtc atcttctaat   9420
tcgaatttag gtaaataaag aactatttct ttcaaagtca tatctttttt agatattatt   9480
ttattgatat tcttaccgtt attgagagaa tcaactactc catctatacc tgtaactgaa   9540
tcaggtatga ttataaacat aacaaatcta taatcttcgt attctaacat aactacctga   9600
cttcttatat cttcatcatg cttatagtaa aacgcaacgt cttgtatcat catcgtatct   9660
atcataacat ctgtcccgtt atattttttg aaaggatgtt tagaagttaa ttctgtatcg   9720
aaaggatatt tccatttaga tttaaagtat aatacgttta tgattgccag tcttatatca   9780
tctgctagtg aaatgctaaa atctttaata agtcctctcg tagatagttc tacccattta   9840
tttatagttt ccgatatagt atcatctgta aaactgacta cctttgcgtt gaatatatcg   9900
```

-continued

```
taactagagt ttataaaatc tctttttata gggtatcctt cttctattaa cataatactc   9960
ttatttatga gttcgtcctt gtcgtcgtaa tactctacgt aatattctga cttatcaggt  10020
ataggaacgt agttaccaaa tattcctaat agatctttta ttttatccct cgtctctttt  10080
ttacatccta tcatgatgtt cattagtata gtatataccc ctctagggga aatacatatg  10140
tcttttccag ggacatatag ttcttttaat aatcttacta aggaacccat cgtcaactaa  10200
ttatttaaca aacatatact tatatttcca tttctatgta atatgtatat acgaagagtc  10260
aataaaaaca ttattttact ctacctcatc ttcaaatgta gcttttctta ttgttaacaa  10320
catagacatt agtgcttcat ctatagtatt tccgtgatca tactcctcga tagcacttgt  10380
aaaagtttca atgtttttag tttcgcacgc tgctaatatc ttctctatga acttacattc  10440
cttaaaatct ttgaacgcgg gaaaaatatc tttatattta tctagagaac gtttagcacg  10500
tgatacgtca gaacacagat aacacatgat agcataaagt aattgatgtc tggattcgta  10560
ttttgacaac atagtgttca ttctattata tcccacttgt tcaaaaattt taccagccct  10620
gtcaaaatct tctttttgta tagataacct agcaattagc aacatacaat catccgatag  10680
tttattatat ccttcaccgc cataatatcc agatgcattc tcatagtgaa atattgcttt  10740
atctagttct aatatatcat tctcataaat cgcggctata ttcatgtgac atctcgcaac  10800
tgtataaaac tttcctaaac aagtatatac ctctatagct ttagatagac agtttatagc  10860
ttcataacta tctatcttct taaatgcgtt tgcggcatct acaaaaactcg aagccgcggc  10920
aatagaattt ttattctttt gcaatagcat atcacctgat ttaaaaaatg ctttacccgc  10980
acactcccat aactgtacgg acgcaaaaag attagcagcg tgacttacca tgccggcggc  11040
ttcttctatt tctataggtg gcccaaatag attcttaaaa aaaggactta cctttaattt  11100
tattttctgc atcttctaaa atcttggttg ctttttgttc tacttctttg cgatccatct  11160
atactaacta ctataacctc atttatattt acatattata catatgcgat aatctgtata  11220
aaaataaatc tctgttatcg agtactgtat ttctatagga aaaaatctcc aataactgag  11280
tcgaaggaca tcgtgtaatt aatttattta gggatatttc tatggaattt agtatctcgt  11340
ctatacctga tattactttt atcttctcta tatattttaa aatctgccgt gtctagtctc  11400
gttattacag gattcctcgc agtttagaat ttaaaatctc cattaccgaa cattagtaaa  11460
ccatagcttg aattaagttt tatttcgtat atagttttca gttctttctc acaggtgtgt  11520
cataaatgtt cttagcagtg cagaagaatt tatcttattc atattaagtt caaaaccttg  11580
tacttatttt cttccgaacc taccttttct tatagtaatt attaatattg gtaataggaa  11640
catcgtatcc agaacatacg tatcacatat gttcgttatt ttataaagca tgtacatatc  11700
gttgtttcta tgtctagtgg aatacatggt ggattacata ctattaatac catatacttt  11760
atcaacaatt tatctagagt gtgacaaccg caaggtcatt ttattattcc tgtaatatta  11820
gataacaaga aagtatctag atcatgacct ctcttttacc ttatcgaata tatcgtataa  11880
gttctaagta aactcggcat taatgactct ataatgttgg caagaaacct cgaacgggta  11940
ttaatatgaa atgcagtcat attaacgcga taataaaaat tacattctca aactatcatc  12000
catcgcttac tatattattt ctactttata aaatcggtta accagtctta ttattaactt  12060
taatagcgtc attcaagatc aatttttta tattatcgtt attaagttta cttaatatat  12120
tcaatttacc ctttaatgga agtaaacacc attctgtatt taacgatgat aaattacaac  12180
tattaacacg taccgcggaa cacagcaact ctttcctata tctgcccatt tctataatct  12240
tattcatcgt ataaccgtaa atacgtaagt tgctttgaga ttctataagc ttatctagaa  12300
```

-continued

```
aggcgacaaa actgttatgg tctatgtctt taatatcttc caagatacat atttcaaaaa  12360
ggcttttatc acctatccct ctagtagtca tgaaagctat ttcggattta catttcagcg  12420
caacttctag taatctacta ttttttgcaa tagccgctat attcctatta aaaccttcta  12480
tattaaccgt tatagatgct ttaaattttg aaataattat ataaggtaca agattaagga  12540
taggtatctt gtattcgtca aataagttaa taaaatattc catgattgta taagttacct  12600
gacctatgtt aataatctgg ttacagttag cccctctatc catcaataac ttaagaatag  12660
taggtctata ataactaatt attcttacaa gaggagtaat accgtatttg ttaacatagt  12720
taggattagc accctcatct aacaaaacat tacacgtttt aatatctcca gtacatatcg  12780
ctattaatag agccgtataa ccatcattag tctctttatc tacattagct ccgtatctta  12840
tcaatcgtct tattattttt atattgcccg ttttagcggc aatatgtaac ggagtgtagg  12900
aatctacgtt cggtgtatta ggatttacac ctttatacaa taactcaacc acctttttta  12960
tattaccttt agcagtttcc ttatataaag aagtatatcc atcgttattg acaccgtcca  13020
tttctgtatc catgaataca atagattagt tatattctat gtaataataa cgattacatg  13080
tatataacat atactatttc tattttctta tgttatataa aaaagttatt tatttacata  13140
ataagacttt tcatatcagt attttctagt cttgagaata tatagtgttt tattttagag  13200
taatctatta cccatacacg gccttccgaa tcttaaatat ttatctgtta agggtattgc  13260
attttgtagt ttcatttttc ttgttgacgc tattttaata atacgaggca tggtgtattt  13320
atatgatttt gcgttttact atcctattat aggatcttgc gaacgcattt ttaccgtatt  13380
gtagttttag tgtatagata ttatacagat ttgatttatc tattatatcg ctttccatgt  13440
gtataagcta tttactatta ttccacggct attctcagaa gtggttcacg ccctttcttt  13500
aacaggacct tgcacatttc cgggtttaat aactaatact aaagacgtat taacttttcc  13560
atcttctata ttaggattag ttgttttata ctttcttcta ttataattga gttgttgttt  13620
ttacgtcaag aaggagctag tatatccatg gtgagaatat cggagtctgc accgctttgt  13680
agtaatagtc ttattatttt agcgccgtta aagtttccat ctaagtgggg tagtattatt  13740
atctagagtt atagcattgt gtaattcttt tttccgccgt gatttatcct gatccgggta  13800
ggaattgagc aactctatag cttcattgct tttgattata accaaatcca tatgagaagg  13860
ataccagtca gtcgtaactc ttgttttcat ggataatata aaaatattct aacaataagg  13920
gagatcttct tcatctattt tttctaagat atcatactta atccctaatg gaagatctga  13980
ccaatctttc aatccattat cctttacatt ccgatttttt tcaaacgcct tttccatgac  14040
atcaagagcc ttgtccagag attcgtgtct cagcaatcct ctttcgatgg tatattctat  14100
tagttgcctg taaatgaaga atccttcaca agatatacaa tttaagcatt ttgctatggc  14160
attgtcatcg caattgagac ataagtctaa tagggaacgt ctatcagaac ctaaagtagt  14220
ttttctcatt ttctctactt cttctataca ggaatctttc caatctttca tttcattgtt  14280
agattctatt atctcgagat catttcttct agcttcttcg ttaatcactt tgtggtactt  14340
atattctgtg tttataacca ttgttgatat tatttgttta gctatttcta ttcctgtgtc  14400
ggagtttaaa tcacaaactg aaagaggtgt atttctccct gatgaaacag aagtatctgc  14460
ccagaagtcc aacaaaactt ttacgatatc gagttcagat gcgttagctg cgaggaataa  14520
aggtgttctt ccgcaaaagt cttgaacatc tacgctagcg ccgtgttcca acagcgtaag  14580
taccatatct gcagaacctt ccattaccgc gtgatgaagg gaactaaatg aaagttcatc  14640
ttcgacatca ggtaacgcac ccctggagag caattcaact actaattcat aattgccaga  14700
```

-continued

```
tcttatagca tgatggatgg tgtaaacaga tcccatactc cttgaattaa tcctggctcc  14760
ggcatctatt agaagcttac agatttcaag atttccatta gcggctgcgt cgtttatagg  14820
gcaattaaac ctatagatat cttctgcatc agcgccataa tctaataacg ttttagtcat  14880
ctttacatca ttgagcttaa cagcatattc caggggagta cgactttcgt ggttttcata  14940
attatcagga tcaacattga attccattaa caggttaact atatcataat gtcttaatat  15000
aacagctcta tgtaatgctg taggcgtaga ctcggtgtac agatcaggat ttgcaccttc  15060
gagtaacaga attctagcta tttcagtatt tccattttct acggcgcagt gcaaaaggga  15120
acatccatat tcattaacca tattcgggtc cgagtcattg ccttttaaag ctttaataac  15180
atcagaaaca cagccagatt cgatagcctc aaatacctcc atgttgtata atattggtag  15240
tatccgtgta gatacaccgg atgtaccaag cgatataaaa ataattaaaa tttcaattta  15300
tttaacatta gtatgtttat ttcataatgt cattattagt atttagtagt tagcaagtgc  15360
catattacaa ctaataagat caaaaataaa actgctgatg tataatttat acccataaag  15420
aaattattta taaaatcctc cgccatggaa ataataaaat gacataacca attcatttac  15480
aatgtttatt tattcattta tttataggta tctattaata agttaaatat ttttacaaga  15540
gtaaacacga tttaataaaa tctaatataa tataaatata tttcaaataa tataaaatgt  15600
atatagttag taattgtctt ttaatttata acaaaataaa atctaataga gtaatatctt  15660
tttagtttca tatacatcat taggatttac acatttaact aggttttcag gttcataact  15720
tctataatct ctatagtctc tataattatc ataagtaggc ttaaacattt cttctttatt  15780
gacattctta catttgttgg tatcggtcat gttggatttc aaatcttcat tatatactaa  15840
aggtgccatt gccaaacaga actctgacat aggagacagt ttttctacat aaaatttacc  15900
ttcaccgtct accatattaa ggatttcatc tcttgtagta tattgagtac atccagaaac  15960
atattcggta tcaggatgta gacatcctat gaatatattg aatattatac atgatgtcat  16020
aaacttacat ttagtatcgt aatcgaaagc ctttaatatc gattctggag taggtctagt  16080
tccatttacc tgcatgaata ccatgctatt agtaatcgga gttacttcat taaagcatga  16140
tttgatttca ctacttattt cgcgtagtat aaccattatt gtaaatttta gtagttatat  16200
attactcaaa agaaattacc atttactagt taatttataa aacagagagt attaataatt  16260
cacttatata ttactcaaaa gaaattacta tggttcaatg tatagacata tagaaggaat  16320
aattaattca aaatatttat aaaatagtat tctaccatct tccgtaaaca tctttgtatt  16380
ctgttactat gtattccttt ccttgttctt ttccgacgta atgtactgga aattctctag  16440
cgtgtgtatt attaatccaa tatctgcaat atggcgtttc aacatgaccg actacacttt  16500
cgtttacctt tatactcgtg tatctgtaat actctacatt ttgtgtaaaa ccccgaggta  16560
tctcgtatga cataacacct cccgttacta taccggttac tatccatcta ggatcgccgt  16620
gtttacttcc tacaaaacaa gttattgttg tttcatttct atgcttttct actacatacg  16680
ttatatcttc tttttgaatt tcggtacatc tttgatacgt ttcctctttt ccagaagccg  16740
tacgtagtac acaggtaaag cacaaacttt gaggatctgg ttttttgacc gtaaaagtag  16800
aagtacttcc actaacagtt acttcataca tatctttata aggaccagga acataattga  16860
aagcgttcaa cccgtaaccg cctacttgtt cttgagctac catgatatta tcatcgcctc  16920
tccaagtagc tctcgatatt tcgtctccat ctttggttct acattgcaat tttacagggc  16980
tatccggtaa atcttcttcc ccgtagatat tttttaagat aaatgatatt ataatagcga  17040
ttgctataac catatagttc attttcatat tgattgtttt tatatcaaac gctgaacaat  17100
```

-continued

```
atacgaggat gacatactag atactatact tattcacttt tattaaaaat atgttaatct  17160

taaaaaaatc aaaaattatt ccaaccacct cttataacgg gatttctctc cgtattccaa  17220

aaatgatccc gaaatcagaa ccacggaaag gtcttgacga ggttctttat catcacaaga  17280

tataatagat gctatataat ctctacttag acccttgtaa cttacggtga atatcacttc  17340

ggtagtgaaa tcagtataat ttttattggc gactactttt tcacattcat gatatttctt  17400

gtattctact aattgagtat cttcgcttaa caccacacca cccgctctag catccacttt  17460

tacttcgcta tcttccatag ttctagtcct gtttattata aaatcaatca aacctctacc  17520

cacatcatct accgcataag cgtctactcg aggcattact ctaagttcta taatgtgtct  17580

gtaactctct gtcttgttgt aatagaagat acatctatag cgaccttcgt catttctgga  17640

tgatcttctc ggaagctcga cgttatattc tttatctgga tcgttacaat agcagatact  17700

atcttctccg gcattatgta tgtcaatagt taccttaaat gtgttgtttt tcaggtttcc  17760

ttttataact accagtttag tcgcgtgtat gtcagggggt agaatacaag tcaaattaac  17820

tcttacatcg ttatgtacta ccattgtata ggaattacat tgtataaacg tagtcaataa  17880

gaatagagaa aatgagtata tctttccgta catgattatc tccagtaatt tttttaccaa  17940

gcactagtga ttcaacaata gtgttagtgt tatactttat gttttttttct aataaatatcc  18000

ggaaatcgtt ttaagatctt ccatagataa attcgataca attactctat gtatctcagg  18060

agataaaagc caccatctac taagatgatc tttactagtg tattcattga tgatcgataa  18120

taccgactct atagccgaat ttcttttttc catgtatttt atatgttttt taataaaacg  18180

acgaaatatt attatctgtt taagatctat ccgtcgtata cgttttatag tgttagccag  18240

atcatccagt ttatctaata tcagaacatc gtacaaggat attttcttat cacccgtata  18300

aaatacattg tctttcataa tagacaattc gttctctatt tcgtctttta atgatttggt  18360

ttctttatga ttgtttacga atctcatatt acgtacaaac ccttgtttat tccttataga  18420

agaatcgttt attacagaaa agtataggta tatcacagct aggaatacag caggattatc  18480

atgagtttta tgaatggtaa tgggagtatg aaatctattc ataaaacaca tatccgctcc  18540

gtgttctaga agtactcgag tacactcttt actcttattg cgtatagcgt atgttaatgc  18600

ggtattttta tcataatctg tttgattaac gtcggcacca ttagctaata agtattccat  18660

attacttact ttaccctctc tagaacaaat cattaaaggt gttataccgt aattatccct  18720

ttcgttaaca ttagctccgt tcttgattaa tacttttata ttaccgatct tagaatacat  18780

acaggctaaa tgtattggtg ttttaccgta tctatttctt acgtttacat cggcaccttt  18840

attaataagt agtctagtaa gccttgaggt atttatagaa acagccgcgt gtataggata  18900

catattacaa gcatcgcacg atacgtttat atcatttatc tttttaata gttttcttgt  18960

aattggcaaa ttccttaatt cgtatataca catacaaagt atagaaatag gtagataatt  19020

aacaggcaaa ctaagtatgt atgagataat gctataatac cgtttacata ttgcttctat  19080

tagtatatcg ttacaacacc ttattcgagc tccgttctta accagaatat tgaataattt  19140

tacaccgtgt ttactagaca ttatagcgta ttttaacatc gaatatatat ctcctatatc  19200

cggatctgca ccatgattta ataatagcat taccagggta acgttttctt gttctacagc  19260

atgatatagt gcagtatgcg agttttcaca tattgtagaa ttaatatcaa taccagaatc  19320

aaggaatagt ttcaccattt tagggctatt ggttttaaca gcttctagaa aataatcttc  19380

taacgctgta tccgtgtccg ctaataagtt attagatata aagtgtttca ccagttctat  19440

atttactgct ctaatagcac acttaatagt aattcttctc atataatata aactgggatg  19500
```

-continued

```
tttagtttct tcccatagaa tttggcatag aggtatagta ctaaaatatg aatatcctat  19560
agcgtaaccg gttttaatgc aatacgaacc acccttgtaa aaatctaata cgtaagatct  19620
acataccatt ttcaagtctg ctccgtgttt tatcagaagt tttactattt tggtgtattt  19680
ttctgtatta ttaaccgtta atagacgtct tattctttta ctaggtttta cgggcttgtt  19740
atcattatat aacatcattc tacctcccgc taatatcata gctatgttga tgggatgtgt  19800
ttttattgtt tctcctccgt tgataacggc attgttgtct agtagcattt ctactatttc  19860
tatgtctgaa tgttctatag cgatgtgtaa aggaagtagt ctattgctgt cgtacatgtt  19920
tattacatct ttatctgatt ctatcaattc tcgaagtctg tctacattat tttcttttaa  19980
gatgttatgt aatgataaca aacgatccat agtgctgtat ttgtacgtta acgtcattat  20040
tttttcttgc gttatgcaaa gataacagtg atttttaata tatgaattca tttattttag  20100
aactaagcta ttataataat atattttaag aataaattac ttattatata ataaaacaca  20160
attctcatta ctttatttat ctgttaattt ttgtttataa ggattttgaa taaaagacgt  20220
catacccgta ttaataacac tcttgacgat catatgtgta attttttgca ttatgtttgt  20280
aaggcatttt ccgtttatat gcgatctata tttgcaaatt gatgttttac atttagttaa  20340
ataataaaat attgtatcct tgttattttc ataagcatta tatatatgta aacctataat  20400
atttaggtac tttataaaaa ttttgcaaca tgtatttctc ctttttcttc ttttatatgt  20460
cctttttcct tttatagagt attccatttt tattcataaa aaacatttgt agcgtgggtg  20520
atggtaagta tataacgagt tacttataga tatatttaat atcttatcga cggaaggacg  20580
aagatccatg gtatgtgtta tgatgtttct gtccataaag ggtaatgatc aatactataa  20640
tgtttttacg atccctaaaa tctaaatata cgaatctaga tattgatata aaagcgtatt  20700
ggataaatac ggttattcat ataaagataa tatgactgtt actaaatctg gtgttataga  20760
agagttagaa aactaatata aaataactaa ttgatgcaat acactacttt gacaatagca  20820
ctgaagactt ctacaaaata agcgatacgt ataaaataag atttatatct gaatagtagc  20880
tttatggtaa accggtaaat acgaatccat ctacttatga aatacgcgga aaaatatttc  20940
atagctaaag gtatttataa cgattatacc aagtcataaa aatctatact atagagagaa  21000
cgaatcttct ttttttatac actaatcgtt atcgattgta atgtcgctat cgctttcgtc  21060
agactgaagg tcatactctt gtttacttaa aactattttg aatagttgat cgcgttcata  21120
actagaaagc aaatcacgct ttttggaatc ttctagttct ttccaatctg tagaaatagc  21180
ttcaagagaa tcaccttgtt ttataatata gttaataata ctttctttat ccggtaattt  21240
aaaatagtat ttgcttacca tacaatacgc gtaatacggt tctgcatctt cattactttc  21300
atcaatatat tctatttcat agcatttagc gtgttcttta ctagatattt tcattaattt  21360
gtcaaatagt tctttatcgt taggcaagta gttgtcgttt tcgttactat ctatactaga  21420
ccaagctata tcgttaattg tatttttctc tagatacgct actgtatatt ctctattaaa  21480
tttagaaacg ctaacatcct gaaaagaaga aaatacaata ggatgttcta tgctatgtat  21540
tttgttgttt atatgcgtta atagacattt tccctttcta tttatcaaaa taccagcacg  21600
cacaagtttt ttattacagg gcggtgctat atatataact tcacaataac ataatgtatt  21660
attgttttcg cggtcgtata aattaataga aacatccaag tattctattg tatctactat  21720
acctttttct gtttttaatt tcatcgtgac gtcaagtaac gctacgtacg ttacaccgga  21780
ttcaactata gttgtttcat gatatacgga tttatcaaac agaacatcgg atgaaatatc  21840
taatgaattt attcctttaa gatagaattt tgtttttcct ccttctgtag ctttctgaag  21900
```

-continued

```
tagtaataat atgtacatgc atagtgtatt ttttgatttt tttttacagg gtttattatt  21960
tgtttttttt aaatagtccc ctacaccgta aacaacaaaa gttaccttgt tttctacgcg  22020
tacttcgcta actatgtatt ttaactgcga tactataaga ttctcgagtt tagtagttaa  22080
gtctttacag agggattcat aaacaatttg cttagattta caatgttcta agtcgagtat  22140
ctcgtatcca gtatgttcat ctaaaattct tgactcgcta aagtcatagt ccatatagtt  22200
agtttctatt tcttctatta acaatttctt gaaatcagaa aagtaatcat ctgaaaatat  22260
atgcattttt ggaataccat ctcttatata cgtgaatgac atatttacaa aaaaatatat  22320
tatttatgtt ttatatgaat ctatataagt aataaatgaa attaaagtta tcaactatta  22380
tagtatacaa aaatggatac cgattacggg acggttcata cacagcagtc tgtaaaggga  22440
aatactttga ttctcttaat atattttata tcgtttatag taggatttcc tggtaattgt  22500
acggttatat ggtttacggg atatagatgg aaaaaatctg ttacgactat atggtttctt  22560
aatctggcaa tagctgatac attgtttgta atatttattc ctttcgagat tacttatata  22620
ttaatgggac actactggcc gtttggttta ttcgtgtgta gaataggatc tcttatgttt  22680
aatacaggca tgtacgctag tatatttttc cttacattta taagcataga cagatattgt  22740
ctcgcatttc gtagggatat atgcaacaaa tataggtata gaattaacat aatggttatg  22800
ataatcatta gttggataat atctatactg ctatctactc cttacatgta ttttaaaaac  22860
actaacgaaa aataccgtaa taacagagac tgcttggaag attaccattc ggataataat  22920
acttatttac tgcgtcgtgt agtattttgt atatcgttag taatgagata tttagtaccc  22980
tccgtagtca tgttattctg ttattgctta ttacttttca aacacagttt atttctatct  23040
aagggacaga cttacaccat agtgattatg ataacttcat ttatggtttt atggacgcct  23100
tacaatatat tatattttat agatgttata ggtagtcatt actacaacgc agatacgata  23160
atagatgctg ctcctatatc tatctctttg atatttttaa gtagttcaat caatcccatg  23220
atttacatgc tggttggtag atatgtatct tttgaaaatt attctatgcg cgaatcgcta  23280
aaattaatat tatctgaaga aagagacaat caaacaaatc atgaaaacga gattaaaatg  23340
gaaaatatta attaataaaa ataatataag tatatcataa tttttctagt tcattatttg  23400
ataaaaaaca acatataatt gatcttattt ctaaaggcag catatgcaga tatggttctg  23460
tagtcagtac agccctttct agtagagtat atctagttag tgacatgcct atgtttttat  23520
cagctagttc tttgtacacg ttagctgttt gttttagtac ctttaatttt ggatgattca  23580
caaatctggc tattacgtta taatcttttt ctattacaaa atcgaataaa ctatatcccc  23640
taactagttt ttggttaatc agttcgttta gttcattttc acattgtaac attatatttt  23700
tataatattc aattccgtta atgaaagaca cgcttcttat cactaatgga tcttttatta  23760
actctttatt cttcttaatc ataataatta ggtgagatat taatgttctt atagtttttt  23820
tacacggaca cgcttcttct ataggagttc ttccatttgt attaacgcta ttgatatccg  23880
atcctaaatc taatacgagt tttattttct tatatttaca acacgctgct aaagtgtgta  23940
atatagtatt cccgtcagag tttttagcgt ttacatccgc tcctttttgt aataataaat  24000
taaacacgtt atcagtttgg taaatgatag ccgtttgtaa cggtatgtta ccgtaaaggt  24060
cgcgcttgtt tatattcgct cctagaccga ggatgagtga tacaatttca ggattatttg  24120
tttttataga ttcatacagt aactccgata agtaatcttc tgataatgca atatctttta  24180
ttccgtgcat taaattcttt aactcgtcta tactgcaata gtacatggct aaaggtaatg  24240
ttcttttatc catgttaacc ataaactcta cggtataaaa ttttataagt tcatctaata  24300
```

-continued

```
taattttatt ctttctctta atagcgtaat acaaaggaga tacagagtgt tcgtctaata  24360
ctttaggatc gcatcctata tccagtaagt atcttacagc ttccaacctt tctgcttcta  24420
cggcgtagtg taaagcggtg gttccttcgg tacctaatat atctctgtct aacgataata  24480
tctttagtac ttctatattg taatgagtta ctatacatct ccgcaatatt tttattcttt  24540
ctatattatc cgtaattgct ttgttttcta ccaataattt gattaatgat aagttacctt  24600
tcttaaccgc ataatataag gcagtatgtc cgtagcgatc aggtatatct aatctaatat  24660
tattctttat tagtaacgaa catgattcta atgttagttt gtcatatatc atatcatgac  24720
caggatatgg accgctaggt tctaaagaca gtaaataatc tataatttct atataacccg  24780
tctttatagc cgttaatagg ggtgtttctc ctttgtaaca aacatctaca gaagcaccgt  24840
aagaaaccaa tatttttgcc atcgtaagat ctttgtttct aacagatatt attagaggag  24900
gtactttaca agcggacatt tttgatccgt tactaagaag aaattcagct actttatggg  24960
atttcatact taccgcccta cataatatag tgcggttttt actacctggt ttattaagat  25020
ctataggttt gtaagaaagt aatttcctta ttatatctac atcatcttca tctatagcgc  25080
gtttaaacgc gctttttctt ctataggcca ttatgtgtgg tataattagc ctatgcacat  25140
aaatttacgc tatatatttt caataattgt tagttaaata tagttattca ttcaactaat  25200
agaacaagat gtggatctcc acccatctaa atcgtattct tcatccaaca attccgacga  25260
tattctatca ggaactatat ccttactctt tttattcttt ataagttttt cacatctttt  25320
agccatgttc atgagatttt catgagattc tatacattcg agattttttta ttaaaccggc  25380
cggataatac attttatcat taaacagttt tctaattaac attatctgta atattattat  25440
agagttcagc ttttcgttgt cgtaagacat tagattagta aaaggagtat ttccttggtt  25500
atcaattata tttatgtcag cgccgtacat aaaaagtaat ttaactctat tgtagttatg  25560
cattgcttgg aatagaggag ttgttccatt agaacatttg atattcggat ctgctccatt  25620
atccaataat agttctaata gcgcgtagct gtcttcatct atagccgcta cgtgtaacgg  25680
cgtaacaccc gctttatcgc ctatattagg atcggctccc gattctatta gttccttagc  25740
tatattaaag tttccggagc ctaccgccgt atggagtact ttggtgccta tagaagaaga  25800
cgatgaagaa tttggatcag cgccgctatc taatagtata cttactaatt ctatattacg  25860
agtactaacg gcacatgcta aaggcgtagt tccataatcg ttttctatat ttatatccgc  25920
tccgttttta attaaatgtc ttaccatatt taatccgttc ctgtaatcac aggcatagtg  25980
taatgcggta ttacctatat cgtctttgaa attaatatct atccctttag acaacagtat  26040
atccatgatc tgaatttctt ctatttgcct gctaggttcc attcgcgata tagttaagca  26100
tttactaatt tcatcgtctt tacaataatc cattatcatt ctcataagtt caactctttg  26160
aaatgaataa ctagtttttg atttattcaa tctattgata acttctagca attctgtata  26220
tgtatttgag caccaattat cgagttcgat aaatgatgaa ttcggaggca tagttaaagt  26280
atgaagtgag gtaataccgt gtgtatctat agctacagga tctacatcgt tattcagtaa  26340
tagtcttact gcctctatat ttcttagttc aatagcctta tgaaggagaa tctttaatct  26400
gtaagttgta ggtcttagat ctatacagtt ctctattagt ttatacagta tactatctat  26460
tccagttgta tatctagtta ttttagtata gtccattata caggtaaata ataatttaag  26520
tttaatatcg taattgaata agatataaaa attggttata tttatttgtt aactgaatca  26580
attatagatt ttaaatcttt attatctaac atttccatta tcatatattt tacgttaata  26640
ggtactgaat ttatcatact tatattatta ctgtattcta tagcatcgtg aatcagttta  26700
```

-continued

```
tatcgtatac ttgaagataa tttagttttt tgaatgtatt ttttatatat actaatacaa  26760
gaagataatt tctcgacctt ggggtggttc aagaatctaa ttagaatatt attgttatta  26820
tccgaatgaa gaaatatcga tagcgaatat cggtgattca actttatatt ccttatactt  26880
tttaattcat cctcacaatt ttttctaata actttaaatc tatcattttg gtctatacat  26940
tctatatttg ctttgaatcc atccaataaa aatagattac tatctttttc taaatctaat  27000
actatcttag agattatgat tgtagctatt ttatcggata tgtaattaat acaggataga  27060
ggcgtgtgac ctaatttgtt aatagagtgc acatcgacgt tgtaagacat gagtaattct  27120
acgctatcta gtctattcga taagatagcg ccatggagag gtgtattttc attgctttca  27180
tttttcatat tagggttaga tccgtaccgt aatagtaact tagcaaattt tatttgcata  27240
aacgtaataa tggctatgta taaaggagtg taaccttctc tgttatatat atttacttcc  27300
gccccatgat tcagaatttc agaaagtata tttatgtctt tggtttctaa agctttatgt  27360
atcaaaggat ttctactttt taggcgagtg tttgcgccgt acattaggag taagtttatt  27420
aaaatcttgt tcctgttacc tacagctata ttaagaacgg tatctatagt atcgttatgt  27480
atatttacgt ttgcaccttt ttctataagt aatgtagtag cgattatatc gttcctcgat  27540
acagcgtaat gtaaaggagt gcctagacac gaatctgtta tattaggatc tgcgtcataa  27600
tctagtaata gtttaagtat gtcgtgtttt ccagcactaa cacaataatg taacgaagtc  27660
ctttctaagt catcttgttc gtttacgggt acgccatatt ttatcaataa acgtaaaata  27720
gaaatatcac agttatgttt cacagccgta attaaataat gattattata tccttccggt  27780
attgttaaag aagcgttatt ttccaaaaga agcttaataa gtggataatt tgtgcatttt  27840
atagcataat atataggggt tttaaaatga ctattttgaa tatttagact tactttatac  27900
tttatcagta ttttgaaaat atctataggt attttattat atatagcatc acaatagttt  27960
atgaataaag tattaggatc agcacctctt tccaaaagat atttagtaat atttgtatta  28020
cgtttacaca aagctagata taaaggacta ttacctaaat atactttttc gatatcggca  28080
ccgtgatcta ctaatagttt taccatttct acattaccta agttaatagc cttatgaagg  28140
ggaggagatt tacatttatt tatatctgcg ccgttatcta gtaaaaattt aacaatatct  28200
atatcggaat tacttaccgc taaatataag ggtgtcgata acgcattttt gttagaaaat  28260
gtatacttct taaggataat atgttttacc gcgtttaaat ctctagttct aatagttcta  28320
tgtaaatctt ttctaagttt ttcattgccc atgttatata atcattattt actctaatat  28380
aatatgtggt cgtatgaacg ttaataaata taagttttcc tctttttttgt tatattacct  28440
atattgataa aaaatcactc gtaccaacca gttactttaa tttttgaacc cctgaatgct  28500
tccgccaatt cgatgaaacg atttttattg tcttcatcat ccgcgctcac gtagcctatg  28560
gtaacgtgcg gacaccatac aggatctgat aacacagagc cgaaaatttc tctaggtgtc  28620
ggcacaacgt taaatagtac gtttctcaag gctttcacat catcagatgc ctccagcttc  28680
ataaccactg ctctaccgtt cgctcctaat tctttagacg cacgactttg aggaaagcaa  28740
atcacttcct tgcacgtgaa ggaaagcgat gtcaaatcta tattttttgt taactcttta  28800
aatcttttga agtttgattc ttggtctttg tttgctattc ccaacgttac gtggggaggt  28860
atatcacatc ccgtcatgta tttgactgct atgctttcca ggtctgatat tccctttttct  28920
aatctaatat cgtagaatga aatggaggcc caattacagt aatcccaagg aacttctact  28980
tctaatccca ttaatatagc atccttttta ttttgctttt cttttaccac gattttctct  29040
aactccttct gtatagtagt agccattttg gttagagtac caatggctct ccaataataa  29100
```

-continued

```
aaagattaaa atttcactta ttttgaacac gctgctataa ataatataat ttttaagtag  29160
ttcgaatata tatttttatt aattttaaag taatatacgg aaaaaagtat cctttatatt  29220
taccagtttg atgtttttaa tgtatagaat gtttttgtct ctgtcttctg agtaggtgac  29280
atataattga tatattttg attatcgctg tataagatag aaatctgcgt ttgtaaatag  29340
tatcgatatc gtatgagaac atcaggttat atccaatata tttatgttta gttctataca  29400
gtaatatatg taatactcca ttaagtatta tttatcgaag ttattatctt atttcgcata  29460
attctttatt agtcatcttt tctacaataa tatatataac ttcataaggt aggttagtga  29520
tggtactcgt caagctatta acaacacgat ctaattgttc ttttctatat aaaccaatct  29580
ttatatactg atctataata tcaccgtata tctgaaattc gtttttatta actcctacga  29640
gtaatagttc tatacatctt gctagcgtgt tatgatcatc ttgttttcca gcttttataa  29700
aatcaaatac cgtcaattta tatccagctc tgcgaatttt catatttcta atttcttcct  29760
cgcataaatt tttataatag ttaaaccggt agatactatt agtaaagtct tcgtttattt  29820
tgaatcctgg tgttaattta actttatcac gaatatgaga tatcataaca gccgatgata  29880
taagatcctt gacggtcatg gatagagaat ttccatggca gtaacaatac catgttagcg  29940
gtatgtgatt gagttttata ttcaagaaga aaggattagc gcctctatgg agtagcattt  30000
ttattataaa ggggtccgtt ctgtttacac tagatagaag aatggtatac ccttctatac  30060
attttgaatc cactagagct ccgttctcta gcaatagtga tacgatgttt atatttttgt  30120
ctaaaacagc attatgtagt accgtacgtc cgttataatc agctatctcg agatttggag  30180
aatattggag taaaatgttt accatctttt catcgttata tgttacagct atctgaatcg  30240
ggatattacc gttttcgtta gtaatatttt gatcagcacc ggaatctagt aacagttttg  30300
caatatcagt attttttgt tgaatcgcta aatgtagagg agtattacgt aaataacatc  30360
tggtattgtt aacgtcggct cccgcgtaca atagtatact tacaatatct ttgttaccta  30420
tatctacagc aaagtgcaat accgaataac atgttaattc ttcttcatag tattcatttt  30480
cattaacatt caccccgtat tccagtaata tttttatgat atctattctt tcgaacttta  30540
tagccattct tagtacccgt attccttcat ctttcgtatt accttccatt aatcttctta  30600
ctaagtttat actataaggt tgtactgtag attcttcatg cggtgtatca tcatctaaaa  30660
acatagttgt aatagtcaaa taacattcta tgtaaaaact aattaataga ttttcatttt  30720
tcaaataata tacccgttct ggaaatagcc acataactga aaataaaata cttaagtata  30780
tattatagga taacaatgtc tatgaataat attacgagta aaatgaatca agatagttat  30840
ggatattttc aattacatat gagcgatttt acacgtgtgt cgctatcgat tgtatttaca  30900
ctagtatttt tggtaggtat aataggtaat gctgttatca tttggtttat aggattcaaa  30960
tggacaaaaa ctatttctac gctattattt atcaacctag ctttagcaga ctcgttattt  31020
ttaatattca ttccagtata tactgtttat gtattatcta actttcattg gtatctcgga  31080
gaattcttat gtagggttag ttctttcttc tttactacta atatgtacgc cagtatgttt  31140
ttacttacgt ttatatctat agataaatac ttaacactaa ccagtcaccg tttagtgtat  31200
aaataccgaa aatatagaaa ctactacgtg tgtataggtg ctatttggtg tatttctata  31260
gctttaggtg ttccaacttt atattataag agggttatat tatcatcatc tagaaacgag  31320
acacggtgta ttagttatta cggcgatgat aaacacacgg ctattactat ttatagaatt  31380
attgtgtgta ttagatttat tataggatac gtgtttccaa tgacagtaat attgctatct  31440
tatgcattaa tagtatataa ggtaaaattc ataaataaac caccgaatag aagtttcatg  31500
```

-continued

```
ataacaacgg catctatatt tgtatttctc gcttgttgga cccctcatca tgtattaaat  31560
attatatcgt tgtatggatt aaaatcgaca tctatgtata attatataaa agaatctatt  31620
ccgttcgtaa atgctattgc gtttgtttat agcgctataa atcctattat ctatatattt  31680
gttattaggt taacgagtac ttacgattcc gataccatgg atgaactaag aagtgcgtta  31740
ttagatgaag aaactacgtc tacagaagat tgtagcgata tagaaattag cgatatatct  31800
agatagattt aatttttgta aacataaaaa aaagtatata gtatcaaaaa actaccatgg  31860
aagaaaatat tttagtaaaa acctttgacg aattatacaa aaatagattc gtagatgaga  31920
tctatcataa cgataaactc attacgttta ataaaaagaa gggtaaagga aacaacttgt  31980
gttattctat aattgaatac attaatccca tttatgattc ttgttattct gtggctaaag  32040
ttgtatatat aactaacgga gttatgtatg ctactttaaa ctatatggga aaacctgtag  32100
aaaatcgtga gctcgttcct attaataaat tactatcgga ttcagaaatc ttatctatgg  32160
gagtaaacgc taaagatcta tctactaaac attacgaata taaatataag gtatctacta  32220
accacgataa aaaaagggac tcgtcattag ttaatataat taaagatgat agtttgttag  32280
aaaaattaga ttattttctt gaaggttacg gtgattggaa gattaccact ataagaccca  32340
ggcagtttcc taataagttt tgtaaataca ggatatctaa atactacttt tcattgtaat  32400
gtttattata tttttatagt agatgccgca tagtgaatca ttatcataaa cttagtttag  32460
actaactata caagatagat tcaaaccgat tgattagcta gtatcgaaga atcaatcatc  32520
tctctatgct cctgaaattt attatagcat tatgattatc gaatttatat gttagctcgt  32580
gattagtagt gatattgtag tttagtaaat cctaatagat tattacgttt atctttaact  32640
atataataaa tatctgtttc ttctataatt aagcctatgg cttctgatca tattacatag  32700
tattatctac tactataggc ctttatttag tataagtata gtctaacaac tgttacatcc  32760
gaatgtataa taaaaataat actaatggcg tgttcacgag ggtaaataaa tttcggccat  32820
agttacctct atataataaa aattttatta atttttattt cttgtttttt acagaatgtt  32880
taaatctcga atgtatacca acgagatttt tcactctgtt ttagtagtaa ctagcgtatt  32940
atatagcatg tatgtggata ttttctggta tatacaataa ttcataattc tataaagtat  33000
caaggttatt ttataaaaat attataatgg ttttaaagat ctcgtcaaag attcaaacat  33060
ataattagga gcaggaccta taactaaaac agtattacat ttttgtcttt tatcgttttg  33120
tacaatataa tagttaacgc ctatagctgt agcgttttct ctaatatcca tcatttcatt  33180
ttcgttatct actttgacag tttctttaac ctggccattt tttaaccatc ttttaagata  33240
atcaggagaa tattttttag atttctcgta ggcacttata gcaccatggc agcattgaga  33300
aactatttca cctttagtca tttttaaatc atctctaata acgaatacca tttttaacat  33360
atctctgtaa gaagagttat caaaaacatt agccattatt agcacaatat gataatctgt  33420
attatttatt tatgttttca gtatttactt aatacaagtt acataaaata tatccttctt  33480
tttacaggta catatactac atgtaagttt ttaagtaagc tacattagaa gatgttttgt  33540
aaacattacg atagaaactc atactcgtta ctgtttctat atcttttatt cttactctat  33600
gaagactgaa tattttcctc acataactta cggaagttat attctctcta gaacacgatt  33660
cgttataata ggtatcgcta ttgggtacta caaatgactc tgttttaata ttagagtaac  33720
aatcatttaa ggaagaatct ttatccttac agtatgttag tataacgaaa taatccgaag  33780
gtatataaac tttgttatta taaccgcttg acatagatat taaccaatca ctatctctta  33840
taccgttgct gttgctatcg aatacagggc ctaccataac gttaacgaca tgatgttttt  33900
```

-continued

```
gtacatattc gataagaata gatgacataa atacttccca tatctttttg aaattacgat  33960
acataggtac agtatttgtc tccaataggc tttgaaagtc agttgccctt gcggggtaaa  34020
gatatccata agtaacatct ttttgagtac tatagtatct acatggttct ttataataca  34080
taactctcat atcctgaaga tagcaggtct tgttatatat atttgtacta ttatatgtaa  34140
tatcgatact aaaagacgtc caaaggggaa gtctatttac cttactgtag gcagtaacgt  34200
aattatcatt tttaataata caatgatggt ggcgattgag tagaacagcg ggtttaccaa  34260
acggtagatt atatatgtaa gatgatgaac gtgttctgga actgtcttct ttatttcctt  34320
tagaagagaa tctgtctatg ttcttacaag tacaaccttt cagatgatct ccaacatacg  34380
cgtgtctatc gcactcagat tctattgtta ttatatctag agaagaaacg tgagtatatc  34440
tactatttct aagaatatta ttcaaagatc ctacagtacc gttgttgtta gcgggattta  34500
tgcctaatat ttcacacatc atattataga gttcgatgtt atcgaagatc gggactctta  34560
catcatcgag aaaagcaggt ccataaccta agaataccgc ggtcatatct tggaaactat  34620
tatcagatcc gtggaatcca cccgatcgat gttttaagtt gccgttttca tcggttgact  34680
gccatccttc ttctagatat actcccagta tctccgttct gaaccctgat ccgtaatgca  34740
atcttttagg tagcctgctc ctataactta cgatgaaagg ttgatcgtcc atcacacaac  34800
tagtagaaga tataattccg tcataatcga ataatcttat atggtttaaa ttttgaggct  34860
ttattactgg agtagctcct ggttttataa ctacgtcatt atttgttatg taatctttca  34920
gatttactat ctttttggga tctacattag acataccatg atccgatact agtattaggt  34980
tagcgcatcc tattaattgc aaatctttta aacctttcat cagtaaagcg attgctttgt  35040
caactttttc taaagctttt cctactcttt catcatctgt accgtattca tacccagaag  35100
acccgggttc ttcaaggtat agcgcataga agtagggtct atatcccgta tccattttta  35160
accacctcaa tacggtattt attctttctt cataaggaac cgatttatta tagcttctat  35220
acatggtagg gcgttttcta ggaacaactt tgtcagatcc tggccaaaag aaggttgctg  35280
atttaaatcc gttcttcatg atagtagtcc atatgggttc acctccaaac cattctactt  35340
cttcagtttc ttccgaagct atcgtaaact cgatatcggt tcccctatct atgaattcat  35400
tatccgttat accgtgagat atgggataca atccggtaac tatactgtac aagtttggga  35460
atgtattcgt aggatatacg ggcctcatag gtgccgtaac tccgtgttcc attaaatctt  35520
ttatcgtagg aatatacttc tcccatttat taagataatc atatctaaat ccattcatcg  35580
ctattagtat gagaggcggc ctttcaaatt caggaggaca ggttacctgg aatgatatac  35640
aacccccgaa cctcgaatct ctatatccga ataacaaaca caaaggtatc attattacgg  35700
atattgcagc gatagtagct agtgaataca ataagatatc tctagtttca cacttacgct  35760
tttttattgg tatagtgtaa aatatatcca cctttttttc tttgtcgata atagaactat  35820
tatcttcatc gcttatgcat tctttagatt cttcttttac aggatacaat gtataattat  35880
cactgtgtat agacatatct tcatcggact gatatccatg atccatagtg gtactatttt  35940
tcatagacat tcgtataaac taattactta atccatcatt tttattatat attattgttt  36000
gaaagaaaaa aatacgcgat aaaataacaa ttattatact tgatacgagt ttgaattctt  36060
atttttcaac aatatcacgt tttacttcct gtcatgatct ttaattcatc attatttata  36120
taggtaaaga tatgatcctt aatttcatta ggtaaattgt tccaagagga tgtattactg  36180
tcattatcta gaaataaatc ttctaatact ttacttgctt tattaagaag tacgtgtctt  36240
gacataaaag tatctataaa atctgtatat aaaatattaa acacggtaag ttttttatca  36300
```

-continued

```
aaatttacta taaatctatt atccttattt atgcatctta gtaataaatc aacattatta 36360
ttaacgaata aatcaaaaag tgtaaatctc gagtttatac ttacctgttt cattttctca 36420
atatctttta aacaatgtat cgctatacgt tgtaatcttt tattatcttt aactagtttc 36480
ttattatggt cgaatccttt agttttatta ctcatacaag tagaataatc taatctaata 36540
acgtgtgaca ctaataatga tattatttcg tagttattac aactcatggc gatatctaaa 36600
ggagttaacc ctgtattttc ttcttcgtta tctcttatat taacatctgc tttataacgt 36660
aatagttttt ttatgatatc tatactagcg ttataaatta ctgctttatg taatggtgta 36720
aatccatcat tattagtaat attagtatta gcaccgtgaa atagtaatat atcaactgtt 36780
atgcggttat cgtttttttac agctaaatga agagctgtat ttccacatgt aagactacgt 36840
tgatttatga tcgctccgtt atttaatagt aattctacca attggtggct attaaatcta 36900
gatgctatca ttaaaggtgt aagattatct cttatagttt cctgaaagtt aatatcaacg 36960
cctttttttaa caagatatct tacaacatct atataattac gtttagtagc tactaatagt 37020
aaactgtttc tatcaagtct atattttgga cataaagtta ctattccagt aatgcgtaat 37080
aactctatta gaaaaggcat agttttagtt atataatcaa aattataaaa ctttaaaatc 37140
aatttagatt tttattaaac tacatgttta taacacaacc ttcgtactca atgactgttt 37200
cttttagtaa tttaaacaga tatccattcc tagtacaggc gtatccacct cctctatgac 37260
gttgagtagg actcctatta atatcaccta tacatacccca tcctttttta tcgtaaagtg 37320
aaacaatcca tttagaatga tcataataat taataaacga tgttccattt acgtttatcg 37380
attttatgtt atgtacatgg tattttgacg agcaattggt tatcatactc tctcctctac 37440
gttgccatgt ttctgatagt aggtcagatt ccaaagtcgg acctatccat gcactcatta 37500
tatcatggcg aaaatatttt gacttagcaa atgttaaaaa cttttctcct tttctagatt 37560
ccatccacct agaaacattt ttatataaag tcgtatagtt tttatcgtta catagatggt 37620
atagattatt cagattctta tttgttactg aacagttata cacgtttggg ttattaacag 37680
gtagtgtatt gtctaaggcc gtaagacctc ctttgtaatc caagttaata cataacatag 37740
attgcccgta tacataacca gagtaaggat aattgtatcc caacacagga gaaggtggaa 37800
atctaggtac agaatgtatc aaccaaaatc ctgttacgct atcactattc catgccataa 37860
cacctttagt atgacctacc ttcgatgaat aatttttgct tcctgggatg ccatcattat 37920
aaaaaatgta ttctatatat ttactatcat ataggtcata aataggatat agtgttttcc 37980
ctattatact gtatctagag tttataggta ctttacctcg tttccattta ggattattac 38040
tatctatgta taaatattca ttacctttag tgcctaattt ttggagctta gggagcttgt 38100
atacgaaata ccagtctact acttcgcctt cttcatttac acaatttact ttacctttat 38160
catattcgtt aaagtttgaa ccgatggaat tcagtatctt agagatattt gagatatcta 38220
tattattacc gatataatat gtaatacata tgcatacgga caatgtaatg ccgtaggtga 38280
tatcatttta ttgtatttat tatacttatc tatatttcat taataaacaa cttgtattta 38340
tagtattata tagtgatatc tttctactat aaacatataa agtaataatt gaaaggtagt 38400
agtcttattt acgtactata aaaagtatat catatggatt ttattcccta acaactagaa 38460
ttagttttaa tattattgta ttttggaact aacaagataa taggaatagt cgctaccata 38520
gcaataaata ttacgaccat tattaaaaca tatggatcta tgaatttatt aatttctttt 38580
tttataattt ctaaaattag taccatctta atattaattt aattatatca ccatattcta 38640
atattgtatt atttttatgt tatttattat atcattgtgt ttgtatattc ttcttaattt 38700
```

-continued

```
ctaataacat gatcgttaag atataatcca atctagtaac cgaaccgtat tctcttaatg  38760
catctactaa tatatctaaa ttgcatgtat cacaagattc tacgactttc attattaacg  38820
tgtactctct ataatcaata aattgagcat aaagttctgt atagtatccc actatcaatc  38880
tcatatcttt atctcctata cagaaatggc aaagtatagc tttgagaaat tgatctttaa  38940
tacgatgttt aagaataggt agtctcatgc atatgatacc tatttgttcg tatacagacg  39000
cggctttatc gaattgtttc attcgtgtaa aacagtcagc tacttttatc atacaatcgt  39060
tagctgattt tatggatcct tcttctctat agtattcggt agcatattcg taatgcatac  39120
atgctttttc taaatccata atacacgatt catatatttc agctaccgtc atttggtgtt  39180
ttgccgccgt ggtgaaatta tttatcgatt tatagacttc tatcgcttgt aacaggcatt  39240
ctatagattt tttaggatct atctttctat acatattact cgcatttaca aaatttatag  39300
cagtatctaa tacgaaatca gattcctgag attgtaacac agcagcttta agaaatgaat  39360
atccagctaa ctcccagttc ttgaccgctt taaaaagtat agctgaacga atcaataagt  39420
ttccaacttc tttaacgtta tttacgtttc ttaagaactt ccaagaaaat aaaaatccca  39480
catcctttag tctacgattg gcttccgata ttagtctata cgcttcttgt tccatgtcaa  39540
aataatatcg tatcttaatt ggtaatattg tatatttatt gaatgagtgt attattataa  39600
ttataacgtt tcttatacgg aagaaatctg gactcgttat gagatacttt ggattgtatt  39660
ttactataat ttataggctt atcatcggtt aaaacggagt atggtagatg ccattcatag  39720
atgtctccta tgtattccat aaagagcctc ggcgatccat aatttatcct atgtattaga  39780
ttcatatttt gtttatacgc acaaaagtca tttagtacga tgttgtcaac ttttagtgaa  39840
atcagatatg atacagtata ttgtgtaact tctttcgaac cacctgttat aaccatatta  39900
acgggtgttt caccaaatac atttctgaca tttatatccg cgccgttgtc taataataat  39960
ttcataaatc ttacatcttg taaactggct gcaataaaga taggagtatt acctacatcg  40020
tcaaagctat cgacattagc tccattatta attaatacaa aagcggcttc ataattacgt  40080
tcttttatgg ctaaatgtaa cgatgttcta ccaccgtgta attctttaat gtttacgtct  40140
gcgtttctgt ttataagtaa catggtgccg taaatattat tacgttcgac agctacgtga  40200
ataggcgctt ttacatgatt tattatattt acgtctattc ctttatctaa tagaactgcc  40260
ataacattat ggtatttatt ggaagtagat agaaaatgca acatactata cttgtttact  40320
atggatatat cagcattttt ttctaaaaga aagcatacca tatcgtaatt attgttacaa  40380
attgtatagt ataatgctgt atatccttta tcgtctttta catttatgtt aattccgtgt  40440
aagcatagta gttctatcat ttttttattt tcatgtgtta tagcactatg tagtaaccta  40500
taatcatttt tatttattat agatccagca tctaataata tcttagctat gttgacgtca  40560
tctacttcta cggcgtatct taataaagta tatcctacgg aatcagctat atttatgtta  40620
aaatttttat ctataaagat gtttactaaa ttgtgatcgt ggtttaaaac cgccttcctt  40680
aacatgttaa aatgtttata agtattaata ttttcttgtt gatttaaaat catacgtact  40740
acgatatagt cttttaattc tatagcctgt tctaatagct ttatacagat aggttcgtgt  40800
aatccaaaca ttttagtttt catatttgta tgctaaatat atctatatag taaaaatagt  40860
ccattaaatt tctattttaa tcaataattt acctcgcatt cgtagcttat tagacaaaaa  40920
gtacatacct accaccagtc taacaaatta aatagcacct ctagtattac ttccccgaag  40980
ataagacatt gatatgttaa tatccttcat ataatcttac gtattccgaa tataaccact  41040
tcaaaatcat tgttagttat gcattctata aggtagtctg tattacattt tatagctata  41100
```

-continued

```
atagacagca tgtcaatgta tgtaaattta gtactagtgg atgtagatac tcttatagta  41160
agtccactag aatctatata agatccatag attattattt catctccaga ttttatatga  41220
tgaatacaat tatttatttt atttagtcta aacattccta taatgttact agtatctctt  41280
aagtttaata gttttctcat tataaaattt atagaatttg ggaacatggt atgacaagaa  41340
cataaatctt ttatcttgtt tatatagtta atcacatcct tatcatgttc taattctttt  41400
atgtttatat ccattgtgct tatataagat tttaaattgt attttcatta attacgtacg  41460
agaaataaaa aatacgataa tattatactt gctatctgta gcaatactat tttttatatc  41520
tatactgtta tacggataag atacaaatct taccatatta tttggatata acactataca  41580
ttttccatcg ttatgtaata ataatccaca gtcttccgaa tctatacata atattataaa  41640
atttgaatag tttcccactt ctaaagtata atcattaata tccattacaa gcatgacgtg  41700
agctaaatat tcattattaa gaagatactg agatagaatg ttagttaatg tttccgatac  41760
aaatatatta ataactttag tattattgat taatctgtaa aaatctgtta tccttgaaca  41820
ttccgtatat agatctatat catcaataaa agatatcatg tgataattca tactgtatat  41880
atacgtataa tatttattat atttcatttt catgccatta ttgtgacttt tcagactttt  41940
tactcaagct tattacgtta tagttaagca ataagtgtag agaagaaacg accataaagg  42000
gcgatataca agcacctatt acagcgctca tactattcca agttagaaag ttatacacgg  42060
ataacaagac attaagcgcg gaaatgatag cacttgtcct taacatactc atgatgtaga  42120
atactaaaaa ccatgacata tccagaaata attgcaagaa ataaaaaata atgatatgtc  42180
gactgatctt ttcgccagag gtcatcaaat acatcgcatg ccccatacaa gcataactta  42240
tagctgatag cacacatcta aagtagtatt cttttactac gtggtattta ttatatccta  42300
tgtaattgta aaaactgtat ttttctatta tctttacgac tattaaccat aacgtaagag  42360
atattagaga ataagaatga tcgcatatat attcgaatag cgtcatttta atcctgtaga  42420
tccaaatcct gaattgcctc tatccgttat attgatttcc tctaaagtag ttacttctat  42480
tatttttggg tatgctattt tttcgaatat aatttgagct atcctatcac ccttacatac  42540
attaaattga gttgatccga agttaaataa taaaacgccc acgtttcctc tatagtctga  42600
gtcaattacg ccagcaccta cgtctataaa ataattataa gcaagccccg atctaggagc  42660
tattctaccg tagtatccgt taggtatttt tagaattata tctgtttttta tcagttcttt  42720
attcataggc tctattacat aatcatacgc gctatataag tcataacccg ctgaataact  42780
agtctgttta tatggtaact tggccctatc agaaatttta tatactgtta cttcctccat  42840
ttacgccgat aacttatact ttcaatttcg taataaagta taaaaagtta ttacatataa  42900
aaggaacata ttttaaaaac tgctagtgaa gcaatgatca acgaggctgt aaaaatacaa  42960
tatgaagctg tattgaaaat atacgaatag tttttatata tacgaattcc attccaataa  43020
tcttggtcta tgaaccaaga tctatattta gatagtatgg catcagttat cgcttctgat  43080
attattccat cgtagtactg aggtgaagta tcttgtttaa cttttttaga atagtatgca  43140
caaaaggcaa taatagttat tattctaccc caattaattt tatcttctaa tacttgcgtt  43200
actataacgt taaaatcaat attcctagat ataattatat caaattcatt ataattggtt  43260
tttattactg atttacacgc tgcctttaga acatcatagg atatagaatc tattacaaaa  43320
ctttttcttg gtttatttgt gttatattct atgatatagt tctgtatcat attcaaagcg  43380
atataataag tttcgtcttt catattacta ctagccatta tgtatattat gattgatact  43440
atcttgttat agcttcaatt ttttagaatg aatctctaag taccccaaag tatatacaat  43500
```

-continued

```
ttcctgtcac tctgcattgt aatatgaaaa taaatggttt tccaactaca gtttcgctac  43560
atgaagaaca gtttattttt gggtattcgt tattagtaaa ttcaagttct atatctgtat  43620
ttaaactaat ggattcagcc ttaatttcca taatagaaga ttgtgctatt ctttcaacaa  43680
ataaagtagt ttctgggaat acatttgaaa acttaatttc cataaggttc aggcctaagg  43740
atttaagtaa ttctacgata tcataagacg atgacatctt tattttagga attttaagcc  43800
tgtgttgagc ttttttcatc ttactattat ctatccaatc taataagcta tctacgttga  43860
tactattttc caataaattg aatatctctt ctttatcttc attaggagat atcgtagtaa  43920
ggatatatct gttgctagct aatgaagttc ttacgacgct acatcctata ttgtccaatc  43980
ttcttaacat atgaagacgc ctcttagcgt cgacgagaat ggatacaatt tccaccgagt  44040
tatgccgttt ccttatttgt tcttcggtag gagcggtaaa cggtctattc catagagctt  44100
caaattctaa cacgttcttg aatttaatac tgcaaccttc tgtttcatct acggtacatg  44160
ttttatagca gttgtagagt atgttttttg tacgttgatt gatacataca ttatttaatc  44220
ctagtttaca gaaataatct atatcggaac tattcatatt atcatttatt tttttcatgt  44280
atagatctat gttttggcat tctatgttta atatatcata tattttatca gctgttgagt  44340
gatcagttag tttactcaac gcgcataaag aagaaattat actacaaggt gctattatta  44400
tattttcagt acctgtagat tttatataat tgtatatctt gatagctaca tctaactgta  44460
tttttatgat atccatactg ataataattt gtattaatag atattatttc agtttatata  44520
tctataatat agatgtatat ataaaatacc gtaattttta tgaattttcc tcatccaaag  44580
agtcatagtc ttcaatatct cccattttaa aaagattata tagtataatc aaaggcataa  44640
gcgatataaa tattactagt agtgctaata tataaattat catatgacct atcgtaaatg  44700
cccacgtatg ttcttttttct attaaacaca ctactacacc ggtagtatat accgtcttta  44760
caccgtatgt tatatcgtag tatactgaat tgggatatat aacttttttta tgtgagttct  44820
tagtagattt tctacatacc ataactttta acgagttata tatatcgcta tgagtaacat  44880
tatggccagc gtatttgcaa ttatttagat aaggtaagtt ttctttatgt ttatttatat  44940
cacatatata gcacttataa ttatcggtgt ctaataatgt aacagatacg tcttttccta  45000
gcctgatcac tttccatgct ttattactgg gtatcatata ttcagatctt tgatatccca  45060
aagtatactc gtctatgtca gttatcctac caaaacgaca tacaatattc ggagaaatag  45120
gtttagcatc gacatggtac aatacataaa gtataacatt aataattatt atacgcatga  45180
tggtcgcggg taattaacta cgtatagtat tctacggttt tatgaaatta tttttctatt  45240
tattaattgt gtataaaaag tattattctt caggaggaga tatagaaacc gcgtataact  45300
gcttaatatc atttagatta ttagccgttt catacgtttt gtcttctctt atcctagaac  45360
atctaggaaa ccgtatagat atattagaag ccgtatgggt agaagatctg gtgaattcag  45420
atccaattat ttcccataca ggtgctaatg aaatatctga gattatcacg tcggggtagt  45480
gtattttatt aatagataac caatcgggaa ttgcatttct atcgaaagga actacagaaa  45540
gattatcgtt aatttcctga agctctagat cagtatgccc accagaacac tttgtaacag  45600
tgcaccattt ttcagatttt gtatcgtagc atcccataag aaaactggat aaaataccag  45660
acttgttacc ctttccgtaa taagcaccca aaactactag atcagcttta tccgccataa  45720
cacatccatc taagtagtct ttttttattt tcagccatct acgcatacca ggttcgtata  45780
caccttttgc atctttgagt acaaaccctt ctatattttt acttaatact atgtgtaata  45840
atttagataa ttcttcatcg gtactaatat tctttacttc tgaaagtaaa attctattag  45900
```

-continued gtatttcctt tatattagca tgaataatat ttcgtctttc aattagtggt ttatctataa 45960
gtacggtatc gttaaaatac agacagtcga atatgaagat acatacacaa gcgttatggt 46020
acatactttt tttgttaata cctagagtac cgaacggtag aggttgatta gtttctgtat 46080
ctattagtat aatttcacca tctagaatca tgttcttagc ggaaggaaaa gctctatcga 46140
gtaattcttc aaagtcagta accttatgag gtgtaatagg tttaagactt ctactaaaat 46200
atttaaaatt tttatcatgt ttatgtattt gtattctttc tccatcgtac ttaaactcta 46260
caattatacc attagggcat ttttttaccg cttccgaaaa tgtcttacac gcggatgcta 46320
acatcggctg taaaggcacc attaattcta ttagtggttt aatattatct tccaaagatc 46380
gttgtactac ctgttctaaa ttattacata atttgaatat tccataagcg tctttatgga 46440
gccctgataa cacatgtttt ggaccaatgt tcattcgtaa atcatgtttt attaatctta 46500
tgatatgtcg aagatcatta ggtgtacatc tgggtattat tttttttatt tctttgattt 46560
gatcattttc tctagttact gtagataatc ttgttagaaa acaatcaact tcatgtaacg 46620
ttaatgtact ttctgtggca taatctacca cagatttact ctttttaaga aatgaaccta 46680
tcacataagc tacatctcct atattaatta catatttata catttcatca gcatcatgac 46740
aaaatatttt actaaataac tttactaact gtttatcgtt tatattataa attagtttac 46800
ccgttcccgg tagtaataac tttgtaataa tatatacatc attataatca cgaccgcgat 46860
gtataaattc tgatattagt tttgttttct ttacatagct tgattctgtg gatatagatg 46920
tacatagttc tctaaattct ttcaatgtta cttccatgtc tttataataa gccaggtatt 46980
ttttacgttt ttattcaggg tcttttattt tgcccatgaa aaccacagaa cctgttttat 47040
tatattttat tacgaatata aaaggtctat ttatatggta gttgttatta gatatttttt 47100
cccatttctt ttggtcacct agtacaatct tattatttat aaaatctact tgtgatttaa 47160
caaacaaact ggtaatagaa aacttgtctg gactaactga tttcatggaa caattttcat 47220
caaaaatatc agttatacct agttctacaa agacagactt gatgttatgt tgtgtttgta 47280
tagaaaattt tgggatacta actgatattt ctgaatattt catgttactt actcctatct 47340
tagacgataa taaaattcga ggcgtaatat gtttttccaa atatttgaaa ttcttatacg 47400
tatcggcgaa gaaaagtaac atactataag tgttatgcaa gtaaggtatg ttaatgatat 47460
tggatttaat ttcatgacaa tacatatgtc caaacattcc actcgtaatt atgtacggaa 47520
cgactttagt taaatactta gtcacaaaaa acttatgact gtcattatct gaaaacggtg 47580
attcccataa atcagaatac ttaatattaa atagaatgct cgcttctgga ggtttccgga 47640
tactagataa catatcttct gtattatagt ttaattcact cattttatta cataatacag 47700
taacatctcc cgaaaccaat gatgttatat tagatttact tacatacttc ttgtaactat 47760
catgaatacg tttgttatga tctataaaga agatggatgt atattctgtt ctagatagca 47820
gttctttaag tatcttgtct gtattactat catcgtcttc atcatcgtct aaaggtagca 47880
tatataataa atctaatagt tgatttctcg atctatcagt actcgctttc aataacattt 47940
ttactataag cataatagaa ggcggtgata tcactatatt tttatcgggt attcttttag 48000
taattagttc gtagaatttc gtagagataa aagccaattt gttgttgata ctgcttacgt 48060
tactcatgtt tcttgtttct gttaattaac aggtataccc ttacaataag tttaattaac 48120
ttttaggttt ttgtgaagaa cttttagctt ctagttccct tatccataat tgggtcttag 48180
atctagattc ttcccatgta taaaggggga catacccaaa atctttaaat gctttgtccg 48240
tttctatagt aaatgtcgta cattccttaa tcaaagtata aggatttagt aaaggcgtgt 48300

-continued

```
aagaacaaat aggtgatagt aatactctta aacctttatt aatattagcg ataaacctta  48360
aacaccataa aggaagacat gtattccgta gatccatccc taattgatta aagaaatgca  48420
tgttaaaatc atgataatgt tcagtaggag aggtatcgta acagtaatac acgttattgc  48480
agagaggact atgttgacca ttttctatca tatttcttgc tgctaaaata tgcatccaag  48540
ctacgtttcc tgcatagact ctgctatgaa atactttatc atccgcatat ttatacattt  48600
tcctgctttt atacgatctt ctgtataaag tttctagtac tggacagtat tctccgaaaa  48660
cacctaatgg gcgtagcgca caagtgcata atctaagtcc tatattagac atagtaccgt  48720
tagcttctag tatatatttc tcagataact gtttactaag aggataagcc tctttatggt  48780
tagattgata atacgtattc tcgtttcctc ttatcatcgc atctccgaga aagttaggac  48840
ctaccgcaga ataactactc gtatatacta agactcttac gccgttatac agacaagaat  48900
ctactacgtt cttcgttccg ttgatattaa cgtccattat agagtcgtta gtaaacttac  48960
ccgctacatc atttatcgaa gcaatatgaa tgaccacatc tgctgatcta agcgcttcgt  49020
ccaaagtact tttatttcta acatctccaa tcacgggaac tatctttatt atattacatt  49080
tttctacaag atctagtaac cattggtcga ttctaatatc gtaaacacga acttctttta  49140
aagaggattc gaacaagata agattattta taatgtgtct acctaaaaat ccacaccctc  49200
cggttaccac gtatactagt gtacgcattt tgagtattaa ctatataaga ccaaaattat  49260
attttcattt tctgttatat tatactataa taaaaacaaa taaatatacg aatattataa  49320
gaaatttaga acacgttatt aaagtattgc ctttttttatt aacggcgtgt tcttgtaatt  49380
gccgtttaga atagtcttta tttactttag ataactcttc tatcataacc gtctccttat  49440
tccaaccttc ttcagaagta catgtgtact taccgaagtt atcatcatag agattatata  49500
tgaagaaata gcacatatca ttattatcag gtccacaatc gacgatagtt ttgttatgtt  49560
tatttaccca gacgtaattg gcttgatgag attctatggg acaacttaaa acatgatagg  49620
atgatgaact taaatacacc tttctactaa aaggttctct ctttattaaa ctaccggaac  49680
atatattttt aggaacatcg tatatatctt tttgtaggag tttcttttct ccaccgtaaa  49740
cgcagtcaat atttgtccat ccgcaatgag ggtctctact caggagacaa ctatcgcacg  49800
taccgccgta taaatggcaa aatgctaaag gtagttcgat agtactatcg ttgtaagata  49860
caaataattt ttccgaacgt tcgtccgaca ctagagcgag cacaggagat ggatattgtt  49920
ttagagttaa ttctatgaca tttataactc catcttcgta aactactact ttgtgtattt  49980
taccatcgga cgtagaaaga tagaacgtgg taaccctgta gtctttatgt tggtagttta  50040
taacagctgt attaattact atatgtgtat acgtatattt tgttttaaat ataaaatctc  50100
cttttacacc atataatgtt tcaggatata aatcgattac ttcaaaagta tctctgggag  50160
ttgatgtgtt taaacaagta cctggcctaa ccgacagaac tttaccaccg ctataccctt  50220
tcagtggaga agtattaaag ttattctgta ttttatcgaa cttaaacata catacggcag  50280
aatagttcca ttcattaaag aatagtccat atataatagt ttcatttgga cttttacctt  50340
tgattacgac aacatctttt agataattaa atcgtacatt cagatcttcg cagatcatta  50400
tcgatttcag gaaggtagac cattttgaac ccgataatga ccccgatcct ccctgatcgt  50460
gtttacatac tctagatact tttgccattc cttcttcctg gaagaatata tatattgtat  50520
catttatact gtttgtttct tgtagcgata ctaaatgtac aaatttagga tttttcattg  50580
tagaactaga tgtatataat acaggcttac ctacgattct actaaatcct gtacttagat  50640
gactatattt ttttatagtt gagtatattt ctttaccatc tattaatacc agtcctgtca  50700
```

-continued

```
tatcataact ctccggagag agtcctctac cgtaaggcgt gggttctttt atggtaccgt  50760
tgatatacca gcatgtgggt gaactagaat tcgttccaca cactagaatt ttgtcatcat  50820
atccacctat aaatgtaata taattagcgc ctgattgtgt cgatacatta tcgggtgaaa  50880
agtccaccgt aatattgctt ttatcggttg tatttaccac gtatacagta tttgttactc  50940
ctataattag tcgggtatta caatccgtgc gatatataac cacatcttcc atataagttt  51000
tatacctaaa ctcgatatta ttttcagtca acttgctctt aacacgggga gatattattt  51060
tagcgatatt acacggtatt accaaaagta taacgatgat gatacttata taaaacatta  51120
tggttggtat actgttatat tttataatac tattgatatt ttgtgtatcg tatagattat  51180
atattcatat attacgtcat attaatacat atctattttt tatgttttac gatatagata  51240
aaaatgaata taataattta attacttatt agtatcttgg gttttgtaag gacattctgg  51300
ctcacaacaa cccccatcag aaggtttagg tccggtattt acgcctttat catcggtaga  51360
tggaggttgt acattccctt ctgggggaga atcgattgtt ggtttttcag ctggagattc  51420
catggcttta gggttcaata atattaatgt ttctttttca tttttaatgt acgttatttt  51480
gtaataatgt ttatataaat taccatactt tagatattat aaatattgaa gtaaaagaat  51540
agtctaaatt acctaacata gaacatcatg tccacgagtt taatagaatt ctataattgg  51600
tctcttacca tacgtgataa gcgtgtagac aattggctgt taatgaattc tcctattccc  51660
acaatatgta taagtacttt atatctaatt atagtctggt taggacctaa atggataaaa  51720
actagaaacg cgtttaacat tagatggtta ctagttttgt ataatttttc tatggtattt  51780
cttaatttct atattctgaa agaattattt gtatcgtcgg cagcaaaagg ttatagttat  51840
gtttgccagc ctatagatta ttcagataac gttcacgagg ttaggatagc cagagcatta  51900
tggttgtact atatatccaa agggatagaa tacttggata cggtattttt catacttagg  51960
aaaaaattta atcaggttag ttttctacac gtatatcatc attttactat gtttactcta  52020
ggatggatag gtattaaatg gtttgctgga ggtcaggcat tttttggagc tcagctaaat  52080
tcttttatcc atgttattat gtacacttat tatggtatgg ccgcttgtgg tcctatgttc  52140
agaaagtatc tatggtggaa acgttatctt actataatgc agttggtaca gttccatata  52200
gctataggac atactgctat gtccatttac atagattgcc cgtttccaaa atggatacag  52260
tggtcagtta ttatctattc tattagtttc atattactgt ttggtaactt ctattttaga  52320
acatacaaga attctagtaa gaaggttaaa taagcatata tctaaaatga catacggtta  52380
tcacaaatag aaatttatat aaatagcaaa ttggtaatat aaataataat gtataaaaaa  52440
gtcaaccttt ctggtatagt tatatcagaa ccaaaatcgg taaaaaaatt taagacaaaa  52500
gattctatag ttaatgtatt gccagaatac taccatacta ttgctgacaa aagactcgaa  52560
atacgtaaag ataaagataa ttgctggttc tgtaaacaag atatgaatac atataatccc  52620
tattttatag agactctata cggtgatcat atagggggtat tttgttccaa aatttgtagg  52680
gattctttcg ctaacatgat aaaaagtgta atagctttac gagaagaacc taaaatatct  52740
cttctgccgt tggaactata tgaaaagccg gaagaagtat tagaagtaat caacgatcta  52800
agacacaaag aaggaatata tggaagctgt atacttgaat ccgacaaaaa tatcattaaa  52860
ttaacactaa gatgccattg taatactaat taaataattt tcacttacta taaatgaata  52920
attctataat aagttcggta attaactcta tagattctag cagcaagcga actaacatat  52980
ttagcttcga tgtacaacag cccacggctt atatgccaca atatatatcc gttaacggat  53040
atcataataa aaaagacaat gacgctaatc aagtatgcag cgtgtcattc gatattaggg  53100
```

-continued

```
atcagcatat agcagctata aattatttct ttatatcaat acaattgcca gaagtatcgg  53160
gagaaggtaa gtttgcttac gtaccatacg taggctataa atgcattcaa cacgtagcta  53220
ttacctgcgg ggatattact atatgggaaa cagatggaga agaacttttc gataagtgtg  53280
tagatgataa gatagcgagt ttatccggtt attctccaga gttaaacgat atctccacag  53340
gatatactcc taacgatacg ataaaagatc ctactactct atatgtatat ataaaatctc  53400
cttttgatgc ggataaaact attagtagtt tgaaactagt taataataag ataaccgtta  53460
caataacatt cagaagtatt aatgatgtaa tagtttatga ttctaagttt caagtagaga  53520
ggtttgttaa agactttgtt tattctactg aattacatct aatcgcttac gcggttagtg  53580
atataaaacc taagtctgct tatatagagt tggatcgtag agtagtctcg tgttctagta  53640
cgcctacccc tatacccgtt atttcagatg tatacgcgtg tactgctatg tctgtttatg  53700
ttaagcccta ttacggaatg atggaaaaca aatttatatc ttaccccgga tataaacaaa  53760
ccgaatctga ctatgtaaga tgtatggtaa atcgcttgct agacgatctt gttgttgtgg  53820
cagatacagt accaaaaggt tttccgagca cggcaacatt tgtaaaagtt cctgttgatg  53880
gacagataaa tctacaagat gttgatataa tagttaaaat agacaacgta cccgatgata  53940
aagatatata ctaccatact aatctattaa tattcggaac aaggaaaaac tctttcgttt  54000
ataatatatc caagaagttt tcatctataa taggtatgta ttctcctaat acagatagta  54060
tcaacttttc taaagtaaac cataccatca gtattacgga tgcttctata cctgttagct  54120
tctgggtatc acaaaagaac gtctatcagg gagataacag atctaactat tctaaatcta  54180
aagacttagt agtaaacgat cccttcagga aaggaataga tatggttaat aaaacggatg  54240
taatttctag actagaagta cgttttggaa atgatcctat atattcagaa atctctccta  54300
ttacaaaagt atttaacatg ctacttactg ggagtagcat aaatatgagg aagattattt  54360
ttaatatgaa tccggctaat atatttagac ctaccactct caatgctaat actaagagag  54420
ggaaagataa actcacagtt aggatatctt atatcgatac agatcctaat aatcctatac  54480
attatgtagc taaacaacta gtagttatat gtacagatct atacaggata gattatgatg  54540
ggaatattaa tataactaaa attactgaat aaaaaatgat tttataaata aggtattaat  54600
aaaatgaata cggacaggat aaccgctttc attaaaaatg gcatttcagc aagaatgcct  54660
ttttatgata ctttgccaga tatggatctt gtttttggta aaaaccattt gcctagtcta  54720
gaatacggtg ctaattattt tcttcagctt tcaaaaatta acgatattaa tcgtttatct  54780
actgaaatgt tatctctata tacacacgat cttaacaaag aatctgatat tagtaaactt  54840
tttgaacctt ataacataaa gaccataaaa tcttacggaa gatctattca agcagatgct  54900
gtagttgtag acctgagacc tagcaactcg ctttataaga acgaacatcc ttactataaa  54960
tctaataact acttaaaaga aaataatcta tatatatgcg attatactat gataactttt  55020
gagatatatc gtccgatatt tgaattatcc acagagaaaa catgtattat taaggtacca  55080
actctttttg gaaaaacaat cgtaaacgca gtgcgcgttt actgcagtct atttagatat  55140
gtcaagcttt acaaactatc ggccgatagt tggttaaaag atagtgctat tatagtgtgt  55200
caacaacccc atgccgcaaa cataaataaa tttataactt atattagaaa agttactaaa  55260
tcacaaactt ggctagacag caacaatgta aattttatat taatccacga ttctgtagaa  55320
agagtattta tagaaaaatt cttatcattt tcatataaaa tatatgaatc tttatattac  55380
gttcattcgt tactctacag tagcatgaca tctgatctcc aatctctaga taacgaatat  55440
caaaaaaagt tgattaagtt gttacgcggt taatcgtatt aataatatca tagctgttac  55500
```

-continued

```
caatacttta ctaatgataa tttgttcaac aaattacata tagttaaatg aacacgtacg  55560
ctgcgtatat tgattatgcg cttaagaaat tagatacctt tcctgtagat atgactggcg  55620
ggaacgataa tacggtttta ttgaaggatt accaattatt tgtagcaaaa gttttttag  55680
gactcaatag tatgaactct atactattat tccaggaaac aggtgttgga aaaacaatta  55740
ctacggtata tatgctcaag aaccttaaaa aaatatatag tgaatggact attatcatct  55800
tggtaaaaaa ggcattaata gatgatccat ggacgcatac tatcttagat tatgcaccag  55860
aagtaatgaa agattgtatt atcatgaatt atgatgatca aaattttcat aataagtttt  55920
ttacaaatat aaaatctata aacgtaaaaa gtagaatttt catcatcata gacgaatgcc  55980
acaactttat atctaaatca ctgaccaaag aagataataa aaaacgtaat actaaacttg  56040
tttataacta catagcgaaa aatcttatgc aaaaaaacaa taaacttata tgtttgtcgg  56100
ctacacctat tgtaaacgat gttagggaat ttcagatgct tgttaatctt cttagacctg  56160
gtatattaac tcctgataag tctttgtttt ataataaaaa gctaatagat gaaaaagaga  56220
tcatttcaaa actgggatgt atatgttcct atatcgttaa caatgaagca tctatattcg  56280
aggacgtaga aaatactact ctttttgcta aaaaaactgt acatattaag cacgtgttta  56340
tgtctaaaaa acaagaagaa ctatatctaa aagccagata tttagaacgt aaactcggca  56400
tatcggtatt caaaatatat caacgtatgg cgtctacttt tgtatttgat gatattccag  56460
ataagaaaaa gttaaccgaa gaagaatatg aaaaatttgt agattcgtta tctatagatt  56520
ttaaaaatac cttatacggt aaaaaaatat ctaaacagtc gttagatata ttatcagctg  56580
gaggtacaat taatgatatc aaagacgtta aagatataga attatataac tatttgtacg  56640
agcatagttg taaattcaca ttcgtatgtg tttcaataat acaatctaaa ggaaaatgtc  56700
tcgtatttga accttttata agatcgtcag gaatagaaat attgctacaa tactttaacg  56760
tatttggtat aacatatata gagttctctt ctaggacgaa ggatattaga tctaaaagcg  56820
tatccgattt caataaagta gataataccg atggtgaaat aacgaaagta tgcgtatttt  56880
cccaaagtgg aaacgaaggt ataagttttc tttctataaa cgatattttt atactggata  56940
tgacgtggaa cgaagcatct ttaaaacaaa ttataggacg tgctatacgc cttaacagtc  57000
acgttaataa cccgccagaa cgtagatacg taaacgtgta tttcgtggta gctaaactat  57060
cgtctggtag atctagcgtg gacgatattt tgttagatat tattcaatct aagtctaaag  57120
aattttcaca gctctataag gtatttaaac attcgtctat agaatggatc tattctaact  57180
atacagattt tcagacagtg gacgatgaaa aggggtttaa aaaattaatt tctaggaata  57240
tcatactaga tgaaaataca ataacaaata aaaaaaagtt aactatgggt gaaaatatat  57300
ggtattcatt ttcttcttct ttagtatcca ttcacagagg tttcaaatcc atggataata  57360
aaatttacga ctctgaagga tttttcatca cagtattacc cgataagcct actataaaaa  57420
tatatgaagg aaaattaatt tatatattaa cagttagata gatgttaact attgctagcg  57480
gatgttctta cagcgtttat tatatattta attacattag tatacaaata atctttgtta  57540
atatctcttg cgtctataaa tgatattcct ttaatttctc tattagggat gaatctattc  57600
aatatttgtc tactcgtaag atctgtttct acgtaaaggg ctataacttc aaaatcttta  57660
tctatcaatc tgtcgtatat agaaccgtat acaaaacagt tcttacagat agcgagataa  57720
gaggaatcga tatttaattc ttcttttatt tctcttacta gacaattagt tatactttcc  57780
aagtctttta ttttaccacc tgggaagatt atatctatat ggtttgtatt atagttatta  57840
ggaagcgata gcttataact taatatatca cgttcgatgt tactcatata ctttgaatat  57900
```

-continued

```
ttcttaaaga gtcttatttt ccgtcgttta tcttttgtaa atgctatttc tgaaaacaag  57960
aaactattgt atctatggca taaaacaaac ttgtcatcta ttgttttcat tatacctatt  58020
acggatagtg gatatttagc atgtagtttg ccatattcat atgctaccag tttgattttt  58080
tgtatattat cagaatatac agacggccta aggagcaatt tatttttata atactccccc  58140
atatttatat gttaataagg tattataaat aaaatgcaag tattcgtatt tttcattact  58200
tgatcgatca aataatgatc ctaattcttt gatttctatg ttatataaag gtttaatgat  58260
ttctgaatag agttggtcta taaaacacac tatacaatac ccataaaatg ttctacgaag  58320
tatcttatct tctatggtaa gttttaatat tttattacca aatgttttta tagtaagtat  58380
tccatcgctt tcttccgata gttctctact caggcattga tatattgatt ctttattttt  58440
aactcttcct cctaataata ctaactcttc aaagttgttg aatccgctat atgtgaatgg  58500
tactattgat ctaatacata tttctttaat ttcgttatta tacatatact ttagatggtt  58560
tatatcgacg gctaatattt ctgaaaagct tcttcttttt gatataaccg attgatacat  58620
aaaagacgtt cttcttatac cgattatagg tatattatct gatgtaatac ataacgcgaa  58680
tatgtgaatt cgtctatcgc taagtatatc ttttatgtta gtgttttcta tagttattct  58740
ttctctattt gtttcgaaag taataacaca atctttattt ttttctaaca tattttgttg  58800
ttctctggat atatcgaaca tgatcttagt ttttatagtt gtttattttt cacttatgtt  58860
tgataaacta tatatagtga aatagcatat cgtaaactat ataaaaaaat actagtgtat  58920
cccatttatg aatatatttt tttaattaag atataaagga atatatgata taattaaact  58980
aataagttaa cgattatatc gttaaagtag aaaaatgtat tgagaaatta ttttacttta  59040
tagcaatata taccgcgtcc ctgagatgat ctattctact atccatccac cgtacggact  59100
tttttgact ttgcatcttt ccataaaatg tgatccttcc tctgaagtat aactatgatc  59160
agattctgta tctgataaag gagataatga ttttaccagt ctaaatccaa catttccaat  59220
atctccacag gtaactacgc acatatactt acctgttgat tctcctgttg taggatttgg  59280
gatacttagc gatcctatcc ctccataagt atgtaacagt aagttaactc ccgaagtctg  59340
ttgttcccat tttcgtgtaa taccgtcaat cttccaccat tttatgttga cttggcttct  59400
accatatatt cgtcgggtac taaaagcaca ttcaattttt agcggccgac catccgacat  59460
atctactctc gatcttcgag gggttatact tacttcgtta tgcatgtagg tttttttga  59520
aacagtaaac actcctagat tcattttttt ataatcagcg tcgccgttta tccatacaac  59580
acacatatat gaaccttctg cttctttaga taccttggat atatgtagca tggtttggcc  59640
cacttgtcgt gtcgtatccc aagttgtttt tattccttga gtaacttctc cgtcaccctg  59700
ttgccacgct acaattactt tatcttctcc agcaccctga tcatctttaa taaaacaagt  59760
aagatttata tcactacctt ccggtacgag tacataggga ggtgctttta cttctacaaa  59820
agtttttgat agatatataa agcagagaaa tattatcaac gtcaattctt tatgtcgaat  59880
actattttta catatcattg tgtgtataac taatatcttt ctacatgata aagaattcaa  59940
tatactatta aaatatttat agttattttt gattttacaa atattactaa atgctatcca  60000
tgtttaataa gctatacgtt acatgatgta ggtattatgt aaattaatct ttattaaagt  60060
attatttttc aattatgtta cctaagaaaa caaaagatga ttccattcca gattgggctt  60120
cttttaacat aacagtaact gtactttcat tagcgtagac tttaccgttc tttatgaaac  60180
agtattttga attatcatat gaaacagtac cggagtcgct tctgatttta caaattagat  60240
cactacaaac taccgaaata tcagattcgt ctgtaatagt tagtatacca gaaactatat  60300
```

-continued

```
cacctacctt atagtattta taatctatgt tacatgtcac atgaacaact atttcattat  60360
taactaactc cgctaatggc atgggggtat cttctactat ctgtatcttt ttggccataa  60420
acccagatgt ttccttgtgt aaatacttat ttataactgc cttttttata ttatccatta  60480
gatctaaatt taattcatgg ggttgtataa ctacgggtaa atacgcgttt gtattaaaca  60540
acgacattta gttcctttct aaaattaatc atccaagaat attctgtaaa caatagattg  60600
aaaggtacta ctataatatc atttttatgt ttatataaca atgatttttc aaatacttta  60660
ttagtaacga agaaatggtc gtctgttatc ttctctatat atttttgtgt tttttctttg  60720
gatttaaaaa tactatttac cattttaaaa agtttagcat cgtttatact tactctagaa  60780
ttgtggtaaa aaaattgtct aaccagctcg cctaatacaa catccgttat ataaggatgg  60840
ggtgatgatc tatagtttat agatagatct tttagtatgg aataaattcg ttttgtttct  60900
ttcgttttaa actttagata aagtagtttt ttgatatcga atggtaaagt atttatatca  60960
tctatactat aatcatctag agaagttatt gtatcgttaa aatctgaata aaccgtagct  61020
aataggtata cgttaacagg tttcgaaaca tctttatacg agaactttct aatagatcta  61080
cccaaaatct gattgtattg tgaaaaagta tcaggtatag tcataaacca gatgtttctt  61140
acttccttca aagtatatga ttctgacata atattggagg aaaataaaaa cataatcttt  61200
tctccgttat cattccctgg ggaattatac acttccaata aatcttctaa ggatgacttc  61260
atttactcg tgactatagc aaatgtttta agatgtccgt ttatcatttt tggattggta  61320
ccttgcgaac cggcgtattc agaatatccg ttgttaagca tgatatactt gatgactaat  61380
ccaccgtatg tagaattaga aaaatagata aaatttttac ccgtaagatt cccgatagta  61440
tctataaaat atttaaattt tgagcttata ttaagtttag ttaattcgtc tccgtataag  61500
acaccgtcgt ttattttcaa attaggataa agttctttat cctgttctac gaataacagt  61560
tctaaactat tagccaaatt caaaggtcct aatacagcta aagaaacatt tgtcatgttt  61620
ttttcaaaca tttcattatt gcacaatttc cgtacgttta tgtagtcagt ttcctgtagt  61680
ttagacattt tacaataaac tactttcgta tctaaaaact ctttaccgtg aaagatgata  61740
ctcggtagtt ccgtatcaca taattcatag taggatatct tattcttcag aatatttttt  61800
aatacgctta cacctttttc gtttaatatt atctgaaata ctttctttcc ctggattata  61860
atatcgttaa agtttatacc ttcatccgac ataatactaa taatattaga tagtgtaata  61920
ggtgtattag tgataggaga ccctgatagt aaaagaaaag gtaccttatt cttattttta  61980
ataatagtca ttaattcacc tgtattgttt ccgaatatgt tatgagcctc gtctatgatg  62040
aaaatagagt cgttgtactt agataaagca ttgtagttca ctacattatc gttgtagtta  62100
agactataga aattaatcgt cgaataaata tgaatatttt caataacata ttctgtattg  62160
atgagattag ttgccaaatc taaattatac gtaaatatat taagtatatt aatattaggt  62220
accaatatgt aaaccttttt aaactttgac acgataagtg caaatagcag tgctataata  62280
gttttccctg accccataat atgaaacaac aaaacacttt cattatgatc tagtatagtc  62340
cttaaaagat aatccaaggt agctaattga tgaggtaaga tattaggaat gttatctatg  62400
tgcccattaa agagttcaag tatttctagg ttcatttata gtattcaaat cttctatgaa  62460
tataaaagac atgtattcat cggccaagtt catatatttt ttattcttca tgataaaact  62520
gtcaatgtct tgcccgtata gttttacatt aaaatggaga cttaatttct gttgaaatat  62580
gtttaattgt agtacaggta ttccatcatc gtctgttata tatcctaatt tcattaattt  62640
atctacatat ttcacatgcg tagaattact aggaataatg agagattcta cttttaatct  62700
```

-continued

```
gaacttaaag tctggtattt tatctggtgt tggtaatatt cttaagttag gaacatgata  62760
tttactaaac catcctaaaa gtattttcag aaacgcgtat ctaaaataat tagattgaat  62820
ttttgaatca agactttcgt ttaacggttt aataaaatca tactttgagt tatgcacctt  62880
ctttttgta ttagtaaagt gagttttaaa attaactaga gctatccttc tcattatagc  62940
gttatctact ttatcgaata cgggtttata gttggtatct attatgatag tagcatgatt  63000
cctgttattg attttattag aataacaaga tcttcctact acacagggtt ctgttaactt  63060
cttgatattg tcggatctta tttttttgga cgtattacaa ctaaaatcag gaagttcgct  63120
acaaaatact actctcttca agtgcatgtt agcgataaag ggattaggac ctttatccat  63180
ttgttctgtt agaataacct gaccggtttc tagaaacata ttatgcatga cagattttag  63240
taattttta gtcgtcgatt ttccagtagc tgtttctcca taaaagaaga atatgcattg  63300
ttttgtagta cccatgagac aactcgaaag tatctgttcg tagagttctc tattttcaaa  63360
attttccttt gtctttggtt ggatatcgtc tagtatagac attagttctg tagttatatc  63420
atcaacattt ataccttctt cgtatttata cccagttgat acagtacaaa caaatttctt  63480
tgcgtcatta ccttgataga atatagaatc ttttatatca tacacaccgt taagaaattg  63540
taatttttct ggataagtgt cggtttctat cgtatctatc aacatatctt taaggttatg  63600
ttctatgact ttccgatttc taggacatag taacaaatcg gtacagtcgg atgataagtg  63660
atctctcata tatagtatta atttggttat attattatca tcttcacaca ttctccacac  63720
gtttttcaac caaactagat attctcctct atctgaaaca ttaattacat taagatctat  63780
tatttgctgt gaaatactga ataatttatt accttctaag gaaatagttt taatcttaca  63840
gctattggga tttccggatt tatatattct tatacaatcg ttactaatca gtaagtgatg  63900
aggatgttta tgagatactt ttttacatag attacaaggc gtggcatagt aaatatctaa  63960
aggagttact gtaaagtttt cagctgtaat atcctttaga ttaattatgc tattacctat  64020
agctttagat atttttttga tagcgtcgtg aaaaggtata tattcctctt tccagtttaa  64080
gagatctgga gattgatgtt gttgctcgct gacgaaataa taacagtctt cttcattata  64140
atctacatag gtgaatagat aatttttaaa atgaatattt tgtttagtct ttttatgaac  64200
gtgaatgtta atcgaatctt tcttagttcc cactatccta agagatggct tatgtctgta  64260
aactgatgta tctatagctt ttactaaacg gttatttgat tcttttgtca atacaattaa  64320
tttttacgc atatttatga gagtatccag ggtagtatag caattgaaaa atataagatg  64380
aaaacttgtt ttttctttat cggtagactc ggttattgaa aaattcgatt tcatatcagt  64440
tatcatttta tctttatctc tatgattact tatcatctta caatcgttat aggcgtaatc  64500
tgctacaaac tttgtaatga tgtttacaaa attatgagta gcctgatatt tatcatctaa  64560
cctcccatcc atatccacat caaaaaacac cctgacattt gaataatact cttcatcttt  64620
tagcgtttcg aataacgtac aatctggatt gctatagata tatctttcca gttcatcgca  64680
tgtaaatgat tctacatatt tgctgttatt attttctcta tgttttgtac gtacacctat  64740
ctgcttaagt acaaaaataa tgtgattgtt tcttatcaca gaaagggcca tttaaatcat  64800
taattaaaat ttcactaaaa ggatatagtt tcttctataa gtatttacta tttttaaagt  64860
tagatataat gtaaatattg tttgataatg ataacgtggt tacaaacaca aacatacagt  64920
ataaacaaat atgactcttt gtattaatat aaattgattt tctattttaa atctcgttat  64980
cgttatacga tttaaatatt atgtaactct gtatttattc gacactatta atctagtaca  65040
tacagaattt ctttcgtatc ttttaaacaa tataaacttc aatactcgtc gccgaagtaa  65100
```

-continued

```
ggcaatccta gtacacttct actatttgaa atatcacaaa atgtattatt ggaagcaata  65160
gcgggaatac tttggttttt acacgaatgt agaatgttct atagtttata acagcataag  65220
ctgatatact atttatatta agatctctat gattatgaca agatttattg tctgtatcta  65280
cgttgaatta tatttctttg ataaagatat tatttataaa aagtattatt atttttagga  65340
atacacagta gagatatata agactatgat tagatatctc ttaaccccaa tactcatctc  65400
cttcaatgaa attatagcta cgtctatcta cagacgcacg aattacataa cttaaacgga  65460
aagatagtgc ggttactaga tatccccatc tctccagaac agcagcatag tgttaggaca  65520
atcatctaat gcaatatcat atatgaatct cactccgata ggatacttta ccacagctat  65580
tataatctta atgtatgttc tatcatattt taaaaacaga aacaaacggc tataagttta  65640
tatgatgtct atattatagt gagtatatta taagtatgcg ggaatatctt tgatttaaca  65700
gcgtacgatt cgtgataagt aaatataggc aatggatagc ataaatgaat tcacatctaa  65760
aaaactatcc atagaaggaa atatatcttc tggaaagaca gacgtcctaa atatactaag  65820
aaatattaat aacgttgttt ctttccacga cgtagaagat agatatactc ctatagaaaa  65880
agaattaata agaaaattcc atgaaaatcc ttcaagatgg agttacgcgt tacaaacgca  65940
ttactgtatg aagagagtca gaatgcactt agaatgtttt gtacctagcc gcgtaaatat  66000
attagaaaga tctatattta gcgataggta tgtttttgcc gaagcagcca cagccctagg  66060
atatatggat gacccagaat gggcactcta ctgtaaacag cacgattggt atacggataa  66120
attagagatc cagtttgatg gtattattta tttaagaact ataccggagt cgtgtaaaga  66180
acgtattaat gaaaaatcta taacggagaa aaactatcca aatataagta tagactattt  66240
aaagacactt catgaaaaac acgaattatg gctgacgcaa tgtaaaaaag ttccggtatt  66300
aataatcgat ggagaagaag attttatatt cgatccatgt gcaaaaaaaa aattaataaa  66360
cgaggttacg gaattcataa attctatata aactattata ttaaataaaa ttgtcagtta  66420
acggtacaaa taccgttaac cttttctgga taaatctgaa cattcactac caaaatagaa  66480
tcctatatta tcgtttttac tgttttctgg tatgcaaacc gccgaaccgt tatttctcac  66540
cagtaagtat cctctatctt cacaggaagc atctgatttc ctgcagtcta taacatcatc  66600
ttcgttgagt gaactagatg aaacttttgt atagtcattg cagcatccta gcggattgtt  66660
ggctctaaga ctatctacat tttctcttaa atcacagcac tctccggtac atcctcgatc  66720
cggcagaggc gggcatttag cgatgcaatt acggaggtct tctcttgttt ttgaagtata  66780
gttactggat aggcaacact gtaaaatttc acctatacct tcattgctgc ttgccagata  66840
ttgaagatta catagtaaca cgcataggtc tctatcaata gcagcatcat cgtatttttt  66900
acccgccata cagcactctg tttcgcatga taacggcata cagagtatat tatagaaatt  66960
tattacaaaa aataatatac ttaatttgta acgcgtatac attttgtaat ccttttattt  67020
atatttaaaa aaaattatat tagaataatc ttgaaattgg tatatactta agagatagag  67080
gatagctctg cgcagctata ccccacttaa taaattatac cgcgcagagt ataaaagatt  67140
atattatcca ttactattta taatagagat aacagaacag tataatattt catatactaa  67200
ctcattagta cgagagatgt ttttaaccat ctatcgtatt attaaattat tagtactacc  67260
gacgtacaag tattatccat tttacctatt tttaaatgta tcgtacgtag tatacgatac  67320
tcgtatagca aaacttacca tactatagcg tataatgtcg ttattatatg ttattttagc  67380
aacttatttt tatgttatta atactgttat tactaggtga tttaccacgc ggatattctt  67440
ccaacatcct agttataagt ctgccggcac caacgttcat accgctacaa tttggaaata  67500
```

-continued

```
tggcaccgat tgtttgtgga taattacctt tatccgtctc attccctgtt atgcaataag  67560
ttttatttc actagttgtt aataggtagc cactgtccgg gcatccgggc ccagttttgg  67620
tacaatttaa aactttccaa ggagcgggaa ctggtccgta tctgccatta cagcaatcat  67680
ctctacactc gtacgttagt ataaaaggat tgtaaaaaca ggatcctatt acagttaaca  67740
cgtatataga aatattactc tgcatatctg cgttaattaa gatacttgta aacacttaat  67800
agtaattcat ctgttaatgg ctatattatt tttaaatttt tttaaccttt tataaaaaca  67860
ttatatttca aatccttgta cccaatttat tctgggttcg ttcttgagtt ctaataacgt  67920
gttaacaatt tcgaaagttt cgtctgtatc gaattgacga ttcctagccg ctggatgata  67980
gcctactact acagtagttg gagagtttaa tatagatcta aaattcgaga aatcgctttt  68040
acctaaaaag taaaacacgg atacgtaggc cgctatatgg ttgatgaaaa catccgctaa  68100
cctttcccag aaaatcttgt gactttttgt ttcgccttct ctgcaactta agtaatagtt  68160
ccacgctaat acaccttcta caaacaaaaa attgtagttc ttgaagagtc tgacgttata  68220
tcttctagaa atattttctg ctatagcctt aatagttttt tttgaaaaat ccggagattc  68280
gaaaggcacg ccggtagcat ccgtggggta aggatctata ccgactatac atactctttt  68340
atcttttagt gattgtttaa gttgtttaaa aatattttca tgagacggtg atgtattttc  68400
ttctagcagc caaggtcctg tctcttctat aacatcagat atatggttaa taatattttc  68460
ccaatcctcg tggtattcta taggatacgg ccaattattt aactttaacg tcttcattat  68520
agattacaat tattcatatt tattttgttt tcaatttcgc tgtatcatgc acgtgataga  68580
acaggccagt cattatacca cttattttta tctagtaaat tcaattttaa atcatcccac  68640
agttcgactt ctttactgat atctaacatc caaggattaa atggaagata tttatattga  68700
ttattatcag gtgatattac tttattattt tgtttatttt tattatccat agaagattta  68760
tacttattat acctaataag ttgtatcgat gctacttctt tccaaaaatt tctaaatgta  68820
atacgtttac aatctaatcc tagtttatta gcttgttttc ttactatacc aaaagcgtat  68880
attagtatat ctcctaaacc gcaattatta gttattttc tacccgtcat tcgttttaga  68940
atacgtacga tggtgtccaa attaatgtta tgtgtaccgt attctcctat aatccatagt  69000
ctaaaaaacg ttatactggg ctttccgagg ggccatctta aagcttgtat taaactttta  69060
tttttacttt ttagaatatc tgaaatcttg tatttataat gatatatagg attacaaatc  69120
cagtaagcgt ttatagaact aatatcagta acttttatat tagttctatc caggtaatat  69180
tcactcgtaa tacatttctt agttattcta gatatactgt gttttacaac acgtgttttc  69240
ttttttcta tataccattt accgatgata aatccacaac caactagtaa tgcttttta  69300
ttattctgtt ctatagattt atatcttaac atgttagagt cgtagtaaca tattaatatc  69360
ttatatttt taccaagagt taatttatat tgttcttctt cgttgttatt tattttaaca  69420
gttgtaataa ctatatggtt agtatgttct gaagaattta tcaccatata gtatctagcg  69480
gacagtcttt tcaagaacag ctttaaccta tctattccta ccttcagttt aatattatcg  69540
ggtaaatcca aaaccagtat taataaatgg gaattatgta attttaatga tattgttgtg  69600
tatttgttaa ctattattcc gttaagcatt ctaatattaa taatattacc aaattttgat  69660
agaaacctat cgaatctaaa tctatttacg cttatattct tttcatctat cataaatcta  69720
tccaatgaat aattattgct taatatatta gtgtatgtag agatcatgat tgtatatatt  69780
atagacaagt aaatttttat tttttttca atatttgatg cgataacata ttttatagga  69840
gattaaataa agtacaatta ttgcctatag ttgataacaa ttaatatatt attacgtgct  69900
```

-continued

```
tttaacagtt aaataacata cgttttataa taaattaaat gaatgatgat tggatattgc  69960
atcataccat ttataatttt aacctcaatc tattaaatgg ggagagtttt gactttaaaa  70020
catataaaga taagatatgt atatttgtaa acgtagcatc ggaatgacga ctagctgaca  70080
ggaattataa ggaacttaca aaattatacg acaggtattt ttgtgatgga ttacgtataa  70140
tggcatttcc ttgtaaccag tttggtggac aagaaccagg tggtgtcaaa gaaataatgg  70200
aaaccataaa gaaatattcg gtattatttg atgtgtccga aaaggtaata gtaaatacca  70260
tatacgcgca tcctttatgg aagtggttac aaacaaggcc tatactggga gatgtgcccg  70320
gtcctataaa atggaatttt tgtaagtttc taataagtcc ttttggttac gttattaaga  70380
gattcgatcc tgaagtcaac cctatgtcga tacaaaaaga tatagaacat gttatagaac  70440
aacgtgctaa tgaagaaatg actataaata gatgggtcat gcctgacacg cattgttctg  70500
aggaagaatc tctttctaaa gatgtgttaa atgacgtata ataaatggta tctaactact  70560
gtgttgtatt catgttaaat aattattcat cggatgatta taaaaaaata aaatctctag  70620
attatcacta tctaatactt gataaacatt cagatagttc tcataaaaca atatctggat  70680
acgtagagtt aaaagatggt atatcttgct cgataataga aaacataaat tctcgaatat  70740
tatataaaaa actacaagga aacaaggatt ttttaagaat taataaaaag aatatagtag  70800
acagttttaa atctaaaggt tgttacgaag aatacagatc gagaagatta gatcttagta  70860
tttttgatta ctataagtaa attcatttct aagtttacgg cttttagttt ttttatacat  70920
gtctttgttt aatattcttt tacatattgt ctttctactt aataccgtat tttttagcat  70980
agataggtat tccgtaaagt gatacattat atggtctaat gaattatcgt ctagtttaaa  71040
agtatctatg gaatcgagat aattatcctt taaaaaccga gtatataatt cttttatttc  71100
gtatatgttg taaaggttat attcagaaac atctaggttt aatatatctt ctctgcattc  71160
tccgaagtaa cacggactta taccatcgtg tttaagaata tcatttactt catctatact  71220
catttcttga tattcttgca cgctatcaca tctgcaggcc ttgcttttaa tgtataatta  71280
tatttatgtt ttttgttttt tttccttatt atattaaatc taaaaagcaa ataagttgtt  71340
atgtttcttc aggctgaata gttatcttgt aaacagtaaa tcctcttatc ctttttatca  71400
attccttgat tttaggttct atagtgtttc taaatgtaac ggttttgtga tatttaccca  71460
ttctgctaca ttgtagtcta taacagaaac gttgataaac cgatttaaat gcataattag  71520
tcatttcatg aaatcgacat aatattacat ctatgtcctt tcttgaattc atcacaaaca  71580
ctatttttac catgattggt gatataaaca tatagtatgg tatttatttt tatatattac  71640
agatcacgat attattttg ggtgcgggta atccttaata catgtattgt atatcacaga  71700
agtaattaaa tcctgctgtg atactattta ctatcattac aaaaagtaat gataaaaaca  71760
tccataacta cctaccacgt acgataacgt gataaagaac ggatgtgaca ataaatattt  71820
tataaattaa ttattaagtt aaaacattaa tatataataa tcattatttt ttgctaattt  71880
cctatttcgg actagagcaa aatatatgta aaaagttatt acattaactc aattgattta  71940
aattaaataa taatattgga taaatgctcc aacagttctt tcaaaaatta atttctttat  72000
tacgtaaacc actaaagata tctgtacggg gtttgctaga agagcctttt tcgggttcgg  72060
gagtaggttg atctgatggt ttactagaag agtctttttc gggttcggga gagggttgct  72120
cgggtggttt actttcgcta ggttggggct gtggctcaga accagcatca ttagaaggag  72180
gcatcgtatc aatatccgac ttctcggtgg gtgctttgct actacctcca gccaatgttc  72240
taaatacgtc actaattaac ttagtcatgt tgtccattct gccacgcata tcttcgtggc  72300
```

-continued

```
agataagtag ctgcctggta aagacatctt tggcctcttg gcctttgagt ttttcatact  72360
cttgaatcag tttcttttcc atgatttata ggctataaaa aatagtattt tctactcatt  72420
attttactgt tacttaaact aaaatacagg attatttata ttcttttttc tatcatttca  72480
taaacggttt tgatagtttc gttttcttct ttacaattac ttagttgtcc gctataccaa  72540
gctctaacaa atgcatgaaa cttatctcta tcgtaatcga attttactaa tttttctata  72600
tcactactat cgaataattc atcagaaata attactttcc aaatgtcagt atcgcttaat  72660
gatactatat gtttatttaa tatacagtaa aggttagatg attcctgttt tcttatcaag  72720
caatttatct cttttctcaa taaaatgttt ttataaaaca aatctgattt atccatattt  72780
atttgtttta taagattggg agatgtataa aaaaatgaac tgtcgttgac ttgataacca  72840
tctataacta tctcttttc gggttttaat aattgatgac atttgatcat cgttatagtt  72900
ttgatatctc cgttacatct gtaacataat acataaacat ggagtttatc cggttgagaa  72960
tacatcttta tatttccctc gttgttgatt acacatgaac ctattacttt tttatattct  73020
ttatataaca ttaaattgat tctttgtttg ataggacaga caacgttgga tgtaataaaa  73080
gaatggtata actcatcttc atcgttaaca cttatttcat aaacataata aagttctatg  73140
ttgttcatca ataatattat tcttttattt ataaattcat ccgtatctcc tagtaaaatg  73200
tatacattat tactactatt acataaatag tctactgatg tataactatt taacctatgt  73260
atttccatct aaatatgata tttaatttat atataaaata tagataaaat atcacatata  73320
aaagaggttt tttataatat tataatagta gtatataatt ttttatatta tatatgattc  73380
aaatatttat ataatgtgta tattgttttt attcttcgat ccccataata tatatgggag  73440
atttaaatat ataatagcgt ctaatagaga tgaaatttat tctcgtgaag caatacctgc  73500
taaattttgg aattctaacg gctatgatgt actcagcggt atagacgtaa aatccggggg  73560
tacctggtta ggcataaata ctgacggcaa gttttccgta gtcactaatt acttacaacc  73620
ttacgaagat cctaatttta taagtagggg aaatttagta tctgattatt taacatctaa  73680
tatatcttct cgtgaatatc tatgttattt atcaaagaga gggcatttat acaacggatt  73740
taatcttatt acggcgtctt tttctaaaga atccgatgat ttatattact actctaatag  73800
atcaggtact gcaccagaaa ggctaggaac cgggatatac ggattatcta attctttgtt  73860
agatatatca tggcctaaag tttgtgtcgg taagaaagta ttcacagata taattcatgc  73920
ccataagaat gatttaaacc aagaatcatt aatcacggaa ttactagaaa tgttaaacga  73980
taccagtccg ctaccgatag atcctagaat acaggaacag ggccaagatt tcataagacc  74040
gatgataaaa gaattttcat ctatatgcgt tagagccgat ggttacggta caagaacaaa  74100
tacgatagta actatagata gtcattatag tgttaatttt attgaaaaaa ccataacgga  74160
tatggacaca aaagagttta aaatatcgag atatacattt agtttattat cttagaaaaa  74220
gtaagtgtat caaagttctt tatttatata ataacatact gtaactttat ttaatatatg  74280
tataatctta taggttaaaa taacactaac tatcagattt atcattaata ttattattac  74340
tattatactt aacctctcca tctacatcct cctttcaaga gaataaccaa ttacgtagtg  74400
gattctttct gtattataat cagatagagt tctatacagt ccttgttagt cgggaggtat  74460
tcctttctta ttttgggtct ttaattttaa attttcaacc gtattactag gttcagctaa  74520
ataaatgatt atctttacaa atatctgcat tactgtattt ttatactaaa cgcgtattat  74580
atacgaaaaa taattatatt tttatattct agatatttat taactacttt tatctatatg  74640
ttcatcatgc atttccttta tagatttaat tatcttatct tctattacta ttccttcttt  74700
```

-continued

```
gctatcttta tcgctaagta ctatatttga ttcagaatga ttagtaatta gtaatacgtt  74760
agttcttctg gtatctagag aattagctat tacaacatgg tgattatatt tatatagcgc  74820
ttgcctagct ttagttacta acatgttttt atcggtctct aatttgaatg acactacaaa  74880
agcatttgga caccattcgt ctactaaatg aaataacatc ttagggacgg tttttaactc  74940
taaagtaata tctgtagacg aatctatttt atgttcatac atttcgtctt ctggaatata  75000
gaaatcagaa acggccgctg caagatatac aacggcatga ctaccgagta tagataaaga  75060
tttagaaatc atttctaaga aatttagata ctgatgtata caagtataac taatagcgag  75120
taatttattt tgttctatag cttcattata ttttttaaa gcagatacaa gttgtgtatt  75180
tagagcgtcg ttaaagtaaa cagtatttcc ttctacattt aatgaactca ataacatatt  75240
tcccgaaggt aataatcttg accaagggaa aatagaatat tcacggtata agaaacatac  75300
agaataacca ttttctatta acttttcaac agaaatagct cctctcatac ccgtactaaa  75360
attctctaaa aatctgactg gttttttttc taaagatact ctagtccctc cagatgtgac  75420
taaagctaca cgcctgtttt tctcttttg taattttacc caattattaa tgttagtagt  75480
cgtgtccatt tttttaatat aagaatttat attaggttaa tttataagaa accaatactt  75540
taaatctcta attcgttgtt ctaaacaaca gttatggttt cttaaattgt tgattcatga  75600
taatattatc gtaataattc tattattgaa atatctagtc tcgtttttga gataaatatt  75660
acgaataaag catattcata tcaaagcaac attagcttta catttaagtt gtactacgca  75720
tacgcacgaa gtacctattc ttatatattc ccaggaaggc attccatttt taataactat  75780
agagttaaca aaagaatgag acgtagaaca ataagaggac caaaatcgtg tatctattcc  75840
taaacagcca ctaatagccg gatattcctt acacttggtt tcgaataggt actgatagta  75900
aacttgttta ttatgtacta tttgatccaa tagttctagt ttattacctc tgtgatcaaa  75960
gactgtagtt ttgttagcga cccatgtaga actactttca caagataagt atattccttc  76020
actggtatta cctacagaca ataattcatc tatgcttcgt ttaccacgat gttctatatt  76080
cggagtacga gtactaaaaa caactttaga tgtatctaat ttatcgttta taagataagg  76140
attagtaaat tggagtaacg atcccttgca tactatacct aatacacata taaagattag  76200
ccttctaaaa ttacaggggt gcgtatggta tgccattctt atttatatat gaacttacta  76260
attaagtaat agaatatgtc tcagtaataa ttgacggtac actgtagtat ttgattccac  76320
tagtaaacac ataaattcct taccattatg tttattatcc actaatagtt ctctaataaa  76380
aaatgtagag ttttgtaacg gaattgttac aggactttta tgaattaccg attccatttc  76440
gctaatgggt ttaccaccgg gaccggccca aaacattctc gctgacgaac ctttcctacc  76500
acaccctaca catattaagc tagtagtatt tatatcttca ggcagtctag taatattaac  76560
gtaggtacaa tcttcgcgtg ttacaggaca gcattctcgc acaccgtcgg aatttttttct  76620
tgcgttttcc ggaagatatc cttctaggtc tagaaaaata gtttcgtcac tatcatcttc  76680
ctcataacta actgtactgt aatctccttc atcgccatag tctatcggat tcaagagtac  76740
gggtattatc aaacatagaa taaaaatagt tctatacatc atgttaattt agatatttct  76800
tctggacacg atatctatcc tactaagtat gtatggtatt tatttatcaa ttaatctgcg  76860
tatgtagtaa ctactacagc gtttctaaga tcatcatgtc ctacaatttt atttctttga  76920
cgtcgtgttt atatcatttt ctgttttggg ataataattt tctctaatat aaaattatat  76980
attaattctt tttctatatt gaagtgattt aattaaagaa aatatgtaat ctttatctaa  77040
ttaggttttt ccttatctaa taatagaact gtatacctgg tgatcttcct acttgattta  77100
```

-continued

```
cgtgacctaa tataattatt tagatattta cctgtttttc gcataaatat aattcctaaa  77160
aatattatta ttaagatatt aatatctatt atccatgata atatatagag aaacattata  77220
ttaatcgcca atcgaatatg aataacatac atagtaataa taaagatagc agttaatggc  77280
aaactaatat tattcatgat aactgctata aaagaagata atatagcaag atatattgaa  77340
gtgtctatca tatcttattt tatggataaa cctttaacgg caacttctaa gttacttatt  77400
ttttggttta ttaaactatt ggtttttttcg tacttttctt ccaatttttt tgtatttttc  77460
tttaatttta atatctcatt atcatgaatg tcgtatagta ttttacttat accctcagag  77520
aagaagccgc ttcgtatctg atcttcatta tcagaacctt ttttaagcct cgtgcaatag  77580
gagttagaaa gataggagtt aagtatcttg gaaaaattaa gtgcaatact aggaaaaacc  77640
caacagataa tatgaggcac gagatcgata tgcacatatg ttcctacaag ttcgtattta  77700
taggcactat ttgatgctaa tccgatttct aaaacggctt tattatagat accgttttta  77760
tagttcaatg tttttatgag ttttttagat gactctagtc tacaccactg cctaaagttc  77820
ttatttccaa gatcacatat tttagtagca tttatatatc cgttgtattt taacatgatt  77880
acttctatgt tcgcatagtt gataaagcaa aagttctcat ctatatgttt aacggtgtta  77940
ggtacaaact ccatattgta atactttcat tcagaatagt attgttttta catttttttat  78000
tataaggaaa aaactggttt attcattttc ttttaaccat gcatacacaa tttacaggaa  78060
ctgatacatg tttagtcatt acagcattat tttcaccaag atacattatt tttttaattt  78120
ctgtgaccgt agaacagtaa gattcccatc ttgactcatc aatgccctta caaggagatg  78180
tagaattagg gaatcccatg cagctaatca tttgaatgta ttgtgtgtat ccatctcctt  78240
tctcagaata tctgcccaaa aattctattt tactgacacc agttccatta acagggctta  78300
cttctctaat atctacccat gtagttacta attcacaagc gggttcgtat aaataaacag  78360
tagtattatc attactagat gtctgggtat cgtataatac agctgcatga tagtactgaa  78420
aacatgttag taacacaagt atatgtgtaa cgtacataat agaaaaaagt ataatttatg  78480
ccttattttt acattatagt taaaaccata aaactatctt aattacaaat aaaatactat  78540
gtagttccat tatttttgat cgcattaaat gaaaggaact attatattgt ttggtaaacc  78600
aaattgcccg ttatgtaaat tttcaaacga aatactttcg aataaaaaga tagctagtaa  78660
atatgaaatc gttagaataa atatagctac attcttcgat aaatcaaagg tcgtagaaat  78720
actcggtatg gataagtctt acgatctatt aaattctatt ggagaaaaat taggaaacga  78780
atatgttctt gtatttaggt atgatgatac tagtaagcaa atggcgtata ttccatttaa  78840
gaaatacata gtaataggac aaatatcaca agattctata gatttcgata agctgcttaa  78900
tgaattagaa acaacacctt acaatatact tcttaaggat aagtagatat cgtttagtgt  78960
actggatata atattattag gtttattgct aaagaccgta tctaacatat cagtattgga  79020
ttcattcaaa agatggtcta tacattggtc tgttactttt atttttatat ccttgttaga  79080
taacactttt ttagctaaca tgtaagtaaa gtagtctaag taatctttac caaaaatcag  79140
aacaatagat tctttgggta tatcttctgt tttaatacca tctgggtatt ctgtatatct  79200
atatatagat ggaatatact tgagtttaga gtaagctata gtattattat cggcgttgta  79260
ttttatttca tttccattaa taactattat acctatacct tcgttaggaa gtttataact  79320
acgtttaatt gttttagtaa atttgcctaa ctttatggtt acgagttcct taagtatgtt  79380
gtctggataa gataattcta tttcttttaa atacgtatca cagtttaatg ctttacttat  79440
aagctttgta tttttagaat tataatactt agttaatacc tttactctgt ctacgttgaa  79500
```

-continued

```
agaattacat aacgatataa atttttccat atatgcttca tcaccactgt ctaaatactt  79560
taatagatta taagatataa gggttctaaa tgacattatt cttagttata ttctttatac  79620
tattcttgtt attatgttat ttttttagtt ttaaacgaac taataaaatg gaaattggga  79680
taaatcctat taagaaaatt ccatggagtg ataacgagca tatatttgta tcatctttat  79740
ttactaataa ggacaaatat ctcaccggtc ctatgaggtt aacctataga cccgatagta  79800
aaacagcagt tttagatttt aaaggtacca actataccta ttatctagac aattttgatg  79860
atgttaggaa attagtacct acgttgctac tgagtaaata gtatatttaa taatacttga  79920
tttattttca aatacattta cagcttttta cagaaacctt acgaagaatc gcggttttag  79980
gtgtccttcc taacctataa tgcactacta aatcatccat actctgaatg ctacaacact  80040
gttttaattc tataccatct atatagtgga atgctagtaa actatataaa aaactatcag  80100
tatatacaaa cgactggcat tcgcccatgc aatagccata atctataccc ggaggatgta  80160
atatccattt aagacctata ctcctgaaat ttatatactt tctatatact ttacaattat  80220
cggacggaga tgagtagtct accccactat cagattcaac atattttta gaacctacac  80280
tcattttatt agttgactcg gtagggaggt ccgtgctttt aatacttctt tttcttatat  80340
cgaatgaata atctacgtga tcatccgagt agagttcttc ttcatcggta atacttaaaa  80400
gcttctttat taacccctca acagatatat atctatgtct gttattagta gagactgtat  80460
agtatctatc atctttaggt tctgtttcat ttacgtagta ttctagaaaa acatgcctgg  80520
ttctgttaat aataccatca ggagctaata gagtataatt acaatgtcta ttatagatag  80580
attgtttagc catattctca gtaagtaaga tacaatacca tttatcagca ggtagtacat  80640
gataatcacc agttccgcat attttattaa tgctacaatt acaaatgact ttcaaaacta  80700
cttcttcgtg ttgagtatta agatatatac aaatactaac gtttagtatt ctgttaacaa  80760
aatatacatc atgagtatta aaatatgcag tattcatgta tttaccactt ccgtacatac  80820
cgtgtaaatc tatggatggt ttgttcttat ggttttcagg aacttctact atggtatcat  80880
agtattcgtc ttgcaagttt tcttcattct ctcctatcat agaaagtatt aaatctttta  80940
tagacggcaa gttaccatat cctattacac agtatactaa acatgaactg ataaaaatta  81000
ttatattacg acataccatt ttaacgcttg acgcatatac aaaattcgaa cgaatgaaag  81060
aaaactactt cttattttaa ctgtacttaa atgattcaac taaataatgg tatacgtata  81120
tttgttaatc attctatgaa aaaagatata tatataggta tttcagattt tgggttcgaa  81180
aaagatataa acgatggaat tctagggata gcgcatttac tagaacacat attaatatca  81240
ttcgataaca agtattttaa tgctaacgcc agtacttcgc gtacgtatat gagtttctgg  81300
tgtgttgctt tacaaaagcg tcattatgaa gatgctatta gaacagctat aagctggttt  81360
tttgataaaa agtatatact aaaaacagat ttttctagaa ttgtattaga aaattatatt  81420
accgaactag aaaatgaata ctattatcgt acagaaatgt atcattgtat ggatgtattg  81480
gcgtatctat atggaggaga tctttataac ggaggccgta taactatgtt agaaaggttg  81540
ccagaaatac gtaatatgtt aagtaaccga atgaaatttc tatccggtaa gaacatagtt  81600
atctttgtta aaagactaac taataacata ctaacgttac taacaaacac attcggtagt  81660
ataccaaagt atcctattat aatacctcta gatcctcaga ttcaggatgc taggagaaag  81720
attatcatga tgccttgccc gttttatact cttcttatcc aagtagataa tacaatgaat  81780
aatttactag ctattatctg tttagtagaa aactataacc ttatagacta tgaaacaata  81840
agcgataaat tatatgtgtg tatttcattc gctaacgagg atcaatacga atatcttttg  81900
```

-continued

```
tataacataa aggatatgga ttttaacata aatagaatag aactagatct cggagaggat  81960
tatattatga atctatatat caactttcct tggctgaaga atgatatatt cgaatatata  82020
cataccatga ataccaaaag cgcgatgctg ttagccgatt taaagaaaaa tatgcataac  82080
agtatactag aacataagtt tatgattata tatcctagtt ttacgaagct attatataat  82140
ataaccgata aacaaaatca cggtatatta gttgtaggag atgttagttt tacaccagaa  82200
aaagatccaa gtatgcatca ttctaacaaa gaaaataata acaattattc taaaactgta  82260
accaaacgca agagtaaata tgttatgtat agaaagacac cgacgactaa taatatagtt  82320
attgattata cagacagtag ttttttgat tacgcgactt tttaccatgt tatgaaatca  82380
aaatatgaaa agacaaattt attttctagg cttaagactt caacaggcat gtgttataaa  82440
cattgttttg ataatgatga tcttaatgaa ttaataaatt cagatacgtt tatacggtat  82500
aatagttcta aaccagctgt attataccaa tatatacttt tagcatattt tgttaccgaa  82560
cgagatataa aagagttagt agattataaa gacgctatag aattagacat gaaatattat  82620
agtaaaaata aaatactctt tggaaagaat actagatatg atatacgtac caaatcaatg  82680
tttgtatgtg gattaatcaa aggacgtaaa ttaagtgaaa aagtcattac cgattatatg  82740
tggaagctaa aaagtttagg attaatatat tatcttactt ctattaaact aggaatatca  82800
aatacttttt atatttttgc atttactata tttccagaaa aagtatataa ttttttgtt  82860
gggttaaaag agataaccaa tcgttgtctc atagtttcaa ataaaaatac aaaaatagaa  82920
gaagatgact attcctcttt aaacaagcag atagttatcg gtataaagta aaacttcttt  82980
ctgttaacat ataaacataa tttctatata gttgtttact agataatctt ataactgtat  83040
tcatgtaggg accgaacaaa atttctcctt tgtaacaata catcttttg cgtctagtag  83100
ttgtattgat tttaactaaa agctgaagat tctttatgtc cttaagagtt tctccggtta  83160
gaatatcatt cctttcaaac atgtctaggt tttcggcttt cttaccaccc ttgttataaa  83220
ttttgacgta ttctaccata ttaacgaaat aattaacata aatttcgaat aatctatcaa  83280
acgatatatt aaaagacttg atatactctt ctgatttttt taacatatcc ttatcactag  83340
gaattactaa taaatcgtta ggtagtgata atttgaattt ttttgcatat actatgtatt  83400
cgtataaaaa ttcatggtct atgcttttaa tcggttttaa aagacacata tcataaaagt  83460
atacgtaaat accttttgat accctaccta cacggccttt tctttgcgtc atcatagact  83520
tggatataaa cagttgatca cctccgaagg gttttgggac gtatacacgt cccgtgtcgt  83580
atacgtgagt agccgtacga atagtaatac tggattcaag gtaaggagta gaaaccaaga  83640
tacatggacg ttctctacca ggtctctgaa cggcgttaag aacctctgta atatcaggta  83700
ttttaccgtg tattattata aagtccatat cggagttact tttctctagg tattttttat  83760
aacttataca ctgagaaacg gatgctaaaa atagtattcc acacatgccg tttctaggtc  83820
tacaccagtt aagagtggtc gatatattct tttttcttc ctctgtatac gctttggaat  83880
cgtaagagta cttgttttg acatatatct ctttaatgga gtagagtacg ggaccttcta  83940
tatggtaaaa ttctacatct ggtaagaatt cttgtaatct gtccctatcg tcttctaaag  84000
tagccgacat taataccaga gaatgtatag tatcgatatt ttttcttaga acggatataa  84060
taatatctgc tattctatca tgctcgtgga tttcatcaac tataataata ttataattag  84120
ataaagaata actagtaagc ttgttcgtag ataatactat accatcgtgt tgtcgtgtag  84180
tatgttctgt ttttcctccg tatcttagtt ctacaggcga accttcaaaa tctgaaaacc  84240
ctaatgactg taaaaaatta ataccgttac ttttaactaa agctactcta ggtaatgata  84300
```

-continued

```
aaactattgg tctagatatg taatcaaatc ttacacgatc taaattatcc catcctccga 84360
ataaatagtt ataccacata atcacttttg gtaactgaga tgttttccct attcctgtac 84420
ttcctgtaac gactatttgt ttgcgctttc taagtagttc gaagatttgt aattgtgtaa 84480
ttaagcttaa agacttaaat ttaattacag taaatggttt tggatttttg agtatgccta 84540
ttgaagattt ttcaggcatc tgtttattgg aagaaaaaat agataatata tttcctgcag 84600
ataatagacc tcttttatca tctagagtta tatcgtaaat actgttatac cccttacact 84660
ttagatagct gtaacattcg aacgtaataa atgttttatc tgaaatcttg tatatttctt 84720
tttttatatc ggtacttata ggacgtatat cgataagatg ttggataggt actctatcgt 84780
aaggttttga agtatctaat tcgatattta gcatatagac attattctga aaacatatat 84840
aagctttgga ccatcggtgc tttataaccg gaaatatagt atacgagaaa aataaaggat 84900
tttttcggtg atattcttct agttcttttt gactatactt cctaggaaat atatcataca 84960
tattagaaaa tgcataaata gaaaatagat cgtttgttgt catgtcacag atgttatata 85020
tttagttagt aataaatgga caagtataca gaactcgtta tcaataaaat accagaattg 85080
ggattcgtta atttactttc tcatatttat caaacagtgg gattatgttc atctatagat 85140
atatcaaaat ttaaaacaaa ctgtaatggt tatgtagtag aaagatttga taaatcagaa 85200
actgcgggaa aagtatcatg cgttccaata tccatactaa tggaattagt agaaagggga 85260
atgttatcca agcccgataa tagtaaatca caattagaag ttaaaacaga cttagtaaac 85320
gaactaatca gtaagaataa cggatttgaa gatataatga ctattcctac tagtatcccg 85380
atgaaatatt tttttaaacc tgttcttaaa gaaaaggtat ctaaagctat cgattttca 85440
gttatggata ttaaaggaga cgatgttagt cgaatgggta tacgctacgg agaaaatgat 85500
aaagttgtta aaattaaaat tgctccagag agggatgcct ggatgaccaa tactagcatt 85560
caccagtttc ttatccccat gtgttacggt acggaagtaa tttatatagg acagtttaat 85620
tttaacttca tgaatagaca cgctatttac gaaaaatcat ccgtgtttaa caaaaatacg 85680
gaagtgttta aattaaaaga taggataagg gataacagat cctcaagatt tattatgttt 85740
ggattctgct atttacatca ttggaaatgt gctatatacg ataagaatag agactttatc 85800
tgtttttatg attccggagg taataatcct aacgagttta accattatag aaacttcttc 85860
ttttatagta attcagacgg actaaacaga aattcatatt tatctagttt agcgaatgaa 85920
aatgccgata tagatatatt atttaacttc tttatagata attacggtgt aaccgctggt 85980
tgtataaacg tagaagtcaa tcagttactg gaatcagaat gcggtatgtt cacgtgttta 86040
tttatggccg tatgttgtct aaacccacca aagggattca aaggaatacg aaaaatatac 86100
acctacttta aattcttagc tgataagaaa gtaacgatgt taaaatctat attatttaat 86160
gttggaaaaa tggagttcac tataaaagaa gtagatggag aaggtatgca acagtataaa 86220
aaaatggaga aatggtgcgc caacactata aatatattgg ctaataagat aacctcaaga 86280
gtagaagata ttataaattg ataatggata actttttaaa gcaaatttct tctaacgtga 86340
aaaaacctat agcagaactt gaagatccgg atgccgtgat aaaattccat tacatgaata 86400
tatcttttaa tttcccggat ctgtattatt gtaataataa tttgtttgat aaacccgaaa 86460
acaacttatt agatatatca aaatcgctac tgatgcttaa ctcattttca cacgaatgtt 86520
ttatattaca agatatattg agagtcattc gccgttacgg ccatgtatac gatgtttact 86580
ttttacctat tggttggttg gtaggacatg gtgaagcgcc taaatatcat gcatcgataa 86640
aattaataag gagcaataca caagaaataa tagacgggat catacgcaga cagttatccc 86700
```

-continued

```
aatacggtat acaaggagac aatttatcaa tttttgtaga ttcttccaat gaagttgcta  86760
taaacaggca ctctattata ggagctagac agttgaatcc tatatgcgta gtatcttttt  86820
atccctttga tccagaacat aaagtttttt tcgttatata tgttggtaga tataaagata  86880
agtattgtgg aatttcctac gtagctgata gagaagatat gtacaaagtt atcaacagga  86940
tatacccgta cgttagttgt ttttacctcg tatcagatgg tataataaat tttcatacta  87000
ctcccgtagc taatcacact agaaatatta aaccccttcc agttaattat tgtaatactt  87060
tatgtgaaat agtatatgat tttgaatatt taaagtttga acaaggtgtt atgtctattc  87120
cggtgttcat gccttttgta ccaaaacagt ttgtatctat tatcaattta ccagatgata  87180
ttctcataac atgtacagcg tccagtaaca tagaatacat aacacatata gataataaaa  87240
agctaaaaag aatacttata ataataaaag ataaatttct aaagggtact atcatgcaag  87300
gtacttttaa aaaagtaaat atcataagac acaagaagta tacatatact ataacgtatt  87360
cttcttttga ttgccctaaa ctagaagata ctaagtcatc gctgccaagt acgtgcaata  87420
aagccatatt agatgggcgt agatatgtta caaaaacttt taatgataca atataaatgg  87480
aaatagctag agaaacgcta ataacgatag gccttactat attagtagtg ttattgataa  87540
taactggatt ctcgctagtg ctaagattaa taccgggtgt ttatagttca gtatcgaggt  87600
catcatttac agcaggaaga atacttcgtt ttatggaaat attttctact attatgttta  87660
ttcctggaat aattatattg tacgctgctt atataagaaa aattaaaatg aaaaataatt  87720
agaatctgaa aatgtcttct ggaagcatcc atgttattac aggccctatg ttttccggta  87780
aaacatcgga gctagtaaga agaataaaaa gatttatgct atctaacttt aaatgtatta  87840
ttattaaaca ttgtggagat aatagatata atgaggatga tataaacaaa gtatatactc  87900
atgatctatt gtttatggag gctacggcat cttctaatct atctgtatta gtacctacgc  87960
tattaaatga tggagttcag gtaataggta tagacgaggc tcaattcttt ctagacatag  88020
tagaatttag tgaatccatg gctaatttag gtaaaacagt tattgtggcc gcgcttaacg  88080
gtgattttaa acgcgaatta ttcggtaacg tatataagtt attatcatta gctgaaacag  88140
tgtccagttt gacagctatt tgcgtgaaat gctattgcga cgcttcgttt tctaaacgag  88200
ttacagaaaa taaagaagta atggatatag gtggtaaaga taaatacata gccgtgtgta  88260
ggaaatgttt ttttagtaat taaggggttt agtgtaataa atttaataaa atattgacaa  88320
aatagttaaa tgaatatatg aaagtacatt atacacggaa tggagttcga tattagttct  88380
tgcagaatga tatattctgt tctcgaacaa tatcactttg ttactgataa tcgttataac  88440
aaccataatc aaaaatttag aattatatta tactgtttaa aagattctac gataaagaaa  88500
tatccgtaca ggtttgtttc tgaaattcac tttgtaagat acataattaa caaattcagg  88560
gggaaaaatc tttacaaaat tagtatagaa gctatagata tatcaaaagg tagacaacaa  88620
ataatcagaa cctaattttt ttatcaaaaa attaaaatat aaataaaatg aaaaataact  88680
tgtatgaaga aaaaatgaac atgagtaaga aacaagtaaa aactcaaagt aaatgtaata  88740
ataacgcatc tagatttaca tgcctggatg cggtgcaata cgctaaagct ttgtgtacta  88800
aagatactaa aatagttaaa tcagtgaaat taactccttc tcatcataat ctatgcagta  88860
atatttctgt gacattagaa cctaaatata atgaaaaact tgtatctccg tttattttgg  88920
tggaaggaga aggaaaaata tatcaaacta gaagtgacaa tttcagtcgt gaggaatcat  88980
acttcctaaa aatacgcccg agtgtaatta gtcctatttt acatcagatg atggaatgca  89040
tttatagtga cttgggttat ctggatccgg aaaatactat ggatgaaaaa acatttaaag  89100
```

-continued

```
atggttatat atacattaat aaaaataaaa tgtcatctac tataatagaa tatacgagaa  89160
acaacaagga agtagctggt agaaaaactc tatccagcga agtagaacat ctatcgaaga  89220
aagatcctca gatggttaaa gctgtactag ttgcttctat atttttcgaa aatgcggtaa  89280
tgtgtaaaat aagctttagc ttgaaaaagc ttattatgga aaaagtttgt aggaaaactc  89340
tgatagatac taacggagaa gtaatcagcg tcgtaacctc cggagacgat gatatagagg  89400
atgaatcggg agagtttgaa tatgaatcag acggtgtatc tggaatttta gaagaaagat  89460
ctgatggtaa caggagaggt ggttacaaaa taaaagaaac agatgaatat gatgaacgat  89520
cattatttaa cgtaaactaa atggaaaagc tatttacagg tacatacggt gtttttctgg  89580
aatcaaatga ttctgatttt gaggatttta tcaatacaat aatgacagtg ctaactggta  89640
aaaaagaaag caaacaatta tcatggctaa caatttttat tatatttgta gtatgcatag  89700
tggtctttac gtttctttat ttaaagttaa tgtgttaaga ttaaatggag caatttgatc  89760
aacttgttct taatagtatt agcgctaaag ctttaaagtc atatctgact acgaaaatag  89820
ctgaagctat agatgaacta gccgctaaaa agaattctcc taaaaagaag gcacaaacta  89880
aaaaacccga gaatagaatt cctctagatc tcataaataa gaactttgtg tctaagtttg  89940
ggctaaaggg atataaagat ggtgtactga atagtttgat atgtagttta gtagaaaata  90000
attactttga aaatggcaaa cttaaaaggg gtaaacacga tgaactagtt cttctagata  90060
tagaaaaaga aatattggcc agaatagatg aaaattctag tctcaatata gacgtactag  90120
acgttaaggt tttagcaaat agattgagaa caaatgccga tagatttgag tttaaaggtc  90180
atacttatta cttagaacaa aataaaacag aggatattat caatcagctt attaagaatt  90240
cagctatatc tatggatatg aaaaatacta ttaaagatac attttatatg atatccgatg  90300
aacttctgga tgtatttaaa aatagactat ttaaatgtcc tcaagttaaa gataatatta  90360
tatcacgtgc tcgattgtac gaatatttta ttaaagctac gaaacccgac gattcaaaaa  90420
tatacgttat tctaaaagat gataatatcg ctaaaatact gaacatagaa actatagtta  90480
tagaccattt tatctatacg aaacacagtc ttttggtatc gtcgatttct aatcaaatag  90540
ataagtattc taaaaagttt aacgaccagt tttatagctc catatcagag tatatcaaag  90600
ataacgagaa aattaattta tctaaggtaa tagaatacct aactatatct actgtgaaaa  90660
tagaaaatac tgtagaataa atgatagtaa cagtactttt tttaattatg ttcttcattt  90720
gcacgttata cagctatcac tatttgaaac catggatctt ctatgtcgaa cgtgaagtca  90780
cgtagatacg aaatggaaat ataaatttat aattatataa tcactacttg tcatcttgtc  90840
tgagatggcg aatctctatt ctaagaaagt tagaaaatcc atacgcaaat ttattcgttc  90900
aggtttaaac ttcgacttat tacatgagaa acacggacgc cgattaataa ttaacaatat  90960
attcgttaaa ttacccccaa aatattataa ctttgctaaa ggtctggatt taaacaatat  91020
actagcgttt gatagcgaaa taatacaact taatgactta aaaaaactga ttatgagact  91080
acctctttta ccagactgtt ttaccgatgt aatatcgtgt cataaaaaat acttattatc  91140
ggatgctgct attgtgaata aacttattaa ctctaatatg gtatctcttt cagatatacg  91200
taatataata gataacagaa taaaaacacc tgttgaaata gcattgctta acagctcttt  91260
agttataccg ggtactccat ttctctaga tgaagtaaaa tatatttttg aaaacactag  91320
tgcagaaaac gtgaaagagc tatacaagag aatagaaaca cctattcaca gcgttctcta  91380
tatggaagaa aaattttcta tatcaccggt tcattcatcc ctatatcaag taactgatgt  91440
tgataaaatt atatatttga taaagaagta tcccgatgat gatattattg attatgtcaa  91500
```

-continued

```
tggaatagta aaatcaaaaa aagattttat agaatcaata attactatca ttaaggatag  91560
attacccgat atatcacctt gcttgaataa atggatatca acacaattac cacccgataa  91620
acttagagat gaatttggta tatactttta tgcgttgttt gaatggatag atatacctct  91680
atacatagat aagtacttgt ttctaaacat aacggaggat gaaactaaat ttatctgccg  91740
ttatatagat atatacaaaa aaaagtcaga gttgtttgta aatgcgttta gatggcatct  91800
atattattgt aatagtatgt atcctcaaaa agtatttccc gttattactt ataaacaaga  91860
ttctaaagaa aaatatgttg taaaagaatc attcaagtat ttagataata aacaaactat  91920
gaaagtacta ttaaatgatt ttaaatataa ctatgctata gggaaataca tacttgactc  91980
gtcatcgtcc aatgaggtaa agatggatgc tctaaacatg ttacagaaac aagtagtttg  92040
tttagaaaat gctaagtgtt ttgatctagg taatttatat tctgtattaa taaagtttca  92100
atatcacccg gtagattatg taatgtatag cgataaactg ttagattata tgtctaaaaa  92160
tagtactttc gataataatg atataggatt attgactcta gcaagtttct tattttctac  92220
cgccaagaaa ggtattatag atatcaattt tctgaatact aactcgctat ggagtccttt  92280
gatgtatctt atagatgatt cgtgtaaagt agatttcacg aggtttatga tggctacaaa  92340
gaatataaaa gccgataaca taaattatct caaaaacaag gacgaaaata ttaataataa  92400
ttttgaacat atagataata tagatatata taaactatta gactatagtc gaataaaact  92460
ttatggaata aacttcatta aaaaagtaat actagctaat gttattttcg aatatatttt  92520
tactttgata attatcagat atcaaaaaac aagctataat ttaagatcgt ttttagaaat  92580
gttattatat agatgcttaa aaggatttgg tatatcacca aaactgtata aaaatgtata  92640
cgttaatgaa atgaatattt gttgtgaatt agaaaaccta atcaataact atgttgtacc  92700
tttcaaaacc tacggaatat taatgaaact attaataacc atttttaata acttaaatgg  92760
aattagtaaa cattctttta gaatcagagt cagaaagagt aaaactctat tatgatattc  92820
caccaaaaaa atctttaaga accaagtgtg aggtagatag agcggttaaa tatttcatat  92880
cggttataaa gaaatatata aaactaaaag aatctacgtt ctatgtagta gttaaggata  92940
caacattatt tacatataaa tacgataaag gagaactaac tccagtagat aatacttatt  93000
atacattcag taaagaacta gctagcacgg actatagttc ctcagaaata acttctattt  93060
gttttactat tactgacgat atgagtattt ctgtaaagcc aaaaacgggt tacattgtta  93120
aagttagatc tgataattct aggtattact aaattagttt ttttactttt tttatatcta  93180
tacatctttc tggattaaac actagattgt tgtaaagact tatgaaaaag aagtatatat  93240
aattaatatc gttgcttgac ataatattat tcttctgtat tgcctgtaga gcatggtcct  93300
tacattcagc acacggtaat gctttacata tgttatacaa gtgacgtttg caagtttcta  93360
tatcgtgttt aaacttggta attataataa atataactat ccaaaagctg cttccccagt  93420
atctaggatc cataactgaa atttaacgta tctaaaaaaa tggatataag gtgcgtaaac  93480
tggtttgaga ataaaggaga aacaaaatat atttacttaa aagctattaa ccgagaatcg  93540
aatgttatat ttataagatt caattattac tatcactatg tatacgatgc ttccaaagaa  93600
ctagaatata aacctaatga gtgtatagat ttaggaccgt tcaaaattat taatatagac  93660
gaaaagctaa gtaccgatat aaggtatgtc gaacctcgaa attactatac ttcggaattg  93720
gtactcgtaa aggatctaaa aagaaatagg gaaaaacaat atctgcaaga atatttagat  93780
ataacttggt tttatctact taataatata acaccggacg ggtgttataa aatagatata  93840
gaacatctaa ctcctataaa aaaagattgt taccattgtg atgatgttag caaagtattc  93900
```

-continued

```
attcaagaaa tacctatctt cgaagttaaa tttacttact tactgtttga catagaatgt  93960
caatttgata aaaagtttcc ttctgtattt gtaaacccta tttcacatat cagttgttgg  94020
attatagaca aggtcaccga atataagttt actttaatta atacagatat cttacccgat  94080
aaagaaccta gtatattaca tcacaaagac ttctctccaa aagataggat aacctattgt  94140
acagaaattg tgatgttgct tataatgaaa aaaattctag aacatagatt cgattttgta  94200
ataactttta acggaaataa ttttgatatc aggtatatat ctggaaggct agaaattctc  94260
gagaaatctt ttatatattt ctctcttcct gatgcgacgg aaacagttaa acttaaaata  94320
tttgaaagat tcgttacagg aggaacattc actaataaaa cataccacat aaacaataat  94380
aatggtgtta tgttttttga tttgtatgcg ttcatacaaa aaacagaacg attagattct  94440
tacaaactag atagcatatc aaaaaatata tttaattgta acgttgctat aaaagaaata  94500
gatgatacaa ttttaacatt ggaagccacg gtaaaagata attctaaaga taaattatct  94560
atattttcta gagtattaga aaccggtaat tatatcacta taggagataa caatgtaagc  94620
aaaatagtat acaaagatat aaaccaagat agtttcataa ttaaagtcat atctaacagg  94680
gattacgaaa taggatcggt acataatata agttttggaa aggacgatgt agacttaaaa  94740
gacatgtata aaaactataa tctggaaata gcgttagata tggaaagata ttgtattcac  94800
gacgcttgtc tctgtaaata tatatgggat tattacaggg tgcccagtaa gattaacgcc  94860
gcatcatcta cttatctttt accacaaagc ttagcgctag aatatagggc cagtactctt  94920
attaaaggac cattactgaa gttactatta gaagaacgag taatctatac tagaaaaatc  94980
acaaaagtaa gatatccgta tataggtggg aaggtatttc ttccttctca gaaaactttc  95040
gagaataatg taatgatatt tgattataat agtctgtatc caaatgtatg catctacggt  95100
aatctatcac cagaaaaact agtatgtata ttattaaata gtaataagct agaatcagaa  95160
ataaatatga gaactatcaa aagtaagtat ccatatcctg aatatgtttg tgtttcttgt  95220
gaatctagac tttcagatta ttatagcgaa attattgttt acgatagaag agaaaaaggt  95280
ataataccta aacttttgga gatgtttata gggaagagaa aagaatataa aaacctttta  95340
aagacagcat cgacgactat agaaagtact ttgtatgact ctttgcaata tatctataag  95400
ataaatagcaa actctgttta cggtttaatg ggattcagta atagtactct atattcttat  95460
tcgtcagcaa agacgtgtac tactataggt agaaatatga ttacctatct agattctata  95520
atgaatggcg ctgtgtggga aaacgataag cttattctag cagattttcc tagaaacata  95580
ttttcaggag aaacaatgtt caacaaagaa ctagaagttc ctaacatgaa tgaatctttt  95640
aagtttagga gcgtatacgg cgatacagat tctatatttt cagagatatc taccaaagat  95700
atagagaaaa cagccaagat agcaaaacac ctagaacata taataaacac aaaaatatta  95760
cacgctaact ttaaaataga atttgaagca atttatacgc aattgatatt acagtcaaag  95820
aagaaatata ctacaataaa gtatttagcg aactacaaac caggggacaa acctataaga  95880
gtaaacaaag gaaccagcga aacacgtaga gacgtggcat tgttccataa acacatgata  95940
caaagatata aagatatgtt aatgaagctg ttaatggaaa gcaaaggaca gcaagagata  96000
accagattaa ttcttcaaag tttagaaaca gatatgatat ccgaatttac acacaacaga  96060
gaatttgaaa agtatttgtt gagtaggaaa catcacaata attacaaatc agcgactcac  96120
tcaaattttg aacttgttaa aagatacaat ttagagaata cagaaaaaat agaaatagga  96180
gaaagatact attatatcta tatatgtgat attagtttgc catggcaaaa aaagctatgc  96240
aatatattat cctatgaagt aatcgccgat agcaagtttt atctgcctaa agacaaaaga  96300
```

-continued

```
atattctacg aaatatactt taaaagaata gcatctgaag tagtaaatct gctaacggat  96360
aaaacacagt gtatgttatt tttcagcaga cttttcggta ctaagcctgt attttcatca  96420
gactaatatc acattttctt tttttagtcc taatttattc attagatatt ctacagcggg  96480
tgtaattttt gtagttactg ataaacctgg aaggtagaat atcaaaaaaa tcaatacagg  96540
atcctgcttt gtattagaaa taataacaga caagttttcc aatgtttcaa tattcaatag  96600
atacagattt ggagatgttg caggaatttg taacgtggcc atattaacag gaaataaagt  96660
tccatcgtat agaccctgcc ggtccagttt accaaagata ggtttgtaat caccgcctcg  96720
tataagatat ttagctagtt ctatatgctt agcatcatct atatagaaac tacccgtaag  96780
gctgtggatt ctaggattaa aagttgtatt tttaaagaag aataatatat tatatattgg  96840
aatgctcgta agcaataaga aacttattaa ctgatcaacg ggtaatatag aaaatttctt  96900
aaagtaatcg tttagattaa cagtagaaat ctggttcaaa tactgtatat ttattttagg  96960
agtatattgc ggaggcggac cttgatgaag acctagcatg aactcaaatt tgtttaatag  97020
acctaatgtt ataggataat agcttcttat atctagtttt tcatactggg tgttccataa  97080
tgctgtttca ggtatccatc cataagcata atcgtgatac aaaaacgtat tattaagtat  97140
agggggtaaa ttcatacgat taaacgtctt ttgatcatct gtgcgttcat gagcgtttcc  97200
tataatatct cttataccac gattagcgtt agtcataatt gccgttgatt atttgtaata  97260
taaatttttt atcattttta gataaatgtt tagtattgtc tagatattca ttaacataat  97320
atatgttttc ttgtagaaac tgtttaaata atataataat agctacttta aaatgattaa  97380
taattgtacg cacaactgat ttaagtatag atttatcatt acaggttgca taaactataa  97440
aagaagtaaa gttttgtaaa caactagatc ccgttatgat tttaaggatt atatcatcct  97500
tatagttttc tattattaac cctaacgatg ctaatttaga atcaagatag tatttcaaaa  97560
gacttttact aaataaagaa aaaacaatag agggtgaatt aagatctaaa tcagatagtt  97620
tttttagctc tcctttataa atgactatgg gattatcctc atttaagtat aaataagtat  97680
tatactcttt tatagcatat tctgtatctt tattatatat ctgacaaagt tttttatttt  97740
ctaacgctag caagtctaca ttttgtgttt ggtatatcat ttgagaaaca tatgtagaat  97800
ttattttcat atcatcaaat ctctttacta aagtagcgtc tgttctgaat atagattcta  97860
tgtctcttct tatatcaaac ttttccgggt ctattttagc aatcacgtta aacaaatcgt  97920
cgtagaatct attagcggat gtaaatgttt tatcatctat aaagttatca tgataaaaat  97980
caacaaaata tgatttccag gtttcatccc tttcgtctat aatagaaagg atatcacctg  98040
gtataccata tattaattcc aacataaatt tcttaatttc gctatcgcta tccaacatat  98100
atacaacttt taacatattc ttattaacac gagcttgttt aatttctgag tagatataac  98160
ttaatacctt ttcgtaaatc gtgatcgcgg gttcattcgt atatactttc tcatcattat  98220
agattctttc tttcataaac aaccaataac tcgtagtact attttttgga aatacaaatt  98280
ctttaaatgt ttctgtcatt atactgctga ctacaggtcc cgttttctgt aatatagtat  98340
acagatcgtg actatcatta tcatcaaatt tcatccctgt atccattttt agcgaatagg  98400
cccatattag aagtcgtaac acacttatcc tgtctacttt gataaatcta gtttccttaa  98460
agagtttgga atatattatc tctaagtctt taataggctc attcaagtga aataaaggat  98520
ttaactcagt actaaagtta acgcttataa tatcttgaaa gtaaggtgaa agttttgtta  98580
cgaataagaa acgtttgtca tccaggagtg tattagactg ttgtttataa atatcaataa  98640
aatctgtaaa agatgtatag tttttacta actggtttag gtataaaaga gttacatcga  98700
```

-continued

```
aagacgactt aagaactata tcgtatgttt cacagtctct tatgaaatgc aaaaatatat  98760
aaaaattggt attattaaaa atgtccttag tcagcactga tttatgatac tttttaataa  98820
tatagttaat agctacgacg tgattaagac aaaagtttga tatcttatcc gctagttctt  98880
gcgtaaagaa attaatattg ttttctacag tatatataag atatttcctt cttataaaat  98940
ccatactaat actatcttat attaatcgat atttataaaa tgtttaaatg atatatatta  99000
taacgataaa caacagtaac ttaatgacat attttactat atctttatat ttatatttaa  99060
ttattactgt tatgaaagtg atgtaatatt attttttatt aacgaagtac taattgtagc  99120
gtccaaatca tatattagat cttgcatagc atcttctatg gcatgtaaca gtaaattctt  99180
ttctatgtct ttgatcacac tttgttttaa cggtactata gtaggataga aacaagttaa  99240
tataggtata ccagtaacac ctactagatc ataatctacg aaacttccgt tcactaacaa  99300
ccatgtattt tcatcatctg tatacatgaa atctttcaat acaccacatg tataatgttc  99360
atcaggatat aacttaatag atgaattatt tactacgtct aacagacagc atttttcatc  99420
actctcttta tagaatattt cctctacgtc ttcgtctgat aatgtgttga tgagaacatc  99480
tctagtagtc tgtactatag attcttctag ttctaatatt ttttctttat ctgcttcgta  99540
agctatttct agaacttcac tatccactac tacgtcagat atgcttcttc catcattcgt  99600
taacgcacta gctaatctat ttatagcatt aggtaaagac ccgtctctat attccataag  99660
ccttgtataa tctttatata gcttttcgag tttatccgaa agttctttat ccacatattc  99720
gttagtactt ttcttatcat atttaaaatc aaatacataa ggcggtttat ctaatacctc  99780
agattctatc cacgtatccc tataatgtat taatatatta gctctgcaag cttcatattt  99840
aggatgggta taaggaacat gatttaggtt actaatatat ccgcaatagt gtccaggatc  99900
tcgttcatct ggccatacgt gcgaaccgca gtatctaacc ttatcagcgg ttgtcttagg  99960
ataaccgtat ttcttataat catcagattg tatagcgcag tgatctctag aagtgattgt 100020
tacaaaacat agaccctcat acttatttat agttctaggt attgtaaaca tgggacattt 100080
caacctcatt aatttagtct ttagatctag ttctgccata cattctcctc cttcaatatg 100140
tttaaaagta tatttcttac cgtctccata atcgttagtc attgactgta tatatcctaa 100200
aacagatatt atctcttccg ctttataagt aagaatatta gctctcgacg tacacggtaa 100260
tacaaccagt aagatactac tgtacgttct aaattgtttc tccgcatcca accaaaatct 100320
atcagggtcg tcgtatgcca tacctagatt tcctacagaa aattcaacat ccaattcgta 100380
agggaatttt aaattcgctt tttctatatt atagatatcc acagtattag gatcgtactt 100440
ttctgtaact agtaattcac tacctacatc tacctgtaac aagaaatcag gagtccaaac 100500
ttctactttc ccgtaatatc ctatacaggt cctaccttgc ttccatgtaa cgcacgttct 100560
tgatctccaa ggcattctat gattaccagt tagatcatca aatattctat ttttaccttc 100620
gtacgtatca atcagtactg attcattatc gtattttgga tttatgaaac ttaccattat 100680
catatcagat ttatatcttt tatcgtaatt attaacacag aatacaccta tagtacgcgg 100740
tttaatagaa gaaaacattt taaccgtata gaagtcggcc aaaggtaatt ctattatgcc 100800
atctttatca cctacggcta caggagtgga cccagaagga cacgtcaaca caaaactcgt 100860
gaagcctcta ttactatcga aagtatttag ttctacgtat aatgttcttg ctctattaga 100920
acatgtagta atatcatcga gtatcataac atcagtccaa taacattctt tgatctgtct 100980
gttagagcaa aactttgcat gccctggaat agtattaggt tttataacgg tatgattaaa 101040
atcgtatttt tcgaacgtaa ataactgccg gtgtttactg ttcctttcaa aaggattttc 101100
```

-continued

```
cagtacccag cgatctctaa catcgtccca cgtagccatt ctcagtaata tgctacatgt 101160
agttctagta atagctacct gggaaccatc gtacggacaa cctttcaccg atagataaaa 101220
gttcttcatg ggaaatatat cacatacgtt actaggaata ctcttagttt cttcaggttc 101280
tccaggtgtg gacatcttta ataattccat ttcgcttata ggtacttcaa aaggttttaa 101340
agtcaacgta gaatcttttc cacaagttaa ttctacagta ctaaactttg aaagcatagc 101400
accaagcctt gtaaactgat aaaactttac attatcttca gtagtaaact tgagcttagt 101460
ataagaagta atatccagtg taggagacct taaataacca ataggacacg ctaccgtcaa 101520
actaaaatcg attataatac cgctagtgtt aagataatat aacacactat ctattgtatc 101580
tataaagtaa gtagccaact tttcagttgt aggcataaaa ctactatcgt ttctatatga 101640
tagaaacact gtaatatcat atcccggcat catacatttt ctaactccca tatgagatgt 101700
atcagataca atatctcgat acatgctaaa tttctgtaca accggatcta aaggtctagg 101760
aacacccgaa aagaagtaat atatatcttt acccgcgtct attaaccctg atattaacga 101820
taatcccata cccgcgaatg caaggtgagg agacgtaact attccaacgg ttgccataga 101880
tgtacctaca gtagttaaac tagtactcac tgcttcaagt atctcatcag tagtatctct 101940
aaatcctctt tccatacgtt ctaatctaga ttgtctattt atagcgttca tggtcatcat 102000
ttgtaaagct agactaaata ccatagcttt atctaccgat gaacctatgc gacgaatgtt 102060
tgactcataa ctattagtac cactatcagc actaacctcg gatgaagtgg aagatcttac 102120
attatcacct cttctgccac ctcttctgcc acctcttctt cctccgccgc ctcttcctcc 102180
gcctcttcca ctactaccat cactacttcc accatcacta cttccgccgt ttattgcatt 102240
ataatgagta ccgctagacc ccgcgtacga tcgacttcta gaacctatag tctcatatat 102300
gtggtcagaa ctatcgctac tatcggatct tataggaatt ctaggaagag ggcggtttgc 102360
gggattacca gggtatccat ctataggcaa ttgtactatt tcataaatac cgttactacc 102420
tacactagac gcactcgatg tagaagacaa acgtaattca ggaccggcca cgctaggtat 102480
tcccgcctgg aagtaaattt gattttgttg aatagctgct gctaccgggc ggggtaaacg 102540
gggtagaggt ggtggctgtg gtggatgagg tggtacaggg ggagatgctc ctccctgcgg 102600
tagttgcgga ggttgtatac cgtatacttg ttgagcttga actgcatcgg cataacgctg 102660
atcgggaatt ctgtttctaa ataaaccctg gacttgtagt ggattaacat agttcatttc 102720
attttgattt tctactctac cttgttggaa acctctagct ctaaaatgat tgtttgcttc 102780
tgcggtatct aaataaatat tttcgttagg tgtgttagcc ggacgatctc taccattatt 102840
accattagca ttattgttag tattacttaa agctattcgc cccaaaatac cacatactgc 102900
cccttgcgag cttctcctac atcttttacg tactatacta tcttggtaat ttttgggatc 102960
attaacattt aagacgccgt atgttcgtct tagaggatga tgtataacat cctgattcgc 103020
tcttgcttct ggaatttttg atggacttaa taaagtagtg gatgtatcta tgttaaacat 103080
tcctgtagac acgcgagacc tactcgtcaa tacattaaga cctttaccgc ctttagatac 103140
ataatctttt agagctttat atacaccggg aggactttgt ttttcttcca tgacaggata 103200
tctatattga tttactctta gactatgttc taatctattt ctatctgtag tgaaatcatc 103260
tttagataat actactgtag tactaataga tgattcgtgt ctagtataac cactattttc 103320
cccttgatat acggggtcga ctctttttctt ttttagaata ctttttatcg aatccgtttt 103380
cttctctaat atagctcgca tacttccaga aactatattt ttagtatctt tttctaactt 103440
aaatcgtacc ttttttttcta attcggcgtt taacatatct aaatcagtct cttccttaat 103500
```

-continued ggtaggcatg taaccttgta atagatttct tgatttccgt ttaatatctc tatagatact 103560
agaatctcct attaccttat ctcttttatt ttctgaagtt gcacctactt gtaagtaagc 103620
agcatcttta ggtataactt cttccaagtt taatattttc ttaagataat cacctatatc 103680
atcatcttcc tcatcagaga taccoctttt agtcctaacc ttatctgtaa taacattttc 103740
aggtttgtta cactgtgaga agtcctcgtc ctcttcatcg tcatcatcat cagtcccata 103800
cttacgatac atacacatta aagcttcttt agagaaagaa gtttttgaat cggtgtctct 103860
ttttcttcta cctatatcac gtcgtttctt tatgtacgct gacaagctag ataatttatc 103920
ttctgttgac tttctattgg taggtacgta atcactacaa tgtttatttc cagtaaccat 103980
acatctataa aatagttctg ttaagtcatc aaccttagct ccattttctt gtagtgttgt 104040
ataaaattct tcaggtatag aagttacgtc cattattaag tccattgtac atttttcaca 104100
gttactggta atagattttt ctacttttac agttccttta gagtttgcag atccagatat 104160
cttttccata acacacttaa gaaatttgtc agaatcgcca tacggtgagt gcgtagatac 104220
gcctttaaag tatacacgta tagtagattt atgttctgat gattgtacct tatttatact 104280
gaatcctcct atagtaactt catctacagt gatatcatta caggaacttc ctttgtaagt 104340
aatatgttct actttaggta gtctgtaatc tactttagac gtagtgtcgt ttatatattt 104400
ctttattgtt ttatcatctt gtgataatag ttcttttgct aacttcttta ctatattatt 104460
catatcatca tttttattgc tttttgtttg cacagtaacg ttaagagcaa tgctgtaatt 104520
atactttagt attccacgag atgaactatc gctacattca cccaggaatg cgtctctaat 104580
ttttttcttt attttatccc aatcaaaaga tttcatgaaa acctcttttt gtacataatc 104640
tgcttttgaa agatatttca aagctgctac agcggcataa tcaatgtttt cttttgattc 104700
tggtttttta tcggtatcgt gataaacagg agtctttctt ttgcaaaatt ctgaatatga 104760
atgcacccat gttgctgtta ttagcgttat tgttataagt ttatacatta tgcatgatta 104820
taaaacaatc aaacttatat aacttaaaac cttttagttc atttttgata tcattatata 104880
ttaatattag taatgttatt ttttaacaat atagtactaa tatttaagtc gagttcgtgc 104940
ataatttcct ccattccttc tttgaaagct cgtaatacta tagtttcttc tacttcttcc 105000
ttgacatcat cgtcttccaa aggtataatt ataggatcta tacatgttat taccggttta 105060
ccaatgtttt ttaacacatc aaagtcttct agagttccgt ttattaatat caatactcta 105120
ttttcatcat cagatggatc atcatattct acaaaatcat cgtaaagata atcgtctagt 105180
ttaccacatg aataattacc cgatgttact gtcttactca cactattatc atagaaatct 105240
attttacaac acgtttcttc atctgaataa atttcttgta aatcatcatc ggataaagta 105300
tttgttagta ccgtataagc tgtatcagca atttgttctt caagttcaat cagtttttct 105360
acgttagcct caaacgctgc ttctaataca ccactatcta tagaaacatc cgtaatacta 105420
cgaccttcag gtgtaagact agtagataat ctgtttatgg attcgggtaa tgaactatta 105480
gcgtattgtg atatagattt atattcatcg tataattttt ttagagaatc tgccaacttt 105540
ggatctatat attcattgtt tttattatat ttaaactcga aggcataagg cggtttcaac 105600
agaacttcgt tttctatcca tacatcttta taatgaatat taatatatga cttacaagct 105660
tcgtaatcag gatgaatata tcctatatgt cttaattgac taaagtaccc gcagtaatga 105720
cccgcatctt ccgatacaga tggagttata taagtatcac aataccttgg tttatcggct 105780
tgttctttcg tgtaaccgct attttttatg tcatcaatat cggtagcaca atgatctcta 105840
gatgttactg taataaaaca catacottcg tactcattaa tagttctagg aatagaaaat 105900

-continued

```
ggctcgcatc ttacagacat catttttgat ttgagatcta aatacgctat acactcgcta 105960
cctgttattc tatagaaagt atatttactt ccatctccat aatcgtatgt cgtggactga 106020
tggtaagcca ttacagaaat aaaatcacta atattataca tgagcatgtt agctctcata 106080
gtacacggta ttaaagctaa aactatggaa ctgtatgtcc tataacttct ggtcgcgtcg 106140
tcccaaaatc tttcaggttt actatatgcg tttcctaaat ttcctatata aaactctacc 106200
ttcaactcat acggaaatag agtagctgat ttatttatgt tttgtaaagt aatagtagaa 106260
ggttcgtatt tctctgttat cataagttct gaacctacgt ctgtttctaa attataatcc 106320
tccatccaca catctatttt accatggaag ctaatacatt gtcttttatg ttgccaggta 106380
acgcagcgtc ttgaacgcca cggcatatta cccaactgtg aaacatcttc gaatactttt 106440
tctttgccca tatattcatc taaatatata attccttcct gatatctttg tgatacaaag 106500
ttaatattaa tcaggtctga ttttaaagcg ctattataat tatctacaca gaatacacct 106560
atcttctttt ccttttttaga agcaaacatt ttaacagtat agaagtcggc caaaggtaat 106620
tctattatac catctttatc acctacggct acaggagtgg acccagaagg acacgttaat 106680
acgaaactag tgaaacctct tccatttcca aaagtgtaga gctctaaata tatagttcta 106740
gatctagaag cacaggaagg tgatgtatcg tctagtacca ttaattctgc ccaataacat 106800
tctgtggcgt gtctattggt acagaattta gaatgaccgg gtatttcatt aggttttata 106860
acagtttcgt taaaatcgta tttctgaaac gtaaacaatt gacgtaatct accattctgt 106920
tcaaaaggat tttcgagtac ccatctctga tataaaggtt cccaagtagc cagtctcaag 106980
agaacactac aagtagtata aactacagat accatagaat tgtcaaacgg gcatcctctt 107040
accgtaaggt aaaacctctt taaaggaaat atatcacata cgttactagg aatactctta 107100
gtttcttcag gctccccggg cgtagacatt tttagtaact gcatttcgtt taatgctatt 107160
tcaaaaggcc gtagagttag tgtaatatct cttccacaag ttaagagcac tacaggaaac 107220
tttgaaagca tagcaccgag tctagtaaat gtatagaatc tagcaccgtc ttcgctagta 107280
aatttaagaa cagtatacgc gttaatatcc aatgtaggcg atcttaaata gccaatagga 107340
cacgctaccg tcaatgaaaa gtcgagtata atattactgg tattaagata gtaaagaaca 107400
ctgtctatag aatcgacgaa aaacaatgac aatttttcta aagacggtat aactatagaa 107460
tcgttcctgt atgacatgta aactatagtc tcagtacccg gcatcataca ttttcggacg 107520
ccagattttg aagtatcggt aacataatcc ctataagcat taaaagtctt aagtacagga 107580
tcttgaggtc gttgttttcc tgataatata taataaatat ctctcccagc atccaataat 107640
ccagatatcg cggataaacc cattccagca aaagcaacct gcggagacgc gataataccc 107700
gatgctgtaa cgacgcttcc tatagtacct atagctgtac taactacatc aaatacaacc 107760
tccgcgtcat ctctatcatc gtcttgtatc ataaatgatc gtagatttct gtccattaat 107820
ccctgagtaa taaattgggc ggctaggcct actgctaaag tcttgtcaaa agatcttgat 107880
attcttctca ttctagctcc gtagtcattg tcactagcat gattattatt accatcacca 107940
ctagaatacc cacttgaact tatactgtta ccacctcctc caccaccact acctccactt 108000
ctccttccgt tattcctact gctactactg ctactactta catgtaacga actatcatct 108060
ctagaactta gtctttggct gctaggaccc gctccggcat taacatcaga ctctgtatcg 108120
ctagaagata accaataaga tgtaagatcc acggaaccaa taaggctact actggacgaa 108180
tctaaagcaa aactacccat tggagaaaca ctaactagac tatccgacga agaactgtcg 108240
ctttgtacag gaggaaccgg ccttctagta cgcggtaaag gagtgagcat tagtaatcca 108300
```

-continued

```
cacatcgcac tcgttaaacc tcttttacat cgtcgattag agtgtgtaac gggtttagta 108360
ttatgatata atatactatt aggtaacgaa gacggtaaac tagggcgggt gctactagaa 108420
tgcatagatt gttctggttg gaaaatagat ttaccgggtt tagtaataac gcttcctata 108480
tttataccca ctactggatt tttgtatact atcgaagata atactttact accacctgat 108540
ttactatatt tatctatact atctttatag tgttctacta cttttctagt tttcgtattc 108600
ttatggttta acatatcttt atctcctaat tgtttttctc ttaactctag atgagtaagg 108660
cgtcttttta tgtcgtctaa ctcttcttct atagatgtac taagactttg tgttgttagt 108720
gcctctttaa tagattgttg tttttggtaa ctaatagatg atattaatcc tggtgtaaaa 108780
ccaccgtcag aatttattat atttttactt attgtagaca ttatgctatt tggtggtgtt 108840
tcaacaggaa ctaaagtaac cattttttct aacttagatt tcatagaatc ttttaatgta 108900
gatattatat cgtcgtctcc taatacatta tcttcactac cgcttatacc tacttggata 108960
taagatgcct tacgaggtat tacttcttcc aacccaaagt attcttttaa attgttcatc 109020
ttgtgttcat ctaatgatct tttaggtctg tttttataag actgtttacg caatttatta 109080
gtatcgtggt actttctatt aggctttctt tttttatact ttttattctt atcaggattt 109140
tttatgcagt tatcgtatct atcatcgttg tcattgtcgt tatcgtaaga caaatacata 109200
cattctaagt cggtatcatc tatatttgtt gtttcatcag tatcttctga atcacccgcg 109260
tttcttctag gccttgattt tcttcgcttt ctactagatc ccgtatacgc acttaacact 109320
ttaaatgaac tatcctttat tttatcagta agcggtatat aatttataca attatcgcca 109380
ccagttactt cgcaaaggta aaacaaatta actaaatcgc tataccctat accaccacat 109440
tcttttaaag aaatattaaa ttcattaggt acttcagtaa cttcagccat taaacccatg 109500
cggcaatcac tgcaatgccc agttagtatt ttctttactc ttactttatc cttttgatcg 109560
ttatattctt cacaggttgt tatcatctct gttacacact cttcaaaaat atctgaagat 109620
tcgtacggtg gactggatga aataccgtca aacgtaatga atatatcggt atgtgcattc 109680
tcgttattat tgtcagtaag aacactataa ttcccaacag taactttgtc tactgtaata 109740
ttcctacatt tattacctgt atatgtaata ctagacacgc tgggtaaaga acaagtaagt 109800
ttattatccg atgttttaca tattagatac tgaacatctt cttttgataa tgatagtgca 109860
ctagctacta tacacgatgt aacttttctt ctcgcgctag tattatcgcc tcttttaggc 109920
tttttaggag cataaatcga tacatctaat acatatgtat aattatactg atatctagta 109980
tgatctttat ctgtcgataa ttcacactgt tttacaaatc tgttttttac agtttgttga 110040
atgttagtcc agttaaaaca ttccgagaat ctctgttctt ccttttttct tacggaacta 110100
aggtacttaa ctgtcgcaga agctttatga tcggataatt ctttcggact tattgtttta 110160
gaaagactat ggtactttgc atgtttcctt aaacacgtgt tttcgtcttc atcttcatct 110220
tcataatctg aataaactaa tgaaaacaat aacacaatta acataaatat tatgtttttc 110280
atattactag tggctatgat ggttataata atagtacatt acttaatatc cgtaagtctt 110340
tttagttcat ttttaatcaa ctaaccaagt aataaaaatg tcattaatgc tcgcgtatat 110400
gaatgaaatg tattggacaa cgttagtttt atactaacta tagtaaatac tatgcatatt 110460
cttgtatttc gtagttaaac tattagtaaa atacctacat cttagggtta atctacagta 110520
atttaactag aaaagctaga ataagattca ttgtctagtt cgatatgttc ctgcatataa 110580
aatcttttta ggatattata tttctttgct cttttaagcc agaaacagat acaaattatt 110640
atcaacaata cggatactga acttatagct acgggtacta aagacgcgat tagaatgttg 110700
```

-continued

```
cttgaagaag attctatgta gtcattttcg gaggctatta gagctagact gatattagcg 110760
tccatctcat caaatacatc atttaacgcg tctgatacgg cattatatat tatagcatcc 110820
tctactatct tccttgattc ttttgtgtct aacggtataa tactaacgtt ataacaagta 110880
gttactaccg ctcccgatcg atttaaatac tcgtatgtta tataagtgtc attaatcagt 110940
acgtacttcg tttcttcttc atccgtgtac acgtagtcac taacttctcc acatatatat 111000
ttatctatcg gataatactt cactgtaaga ttgttgcgaa cgtctataat acaacaccta 111060
tcattttctg cagcttccat aatctctttt aaatcttgat ctgttagagt atgaatgaat 111120
atgtcattgg ttatttcaga tattttatct tgaatttcca ttatcttttc tttatcagcc 111180
tgataagcca gctccaagat atttccgtct acgttcacgc tcgtaatttc tctaccttct 111240
ttggtcaatg ccgttgctaa tctgttaatg gacttaggaa gtgttccatc cgtatattct 111300
attagttttt tgtattcttc atatagttcg ttcattctat cgcttagttc cttgctgaca 111360
tactcgttat tcctatcgtg tgtgaactca aaggtataag gaggtgactg tattacttcg 111420
gattctatcc aaagatcctt gtattctatg tggatatagg atttgcacga gtcataatct 111480
gggaagtaat catatatatc tccgttatat ccgcagtaat agtctgtagg tgtatagtaa 111540
aacgcggttc gttttataca tgttctagaa tgactagaat atttagaggt atacccgtga 111600
ttcttcatcc attcttttc agtagcgcaa tgatcttttg atgttactac agcaaagcat 111660
aatccttcat aatttactac attggctcta ggaatactaa atggatcaca acttacagtt 111720
atatctcgag aattaaggtc taattcagca cggcaattgc cttcggaagt atctattttc 111780
ttgaaataat agtgtttacc atcgccataa tcttcagtct ctgattgcag atatcccatg 111840
gttgacacta tatacccgag ttttatgtct ttatttcttg aagtgcaagg tactaaacta 111900
attaatatgg cactataagt acgtttctta ttaatggcat cttcccaaaa tctggaagga 111960
ttcttatacg cgttacctaa attgtttacg gtaaatgtta cttttataga cgtgggaaag 112020
cttgttttgc ttttcttgac aatatccgga tctatacttt ccatttcata actttccttt 112080
agcataattt cttgactact gtgatgtatg tctagttcta catcgggatt agtgaaatca 112140
acatctccaa agtaacattc ttgtctcctg ttgtcgcaat atcgcgatct gaaaggcatt 112200
ccagatgata gaccagtaaa caatttatcc ctatcgttat agttggattt atgtattccc 112260
ctaggatttg aatttttatc gaataatatt actataatgt ctgatttgta cctagtatcg 112320
taattatgca tacagaacac tcctattctt ttcttttctg tggaggcgaa taatttggac 112380
gtcccataat cacctacagg caattctatt attttatcgt ttccatctat agataccgga 112440
gtagaaccgc tagggcacgt aagtacaaaa ctatcaaatc ctctatctcc gaacagagca 112500
atttttacgt atatctttct aactctagtc tggcacgatg ttacatcttc taacatcatc 112560
gattcggtcc aataacattg actactctgt ttgttagtgc agaaatctga atgccccgga 112620
actccatttg gatctattat tgtgtcgtta aaatcgtact tagaaaaggt gaatagttgt 112680
ttaaattcac cttcttgcct gaaaggattt ttaagtaccc atctgttcct gaaaggatcc 112740
caggtagaca ttttaagcaa gatactgcaa gtggtgtgta ctatcatagt ttgagaagta 112800
tcgtatggac aaccgtccgc caataagtag aacttcttta gaggatattt atcacacacg 112860
tctgatggaa tagatctcgt cgatttaggt tctccaggag tagccatttt tagcaactgc 112920
atactactca taggaacttc ataaggcctg atggttaatg tagtaactct gccacatgtt 112980
aaacgtacta ccggtgttct agatagtaat atccctaagc gtgtaaatac atatttcttg 113040
acttctccat catcgtacat aatcgtgtat gctgtaatgt ctgtatctgg ggatctcaag 113100
```

-continued actcctatag gacaggcaac tcgtagctga taatccagga taatatctga agtattcatg 113160
taaagtaatt cagaattgat agtatctaga aaatatagtt ctgtattttc cttttcgggt 113220
ttaaatgact ttgtatcatt ctggtaagcc atgtatatca tcatactatc tccaggaacc 113280
atacatttcc tcactcctga tttttcgcgg tcgtttataa gtccagaata tgtatccaat 113340
aacttaatta aaggatcttt aggcctttcg ataccggaaa acaagtagaa tacatcttta 113400
acagtatcta taattccagt tatagcagta acggccattc cagctatcat aagttttgga 113460
cctcccgcca aacccgctga tgtcagagta gttcctagag ttgataagct catcgtaact 113520
gcctcgaata ccttttcttc tttagtcata gaatcttttc tttgtataac cgattgcctg 113580
gcttgatgtt gagccgcttg ctgtccggcc attaacatgg cacctccaaa aataagagat 113640
ttatcaagag atgaagatat ttttttcatt gatcctttat aaccaccaga agattttgaa 113700
tttccagatg ggtctgttcc acgagttatc gtagacttgt caactacatt gactttatct 113760
ttaggtatac ctcctatttc ttcgtagatc ggagattctg gttttccggc tagagaataa 113820
gatgattctg gtgatccggc tagcgaataa gtaccttcta gttttggctt gctctgtaac 113880
atgccgcata ttactccgtc tagacttctt ctacatcttc tatgtagatt cttaggtata 113940
gcaccgcttt ttggatttgc ttcttccgga atagcatgca aaggtcttct agacccatca 114000
cgaggagata gtggaggtgg accgtgtgta acagaaggcg atggtctatt aggaggaaac 114060
aagttactag gttttccatc tgtaggtcct tccgtgtata tttcattgtc tagttgcggt 114120
gttctagcgg gtgaaaattg tataccgtta cttaaatgtg tagtaccact atcgggccgc 114180
tttctaatag ctgctcttct agtaagagga gtagttatta cagttcctgt atcaacacct 114240
ttgatcatac tgggtgaata aggagacggt ggttgtttta taatgtctac acctttaagt 114300
actttggctg tattttctaa tttttttgtt atagcgttac ccgctggatc taaaccttca 114360
gttcctttct tcatttttat gatatctttt ggtggaggtg gatattcaaa atcactacta 114420
tcgctgctta gtcgtctacg aggaggtggt ggatattcaa aatcgctact ggtactagat 114480
ctacgaggag gtggatattc gaaatcacta ctatcgctac ttagtcgtct acgaggaggt 114540
ggtggatatt caaaatcgcc gctactgcta ctactgtgcc ttcgtgactg ctgcacgtta 114600
cctagtctca tctcttgtag ttgcctttta acatcttcaa tatccacgaa atcgggttca 114660
gaatctatgc tgctaacaga ttctttccta gaaaattcga ttctagtata aaccggcaaa 114720
ccatgtttac ttttagacgg tagattatta ctaatctcta attccgtgaa caatacctcc 114780
gatattgatt tttgtttttg acctatagtt tcgcgtaccg cttctgtgaa aacatcagat 114840
tttaattttg gaggtagttt aggtggtttt cttactttgg tgtataggtc ttcgggtttt 114900
ccggtagatg gtaaactagg agctatacta gatacaagat ctttagctct ttttttttacg 114960
tcgttgtaga tagccccatc acccgtaaca ccagattccc ttttctgttg gatgcctacc 115020
tgaaggtgcg atgcttttgg aggaagtact ggtttatttc ctaaatgttt tctagcatta 115080
gctgtaaatc ctgtatcttt ttcctttttt ggttctttat cagatctcct atttctgatt 115140
tttgcttcac aaccatccat gttacttaca tcaggatagt acaagtatct gcaatcaaat 115200
tcttctatac tggaggattc tgtttttaat gcaatactcc ttctatgtct agaatgggag 115260
gtgttgttta aattgctatg ttttaacatt tctgctgttt taccaaccgt tatcgaacta 115320
agatctataa attccataca atcgtcgtca tctatcaaat tacacaaata gaaactatca 115380
gtagaattat ccatctctat tcctaattct ttcatggtgt tattaaaatc ttcaggaaca 115440
gatgttacac tcgccataaa tttcatggaa catttctcac atccactaat tacttcatgg 115500

-continued

```
gtataaacgg tatcattatt aatgtttatg gaaatgcatt ttatcagttc gtcagaattt 115560
acgttactac cgtcgtcggt attaatattc gatagagata ctctgacttt caccccattt 115620
gtagtattaa ttatagaaaa gtttacctta ttagctgtca cattattaca attactgtat 115680
tgtaatattt ttgtgcttcc ttttagtata ttagggtcat tttcttcgga tgtatttttc 115740
gtagagttga tatttcctgc catgattaac gattcgtttg aatacataaa tgcttcaaca 115800
gttgtttcgt taacgtctag tactgatatc aagaatttca tagcgttatc gtaatcagaa 115860
gaaccatcat ttataggaat ggaagtagtt tctacggatg attgaattgt agttgggatg 115920
atggtggtaa aagttccatt atctgtaacg gtataataac tgttagtagt taagactaca 115980
gtagtagtta tttcttgtgt tgtagattct atagtgctat ttttacctat agttgcctca 116040
aatacgatag tatagttata cgcgtatgta tcgttaccga gattacaaga tctattaaac 116100
tccgatctaa tatcttcctt tatttttgtc caattaaacg aactaagaag acgagattgt 116160
tctttctttt cagcaatttg taaatatctg aaagtagccg atgatttacg gtcgatggta 116220
tcatcctgta caagcatacc ggtgtcgtgg tataaagagg attttctcgc gcatgttttg 116280
tatccttcag aaacggaaat taaaattaat ataggggtaa tataccacga gaatattttg 116340
atattcattg ttacataacc gcgtacaggc atcgcgataa ttatactaat tattcacttt 116400
atctgtacgc tattaaatag taacattata attatataat ggatatgatg aagatcataa 116460
aaaaatacat aaattcggaa gaagaagcgc aaaaattgct aaaatgggct atagataatg 116520
caaatatata ttacttaaga aatatcgtta atacaaaagt taatattgaa gaaactaagt 116580
ttaaaacagt ccataatata ggaatagagt attctaaaga taataagtat aagctatctt 116640
atagaaacaa gccgtctatc gctactaacg agaaatacaa agaactatgt aatcttatca 116700
ggtccaccaa tggtatagaa aaggaaaccc ttaggtatct tttattcggt ataaagtgtg 116760
ttcacgccaa agtagaatat gatatagaaa aagtacccga ttacgattat agtaactact 116820
ttgatgtact taaagaaaaa tctactataa gatgcgtagc gtgtaagtct aataatacga 116880
ttcctatgat actccaaact agatcatctg acgaagaacc tactgtacgc gtagtatgca 116940
aagattgtgg caaaaacttc gcacctccta ggttgaagtt taattaaata gcgtatggtt 117000
gtaattattt actaataaat aattgatata ctataaatca tgtttgatat cactaatctg 117060
atagaattat acgagtctaa cgattatgta tccggcgact acaagcattc tcagcttcag 117120
aaagcttttt taaaactacc gataacagaa gttgtaatgt tagttaaatc tggattctat 117180
ccatctaaat tatctaaaaa gttctacaag ccaatagcta aattctgtgt tgataagata 117240
tatttattta aacctgaata cgtatcgtta aaagacttat ttacagtaat ttatacattc 117300
gatgacttaa gcaaatataa agaaattata agatattatt attacgagct atctgtttct 117360
aacagctatc aagtatataa aaaatgtaaa aacatcttag gatacaagga tgaatacgat 117420
aatgatatta tagaagaact ttctgaaaat gatttagtag aaaaaatggt aaactttcca 117480
ggttttagaa aaatagtata taaaaagaaa attttatcta taagaatact aaaagagatg 117540
tattacaaac ataaggtatt acctatcaac aagggtataa ctcctatcag agaagaagat 117600
atatgctttt ttatagacgc gttgtatgat gcacacgatg atgacgacgt tctatatttg 117660
ttactagaga ttaacgagca aatactagat tctgacgagg ttaaagaaac aataataaga 117720
aaaatatgta aaggcgaaaa tatagatgta ttgcgttatt atgtatctca ttacctaata 117780
gatcatgcaa agttgggcgt atactataat atctttttct cagaacgcga tattatttca 117840
gagtatggtt taaccgacga atcattaaaa gtaatttgta agtatataga cagatattcc 117900
```

-continued agttctattc cttctataat aaaattacta ttggataatt ctaattatac attattagca 117960
tcagtaatag actatatacc agaagaaaga ctcaatgaaa atctatatat gcaaatagtt 118020
agacattcaa acgataacaa acctaaaatc aagagcttca aagcagaatt tttatcagaa 118080
tgtttgatgg taatgtgtta tctgagagga tacgaagata ttgtagattt ccttatcgct 118140
ttagatgtag aaactattgt acgaaataga ataaatcctt ttaacgatta tacgtttaca 118200
acggattggt ttaataaaaa cactgaatta gtacgtcttt atatatcctt ttattttata 118260
gatcctgtta tgatgcgtaa gctactattc gaatatcccc tttgtgagac ttctactaca 118320
gtagcgatag aagaacttaa gaaatacaga tcgtcaataa ataataacta taatatagac 118380
tatcacgaag aattcaaaat tgtagatttg cctagatcat ttaacatacc gataagcgag 118440
gtagtttcaa ctaaagaata taattctatt atttcattta tttcagacaa aagttataaa 118500
tttaagataa cttcacagtt actaaaatat aacatattac aaactataaa agtagaaaac 118560
ttatgttact ctcatatcaa taacctacat tccttttatt ttaatattac taaaccaagt 118620
ggtataatcg ataatatatc tagacttata tatcagatag gtgatttagg cagactactt 118680
agacacgggt tttatcgtt tactgataac tattttggaa aatggatacc ctcattaaat 118740
tattctaaaa tactggatca ttatcagtat aatggacctg attatgtatt atcttggcaa 118800
ataggtaaac tagatctaaa ggcgttcgta aagtataaag attttcctaa attcttttta 118860
acaaaatata atatcgattt cctgttagaa aaagaggtac tattatacta ctgtatatat 118920
tcttatttat tgctgtatat actagtgggt tcggtaacgt acgtagaaca ggaaaacata 118980
tattatttta ttacaaatat aataaattcg ttcattcaag gattgggtat acgtaattct 119040
atagattcac tatcagaaga ggtagtaaaa gagttaataa ttatacaaaa attaccagaa 119100
aataaacgta aactatcatc tatcagaccc gtaagtctgt taaacttatg taaaagagtt 119160
tgtgctttta tatctagaga tggaaagaag tagacaagta tactatatta ttaacgagta 119220
tttaggtaga catccatcat ctaccgaata ccaagtatta aaacaccaag tagagaagat 119280
ttcaaaaatt aataatttta ataaagaaac tttctttttt ctgctaaaaa aaaataaaaa 119340
caaatttttt aaggatctag aactatcaga tgatttgctc aaaaagagaa tagacgaata 119400
tttttcaaaa cagaaacacg cgaaaaggtt aggcaactta ttcgctatca tggaattaca 119460
gaagatatta atttctagtt ttactaagac tataggtatc ctaacaacca aagtaccaga 119520
atattatcat tccactataa aactggaata ttcgtctatg gaaaaaatag cggatgatat 119580
tttagattct tataatgttg ttgaacctag taaagaagta aaaggtagac acaaggtatc 119640
cgatctagta ggtcatgttt ataaaataat ggaagaatac cttagaagac atagcaacag 119700
ttgtttatgt tacggatctt attctttaca cttcttaaac aataaaatag aatacgggga 119760
tatagatgtt ttacaaacaa atgctagaac atttttgatt aatatagcct ttctaataaa 119820
atttataact ggaagacgta tagtccttct aaaagttccc tttttgaaga actacgtaat 119880
aatgcacgat gaagaaacta atcacgttat ggatacattc aatatacgtg aaaaaaccat 119940
gaatatgata cctaagataa tgatcgataa tatgtatata gtggatccgt gtatacaatt 120000
acttaatatg attaaaatgt tatctcagat tgatagattg gaggaacttc aagccaaatt 120060
cgaaaaattg agcgtacgac taggaacgtt gttagaatat acgaggtata gatattctat 120120
accactggat agcgaaagta tattagaggt acgcgctaaa cttgataaag ataaaagaaa 120180
aataacagtt gacttcaaga aatacaaact caattatata aaatgttatt tctatttaga 120240
tgaagtcgaa ctaaagaaat ttataagtaa aaattctggt ttagacgaat acgaagattt 120300

-continued tgaggcggta acaaattcag agtacgctat acgtaataaa acgatgtaca cgtacttttc 120360
aaataccgcc cttatgagat cggaaaacga aatacatccc ataacgataa acgcgttaac 120420
tagtcacgca cttttatatc atgttatcac aaggaagttt tacgatgatt tattaggcga 120480
tctagttaga tctcttatga tcgtggaaaa agttcctgta tttaaaatca tacctagaga 120540
taaaaaacaa ggtaggcaca cgatcattga tattgaaaag gatatcatat ttcactgatt 120600
tattactctc gctgctttat ctgttgtatt ggcaaacaaa ttagataatg cacctgtatt 120660
aataaatctc aattgcggag cttgacgttg ctgctgaggc gatgtttgtt gcatataaca 120720
ttttggtgct gaatccgaag aactaatagg gcaaggtgat tggggcttat ctactttcag 120780
tacgcaactc gtttcttgtt tcatgcaatc tatagttctc acattgcata gttttatagc 120840
ttttagaact aaatatcttc cttcatccgt gtttagaatg aaaggactaa caaagtattt 120900
tggatcgtga aatggggttc cagcactttc ttccatttat agtatgaata tttcttcttc 120960
ttgtattggc aaaaacgtat aagtcagata caaaaataaa ataattatat aaatgtttaa 121020
aaattacaag tatactctgt tatctgaaga tactaataat atgaaactac ttattccggg 121080
attggaagat gatatggaag caggaacaat agaaaattcc ggatacagaa atatatctac 121140
gaagatgttt aaagatcaag taaaagacat agttaagaaa acttacaatc agacttactt 121200
acagttatta caacttcttg aaaggtctaa tgtagactgt aacgaattag aattgttata 121260
tagaataatc aatattaatc caagaatttg tcatagattc tatataaata gatacgatag 121320
tatatttggg tcttttaata aattacatga atttataagc aacgttatga ttaaaatatt 121380
taaaataggt aattctatat atattacgtt tatcagtgat aatactagtc tagaaattaa 121440
tgtagataac gatacagaag gaagactaat gaatatagat tacactatta aatttggtga 121500
tgtaattata ctacaattag gtagaatatc tataaaattt agcggtaatt ttgtgataat 121560
gaaagacata cttttcttag tcacggattc taacaaaata gtatataacg aagatgagtt 121620
tttattagag atatataata cataaaattg ataaaataat cagatatcgt agattgggat 121680
atctgtcgcg cacatatgtt agtcaattat ttttaaatat aaaatatacg aatacaatct 121740
atttattgct atttttaaat aagataacaa tgaacgtatc aagattagaa gagttaattt 121800
ctatgaatcc atttagcgat atggaaaata tagtcatcaa cgaaaaagaa aaatgtatat 121860
taggaaacag gtgttttgtc aaactttcag aggtatataa tatgcctatg tgttgtatag 121920
ataccaatca atgtttaact atgaatagat ttaaatttag cttaaatgaa ctactctaca 121980
caccttttta ctataaacaa ctacaatatc agtatctaac accccagttc atatttagat 122040
gtatacaaga agctaatgaa aacaatatga gttgctatta ctgttatact aagaaaaagg 122100
aacataacgg attaaatatt gatattttca ttccaactgc aaattcaaag tcttatatag 122160
ttataggact acgtataaaa gatttttgga aacaatcttt taaagtaaat aagtaaataa 122220
acattaacat ggtaaaaatc tatatattta tgtgcattta taacttatgt acgttagtac 122280
acaatggtgt tataaatcac tttttgttat taacttaatc aataaaatta tatttttata 122340
tacatatttc ccaaaactga aaaaaaataa aatcttgaag ataaacaggt gtttattgat 122400
aaattatata tatcaataaa tattttatta taccatggcg atatttaaaa ggctaagaag 122460
atttctagga atcgaaaaaa atagacttaa gaaaagatac ctagcatgta tgtatcagaa 122520
ctagacttat ctaaaggctt tatggtcata tccgacataa aaaccaacga gataataaat 122580
atagatctat acaatcaaaa aggtttttca actataaaca acaatcatga acaaaatcat 122640
ctgaatagat tatctaaaag ctgttctgat atacataaca agataatgtg caaggcagag 122700

-continued

```
atgagaaaat tatgctacta agacactaac ttttttttagg aaaaacacta catatttatt 122760
ttaacaaatc agtctatata tgtaatattg ttactcaaca ttatgctact aatattataa 122820
tctaattctt ccattaatga gcccaaacca agttctattg aatataataa tatatttttt 122880
tctacttcgg atctcgcgga tcctatagac agaggtatca cgttatcgtc taagcaggtt 122940
acgacgctag cttctgatac cgaaaacatg tcgtagtcca tatgagttcc gttaataagt 123000
acagtgattt ctgttgtgtt gccggtgtct tcttcgtata taaaatcatc tagagtaccg 123060
catgtataat tacaattagg atacacctta gtactggtgt tgagtttaaa atctaaaagg 123120
caacacatgc cgtattgctc tttcattatt atctcataaa gatcattatc tgataacgtg 123180
cttatcaata cttctttaga taaatctttt attttttcct ctaattgagc catcttttcc 123240
atatcagcta aatacgctac ttctaataca ctgctatcta tgttaacact tgctatatct 123300
ctacctttat cagataacgc accggctaat ctattaatag actttggtag agtcccgtcg 123360
gtgtattcgt acaactcttt gtaagcttga tataagccgc gtaacttacc tgatatggta 123420
ctatctatat attcgttttt gctagtatcg tatttgaaat taaaagcgta aggaggttcg 123480
tctaatattt ctttttctat ccatgtatca ctgtagtata tgtgtatgta tgacttacac 123540
gcttcatact gtggaggata ataagttccg tacagagaac cgtaaccgca atagttatct 123600
ggaacgtaca tgctgatact aggatattta tacatgtcac atcttcgtgg agtattagca 123660
tgcgaagaag aatagcctct atactttgaa gaatctaaag tagtaccaca atgatcctta 123720
gacgatatag tgatagaaca tataccttca tactgaggca gagtagacct aggcaaagaa 123780
aactcttcgc actgtaagga taataattta gtagtcaagt ctaactcggc ggtgcatttg 123840
ctcccgctta gcgtagtaaa cacatacttt ttaccatctc catatttatt agtaagggct 123900
tgctgatatt gtaatataga tattctctga ctatgatatt ttatgatatt ctgtatcata 123960
ttgcaaggta ctaatacaat aagcatagaa ctgaaagttc tgaatttctt tttcgcgtct 124020
tgccaaaatc tatccgctgt atcatacact tttcctagac ccgataatga atacttaagt 124080
tgtaacttgt aaggaaaata atggctggat ttactgatac tggataacgt agcaatatcg 124140
gggtcatact tttcagttat cataatctcg ctacctattt ctgtatctac tacatagtta 124200
ggattccata tatctattct tccgtgaaag ctaatacacg acttactacc cactatatta 124260
gaacacgtcc tagaacgcca cggcatgtga ttgtatacca attcgttaaa tagtttattt 124320
tgtccatcgt aggtatctag aggcaataca tcctttggaa aattaggttc tacaaatttt 124380
agtattatca tgtctgatct atatcttgta tcgtaatcgt ttacacaaaa tactcctatg 124440
tttgttttct taaccgaggc aaacatcttt acagtaaaaa gatcagagaa tggtaattct 124500
ataatcccat ctttattacc tacagcaaca ggagtagatc cagaaggaca cgtcaacaca 124560
aaactagtaa atcctctact cccggaaaac aagtatattt ctacgtatat ttttctaaca 124620
cgattttcac aggatgaaat atcatccagc accatgacgt cgaaccagtg acaatggttg 124680
gactgtctat tggcgcaaaa cttcgcatgg cctgatattt cgttaggttt tatgaccgta 124740
tcattaaaat taaatctatt aaaagtaaat aattgtttaa atctgttttt attatcaaat 124800
ggattttcta ataaccatcg tctattttct tcctcccaaa tggacattct taataataca 124860
ctgcacgtag tataagctat agctacttta gaattatcaa agggacatcc ttttactagt 124920
aggtaaaagt tcttgagagg gaaaagatca caaacgttag aaggcatcga cttggactct 124980
tcgggttcac ccggagtagc cattttcagt aattgcatat tagatagagg tatctcaaat 125040
ggttttaaag ttagagtaac ttctctccca catgtaaacc gtactatagg tgacttagaa 125100
```

-continued

```
agcatcgccc ctagcctagt cacttgataa aatctaactt cttcagtaac atcttttaaa 125160
gtaacaaacg catttacatc taaatcagga gatcttaaat atcctatagg acacgcgata 125220
gtcaaggaat aatccattat tatattacta gtattgaggt agtaaactat actttcaggt 125280
acatctataa aatgtaaatt aagtttctcc aatgatggtt taaacgagga atcatttcta 125340
taagctaaat aaataactag atcagatccc ggcataagac aggttcttac acccattctg 125400
gtagaatcag aaactagttc gttatactga ttaaattttt ttactagtgg atcctcgggt 125460
tttggtttac ccgtgattaa ctgataaaga tgatttccta gatctaataa tccagatatg 125520
aatgataatc ccatgcccgc aaaagctaca gtaggagatg ctataattcc tgcagaaagc 125580
atagcgttac ctacactact aaaagaagca ctaactgctt cgaatatagt ctcggcttcg 125640
ttaaagtcaa cgtttttaaa attttcattc ctaattctgg cactaatcat accttgaact 125700
atcaactgtg tagcagatgt cagagcagcc gtcttatcga actttttagc agtttctatc 125760
attttctctc tgtatacttt cttgctttta atatctagct ctttaattga tggttgatat 125820
acagatcctt ccatatcaga tctggatgta tctccttgat atccgctttc cgaccgtaaa 125880
cgattactac gagttccacc tgaataagtt ctagatcttc catataagct gctatcgata 125940
tcatctatat cactgttcga tatccaactt accctactac gagtcgatcc ttgtcttacg 126000
tactgtctac ttctttcatg gttatctatc ttagattcat ccgagaatgt tacatgggat 126060
accgtatgtt ttatacccga tctgcctaat atactagtac ttatgggaat ttttggtact 126120
cttaatggtg tcttagaatt tcttaattta tcaatcaaga tattaacagc cgtgttatgt 126180
tttacgttat tattattatt tttacccata tcaggcacgc gtcctaatag tgcacaagcc 126240
gcggtattgc cgaactttcc gcaatcttca atactatttg tgctcttagt ccttctcaat 126300
gaatcaaaat tattttcttg tattgtttcc atagttaggc tatctatacg acgaccaaat 126360
tccttcattg aactctcgat gctatgacgt ctaggtttta cgatactcgt actagtgtct 126420
acattaaaca tcaaactgct ctgtctttga ttgtacttag taagtaatac ttcaccgcct 126480
gtgtccctaa agtctctaat tttttctttc atagtgtcaa atattgaacc agatacaatc 126540
tttttggaac tataactagt tttgacatct ccgtgtaagg cttttgattg ttttgttatt 126600
ccatctcctt ccgtgagata ttcttttatc accgttttat gtctgttatc gtcggataaa 126660
gcagataata cgctattcac tttattggta gccacgctgt atactccagc aataacggga 126720
tttttactag gaggaggaag gtttgaagtc gatgtcctta agacatcccg aatactatag 126780
gggtctgtat ccagaggtac tgaaggcata taaggcgcga aagcttgtct agcttgtaaa 126840
gatagtctgg atatgagctg accgtcgcct attattccat cattttcact ccctccatgg 126900
attcctgttt gtatatgcga tactcgatcc ggtattacct ggccatctac acctagataa 126960
cgagccatca ttttagtttc atcatctgta tctgtattta tagagggtac tattgtcctt 127020
ttctttctgg atttagcaat ttctgctttc ttactattaa cacattcggt atattcagtt 127080
ccttctctgt aaggttcgta agcttcatac atacattcaa gatcttcgct gtctaaaggt 127140
atctcgcccg tatctctttt atgtctgtta ccctttgtat acatataaga ggataaaatt 127200
tttgttgctt gtacagcggt atccgctgct aacgaaacgt agttcgagca atcgggatta 127260
ttttccaaca tacactcata aaacaaacgg gtattaacat catccttaat ggagaaattt 127320
ccaataatat taagatatga attaggaggg gttacaactt ctgccatcaa agacatacta 127380
gcatgatcgc aattaccagt tagtgttttt ctaatagtac ttataaaaga attagatgtt 127440
ttacatgatt ctactatctt attaatacag tcaggaaact tatcagaatc catatacgga 127500
```

-continued

```
tgttggacag atacaccgtt aaaatttata ataatatctt cggcagcgct gcgtgaatcg 127560
gtaacagaga aattacctat tgataccgta cttatagtaa cgttattaca cttaggattt 127620
tcatatttta cgtagtctat atccggtatt ttgaaactgt atccggatcc gctggttgtt 127680
acgtactcgt ctatactatt agcagtagtt aattgttgaa ttaaagacat aagtgtcttt 127740
ttcttgctgt ctccgatctt ggttccctta gttacttgta ccattaccct taagacatat 127800
ttgtaagagt agtcatactt atagtgcgta ctcccgttgg attttttaat acacttagtc 127860
ttgtaggcat cttttacttc ttttcttatt ttttcccagt caaactttcc catgaacaac 127920
gatttttctt tttcttcagc gagttctaga tatttatgta acgcttctgc tttagtatcc 127980
gttgattgtt tgttctcgac tgagttttgt gcagaatgat acataggtaa atttttcata 128040
catgtttttg aatccgtttt atgtatatat atgaatgcat atatcattat gtatttgtac 128100
attattgtaa tttataacat actatattaa agctataaag tttttagttc aattttgatt 128160
ttttgtatat ttatatacat aacttaaaga agtaagttat taacattttt gcacattaaa 128220
aatagcattc atcatatttt acagtaataa aataacatac attactctta attcgtttca 128280
aaaatgggaa atatttttaa gcctattcca aaggccgatt atcagattgt ggaaacagta 128340
ccacaaagct taacagctat taattctact aatctttcta cttatgaatg ttttaaacgt 128400
ttaatagatc tagcaaaaaa agagatctac atagctacgt tttgttgtaa cctaagtact 128460
aatcctgagg gtactgacat actaaacaga ttaatcgatg tttcgagtaa agtttctgta 128520
tatattttag tagatgagag cagtcctcat aaagattatg aaaagattaa gtcttcccat 128580
attagttata ttaaagtaga tataggtgtg cttaataatg aatcagtagg aaacttgtta 128640
ggtaatttct gggtagtgga taagcttcac ttttatatag gtagtgcgtc tcttatggga 128700
aatgcgctaa caactattaa aaatatgggc atatattccg aaaataattc tttagcaatg 128760
gatttatatt tcagatcgtt ggactataaa attataagca agaaaaaatg tttattcttt 128820
accagaatgg ccacaaagta ccatttcttc aaaaaccata acggtatatt cttttcagat 128880
tctccagaac atatggtagg tagaaaaaga actttttgact tggattgtgt tattcattat 128940
atagacgcgg cgaagtctac tatagatcta gcgatagtat ctcttcttcc tacaaagaga 129000
acaaaagatt ctatcgtcta ttggcctata ataaaagatg cattaatacg ggccgtatta 129060
gaacgaggtg tcaaactacg agtgctatta ggattttgga aaaaaacgga tgttatatca 129120
aaagcatcta taaaaagcct taacgaacta ggagttgacc atatagatat ctctactaaa 129180
gtatttaggt ttcccgttaa ttctaaagta gatgatatta ataattctaa aatgatgatt 129240
atagatggaa ggtatgctca tgttatgact gctaacctag acgggtctca ttttaatcac 129300
catgcttttg ttagctttaa ctgtatggat caacaattta caaagaaaat agctgaagtg 129360
tttgaaaggg actggatatc tccttacgca aaagaaatag atatgtctca aatatagtat 129420
atatgataaa aagatcctaa taaataaata tagcatggca ctaatagaac agttacaatc 129480
ttctgaacaa tcaatacttt caccgtttag atattatggt tttaaagatt ttcataatgt 129540
aatttttacc acaatagatg acgaaacatt aatagtaatt acagtcaaca atgtaccatt 129600
agtaactagg ttaataacgt ttgaaaaaat aacatttttt agatcgttta atagtacttg 129660
tattataact tccaacaata attcggatat tgatacagat acttatttta taccaaattc 129720
gttatcacta ctagatattt tgaagaaaag agcatatgat gtagaactaa gagatctatc 129780
atttgctata atgtcggaaa tgaataacga tgaattgaga aatagtgata ttgtatctct 129840
aaacaaatgg ctacataagc ataatttact agactacaaa ttagtactaa taagtgatat 129900
```

-continued

```
cgatagaaga tataaattat acaataaaaa aaatacaata attgatgtta tatccgtaaa 129960
tggtagaaat tataatatat gggttaaaga tgttatagaa tattattcac cggaatactt 130020
aagatggtct atagatatta aaagagccac agaaagtaat aactggttac cgtatagcca 130080
gtctataaac cctttgaatg aaaatatata cgcttttgaa tttatagcta ctttagaaag 130140
atccaatgag cgcttaaata tcggagcgat attcctgtat ccggatataa taattacagg 130200
tagaaacaac gaagatataa tagaaaagtt tttagatcag ttagaagaag taatatataa 130260
aaaaaattct gatagtattg ttttaacagg ttatcatcta acatttttag agaatactat 130320
tttagagaga tatatcagta agtataaaga ctggattttt acatgtaatc gtctagtaca 130380
ttgtaaaacc ggcactgaag tattcttatt tgatgccgct atatttttc catcctctaa 130440
taagaaagga tatgtaaaac attggacagg taaaaaatta aattttaaaa actttttcca 130500
aaaagatagt cagctagaaa aatacataaa taataacagt gtagcagaac gtatatatta 130560
tttacagtct tctttacaca agcatatatc ctgtctaata gaaattttcg agttaaatgg 130620
atttgatttt aatttttctg ggttgttaga tatacttatt ttcagtattc gtgttaagaa 130680
taataatggt aattactatt accctaaaca ttcttcagct gtgaatttga tgttgtcatc 130740
tatttacacg gactattatg ctattgatga tatagataaa gatagtaaga aacttgtttt 130800
taactctatt tttcctttaa taatggaagg atattaccct gaaggaaaac cttattatac 130860
gaaaacaccc aaagaagggt atttgtcaat atgtttatgt gatgtagaaa tatctaatga 130920
tataaagaat cctatattgt attgtaaaga aaacaagtca gctaggaagt ttacaggagt 130980
attcacatct gtagatatag ataccgctgt aaaactaaga ggatataaaa ttaaaatatt 131040
agaatgtatt gaatggccta ataaaataaa attattcgac aatatatgtt atctgaataa 131100
attatttata gaacatcagg attacacaca cgatgaaaaa tctttacaag gctatctttt 131160
ttcttattta cttaaaggca acgttaccga agatgtttta gctatgaaaa gttgtagaaa 131220
taatctttct ataatatcat ttataataag ttactgcaga aactatactt acaaactatt 131280
agaatgtcca gtatacgaat caagtaatat agttaaatgt aaatataatc aagttatata 131340
taagtaaaca atataattga aaataaaaat ataatatacc agcagcatgg atactaatag 131400
aaaaagatca ctagatgaac atgacaccgg tgaagaatca cccggtaaat tacaaatagt 131460
tgaaattaac gatgaagaag atatcacatt tacagataac ccatattata aactagtgaa 131520
atctcgcgat aatagtatta atctcgtacc tttagtcgga tgtgttatga ttaagataaa 131580
tgatattaag ggtgtaacag ataaagtaaa taaactatta cctaaaacat ctagtaagac 131640
aaattctact agttgtataa atattcctat agatagtatt cctttgaatt ttctggatga 131700
tggtaataaa tatttcaatg tttccgaagt gagtatactt caggtaagtc atggaaatga 131760
tatgatgaac atagataaat atgtcgatgg tagctttgat tacatagccg tattatgttt 131820
aaaaaattct ggtagatctg tgattatgtt aaatcattgc aacaaacaac acgtaatgca 131880
agataatttc tgcttaatat tcagatcttt ctatggtata aacatattga ctcaaataat 131940
tggagaatct gtatatttat tagttaaatt atcacctagt gatttattta aaataagatg 132000
gtcgtctgtt atcgactcta atagattcat ggggaagaaa ttctatatcc gaaatttaca 132060
agaagacgcg tgtatagaaa aaatgaaaaa tatggaaaaa gatatctaca aaaacataga 132120
gtttataata attaatagcg ttttattgga agatttaaaa tctcgtcttg atataacaag 132180
agagttaaat cacaccatag ataaaatgtt taatcataat aataatacac tgtttagtga 132240
tataataaaa ttatcagaag aaattataga taaagacttt aaaaacatgg aaaaaatgtc 132300
```

-continued

```
tgatagtgta ttagcagatg taaaacaaat atctaaaacg aagaataaat tacgtgaaag 132360
acttttaaaa gcagcgattt cctctaaaga agtagaagaa atattatccg atatacccgt 132420
tatagaagaa ggtacaataa aacaattttc tttaaatcaa cgagctgtat acgatcacta 132480
caaaaaagta atctacaaaa ataacagtag cttggactta ggatgtatga atatagaaaa 132540
gagttatatg ttcaacctat acaaggtata cggacaaaac gagtacatga ttacatatat 132600
actaaactta ataaatagag taaaaaaggg tatggatgct ataaaaagta acctaggtga 132660
tatatacaaa tataatattg ataatattaa tttagttgta tcagaaagaa taaacaaagt 132720
tatatcaggg gaatctctgt aaatattaga tatataaaaa tactgttagt tacgtatata 132780
aaatcacttt ccgtatagtt gtatttgctt ctacattaaa tggaatttcc ggacatacat 132840
gcttataatt ctaccaagta tttagaagat ggagacacta cgatattagg agatactatt 132900
cagtttcagt ttatatacga aaatatagac aataaggagc atatctcctt accaaaaata 132960
aagattttca agtattttag agataagata tcttttgaaa cactagatag aattattaaa 133020
aatgattaca taaatccttc ctattttcag ttaaaagata aaaagttttg tgcgcacaat 133080
agggattttt accatctatc taccggggga tatggtatta tttttaggat ggaaaaatat 133140
gtagttaaat ttgttttcga agacgggagt aaaaaatata aacctatgga agtaacatct 133200
gaatttacaa ttcctagatt tttatataat aatcttaaag gtgatgaaag gaagtttata 133260
gtttgtgcaa tcgcgatggg gattaatttt aagatagatt tcttacgtac aatctattat 133320
aacacgatga gtttaatgtc tgcgttattt aacatcatgg aaggagaacc tctagaaaac 133380
aaatattctc atagaaaagt attacgttat ttcgctaagt acaaacaatc taatgatttt 133440
gtaaaattga tatcacagtt ttatccgtat gttgttaact ctaatatcaa tgtaattaat 133500
aactttaatt atctaattaa ttttttgaa cgtagtagga gatcaaacgg ttattttaac 133560
agaggtaaca taataatatt ccctttagca aaatgttccg cagaaaaaat aactccggat 133620
aactatgcac aatatggatt ttctagtata gtagaatata ctaaatttat gtttttacaa 133680
atagctttat tgtacataaa aatttatgaa ttgccatgca gtaactttgt tcatttagac 133740
ttgaaaccgg ataacatatt aatttttgat tccaaagaac ctataaatat atacgtaggt 133800
gatatgcatt atgtgtttaa agaacctata agatgtacat taaacgactt tgacttttca 133860
cagatatcgg aaattattcc taataagaaa gctgtaaccg ctattaacaa agaacagaat 133920
tggtattacg acttccactt tttctcgcat gtactattta aagtatatcc agaaatatct 133980
aaagacgaag attttacttc tttgcttaac gaatttacta tctgtgataa atatatctgt 134040
gaaaacttta gactacaagt aaataaatta ccttctatat cgtttttaat aaatatagtt 134100
tctagagata ttttttcaaa gtggatagat ggaaaatcaa caagtcatca gtaatctata 134160
ctatttattt tctgaaaagt acctagagaa attgaatcaa cacccagaca ctagtaacgt 134220
tagatgcgga atacatatag gttatttaag cggtgaagca aaaaactgta tagttagtat 134280
aataaacgcg tgtaacagta atgaacaaaa aagctttcaa cttctgatag aatcattaat 134340
tgaaacaata gaaaatcttc cagaaaaaca acaaaaagaa atagctaaaa gtataggaat 134400
caacatagat gattacaaag cgggtaaaaa gacagaatta cagcagcatt gtgaagccta 134460
tgctaatctg acgcagcaca tagatataca acacttcaac ataggtacgt gctattctcc 134520
taacgataaa tacactgata taaaaattat aaatacagga tctgctttat caaactgcgg 134580
agtagaaatt attctaaata aaattaaaac aaataatcct atagtaccta tagataataa 134640
actatccatg gagtcttttt caataaaatg gtttattata tatatagttt tatgtgtgtt 134700
```

-continued

```
aatattatta ttgctgggtt atatatatag aactgtcagg ataaaatata cctacggtgt 134760
atatatttaa atctaaaata ataagaaaat aacaaaaata aaatagaaaa ttaagtccaa 134820
gaatatctta ttcaatcagt attcgggtac gtgcagtaca atggctgata ggaatgttaa 134880
gtcttctaat aatcttacaa agaagcgtat caagaaagtt agaataaagc agcctgatcc 134940
tactaccgaa gaaatagata cttacggcgc cgatataaat gttaaactta ttcaacctaa 135000
tataagtata gaacaagatg acggtgaaat acaaactatt catatagatg actttaatta 135060
gttgataata attacaaaaa tgtccggaga catttcattg atataaattt aaattctatc 135120
aagtcatgat atgaaggata catactgtga ataagttata ctactggtta tgggttatac 135180
tacgataaac tgacaatatc cataatgtgt aaatggtata gaaaggaata acttcactag 135240
atgttgttct acatggcgat tgttatacca catattacat atttgtattc taaacttgtt 135300
atgtatatcc tacctacttt tggatatttt catgcgttat tatatattat actatacctt 135360
aacagtatta ttacttattt tattaagata gtaaaataac gtcatctttt tttctaataa 135420
atagtaatta tgtctagaat aaaaatacta ataggtataa caggtagcgt agctgcggtt 135480
aagttacctg acctgataaa agaattaacg cgtttggaaa acatagaatt aagaatagtc 135540
gctacagaaa attctatgaa gttcacagac caaaaaacta taggtattcc tatttataca 135600
gataaagacg agtggactac gtggaaaaaa atacccgatc ctgttttgca tatagaactt 135660
aggagatggg cggatgtttt tattatagcg cccttaacgg caaatacgtt agcaaaaata 135720
gctaatggta tatgcgataa tttactgacg tctattgtaa gagcctggga tacaaacaaa 135780
ccactcattt tctgtcctgc aatgaatact cttatgtggg aacatcctat tacagaaaaa 135840
catatagata cgttaaaata tatgggtttc atagaaatag aatgcataga aaaaaaacta 135900
gcatgtggag acgtaggaaa tggtgctatg gcagaagttg cagaaatcta tagggttgtt 135960
agagatataa tgagagttta aatatataaa aaatattatg tataactaaa gcatacttcc 136020
tttaattaag ggcatgtaca agtttacaaa gacggatgaa aagatagagt ttagtagaga 136080
aatttcttcc cgtaagataa aactacggta atatctaaac atttcgtttt gacgtaacat 136140
gaatacgtca aaacatatag agattatcag tatccaagac actaataaac acgtagcttg 136200
tataactatt actataagat aaaatacttc tatcttacgt ataacaaaaa tgctaataga 136260
taacggcact aatattaact tatctaaagg gctaacacct ttacatatag cgcccaaatc 136320
gttataatat ataattaatt aacaaagtac tcaaagtaaa cactttgtaa agaaacataa 136380
cagagatata atactagact cttttattat gcacgatgag acaggtttac tttagatagc 136440
ggtactgatg tccacacgcg ttagataaat ataataaatc tcatctacat tatgctgtgt 136500
ttacgtaata tctataaaat agcagagata taaatataag agatgaatca acgatacgcc 136560
gatattctac gtttttcatt cttctagaaa catttgaact attattagac aatggagaaa 136620
agtgaatata cgtaataaaa ataaaactat actattgatt aaatatgtca ataccttagg 136680
tgcctatact tcatacttgc tatataatca atctacatat aatgctataa ttagactatt 136740
ggtaaaatat atacgttgat ttagatgagt tatcatataa taaaaatatt gaatacataa 136800
acagaaaaaa gaaataacaa aatataaaat ctggtactct agttattgcc tggaccgttt 136860
ctttcatttt ataaacggtt aatttgttaa ccaagttaat agcttttgta aataatatag 136920
atatagagga atattcccta cgtataaaaa caaaactagc ggtgaacaga gcaaatctat 136980
acaatatatg tttaaataag attaacggac tcttatcacg taacgataac tgtgttcatt 137040
gcctgtagaa attaggtgtt atatagtatc tttttctagg tactatgaat tacttgtaat 137100
```

-continued attgaaataa aagactacat taagtacttg tataataatt ttacattatg gacggacgat 137160
gtctccataa tattatgtat acgggtactt atgatgaaat catgagagct ataaatatat 137220
acgaacaccg taactattct tctttcagaa atctaccgtt acactacgcg atttattcta 137280
gaaggaaaga tatagtagaa accttgctaa agtcgggtta tgatcctaat tctgtagata 137340
tcacggataa taattgtctt caattattat caatgccttt tgatataact atgcttcccg 137400
ttgatgaaga agtacaagac tatgctattt cgttctattt atctaaaaat atgaaacaca 137460
catccatgtt aatacctatt actaaagaag ctttacgcgg gaataggtat ccttcagagc 137520
cttattttag tagcatgtgt agaaaattta aagataatga gttatgtata atggatcttt 137580
tattacggta cggggcttta cctaattcta gaaaggatgg attattaccc ctatatcatg 137640
ccgcggcggc tggtaataca gagatggtag aattactttt aagttacggc gctaagacta 137700
atctacatac gcgttatgaa gattctattt tcatgtgcgc tataaagtct aacaatgtaa 137760
aaactgctaa aattattagc gatctatata attacaaaaa cgatataaac aatatattaa 137820
aaacaataca gttatataat gctgatatgt tattattcct gatagagata ggcttagata 137880
taaacactaa agacaaaaaa ggaaaaacag ctttacacta tgcttgtaat tcgattaact 137940
gtatagaaac tgttaaagaa attatgaaat acggtgcgga tataaatgta aaagatcgtg 138000
aaggactaac accgttacat tcggcgtgta aatacggtga tctaaaatta tccaaattat 138060
taatcgagta tggtgctgat gttaaagtaa aaacaacatc taccgtacta aacttagcgg 138120
tagaatcggg taatgtagaa ctagtaaaat ttcttataga gaagaatccc gaatttatta 138180
catcagacta cttatcgttg tcactggcga ttagatgtaa agatattaat atagtcttac 138240
ttcttttgga cgctggaatg gatgtaaact ctagtaagtg tatatcgaca ccccttcatt 138300
taggagttat tttaggcaat tcaaatatcg tcaagttgct tttagatcat ggtgctaata 138360
ttaacgctat agataagtac ggcgaaacac ctttagaggc agctaataaa cgcataaata 138420
tagattatgc ggaattatat aaatctaata gatttattat aaagtatcta gtattcctat 138480
cacgatatga ctataaaata aagaataata taggtttcat taaaaatatg tatataatag 138540
ataaagatga aacgctaagt tgttttagaa atatgtgtga gacagaatta gataagatat 138600
catctataaa aataggtcag tattctctat atagtctgtt agcatcagat aatgatgtaa 138660
aagaatatat atgtaaaaac agacaggaaa taacacaaaa aattattgat aatctaaaag 138720
atattattat atatcgttct tttatagaga aatatatttc tagaataaat atataaaact 138780
ttttttaaca tattagtatg gaaaaattaa ttatatatag ttttatacta gttgtattaa 138840
accacgttta cggacaatat ctatacttag gaggactatt tagttcaccg cgtaaaacta 138900
ttatcatgaa gttatgttgt ccatccgtag atggagatat gttaccagcg gataaaatcg 138960
gtagtaatat aagagctaca gattgccgat gtaaaagtaa accgtctata atagtatcta 139020
ccaccaaaga agaagagaag tgttttcctc ctaatactcc gtggttggaa caagctataa 139080
aagaaaaaaa tttaaaaata ccgaagtgcg tatactatcc taacaagata ggcgctccta 139140
aaggatttgg ttataagtag tttttaaaac actcgaaatt cttcgaatac agattacaag 139200
taatgttatg cttttaatag ttttgaaata tctatgtaat aaagcaaaat taaacctatt 139260
atctaataat acattactcg cgttacataa ttactctagc tttacctatg tcaagactgt 139320
agctatcggt attaatttca tgatccgtta tagaattagt gtatctccat gagatacgtt 139380
atatagttca tacctatagc acatccaaaa catatgtgta tgaacttatc tcctgcctta 139440
tcagttatcg tataagatga gaaattgtaa caaagacttc ttccttgaca acagtggaag 139500

-continued

```
ttctaaactt gtaacgttaa ttaaaccgga ggaaactata aatatagacc agcatatact 139560
tatatagtaa tacccacata tttataaaaa tcgttttcgc gataaaacac atacagttat 139620
atttatacta actagtagtt agttgcttta tcaaaaaaaa tcataaaaat aaatctatac 139680
acattaattt aatcaggtat ctataatggg tattaaaaac ctaaaatccg tattgctatt 139740
aaagcacagc ttgaaagtac ttgattccgc tgtaaaaagt aaagaaatat acgttgattt 139800
tctaggatta tttatggcaa tcgcatactc ggttacatct acagcaatgt tacatcatat 139860
tataaaagaa aaatttaagt ttatacattc tatagctgat aatgttactg tgtttgtaga 139920
tagaggaagt atttctctaa aaacatcatt aagagagaag agaaaacaat cgttaaagaa 139980
tcaatataaa aggaagcaag aagaactgaa aaacttggaa atagcgatag acaatctctc 140040
tgtagacgat gaaatgtatg aagaacaaaa agagagcttg ttttctaaaa tagataaaaa 140100
tagctattat atgttcttgg cggataagaa aaatatggaa gctattataa cagatgtact 140160
agcttctcta aaaaatacag aaatctatta ctgtgatcat atagatgcgg aatttatgat 140220
gtgttgtaga gcaagggaat attatactaa taacggtaca tggccttcta tactaagtag 140280
tgatcaggat actatttgtc tagtatgcgt tgacacgcaa gaaaaaatat tatacgatac 140340
taaaagcgta tacaaattat ctcccaacaa gtacacatct tatcttacaa aattaatagt 140400
attaactaac ggttgtgatt tctttagagg actttacgga atttctataa ataaagataa 140460
ttatatgaga tacgaattat ttacagaatt taatagagag aatgcattca gaagcatagc 140520
tcataaaaac tatagcttaa ataattctaa taccgatgaa aatatagatg aaatttctac 140580
taacatagat gtgatttttg attttataaa ccactataca tcgttaaatg aagatgctta 140640
caaatttgaa gatttgccgg atatacgtgt taaggatttc ttggacgtta tggtccgtag 140700
taaatggtac gaagctaaaa acaagtacga tcttggatcg gatatattac aaaacattta 140760
caacgtttat aaagtacata gacgtaatta tgaaaaggaa aaagaaacga atatactaaa 140820
aatgatagaa tcttataaat atagaaacat aaaaataaat actataacta catttataaa 140880
acttctagga atagaaactt ctgattctat atgcgtattg ggtatattgg cgccttcaga 140940
attatatata ggtttcgaag gaagattcta ttttaataaa acatctatta ttaaaagttc 141000
tccgaaatta attaatataa atatctagaa tggtattccc gttagtatgt tctacttgcg 141060
gtagggatct cagcgaagct agatatagat tattagtcga acaaatggaa ttaaaaaaag 141120
tagtaattac ttattctcgt aaatgttgta gattaaaatt gtctactcaa atagaacctt 141180
atcgaaatct aacagttcaa ccttccctag atatcaacta atggatatct cattatttga 141240
ttatgtagcg ccaggagctg ttatattaag tcaatctaat cactctatcg taaatttttt 141300
caatccatca gaagaaaaac attcttcttt atatttcggt tatggtatag tagatttcat 141360
cattaaaaat gatatcaact tttctattaa cggattaaat aattttacaa attatattat 141420
agaattcaac acatctggtt ttgctataat acctttaagg gaattcatgt tagataggaa 141480
gtatgcaaaa gtatactact atatggaagg aatatttcca aattatagat tgatggaaga 141540
tactgtaaaa caagcatttt tacacgctaa caaagaatat ggtttcggga aagataaaac 141600
ttactgtttc aagatgatag ccgactgtta tctagatata ggtataaatg ttaaatcgta 141660
taaaatttta ggtaaatata tttatcttag tcaatctttt tgtaccgatg atagatggac 141720
taaagtatta gatactttaa cgggagaaaa tctaattact aggaacagtt actattttat 141780
aaggtgaatt aatggttaac gtagttcctg gctttttttgt tttaaatgat ttcttctttt 141840
taatgcaatt agctagtact ctaatggtat atagataatc cagtatagca aattttctta 141900
```

-continued agtcattatt agtaagtctt attctatctt ctgtgatagg actgatgaca gcaccgtcaa 141960
gatcatgtcc tttagaatat ttgtaagcca tgtctaaaac tttattgttg ttggctatgt 142020
aggtagccaa ttgattcttg acggtatttt cagcttcttc accaacttct tctattttta 142080
atccagctat atattctgga taagtatcct tacacagccc tatctcgcat atggtcttat 142140
acattttatc tagttttgga gactttaagg gtaaatcgat aattatatct atttcttccg 142200
aaaaagacat cactttacct ccggctatag tctctatgtc ttgctggcca gtgagtatag 142260
gaaatatctt atactgcgcg aatttaagta tggcatactt catatctagt agatcggata 142320
cctcacttga cggtcgtttt tttgaatcga ataggtaatt ttctatctcc atgactatct 142380
tcgccgcatg aatgagttga ttggcaagaa ttaaggttaa aagtgtagca gctgtagtat 142440
ttatgagata gttacaagtt ataaaaaaag acttattatg agtcaatcta gtaagaatgt 142500
ttcttaactc attaaattct atttcgtctt gcacgtgtct ttcataattt ctagttttat 142560
caactaggga ttttacaccc gctatagtag gaatagatat atcggactcg catttttgat 142620
atatgctatt tataatgcta tctctattag aggagttata tatatattta gctctagcta 142680
ctataccggc tattgcttta tcgtctaagt agtcttttaa cagtgtttct attaaagatt 142740
tagacaccat gttaaaaatc ctcgattgtt tctggtcttc catttaaatc aaatattttt 142800
aaaaatataa aagtaattta ttacaactag ttaatatcac taaaaagaca tatagtagta 142860
ggttacctat tatccttaag gctcatcatg tatgacctac gtttattata atctcgccga 142920
gtgtgtagtt aatatttttc ttctttcgac atagaagaag ctaataccat cgtagtggac 142980
tttcgctttg aagagttaat gttaatatat ttactccata gattcgatat aatttattac 143040
gggaagctaa agaattaaga aaacagtatc gcgatacgca agaactatta ccattttaat 143100
cggagagctt tctatggata tagggttagc gtctcaagaa atacataaaa ataagtatta 143160
tattacgtat atattatata tacagcatgg atacaactaa aagaatgtgg cctctacaac 143220
tttgtgcgtt aattgctatc tgctttacat ctactactgt atctgctgct agtggtgatg 143280
gatgttgtcc atacggattt tctccagatg gtactgacgt gcctgtatgg aatctgttaa 143340
actgtaccaa aataccggat aattgtgaga aaaagggatt tttattccat tacaaaagcg 143400
gtggtggaac atgcggaacc ggcgatgaag actggtttag tcctcatagt cttatgaatg 143460
atctctgtaa taatggacta accgcgattg ttaaacgtac tatgtccgga gactgtaatt 143520
gcaaatgtac ttgcgatatg gaggataagt agcgtgtata aaaaataaat ttttgctagt 143580
ctcgtatagt acttaactgt agatgtagat ttgatgacac tcactactag tcgttttgaa 143640
ataggtgatt tagaatattg gatttttcta ctctatacta gataatagag ttgcatacaa 143700
tattttagct atcgtatgga taaatatatt ctagaataca aaaatatggt ctaatctcgc 143760
tactggataa atcgaaaaat acttttttatt atatacatat agtctattaa acaaaatgat 143820
agctcgtaac ctataaaagg aagcagtgtg tctgcatcgc ttgctctgaa gatgtcaaat 143880
attataaact gctacatttc tgctggggac aatactaaaa ttggcgacat tgttatgcag 143940
gtttaacaat gggatataga tgacactaaa gaatactatt gtgaacaaca tggtatgaat 144000
tatctaactc cgttagacgt gtgggataga aaccaagtta aggttaaaga aattggagaa 144060
ctcaagagat atcccggcat tattttttcc taaaagttat atacccaaca gaaatgtgcg 144120
ttatttcacg agtaacgata tcgaagaagt caataatgtt attactagtt acttaagtga 144180
agcctattat tgttcataaa aatgcataat gagataaagt gattaacccg gtgatattgt 144240
aaaagaagat tgatcctatt cttaagactt tacgattaca agcaaaggta aaggagagac 144300

-continued

```
tttaaactag aacgcgtaaa aatcaattac agagatttta cgttatgcaa tatagaatag 144360
ccactattta atacggcaat aatggttttg ggaatatatt aatagtaaag tcgaataccg 144420
gtttattata acatgctttt caagtatcca aatctactga gtataagata actcactagt 144480
taataatgct atactaatat tataatccag ttcgtataat aattcctgga taccctcttc 144540
tatcgcgtgt agtattatag catcttctac ttcttttttt gtagctgaaa ctaatggtac 144600
gataattgga tagatacaag tcaatactgg cattccgata acattaacta gttcgtaatc 144660
cataaaggtg tcattaacta ataataaaat ttgatcattg tgttcataaa cgaaatcttc 144720
tagtaaacca catgagtaat tctcttctgg atataccttt atagataatt tcttttctag 144780
atccagtaaa cagcacttct cgtaatcgtt tttgtaaaat atttcttcta agtcttcgtc 144840
tgataaagtg ctcgttagta cttcttgagt agtttcttta atcttttctt ctagttctaa 144900
tatcttttct tgatcagccg cataagatat ttctataaga tcagtatcta ccaatacatc 144960
agtaatactc cgcgcctctt tcgtaagtgc ttcagataat ctattaatag acttagctaa 145020
agatccgtct ctatattcga ttagttttat gttatcgtcg tataatgttt taagcttatc 145080
cgaaagttct ttatccacat attcgttagt actttttctta tcatatttaa aatcaaatac 145140
ataaggcggt ttatctaata cctcagattc tatccacgta tccctataat gtattaatat 145200
attagcttta cacgcttcgt attcaggatg ggtataagga acatgattta ggttactaat 145260
atatccgcaa tagtgtccag gatcttcttc atttggccaa gtatacactc cacagtgcct 145320
aacttcattt gccttattac tgggatagcc gtatttctta tattcgtctc ccttaatggc 145380
acaatgatct tttgatgtaa tagtaacgaa gcaaagtcct tcgtatttac ttatattcct 145440
aggtatagta aacatgggac atttcataga tatagatttt aacgtaagat ctaacgtagc 145500
ggtgcattcg ccccccctcca tatgtctaaa agtatatttt ttgccgtccc cgtaatcgtt 145560
tatctgtgat tgcatgtatc ctaaaacaga tataacaaca ttagcgtcgt atattaatat 145620
atttgctctg gaagtacacg gtaataacaa aagtaaaata ctactataag tccttaattg 145680
tttttagca tcatcccaaa accgattagg atcatcatac gctctaccta actcgcttac 145740
agaaaattca atatcgagtt cataaggaaa tctagtaatt gccttttttta gattcatcgc 145800
atcaaccgta ctaggatcat atttttcagt aattaacagt tcagtaccaa tatctatatt 145860
tagtatataa tccggtggcc atacagcgac ttttccataa tatcctatac acgttctacc 145920
ctgcctccaa gtaacgcacg ttctggaccg ccaaggcatc ctcaccgctt ttaccaaatc 145980
gtcgaatagt tttttttac ctttgtaagt atctactaag acagcgtctt ccggatatac 146040
gggtttgacg aaagatacca ttagtatatc ggatttatat cggctatctt cgttgtgaac 146100
acaaaacacc gctacactac gctcttctgt agaaccgaac attttaacgc taaagaaatc 146160
tgacaacggt agttctatca gtcctaaagt attacctacg gctacaggag tagaccctga 146220
gggacaagat aatacaaaac tattaaaacc cgcgttgcta ttaaacgtat aaacttctac 146280
gtataagatt ctaactctac tattgcaaga agttatatca tctaatatca taacatcatt 146340
ccagaaacat tcttttatat gtctatttgt acaatacttc gcatgtcctg gaatagtatt 146400
aggttttata atagtatcgt taaaatcgta cttatcgaaa gtaaataact gacgatgttt 146460
attactatct tcaaaaggat tttccagtat ccaacgttgg gttttatcat cccatatcgt 146520
cattttcatt agtatactac acgtcgtccg cgttatagaa gtttgtgaag cgtcgtacgg 146580
acaccctttc aataaaagat aaaagttctt catggggaat agatcgcata cattagatgg 146640
aaatgtttta gtatcgggtg gttcaccgga cgtagacatc tttaaaagtt gcatgtctgt 146700
```

-continued

```
cattttaact tcgaacggtt tcagagtgag cgttatatct ttcccacatg taagttctac 146760
gatcggaaac tttgaaagca tcgccgccag cccaacaaac tgataaaact taactccctc 146820
atccgtggtg aattttaatg tggtgtacgc cgtaatatct aaagtggtag atcttagatg 146880
tcctattggg catgcgacgg ttaacccaaa atctactata ataccgctag tgttaagata 146940
gtataaaaca ctatcgatgg tatctatgaa atgcgtcgct aacttttctg actgcggcat 147000
aaaactagta tcagatctgt aacttaagaa tatagtcaaa tctgaaccag gcattaaaca 147060
tttcctaaca ccggtgtgct cggtatctgc aactatctct ctatacatgt taaattttag 147120
aactaatgga tctgaaggtt ttttaatacc ggagagtgaa tagtatatat cttttccgat 147180
atctattaag ccggtaatta atgttaaccc cattccagct agggcaagat gaggagatat 147240
aactataccc gctgtcgaca tagatgttcc tatactactt aaagcggtac taacagattc 147300
aataacggct tccgcatcat ctctaaatcc ttcatgtatt cgttgtaacc tagactgtct 147360
attgatcata ttcatagaca ttgtttgtat ggctagacta aataccatgg ctttgtctgt 147420
agaagatgat agtttcttca tcttttcact atacttagag atagcagtag atttataact 147480
atcatcatca ttagccgata accgagaact tacgctaact acgctacctc ttctaccacc 147540
actactactg ccaccgacat cgcctatcac tgaatatatg tcatcgatat ctaaattact 147600
gtataacgaa tcgtaataag acgatgaatg cgatcttgaa cttcctggaa ttcttgggag 147660
aggacggcgg gcgagattat aagaatccct catacggtca tagtcattat agctagtcag 147720
tctcgccgaa tttactacat cataatatgc gtaaggtgtt actaggttca caaaaggtct 147780
ggcagcccgc tgttgcgtat tttctaaaaa ccccatatta gggctagaca tatagataag 147840
ttcttgtgat tgtgcggtag agggatgcct acgtcttcct tgtaaagagt gcttttcggg 147900
tactattatt cccatagctc ttgcggcctc tatatgtcgt tggtacggat cttgaaaaga 147960
ttcctgatgt acttgtgcgt gaccttgtct tcctgtcgct attcccatag ctcttgcggc 148020
ctctatatgt ctttggtacg gatcctgtga aaaacctctt gctgatgaac tacgcgcgga 148080
gttcatagcg cttgaagccg tatgagcgtc cacataaaca tcgttaggat taccttccgg 148140
tctagatcgt tgacctaaca tcgcacacac tacatcgtta gtacctcgct tacatcttct 148200
gcgcgacgtc gatgaatttt ctggttcatt tcttgaaaag agttctgaca ccgatgtcac 148260
tggtgaacct actaattctc gtacgttttt atatttaccc atcgtgttcc tgatgatagt 148320
ggttcctttt cttgttaacg gacttaccac taccgtagat gtatcgacgt cgaataaacc 148380
ggtaggtgta tctgatacag tagatactac gtgtattcct ttgccgcctt tttttctgta 148440
cgctgcgatg ttttctacga gattatctcc tgttctgtac cgcgcacgtc ctcgtcttat 148500
atggttctct actattcgga tatcctcttc ctcagattcg tacctcgaca ccataaattg 148560
taattctgcg taaccagcat cttcagtact actactatac ccgattctag actctagtac 148620
tcccctaaca gattctattt ttctagctgt tatcgccgct aatcttctag aaagtatatt 148680
ttgtgaatct tcagggactt tatttatagg cctaggccta tttatcttat cgtatatctc 148740
gtcagtgcgt gtatcagccg ggatatttgg taagaaactt tgtaacgttt tcttagctct 148800
atcttttact tttgcacgta tatcgatatc accggctact tgtgtagtag atcctttaga 148860
ataagaagta cttgttccta attgtaaatg ggtggcttct ttaggaataa tgtctcttat 148920
tttcatgatc ttcttcaagt attgtgccat gtctatatta ccatgaccat cctctgaagt 148980
ttctctctta gatctacttt tagatgtaat catacactgt gtaaaatcat ctttttttacg 149040
agtatcgtac atattataaa tacatttaat atcttccata gatatctcgc cgtgggtatc 149100
```

-continued

```
gatatcgcgt tttactcgat gtttatattg ttttatataa ctagatagag ataacaaggt 149160
atcagattga aacttttcag taggcgcgac gtaatctata caatctttac cgtttgtcat 149220
catacaagcg tataataatt cggataacgt atcagatgta gctccgttct tttttaaagt 149280
agtgtaaaat tcttccggaa tatctgttac ttccaccatt aaacctaccg tacacgtctc 149340
gcaattatta attaccgatt tatctatttt cgccttgcct ttaggggaca ggcatccttc 149400
gttgactttc ttcgtgatgc attctataaa ttgatctgaa tcggtataag gttcatgcgt 149460
agagactcct ttaaagatta tcggtataat agatttagat tgtggtaacc ttgctttatc 149520
tccgtctatt acactaaatt tagatattat cactttatct atggttacat tgttacagcc 149580
gctatcggag taggaaatgt gttccataac tggtaattcg aaatacgttc tatcatttgt 149640
ctcgtttata aattgatccg taacactatt gttgtgcaat agtagagtat tgattatatt 149700
tttatttata tccttatatt gcttataact cgttcctcga actccgtctt cagtatcggc 149760
ggatacggta atattcatca tgacggtata attatatttt ataactcctc tatcattaga 149820
acatttatct agaaacattt tcttaacgga cgccaaaatg ctatcccaat taaaagattc 149880
tatgaaagtc tctttgtgaa ttctttccgc gattgacaga taaccgtatg ttgcggtagc 149940
ggcataatcg gtcttttctt tgggatttaa atcttttcta gtatcatgat atattggtaa 150000
ctttcttcta caaaattctg atcgcgttat cgcaacaaaa ataataagta tagtaattat 150060
atccataata actatgttaa taacctttta gttcatttat tctaagtttg ttaacgaact 150120
gacgttatgt ctcattaata tagtacttat attcatgtcg aattcataca tcaattcttc 150180
taacccttct ttaaaagcgc gtaataacat tatctcttct acctcgtgtc taatactttt 150240
tgttctaaga ggtattacgg tggcttctat acaggtaact actggttctc ctattaggta 150300
taataactcg aagtcttgta acgtcccgtt tataagtatc ataggtctga tctgatcgtt 150360
agacatatta ctatattcta taaaatcatc atacatataa tcggttaact caccgcagta 150420
ataactggat aaatcatcta cctttgtaat actattgtct ctgaaattaa ttagacaaca 150480
tttatcttta ttcccaatta tatcgttgat atcttcagcc gacaaagaat tcgctataac 150540
ttcttgagaa gttatactaa tagcatgttc taattcggtt aaacgttcag aatcggcttt 150600
ataagccgtt tcaagtattc taccgtttac aatgatttca gtaatgctac gtccgttaga 150660
agtaagactt tccgataacc tgtttatagc agatggtagc gacccttgct tatattctga 150720
tatcgaacgg tactcttcgt ataatctttt caacgaattt gataattttg gattaacata 150780
ttcattattt ttatcgtatg tgaacttgaa cgcgtacgga ggtttagaaa gtacttcctt 150840
ctctatccaa gtatctttat agtaaacgtg aatataagac ctacaagcct cgtatttagg 150900
atagcgatat cctatatgcc taaacttact aaaataacca cagtaatgat caggatcttc 150960
ccaaacagcc ggaacaatat acgtctcgca gtatctagca gtattagctt gctctttaga 151020
gtatccgctc gttttaatat cgtcttctaa ggtagcacaa tgatctctag acgtaacggt 151080
tatcgaacat atgccttcat atttgtgtat cgtcctcgga atagaaaatg gatcgcaagt 151140
aactttcatc attcttgagg ttaattctaa ttctgcaaaa caattactac cagacactct 151200
agtcagtata tactttttac cgttaccgta atcttgagtc atagactggt ggtacgctaa 151260
actagaaata gtatcgctag tattatatat tagcatgtta gctctcatcg tacacggtat 151320
taaaattaaa acgatagaac tatacgttct atacatattt ttagcatctg accaaaatct 151380
attagaatcg tcgtatgctt ttcctagatc tttgatgtag taatgtattt ttaggtcgca 151440
aggaaaccat accttagatt tttctacgct attaatatct atggtaccag cgtcgtattt 151500
```

-continued ttctgtgatc attatttcat ctcctatatc tgtttctatg atatagtcct ccgtccatat 151560
atctatcttt ccgtgataac taacgcacga tctcttgtgt ttccaggtta cacatttcct 151620
agaccgccaa ggcatagtcc ctagttttgc catgtcttca aatactcgtt ctctacccgt 151680
gaactcgtct atgaatataa cagactcgtt gtacgcttgg gatacaaagt taatatggat 151740
gagatcggat ttaaaatcac tatcataatt atctatacaa aacacgccta ttttattttc 151800
ttctgtagaa gcaaacattt tactcgtcgc aaaatcacct ataggtagtt ctattactcc 151860
atctttatta cctacggcta cgggagtaga tcctgaagga cacgataata caaaactcgt 151920
aaacccccta ccatatccaa aagtatatat ttctacatat atatttctag atctggattc 151980
gcaggaagaa gtgtcgtcca ataacattgt gtctttccaa taacattcag tagtatgttt 152040
attagcgcaa aatttagaat gtccttgaac agtattaggt tttattacta tatcactgaa 152100
attacggttt tgaaacacaa ataattgttt gagttcagga tctttaccga acggattttc 152160
taatatccat cgcttacctg caggatccca acttgaaatc cttaatagaa tactacatgt 152220
agtatgaatg atgtaagtta tggaactatc aaacggacaa ccccgtacca acagattaaa 152280
actttttaga ggaaatatat cgcacacgtt agaaggcata gtcttagttt cttctggttc 152340
tcctggtgta gccattttaa gtagctgcat gtttcttagc tctacttcga aaggttttaa 152400
agtaagagtt atatcttttc cacatgttaa tctaaccgta ggaaaactag aaagcatagt 152460
tcctagattt aaaaacttat aaaaccgtac tccgtcttca ttagtatatt taagagtagt 152520
atatgctgtt atatcaacat ctatggatct gagatatcct agaggacagg ctactgtcaa 152580
cgaaaaatct agtataacgt tactcgtatt aaggtacatg aggacactat ctatagtatc 152640
tataaaatgt aacgataatt tatccaatgg ttgtttaaag ctagtatcgt ttctgtagga 152700
catataaacg agagtttctg ttcctggtat catacacttt ctaacgccag ttctttcagt 152760
atcagatata tattcttcat acgtattaaa catcttgata acaggatctg gagatctagg 152820
ttttcctgtt agtatatgat atatatctac accagcatct attaatccgg ctatagtgga 152880
taaacccatt cctgaaaagg ctagtctagt agacataaac gacccggcta tagacatgac 152940
tcctcccatg ctttccaaac aagtacttac tgtttcagca acagcggtag ccacagaatt 153000
atcatcgtta tatcttagct gtaaatctat taacctatgt acgagcaatt gtgaagctaa 153060
gttaaaattt actgctttat ctaattgttt ggctatcttg tccatattag acccataatc 153120
ggtcatcgga taaccgctgc ctataatgta attactactt tctgtagtat aactggttcc 153180
gctaatactt cctgtactgt atccactgag tatgctatta acgctctcgc tatacatgcc 153240
gtaaacacta tgcgtatcac ctctaccgga tgtgtgtatg ctattatcgc tatatctacc 153300
gctagaatca taatacccgt ataaatcttg cgacgtgtct agactacctc ccgtacttaa 153360
actcggcgtc gatcgtctac gtgaagaatc actatggcga gtaagagata acaatccaca 153420
aacagcgcct attcctcgct tacaccggat agatggttta tgattttggg acgtatagat 153480
ttctgtatca agaactcgct ttacgtcgcg cgatgagtcc acggagcgaa ctcttctttg 153540
aaggacgtcc tgactctcat ccgaggtggt tggtttagaa atgatactcc ttacttctac 153600
gcctaatact gatttactcg gagtagccac gacagaaaca gtacgtcctc catattcttt 153660
ataagcgttt attccgtctt taaaacacga tattatgttt ttatgttgtt tgttatttaa 153720
ctcgatatga tttaaccgtc tctctaattt atccaaatct tcttcgaata tatggtaact 153780
atgtttatta tttgttatca cgctctttat ggattctatt tttgtaaaag ctatgtaata 153840
tagactcgct gaaacgatat tcctaccatc taatctaggc acaggaatat cgagtatatt 153900

-continued

```
taatacatct ttaggtaata tatttgatga aatttctggc atgtatgttc tgaacgttga 153960
ctttaccatg tcctttaacg tattcactaa ctcgccgtct ccactaatac ctttttgctt 154020
cttatacata cctatctgca gatgagtaat atcttctaat attacgctat ctatacctag 154080
atagttttta agaagagtcc taatatcctt cgaagaagag ttcgttccga ttacgtcctc 154140
tacactatca tcttctaaga tagatctttt acgtctgtgt ctataactac gatacgcgtt 154200
atttagttta cgtttatttt tatagtcgcc agaatgttct atgcactttt cgtattcttc 154260
gccgtcgtct aagtcgtaca tattatacat acaatttaaa tgctcgtggt taatcgacga 154320
atctttcagt tcttctttaa aggacatctg tggagtgagc gtatctcttt tagtttttgt 154380
tcttctcttt ttacctgtat aagcacgtaa agtttttatg gaattggatt ttatcttatc 154440
atttatatag atatagttgg tacaatctgt acctcccgta acttcacaag tataataaag 154500
actagccatt ttatcataag gtaatcctcc gcaagtcgct agagatgtct taaattcatc 154560
aggtacgctt accacatcta ccattaaact catctgacag tcgtgacaat tactagttag 154620
ttttgtgtct ataataactt gacctatacg tccaaaggtt ggtgcctttt ggcaattaga 154680
taatatatgt tttacgcatt cagcaaatac gttagacggc tcataaggag gactagacga 154740
tacaccgtta aaagtaacgg ttatagtact attattttta cttttattca tagtaaagtt 154800
tttaacaatc accgtatcgg ctgtaatgtt tttacattta tcattattgt aggtaacggc 154860
atacatgggt ggtacactac acgttagtac gttatcgtga gtttcacagt tagtatattc 154920
aatatcttct ttagataaag ataaagcagc ggctgatata cacgagaata gtttcaaacc 154980
ttcacgcaaa taattatgtc tatttcttgc tttattatga atatataatg atacgctata 155040
agtatagtta tatctataaa ctgcgtcaag acgatcttgg ttactacgtg tatcgcacat 155100
actaataaaa ctgcgcttga tttcttctct aatacttttc cagtcgaagc aattatgaag 155160
acgttctctt tctcgagttc taattatcga caagtatctc atagcggcga tagctttatg 155220
gtctgtcagt tctttgggtt ttatgttgtt aacgatgcga tgatatctag actcttttct 155280
taagcatgat tcattttcag agtcatctgc ataatatgcg aatgttaatg aatagaataa 155340
aatacttata ataattccct tcaaagaaga actctctccg cgtacgtcct tcgacatcct 155400
ttcatcctat ggtgtatata gtattataat aatatatagc tagtttgcct tttagttcat 155460
ttttaataca tggaaaacat gaagcataat tacctactgt aggtgatata tatcaaatcc 155520
tacttgtatg attagtgaga aaacatttag ttattgggta ttctagatat cacgaccttg 155580
aaaaatgcga taaatacgat aaagatattt tggagcttga gatttaccga gaacaacgta 155640
aagagaaaga agaatataaa aaagcaaagt aaagaattat cttatgtcat tagacgtata 155700
gaagagaaat acgataaaaa tactctagaa ctaaatctca agatagaaag aatataaaga 155760
cagtttaaaa caaacgtaat taagacaagt tctcctaata aattacacct tttggtgata 155820
tctcaaaata agaatgatcc taattctttt agaaccctaa gggttctaga ccacatgaat 155880
caggaaatca ataaatatat actagattat aatgtcttct ttagcaatta cgaacctaag 155940
gctgtttcct gttccaataa cttaaaggaa atattagtat ctcatggccg tttagagtaa 156000
gttataacga ttttatttta tgtgatttag agaattacgg agtaagaaaa ctatataatg 156060
atttactaaa tcttgactta gtacgtaagt aagcttagtt attataactg aattaattag 156120
aatttttacg atataaactt ctagtaacaa aggcggtagg attcataagg aaccaagtat 156180
tgatttcgca acgatagaat ttaccaatac tattcgcgta tatagcaatt aattaaactc 156240
gttaataata ttaattaaaa gtatgcatag ttaaattcgc atagatataa tataggaaag 156300
```

-continued

```
gttatgtaag ctatccggtt tttatgaaaa ataatgccat aatttaagta actagtaata 156360
acattatgga cttctcggat ctcgttaccc gagaaataga tgaccgtttt tgttatatca 156420
aatatgataa attcgattta attatgatga aggaaaacag atttatcaac gctacaaaat 156480
tgtgtaagtt gggagggaag gacttccatc gatggaaacg cctagatggt tctaaagaac 156540
ttatgatcaa agtaaacgaa atgaacgaaa tgtggaaaag tgcccccccc cccccagatc 156600
tggggggcat aattattgaa gtaaacggat ctaatcaata tactgagtac gatatagcgg 156660
gttcgtacgt tcatcaagat cttatacctc atatagcttc gtggatttct ccgttatttg 156720
ctttaaaagt atccaagatt ataagctgct acgtttctgg taaatacgaa ttcaagctta 156780
aggaaaaaga aaacaagata gaagaattac tagacttact tcataaattt aataataaat 156840
acgacaaaga tactttagaa cttaaagaac tttaccgcga gcaacgcaaa gaggctaaat 156900
ctttaaggaa aattaacgaa agaatagaag agaaatatga taaagatact cgagagctca 156960
aacaaggatt aaaggagtta aaagatgaga acaaagagct taaatttgag ttaaagaaaa 157020
tagaagaacg attaagggat aaagtaataa atccattctc tcctaataag catcaccggt 157080
tagtgatttt acaaaagaag atagataata attcttttaa gactttacga ttacaagccg 157140
aacgtttaaa tcaagaaatg aataagtata aaacgaatat tctgtatttt ttaatgcata 157200
cgaacctaac gcagtatcct gttttaatcg gttaaaggaa agactgttag atcaagaacg 157260
cattaaaatc aattataatg attttacttt gtgtgatata gatatttacg gagtatatga 157320
actgtatacc gatttacaga atttgtattt ggtacgtaag tatgtataat gttataaaaa 157380
taagctgatt atcgaataat aatatcgtta gtgaaaaaag aaaacagaat taccataata 157440
cgttacttta cggataaaaa aaatctacag tatgttaata acgctagaat aaatataacc 157500
tagtttacat attagtaatt cttgtatatc atagatatta ataaaagcat gcttgatttt 157560
tgatttaata cgtctctagt taagcgatta ttaagtccct ctgactttgg ctatcgctaa 157620
tcacccatat ctacggtagc tatttacttt attatattca taaagcatct atgtgtttag 157680
tatattaatg atacggttaa ccttgatttt tagtttattc tcaacacgat tgaagtaata 157740
ccaatataac tttaaactaa gaacagttat tacacctgtt agatacctcg ataaaaatct 157800
gttttagtgt acgggtggca agattttatg gatataatta tataatgata taatttatcc 157860
gagttcgtta catcgagtac atataattaa cttttaataa tgatgaaata acatatatat 157920
taataagtaa ttaataaaaa tcgtagaaga agttaaatat atgttagaaa ataataaagc 157980
aatgattaga catatatccc gaattaagtt aaatccgata tctcttaaaa tttaaaaata 158040
atggcgtaac ataaaataat gatatttttc aacaaatcta tttcaaatag gcacgattca 158100
ctatagaaat agtatctatt tataaggatt gtaacaccca ctatgttata tagactctat 158160
tttacatact ataacgatgg tcataagaaa caattaatgc taatagtatt cctgagtttt 158220
ataaatctgt tacagtcttt tgtattagtt aatacaccga gcgtttatat aattgtaccc 158280
agaaacagta gtataaacct aacttgtgat tttaccgatg ataagggata tggaatagat 158340
gctgtacgtg tgacatggac acggtcagat aagagaattg aggaggaaat agaaactact 158400
tggaacgaaa ctagtcaagt gggagaaact gtcttgcatg tacccagtgt gtcggaagaa 158460
gaagaaaaat ttcgttgtct ggtatacgta aatctaagcg ttgattataa aaacataaaa 158520
atacaaacta ttgatattac acagaaagtt aatttagaca gtgtattaga aataatcccc 158580
cctagtaaac aagtggatat atgcgacgga cccccattaa aacttaattg tagtttcaaa 158640
tttccaaact ggtgtttgaa acaccaagtt aaggtagagt ggtgggagta caataatgat 158700
```

-continued

```
acactagcat ggaaaaaaca tgtcgatggt attagctggg tcgcaactaa ggggggtggg 158760
actgggtggt taaatatctc aaatcctgga gtagaaacca cattcttgtg tgtagttaca 158820
tgtggttata ttggaaatag cggtgttaga gtatccgtgc cggtaccagt tcacaaggga 158880
caaaaaatac aaccaaggca tagccaatac ccggcagtaa aaggaatgag cgttatactg 158940
gtatgtaata tcgatgatag ttcgtacagt gaaagcggat ggtggtttaa cggaactaat 159000
atagataagg ggaataaata taccctctcc aataaacaaa aatcaatgga attagtaatt 159060
ggaaatgtag gtgacgaaga taaaggaaat tatacttgtt gggtagctaa agacgggtcg 159120
tgggatgctg cgtcagttaa tgtatacatt acagaggaag acattgatgg ttcaacgtaa 159180
aacaagatcg ctataaacta gtaaattcta ttatatcgtt atcttggatt tgcttgtacg 159240
gtaaaggtat tgttggtcta tggcatggga taatgctttt gtgctacaat gtgtatttta 159300
tattactaat gtgagtgatg ttatagcaag actttagttg ttactagaaa actaatgcgt 159360
ttgcttgcat acaaagtgta taaataactt ctaatagaac taacccgctt atacatgcat 159420
agctaagtca catatctctg tatactgtga aaacagactc tggggactag tgtttcctat 159480
ctcaaggaac ttaaatgaag agttgtagac aaacttagta atcttataga aagtttatga 159540
agatttataa gatacgtgaa ataatatacc atatcaagtt taaataacaa atgaaaaata 159600
aatgagtttg cgtataaaaa tcgataagct tcgtcaactt gtaacctatt tttcagaatt 159660
tagtgaagaa gtatctataa atatagatgt aaaaagcaac gttttatata tatttgccac 159720
tctaggtgga tctataaata tatggaccat tgtccctcta aattccaacg tttttataa 159780
cggtgtggaa aacaccgtgt tcaatctacc cgttttaaaa gtaaagaact gtctatgtag 159840
ttttcataat gatgcagttg tatcaataac agcggatcat gataataata ccgtcacgct 159900
atctagtcat tataccgtaa gcatagactg taacaacgaa caaatacccc atagtacagg 159960
aacgagtatt tctttaggta tagatcagaa gaagtcctat atctttaact ttcataaata 160020
tgaagaaaag tgctgcggaa gaacggtgtt tcatcttgat atgctacttg gatttattaa 160080
atgtattagc cagtatcaat acctcaatat atgttttgat gataaaaaat tgttgcttaa 160140
aacaccgggt actagggata cgtttgtaag aagttattct atgactgaat ggtctcctac 160200
tcttcagaat tattctttca aaatagcaat tttctcgttg aataagctaa gagggtttaa 160260
gaaaagagta ttagtattcg agtcaaagat agttatggat acggaaggga acatactagg 160320
attgctgttt agagatagaa taggtactta taaagtcaat gtttttatgg cgtttcagga 160380
ttaatcagta aaataaatgg ggggtggttt agttctacct actagggatc cgcccaaaga 160440
acaagatact tcggagacag ctactaatat tcctaaacta ttaaaatcta ttcctggtgt 160500
aaagttagga caacagataa gaataggtta caaacctggt cctgaaactg ccaaggcatt 160560
tccagaattt gatatcaaag aagtaagtaa tggattatac gaacttagca gaaaatcgta 160620
tctcggtgat actaaaacgt gttgtataaa tccttctcta agttactatt gggaagactc 160680
caaaaataaa atatttgacg agtacgctac aggtagaagt cttaaaacat gcgatccttt 160740
aacaaaaact atatctggtt ctacattatg tgataatata ttaacgagct tatgtctgga 160800
cgaaaaatct ggagtagata gaactatgtg taacgaatgg atgggatatg ctcttaatag 160860
acccgatctt tccattccga aatcaattaa cgatagatat acgaagctat gctccaaggg 160920
agccaataat atagtatgtg aagattggtt gcatcattta agaattatag gaggaaaaga 160980
aaatgatgaa gttatagaca acgtattaat gcaacaaacg cctgaattta aagaaaaata 161040
tatgaagtgt agttttccta gccataatac agtatttctg gcagatagag taatagaacc 161100
```

-continued

```
tagagaatgc tgggaccaag aatgtattac gtctaacgtc cattttcttc taagtaaaaa 161160
ctatcataat ttaacattat gtcacatcta tagatgtaac attagtatca ataacctttt 161220
gatagatggt aaatcatctg ttaaaatatc ttgtcatgac gagaatataa gtaataaaga 161280
taagccaaaa gcacgtaata aagcaaaatt tatagacgat atactagggt cctcgtttaa 161340
tataaatttt ggattctttt ttgtgatttt tattatgata gcgttaatat taattgtttt 161400
actttaaatg gggcagcgg ctagtatcca aactacagtt acaaccatta ataaaaaaat 161460
atctgaaaaa ctagaacaaa ctgcttccgc gtcagctact gctaattgtg atattaatat 161520
aggaaatata atttttaaaa agaataaagg atgcaatgtt ttagtaaaaa atatgtgttc 161580
tgcgaatgcg tctgcacaat tagacgctat agtatccgct gtgagagaag tatatgatca 161640
actaacagaa caacagaagg cttacgcacc tagccttctt accgcggcgc ttaacattca 161700
aactaacgtg agtacgataa cgcaagactt tgaaacctat ataaagcaaa aatgtaattc 161760
ggatgctgtt atcaataata tcattaacgt acagagttta gaagtggatg aatgctcggc 161820
gccgcctggg cagattatga cgtttgaatt cattaatact ggtacagcta ctggaaattg 161880
cgctatgaaa tcagtattgg acgttcttac aaaaagcagt gatagagtat caggtaatca 161940
atcaacgggt aacgatttct ctaaatatct atatataata ggaggcataa tatgtttttt 162000
gattttacta tattatgcta aaaagttatt ttttatgtcc accaatgata aagtaaaagt 162060
tctattggct aaaaaaccag acgtgcattg gacgacgtat atagatacat actttagatc 162120
gtcaccggtg ttggtttaga gaattaaatt caacttaaca taatatacat taaatgcata 162180
cctttttaac agctcgtcta caagcaatag aagatgtatc aaataggaat ttgagtatgt 162240
tggaactaat attgacgaga gctatagtta ctcattggat aatactagac ttggtactaa 162300
atctaatttt cgatagtcta ataacatcat tcgtcattat atattcttta tattcatttg 162360
tagccagaaa taataaggta ttattatttt tactgatgtc ttatgctata ttccgattta 162420
tcgtcatgta tttattgtat atagtatccg agtctataga ttgatattag ttgatcgtgt 162480
tattaattct ttcgctgtaa atacatcatt agtagaaaaa tcatctattt caaaaatatt 162540
tcccccatcg atagaataaa ttacacgaac tatgttattc agcgatacat cggataaagt 162600
tatacccata attaaagcat cgttatacat tacataaacc aatgatccgg gttctgtgag 162660
cctgtgtatt tggggtgtat taatatagtt cttttttatc ttaaatatat ccaaatactg 162720
cctagatatg ttttcaaagt gatttcttat aaaccattca aaaaaatagt ttgtagattt 162780
caagtttctt ctagtcatca agtcttgatg ggcagtcata taatctaaat agcacgattg 162840
tgataattca gacttataga gatgagtatt tgtagacaat agtattaaag attctgtatt 162900
aaacaataat actagatggt taatcgacat agatatagta ctcctaggta tagaaactaa 162960
atcgaattta aaatcatctg agaatatgtt gtttttataa agagaatata atatagcgac 163020
tatttgcagt attatgtctt tagttaggca tacagtattt atattcagat tagtacgttt 163080
catattcttg aaatactcga agtagatagt tcttccgtat gtatgatctt taacactata 163140
tactagtgga aatcctagag ctttaccggc ttttactaaa gcagataatg ttacccaata 163200
attagcttcg tctatacata cttgcttacg aatattaaaa tattctccta tataacaaga 163260
aatttcgtat ctctttcttt cttggtagta atcgcataat ctctgttctg taaaaggtat 163320
ttgcctatta gactctgtag ttgcattatt tttactcatt taatcttaaa aaaaacttat 163380
ctaaatgaac gatcttctat tagaaaatct gtttggagaa aaagcattat gcgcgcaagt 163440
aacgagagat caactgttag aaataatagc ggcgggagcg agatcaaagt ttcctaaatc 163500
```

-continued

```
tttactatct atgtacagag taactcctag agtaatgact cgctatcctc tgaaacttat 163560
aactaacgaa tctattaccg gagtggttat cactacagta tataatctta aaaagaattt 163620
gaatattcct cagaataata aacttacaac acaagatatc gaacgttatt atttagataa 163680
aagtgtagaa gttattaatc ttatggttgg taatacgtct ctcggagatt tggcatgtgg 163740
gagacccagg agaacaaaat cttcaaagaa gaaagatccc gttatattct tgggtatatc 163800
agcacctctt atattggtta tgaattctaa gaagtcgata aatacataca tacaagataa 163860
gaagtctgat cccagtagcg attatgttaa tataaatcca ggcatcggag tactagagaa 163920
ctatggaaat acgtatctac tagacatcca taatccgtca tcggtattaa ctatttctac 163980
tatatacggg ctcgataata atatggaact gaaaaaatta agtacagcca gtgaaataga 164040
tgcttaccaa gatgtaaaca taggtaaatc agtagatcta aaaaagttta atgaaatatt 164100
taatacgatg aaaaaacatt tgtctttgtc aaattttagt atctaaatgg atagaaatat 164160
caattttagt cctgtattta tagaacctag gtttaaacac gagtttctat tatctcctca 164220
aaggtatttt tatatattag tttttgaagt aatagtagct ttgattatat tgaatttttt 164280
ctttaaggaa gaaatattat atacattttt tccgttagct aagccttcta aaaattcaat 164340
aaatagtctg ctggatagaa ctatgttaaa atgtgaagaa gatggatctt tgatgatttc 164400
gagaccttcc ggtatctatt cggccttgag tttagatggt tcaccggtaa ggatttccga 164460
ttgtagtttg cttttatcgt caataaatgg cgcatcctca tcaacatctc cttactctat 164520
ttttaacaga cgataacgga ttttattctt atctatccga aaaaagtgat gatgaagctc 164580
ttgaagacat aaatactatt aagaaatata tggactttat tctaagcgtt cttatacgtt 164640
ctaaagagaa actagaaaat ataggatgtt cttacgagcc tatgagtgaa tcgtttaagg 164700
ctcttattaa agtaaaggat gatggtactt tagtaaaagc atttaccaag ccattgttaa 164760
atcctcattc cgaaaagata gttttagata gaggttatac ttcggatttt gctataagcg 164820
taataagact atctagtaaa agcagttata tacttcccgc aaatacaaaa tacataaatc 164880
caaacgagaa tatgtatata aacaacctaa tatcattgtt aaaaaggaat tgaaagaaaa 164940
tattttatat cgtaataaat taaatatgca tgaaggacat caggagtctt ttaaagaact 165000
tgaaatgaca aaaccttata tgttcttcaa tgaactagta ggtgaagaag actataacaa 165060
agagttagaa aattctaata ctaagtttca aggacagggc cagcttaagc tgttattagg 165120
agaactttat ttcttaaata cattaatcaa gaataaaacg ttatgttcag atacagttat 165180
cgtgtatata gggtcagcac caggaagcca tataaatttt ttatatcatt atatggatga 165240
tcttaaaata gatttaaaat ggatattaat agatggtaga gatcatgatc gatctctaga 165300
aagtcttaaa aatgtgtcta taatacatag gtttgtagat gaacaatact tgtttaagct 165360
acgtaatatg attaggaaaa accataaaat tgtactgata tcagatatta gatcgctaag 165420
aggaaaagaa cctactagcg aggacctatt acacgattac gcgttgcaga atcaaatggt 165480
aagcattctt aaaccaatag catcgagcct gaaatggaga tgtccgtttc cggatcagtg 165540
gataagagac ttttacattc cttgtggaga tgagtttctg cagccgttcg cgcctccttt 165600
ttcagcggaa atgagattgc taagttgtta ctcacgggca cccattcgtc taatacgtat 165660
agataagaat gcagctatag aatatgaaaa aaaaatgttt tatttaaata ccaaaatcag 165720
acctaaaata gttcttgatt ttgattatcc aaaccaaaaa tacgattact tttatatgtt 165780
ttatatcctt aaagacatcg tgttgcctac ttataaagag ttttcaacat ataaacaaaa 165840
ggttatattt ctacaggagg caatctttaa cgcgttaaat ataaaaccat gatgaaccaa 165900
```

-continued

```
tataatgtca catatttatc aaaaatattg tgtctaaaaa cagaaatact atacaagcct 165960
ttttccataa ttaataggag tatagttaat cagtataata tagatgttaa gtacgacgat 166020
attacaagta tcgtaaagat tagacataaa acagaaaata ctattttagt attccaaata 166080
tttaacgaat ctaatgtaaa atattctcct atagaatatg attatggtga tcccatcatt 166140
ataacgtcta acttacaaca cggtcataat agaatcccta ttaacatgtt gtatatagat 166200
gtcgtagaat cagacatgtt tccaacgttt tccaggttag acagtgaaac aattaaaatt 166260
ataactagta tattacaatc tgataataaa aaggaacaat ctattaagct acctaaagtt 166320
tcagaaaacg aactatctgt aaaaatatta tatcataaag actatccgct gaaatacgtt 166380
agatattata aaaacaatat ggtaactggt atagaagtca tagatagatc ggtggcgatt 166440
accagttaat aagaacgatt aacgctaata tcgctaaacc taatattaaa tattttggat 166500
cgataatagg aaggtgtatc tcctgttcaa gaggtttaac tgaataaccc gcgtatatag 166560
catgactaga taaacaatca ttatttactt ttaaaatacc atctaataag ttgatctcgc 166620
ccaaagatac gctacaatct ataagattac atcttttcat gttatccctt aaagcggtag 166680
gtattttagc ggttttcctt ttacatggtt cataccaaca ataataaggc aataataggt 166740
cttctccaat tttttctata gtaggttctg gatgaataca tagacagtct ctatctttag 166800
ggttagattc acaatactta aatattgctt catcgtttat aacgttgtcc atattaaaat 166860
ttaaaatcta aaaataatag ttataatcaa aaatgtctgt gatatctaaa gtaagttata 166920
gtttatattc tcaaaacgaa ataaatgcta cagatattaa tatcaattat gttaaggacg 166980
acgacgaagt cggcaccgtc aaggacagta ggctaggcgc aaccgatgga gtattatgta 167040
gaacgtgcaa ccgtactgaa ttagaatgtt tcggtcactg gggaaagtt aggatatacg 167100
aaaatattat tattaaacca gaatatataa gcgaagtaat acgcattcta ggccatattt 167160
gtttaacgtg cggtcttctc agatctcgag aaccttatac tgttaatatt tcttctctta 167220
ctagcggtga attaaaaaaa ctaaaggaca aaatatcgtc caaaaagaaa tcttgttgga 167280
atagtcgttg tatgcaacct taccaaaaag taaacttctc aaaaaagaaa gtatgcttgg 167340
ttaataaaac agatgaattc tgtgtgccta atgctttagt atacgaaaaa ataacatcta 167400
ttcaccataa attttggccg gtattagata ttcatcaaga tccagctact ttattttata 167460
gaggctattt ttcgatacct ccattattga ttagacccgt aatcagcttt tggatagata 167520
acgtacctaa agataccaac gaacttacct accttctagg agttattgtt aaacattgta 167580
acgcaaatgc ggatgaacca actattcaaa aagctattat cgaatatgat aatattaagt 167640
taatatctac taatagtact actaataatc tttcttatat tacttctggt aaaactaata 167700
tgttgagaag tttcgtagtt gctaggagaa aagatcaaac agctagatcc gtcttaggac 167760
ccgattcttc attagatatt acagaagtag gtatacctga ctacgtaaga aatactctaa 167820
cagaaaaaat atttataaac gcatttacaa tagataaagt caaagatatg tttcagcgcg 167880
gtgagattaa gtattacttt aacaaacaat tacaccaatt gacgaaaata aaacaaaata 167940
aatttattaa gaataagata catcttcttc ccggagattg ggtagaaact aacattcaag 168000
aatttactaa tatcattttc ggtagacaac cttctttgca taggtataac gttatatcgt 168060
cttctgtaag aaaaacagaa gaagatacca ttaaaatacc accaggtatc gctaattcac 168120
aaaatgcgga ttttgatgga gatgaagaat ggactatagt cgaacaaaat ccaaaaagcg 168180
tgatagaaca aagtattcta atgtatccaa ctactctatt aaaacacgat gtacacggaa 168240
tgcccgtata cggttctata caagacgaga tcttagctgc ttacaatcta tttcgtgaat 168300
```

-continued acgatctaac ccaagacgaa gtacttaata tcttaggaaa gtacggattg gaattcctaa 168360
ccgattatga aaggaaagat aaatataccg gtaaagatat ttttaaattt ttgatcaacg 168420
aaccagaaat taattatccc ggtataatat gtaatggaga aattatagcc gaaaacatag 168480
atagtaattt tatagtatcg atgaaacaca tgtccatatc cggtcttata acggattata 168540
aatctagcgt agaaggtata aaatttataa acaaagcatc ctatgtgttt aaaagatatt 168600
taaagatata tggatttagt atcactttca gaaatttatg cccggatttt gagtttacaa 168660
aaaaactcag agaacaaaat ataaaaaaga ttaacgatat taaacattct tatgttaagt 168720
atttgtacga cgttgctaac ggtgatatta taccattatc tagatccgat gagatggatg 168780
ctgtcgattc tattctttcc ggccttacca actttaatat tcaggagatt gagaaataca 168840
tgaaagaagt tatatcaaag gacccagata atagcttgat gaaaatgtct tgcgcgggat 168900
ataaggtaaa tccaacagaa ctcatgtata tcttaggtac atacggacaa caacgtatag 168960
atggagaacc tattgataca aaaatatatg gaagagtact accctatttc ttacccgatt 169020
ctaaggaccc tgaaggaaag ggttacatac tcaattctct catacaagga ttgacgggtt 169080
cccaatatta ttatgccatg ttaatagcta gatctcaatc tactgatata gtttgtgaga 169140
catcaaggac gggtactcta gctagaaaga ttatcaaaaa gatggaagat atggtggtgg 169200
acagttacgg acagattgtg tacggtaata ctctagtcaa atacgccgct aattacacaa 169260
agatacaagg atctgtttgt aaatctgtag agttaatata tcccgatgaa tctttaacct 169320
ggtttctaga aataagcgct ttgtgggata agctaaaaaa tggctttata tataatcaag 169380
gtcagaaaat agctaaatat attttagctc cttttaactt caaagtattt atgaagttgg 169440
acgaaactaa tcccatgaag tctaaagact tatatgacaa gatacaacta gtaattaaag 169500
atgtaagaga aaattatttc ttcgatgtca ctagtataga cttcatagaa tacgtatttc 169560
taactcattt aaacccgtct agagtaaaag tttctgaaga tacagcaaat ttaattttcg 169620
aaaaactgta tgaaaaatta aattacacgt taggaggagg aactcccatc ggcattatat 169680
ctgcacaagt gctaagtgaa aagttcactc aacaggcttt atctagtttt cataccactg 169740
agaaaagcgg tggtataaaa cgcaaactcg gatttaacga attcaaccag ttaacaaatc 169800
ttagcaaaaa caaaacagag attatcactc tcatatctga tgatatcaca aaactacaaa 169860
ctattaagat gaattttgag tttgtatatt taggagaact atttccagag attacaatag 169920
aagaagacaa aaactattac cgtatagata taaatgttaa tagactttac ataaaacgta 169980
atcaactaac agaactgatc gtcgaataca tgttagaaaa gtttgtttcc tatagtgtgt 170040
tggttaaaaa ctggggaatg gaaacgaaca taattaacga acatatcatt agatttagct 170100
tattcattgt atttacagag ccggtaaatc tcaataaaaa taaatttatg atgatgttac 170160
caggagcggc aaataaaggc aaaattagta aatacaagat acctatatct gaatatcagt 170220
catataccga ttataacaaa acagtaaagt tatataggct tactgtagaa ttaatgggcc 170280
ttaaagagct tggaaccttt gatctagtta atgtcaatgt tatacctggt gtatggaata 170340
cttacgagat attcggtata gaatctgcaa agagttatct ttgtgaagct ctgctcagta 170400
cttatggaga agggttggat tacttatatc aaccgtgtga tttactagct agcttgatat 170460
gtttaaacta tgaaccggaa tctataaaca agtttaaatt tggtcctgta agtgctttaa 170520
agcgcgctac atttggcgat aacaaagcca tcattaacgc agcattatac aagaaaacag 170580
aacccgtaaa tgataacagt agttgccact tttttagtaa agtaccgaaa ataggtacag 170640
gatattacaa atatttcata gatttggaaa agtttcttcg cattaaaaag actatctcag 170700

-continued

```
agaaacttat agataaaaag ttagtagata taggtgataa tattactgat ttttagtaca 170760
tcagtcatat atacttatct attatttggt tcaagaatga tttattttct ataaaagctc 170820
cccttatata ttttagttca tgatatatat acaaaaagta tattacaaat ggtatatttt 170880
tgtctctaat ctccataaga taacccataa tcatagccga acttctgtta atacctgcca 170940
tacagtgtac caatacggga atctttaaag attcacattt tttaagtaca tatgtaaccg 171000
cgtcgatatg ttttgatata ctaacagtgt cattgtcttc taatggaaag tgtaataccg 171060
ttatatctgt tctcttgagt ttatatttta acatcgatac gtttactata tatttgaaga 171120
atgttttatt aggtaattcg attacatttc tataatttcc tagatataca taatcggtaa 171180
ttttagttat atctctaggc gtaaatttta cacatgtgtt agtagattta gtaataatat 171240
gcttatatag ttgtttttca tccatttata taggttacaa atgggaaacg aagtagagtt 171300
atcggttcat ggaatagaac ttaactatgc tagaaataat attactaaaa atatacgata 171360
tgctagagta tctactttaa tatttttctt tttactttta gtaattagcg ttgttttatt 171420
ctttttccag atatccaata atagtatatt ctcaacactg agtaaatata ctcgtataaa 171480
aaacaattta agctcctgga aaccactagt aatacaaaaa tctaaaataa atagcgagtt 171540
aggaaagcac gcggctctta acagacagga tttaatgaga tttaaatgtg ttgactttgg 171600
tagttacttt ctacctgtaa gattgaataa taataacttc ttaccggaag cggttagaag 171660
aggagatgga gatggatgga tgataaaaaa ggcggggaag tacgatcctg ctgctgagca 171720
gtattgtgat tttatactgg acagatataa agatacaatc acatgcggtg accaaatgtt 171780
taatagccta gggtatagcg gttatttcga atctgggcac tggtgtcaga cctttctaga 171840
tttagttaaa taactatgat gttaataagc attctaactt caataacagt tttatagtaa 171900
acatcactca agattactta cttctatttt aatgtataga ttaaaaggtt atttcgtatg 171960
attatgttat attaaacaat taatttagca ctattatagt tctgaatgta ttagatagta 172020
tctgtttaaa agattacata gaatacgcta aaaatactcc agatagtaac cataatagct 172080
tgttattgat atcgaatata gcgagtccta tgataataac tattgcgatt aaaaacatca 172140
tagtgatatc gtatttccca aatacggaaa atagaggata gtacatgcga tgataaaatg 172200
acggccagtt atccataatc cagccatcta tacgagattt aatagacaat ctatttttct 172260
tgttcttcat gaattcgttt gctagtttat agtcgtgata aacgtatcta tcgttatcca 172320
cgacgtatct agttataccc agagtattct caattctaag aatttctaaa gatatatcaa 172380
agctcggttt attattcgta aaatagctat ataatttcct taccgcttcc tgtctaataa 172440
tataagcaga taacgataca tcaaaactac ctttaaaagc ttctaaatct ggaagtagca 172500
taaggtgttg agagtttcta tcttttagca atttggtatg tgttactaat tgcagtatat 172560
ctacgttgtt atcgttaagt accttggtta tgttatctaa atttgtaata aaaccttccc 172620
cggttattgt attatcgtct tccataatga caacataatt cggtaatttt tctgcattat 172680
ccataatata cctccataga cttatgtggt ccgcgatgaa gattttagta tcttccgtac 172740
atgttagtct acagacgtca gaataataac catctctaac agaaaccatt tcatcgtatt 172800
ctatgtcacc taccttatcg tccgcatttg gttcttgttt gctttttgga agtggtttag 172860
gagacggcgg gtctctgtaa tcatcgtatc catttttaat acccttttta taactccatt 172920
cggatacctc caaattctta aagggtacta cggtagatga aggtctacct atcgtagtta 172980
ttacaaatat aatttgtttc ttgtcgcccg gcgccattta attgttaaaa ttaattatgt 173040
atagttcctt gatctttttg ctattttctt ctatccattc tgttacattg acgtagctag 173100
```

-continued

```
ccaaaaacat gtaaaaacta aattcaagtt cttgtctatt caaactatcg ctaaaatacg 173160
taaacacgtt actattaggt aataattcct gcctaagcat attatatccg gtgattttat 173220
ggttagtatg ttcttgacta atcaagtcat aatgaaatgg aaatggatca ccaaatttga 173280
aaacataaaa atctacatta gatgaataat acttgagaac attatataca aaaagactag 173340
tcaatggaat aattattttt ttcttttcca cttctaattt gatatgagtt gtaaaaaatg 173400
aggcgttgta cgcgtttgta tcattcaccc ttataagaac tttagtagtt ttcttcatta 173460
tatcttcaaa aatttcttta tcttcatcag tgccttcttt tattcttaca ggatgtttta 173520
tcgttatgat ttctgtattc tcggctacta ccttttcgta agtaatgaac aacttagtac 173580
ttgttataca actaggaaaa aaagctattt catctgttct ctgtatctgc ctatagatac 173640
taatatcata gttaggtgtt tttctatctt tcttaatggc tattaaacgt tccatttcga 173700
gttttattct attatagtgg actataagtt cttcggttgc tattttcatg tatgtttccg 173760
taaatagttc tatagtattg aactgcttgg agtcaactgt cctggttttc ttcagaaaat 173820
caaatacgat aactgatata atatgattta gatccgaata gttagtttct tccttttttgt 173880
tagtcatata atacataata aagtccgcac cactgttaag tactataact agggctacta 173940
taaaatggat attcaatatc ttagcagaat agaataactc catagaagac atctgaatgt 174000
caaaaagatt agcggaaagc cttaggaaga atataccttt cttaatttct gtagcaaact 174060
gtttttcgta ttcgtgtctt ttgctgttaa tgtctattag gaaattcaga ataagacgat 174120
ttatattata cttcatattc cacatttgag acttcataat agtatcgaac gacataatcg 174180
tattaaatat aaacctttgg ctatgtgaga aataattata gggttccgac ataaatatag 174240
atttattata agtaacgtta ataagagata ttttcgtgac atcggtagca tccaagttta 174300
gttcctgtat gtttattccg catagattac agtacgctag tccatcttca taatatatat 174360
atttagctat aaacttatta atgttctcgt agtattctag actaactttt ttagcatcga 174420
taatagctat ctcatgttca cagggtacaa aatctacgct acctccttct tcccagaatt 174480
tcaattcgga tacgtatatg tactctatag gattcttcct aggttcgaag gtgacttgtt 174540
ttatattaat taactccata aacaaatcac acaaaccata gttagacaaa aagaagtaac 174600
tatataaacg aggattttta aacttaggta taataacctt accccattcg taaaagtact 174660
tattgtcatt atcaaaatta ttcctgtagg ctttattagt ttcttccaag tatacgtatt 174720
ttacatcgag gtagtcttta ataactatag gtatagttag ttcgtctata acgtagttaa 174780
aaatgtacct aacgttatat tttcgtttag atatttttat acctatgttt ctacacaaat 174840
atgcaaagtc taaatacttt ttagaaaaac gtaactgatc taaattcttt gatacgtacg 174900
ataataactc cttcatgtta aaagggattt cgtttactac ctgttcatat ttatcttctt 174960
tgtatgataa actcgtagta aaacttctgt aattgatatt aaagtcgtta ttaccttcgt 175020
cattcacgag aatgttgaca tgtttttgcc ttattatgaa atctaaagta gaaaagaagg 175080
tatcatacat attataattc atatcacctg tcatcctatc acctaaatcg atactagaat 175140
tgtcatcgtg gatgttcttt tcaaaattat atcctatata agaaaatata gctaccaaag 175200
atttatcatc tatatctatg ttttgttcta tagtaatgta aagtagtttt atatcttcat 175260
ccgtaatcat attaacgtta tatagattac agataaataa ttctttgttt ttttctataa 175320
aatcttgata agatttttcc tttaccgtat catcttttat atacgccttt atcttaggca 175380
ctaactctaa taatacagat tccttgttct ccatttaatg tatagaacta atttataata 175440
aacatagtaa atatgggtaa cttcttaata gccataatta aaattgaaaa aaaaatatca 175500
```

-continued

```
ttataaaacg taaacgaaca aaaaacatta atttaaattt gccaataaca aaccaatatg 175560
tcttggacaa attctgaaga taaatcgttt aaaacaatag atgagcttaa agccaaggta 175620
aaggcggata gcagtcatca tgtttccaac tctgcttctg atacagaacc ggaaatgatt 175680
ccggaagtag taaaaaagcc taccaaaaaa actgctaaaa aaacaaaaaa acaagaactt 175740
gcatcttgta attctagtaa tccaaataca gatccattta ctaaggatct agatctttac 175800
gatcttgatg ttcttagcga tggaaagtgt gcggaagaaa acaaaccgtc gtctatagat 175860
cttgtagaga ctagattggt aataaagact atctctaaat caataaaaga tatagcacat 175920
agaatagcgg cattgaggtc agtaatacat gatttggacc ttactgatat cccgaagaat 175980
acgggtcaag ctatcaagga agtagacaaa ttaaaagaag cgttatgtaa tctaggtgtc 176040
agcgtaccac cacctaaaca acaaaggaaa aaagctaagt aaatggtaaa gaaagttttt 176100
tttcattata aagatgataa actatattac gatgccgcat ataaaaatct agttcctgct 176160
agtaataaaa catacgaaat aattaaagcg tatagagttc ctcctcattt gaaagaagta 176220
atcgtatacg agcaatctct agaagaggcg tctaacagct taatatttat cggagtagat 176280
tctaaaggac gaaagcaata tttttatggc aaaaatcatg taatattaag aaataagaat 176340
cgagataaag ttttcattaa agtacataaa ataataaaaa aaattaataa ttatatagac 176400
aagaatatat gttccgaatc aaatactcta gaatttcaac tagcagtatt catgttaatg 176460
gaaactagct tttatatacg gataggaaaa gtaaaatact ataaacaaaa cgatactgtt 176520
gggttattga cgctacaaaa taagcacctg actgttacgg acgagaatat tactataaaa 176580
ttcacaggta aagataaagt tgttcacgcg tttaacgtca agaaagaaaa cagattatat 176640
gagcctttat taagaataca tgacttttcg aaaccagatt ccgtattatt ttctttatta 176700
tcagaaaaga aagtttattc atttattaag caatattcaa taaaaataaa agacttgcgt 176760
acttacggtg taaatatcac atttttatat aatatatgga ataacgtaat ttctatgttg 176820
aaattaccta gtatcaaaaa actaatagta ttatctataa aacaaactgc ggatactata 176880
ggccacaccc ctaatatttc taagcaagcg tatatggcta ttactatact agaactaatg 176940
aaagaagaaa atataacaga aactattaaa caaaagacat tcgacgagtt tcttaatttt 177000
gtgattaatt atgtaaataa aaaaaagata taattaaatg gaccataaat ctagaatgct 177060
tttagatacc atatttaaag atatgctaaa tacgaaagac gtatatgcat taataaaata 177120
tatttttaaa aaagatcctg tagaaactat attttctaaa aaagacgatg atatatttat 177180
agattttgtc tataacgata atgttctagc atctgattac ctgggtatga aaactactaa 177240
agtagaggat tgttgcagtt gtagaaaagt agtagctgta gaatatatga atacatctat 177300
tatagataat gacttagaag gatatataaa gcaatccgat aaactaaaaa gatttattaa 177360
actatataat aaaaataatg ctattaaaaa agcgagaaac ataaaatcac gccagaaaat 177420
gctaaaagat gctggtatag atgatatagg atatgaattt ataaaagacg ccatcggtct 177480
aataagtcgt aagtaaattt catagccgtg tatgggtcca tacgctttat atctttatgt 177540
ttattcaatt cattagatga tgttaaatcg taccaagcac tataattagt ctttttctca 177600
gataactctt cttgtaattt cactagtgta ttttgagcgg ttattttatc tttgtataat 177660
ccacttagta tcatattatc tttatctaac cgaacagatg ttgctttctt agttaacata 177720
aatagaaaaa aaacgataac tataatataa ataaccaata taactatcat ttaataaatg 177780
gataaatata tatcaaaaac cccacttagc tgttattttg aagaactagt agatacattt 177840
atttctgtag ttaacagtat aaacaaagta gatgaatcta agcatcatga agtcgaactt 177900
```

-continued atcttattta aaccacctat tattaccctc actaacctat ataacatggc aactaccaca 177960
gaatcttata tagagtttac catgttaccc gtagataaac caaacactaa gtttagaaac 178020
agaataccct tatctaagat tcatggacta gatgtaaaaa ataatcaact agtagaaagt 178080
ttggatggtt ttatttggga agaaaaatct cttttgttaa aaaaagacat atcggataat 178140
tcttccgcga ttataaaata ttctattgaa gaaaaaactt tattcgtgga ttacaaaaga 178200
cgtaacgcgt ctattaaact agaacttgta agtgtagtac gagctaaact tagaaacata 178260
gttatagatt ttaaaatgaa atactttcta ggttcaggcg cacaatcagc aaattctagt 178320
tctctattat gtgctttaaa ccatcctaaa aataaaccca gtctgtatat agagttcgag 178380
atcatgatgc aagacaaaaa catatctaaa aagaagctac tcgaagaact aaatatgtca 178440
gctagtgctt tatttctaag tcatccaaag tacattagac tgtgtcctag tataaaccct 178500
atacttagaa ctcacttact caaaaaacag gatattatta atataaatac agacgactta 178560
tatattacaa gcaagacgga tggtatattt tcacacgtct atatagaaaa gaagtctata 178620
ttctgctatt ttagccatct agggtatata aaagagtata cagcgtctag ggaaatagaa 178680
gaaactatat atctatatgc tgaaatgcgt aaagaagaat ctatattata tcttacagtt 178740
attaaagtat taaaaccgtg tatggaagat cggttgtcag aactagcatt cgtaaaaaat 178800
caccttaccg gtatccatga tagattggta tttgttacaa aatgttacga tggacctttt 178860
gaatctagtt ctgatcttgt ggtgtctata gaagaaatgt taaaaacaga acaagaaggt 178920
attatacttt tttactccaa gggagaagat tctacaacag attataaagt taagaaagat 178980
aatactatag atcagtgcgt taatgttata tatagatata tgtctagtga acccatagta 179040
tttaacgata aaggttcgtt cttggaatat aaaagataca gtaatgataa gggttttcct 179100
aaagaattct ctacagggaa attagatctc aacggaagcg ttgaatatat aaataacata 179160
tattgtatag aaattaaaca ccttaatcca tgtaccggta ttactaatct tgtattacct 179220
ataaaattca tagcagaatt ctctcataac gatgaattaa tacaacccag aatagataaa 179280
actatgaaat atctatatga aagcggatac tacgggaatc aactatccgt tattatggat 179340
catttgaacg atcaaaaact gagaatagga gatgtttttg aggaagaaaa attagcagat 179400
atagcagcac acatgaaatt aaaagattct atgcgtctaa atccggacgg taactacttc 179460
ctatcgaaca gagtgagagg agcgttaggt attttatcta attttgttaa gacgttactt 179520
atatcgttat attgttcgaa aacataccta gataatcatt ccaagagaaa agttctagcc 179580
atagactttg gtaacggagc tgacttagaa aaatactttt atggtgagat agcattgatg 179640
gtagctacag atccagacga taatgctatc gaaacgggta aaaaaaggta taacgaacgt 179700
aacgcaggtg ataaatccaa gtactataag tttaattata taaaagaaac tattcgatct 179760
gaaacttacg tttctagtat cagacaagtg ttatattttg aaaagttcag tttggtagat 179820
tggcagttcg cgatacatta ttcgtttcat cccaaacatt atagtaccat catgactaac 179880
ctacaggaat taacagaatc aggatgtaaa gtccttatta ctactatgga tggggattat 179940
ctggatactc ttaaggaaaa aaagaaattt attattcgca aattattacc cgaaaccgaa 180000
aactatttat cgatagaaaa aatagacgat gataaagtgc ttgtgtataa tccttcgagt 180060
atgtctaaac ccatggcgga atacatagtt agacgcgaca cgctgatacg tgtattcagg 180120
gagtacaagt ttaagttaat agattcatgt aattttaaaa ctatcattga tagaaacata 180180
agttttatta acggggtttc gaggttggaa tctaggggat cgacaaaaaa tttcttcgag 180240
ttaaacagga aagctttaga agaatgcaac gacactgatg ttcttgaatt attgagtcat 180300

-continued

```
tatatggtat atgtgttttc taaagaggta tagtgtatta cattgttttt atatatagtt 180360
tctagttatt taaattatat cagggttaaa tatgggaccc gaattatatc ataccgatgc 180420
tatgacattt tcattaagcg ataagtacga tatatatggc atattcagaa cgtttcatat 180480
taacactgac ggtaagtatt ctaaacccgg atcattatac gattattaca taacttataa 180540
tactgacgga gtagaaagtt attttctctt cgaacgtgct acagaagaac aattatataa 180600
aatattaaaa tcatataact atttacttat aaccaaggta actgtttatc ctaatgataa 180660
ttcctacgat agaaggtata aacatagaag agatcgtagg tactaaggac gtgtataata 180720
ataacaacat cctaatactt tatttgtttt aaagctatta aagagttcta acaatatcat 180780
ttttggatgt ttatttgcgg acggtatacg tagggtacta ctttcctttc taataggaaa 180840
ttcttcatta aatgattcta atatattttg actgggaaat ataacaggaa ggtaatcatg 180900
tctatctttg tatacgtttt ttatttgttg atatataatt ccattatcaa atctggctac 180960
tttatcaaag ttatatattt caaacagttt accattatca caaaacgata caattatata 181020
atctgatttt aatatattat ttatatcttg ttggaacctg atgactttat taaacaacgt 181080
atgtatgttt attaatccta tactcttcaa ttctagttcc attttgattg aacgttatat 181140
ttatagctag ctacaggttt acctatttta tcacgattga tatctgatta tattgtgtac 181200
aagtaaaata attactacct ttgtaactat cgagtataat ctatgccttg tagatggtgt 181260
gacgaattat aaaaaaatct caatatgttg tattactata ttagaaaatt agaatattat 181320
tgtgaaaatt ggtgatatac tttttatatt aatgaaaaat aataattaaa agtttggaca 181380
atataaaaaa tgaatatttg tattaacccc gagagtacta attgcgttca ctcgactaat 181440
gatgttaaag cccggactcc cataaaaaat aaatatttac ctgattacgc gttaataaga 181500
tttatgatta aaaagtttaa taaactattc atcgaaaaag gtttacctat aacagctgta 181560
tatagttgga ccgtgtttcg tgaagctgct atatgtagag gtcaatacag aagttggata 181620
atgtcattta tacatactat ttctggtaat aatattgcta attttagatt agatagagct 181680
tactcagatt ccagatataa ttctataata atagactcca catcaggaaa gattatatgt 181740
gaaggaattg gcatcatgga gaagttgaga ttacacgggg tagattttat taacgacaag 181800
ttattcaccg aagaagaaat aataacacat gtatacggag ttcaaccgct tcaggatata 181860
tgtattagga tgatacgtaa tacggtaagt agagacgatt atgataagct agaacttcca 181920
agatcattac taaaagaaat taagaaataa ggcagtaaat atttatgtca aaattgaagt 181980
ataatagcaa ataataagct ataaatgtag gtgattatgt cacatcttca tcttaataat 182040
ggagatacag agtatagagt tattgaagat aatggatttt ccattatatt gcttaaacat 182100
acagaatata taaatgttac aaaattatgc aagatacata acaaagagtt ctatagatgg 182160
aaaagactga tctctgcggg acgtattatc gaaactgttt cacgagatat atcgaatcaa 182220
ggttttgaat ctcctctagt atacgtaaat aggaaaggca ataaagaatt ttatggattt 182280
tatgcccatc ctcaattagc gttgtatata gctaaatgga tatctgaaga tatatttaac 182340
aagattaagc atttaataaa ctcctatacg atatcagata aaaccgtagt aataaaagat 182400
ttttcatatt gtgacgaact atgtcccgac gctataatag gaaagtgttg taaaaccaaa 182460
tcatcatgcg agtacgtcca tggagatata tgcgatatat gtgggtttga ggctttacat 182520
ccaaccgata ttgataaaag attgactcac gaaaaggtat gtatgcaact actatgcaaa 182580
gaagatataa aatacgataa atgcggtatt tgtttggatg ctataaaagg aaataagaaa 182640
ccttatggta ttttatcaga ctgtaatcat atgttttgta ttaactgtat taaaacatgg 182700
```

-continued

```
atgactacta ttaattctaa gaagcaatgc cctgaatgca gagtaccttc taagtatatc 182760
atacaaagtc ctatctggac agtggataag gttagtaaga atcagttaag tgtttcgtac 182820
aagactgtat atataaaatc atgttaacgt tttgtagaag ttgaaaaaat aatatactga 182880
tacaaaatgg cttttcaaga actttgttgt agtaatttgt taaaattcga gaactgttca 182940
ctactcgaaa cgcataaaaa gatatctata gaaggaaata tttctgccgg aaagtctacg 183000
ttgataaata tattatctga taatgggtat aacgttgttc aagaaccttt agaacaatgg 183060
agaggtaata atttactgga caaattatac aaagatccat ctagatgggc atatactttc 183120
caatctcacg ctttttggac tcgaactaaa acttatatag atgctctaaa caaaaataaa 183180
ggtaatataa ttttagaaag atctgtattt agtgataagt atatatttgc gacagcgtta 183240
cacgatatag gatatataga tgatacagaa tggaatattt ataacgaata cagtaagtgg 183300
atgaccgaat ttatggatat aaagatagat ggaattatat atttaaagac atcaccggat 183360
atatgttata aacgaatgtt aaatagagcc cgtcatgaag aaaataccgt taaaatagat 183420
tatttgaatc tgctccatga taagcacgaa aagtggttgt ccgagaataa cgagcacgaa 183480
tttaaagttc cggtattaga aataaacgga gacggcgact tcatcgacga tagtaacaga 183540
caatcaagca tacttagtaa catttatgat tttatatcgg aattatacat ataagtaaaa 183600
cttttatagg ttatagaatt tgtcttctat ttccttattc gttaattctc ttataggcat 183660
tatgcttatc ttatataagt cacataatga tgcattattt acaagttcag catattctga 183720
ttccgtagta taataagtat attcatattt tttattctta gaatataatc ctatttggaa 183780
atgttgatct tgatttctat atttatcgtc agtgattaca tgatagcatt cgaaaattct 183840
aggtatatcg cacgtattac ttatttgtag tgaaataaga tctcctactg caaattcttt 183900
ccaaaaaaat tgctcgtcgt aagatacggt atttacatcg ttatcgtgaa cagttaagat 183960
taatgattta caattgccat tctccataat tttggtttta atatatttat aacacaattt 184020
ataataataa atcttataga ttaaatagag gtttaataaa cgcgtagtta tatatcatta 184080
taaaaatgat acttgcttgg aaaattatat atctagctat tcttttgtat ataccgacag 184140
aaagactagt tttaagtcat accgtgatta cgcgtagtaa gctttccaca gaagataacg 184200
aaatagatga cgttccaaca tgtccgtaca gaatgttcaa taaaaagaag attatgggtc 184260
ctatcgtgtc tgtaaagtca cctgataatc cgacgggccc tatcatggct ttggatgctt 184320
atcataacta tacgtcgtgt aagtataatc aatattgtac tttttttgat ttctgtatgg 184380
cgggtaacac tactattcgg tttggaaggc agaaaataaa cttaatatac tttgtattta 184440
tagaagctgt aaccagagat gattatacaa aaattacaca agaagttacc ttgaagcatc 184500
tagatgatgt tagatttaaa ccagtatccg ttacttttgc agcattatat aaacaatttg 184560
tgaaaatgtc tgcatatcac gaatgtaata aaacaggttt taaaaaacca gttagagatt 184620
catgtagaaa agatagtaac tctgctatac aatatagtaa tgaacaaaaa tcacattaca 184680
atttcttgtt aaaaagtagt aaaaaaatat aaaatgaaaa taaaacaata ttttataata 184740
gcttagataa tatagatttt gattcactca taaacattat taaattagaa aataagacta 184800
taatatttgg aaaaagattg cagatatata tcaggttgct gcttatgtat tgacttatac 184860
atcatagggt agcgttaaaa tacacaagtt gttcagacac tacatgaaaa tataatagta 184920
cgggacctgt aatgatatgt ccggtaataa aaatataata tttagtgaaa tattggaaat 184980
tcttaatagt aagtacaaga aggatatgaa gcttttaaat atagtctatg aaaaatatag 185040
agctattata ttctgggaat tagacgacat taaatcagag agcaaaaaat tgagaacaca 185100
```

-continued

```
atatcaagaa gaacttagta aaaacttaat gtcggattta ctaaaaaata aatatcaaag 185160
ggatattagg tatttcagga gtaaattaat agagttaaaa actagactag atgatattga 185220
aagaaagtta atagataggt ctaatagtct tatgcttaaa tacgtatcag atctacaaaa 185280
aatacaatca tacctatcga gtaaaacaag cgactctgta atcatcgatc ttgttactca 185340
gttaatagct tataggatag tagatggata taaagaagct gaaaaataat ctatttttta 185400
ttacaaacta aacaagtatg atgtttaata gtatgataac cggttatata gatgaagaat 185460
tttgctatat acaatattct ggatttcatc ttgttatgat gatttccaat tgttatatta 185520
acgctagtaa gttatgcgat acaaaggatt ttaaaaaatg gttgcgttta gatagttcgt 185580
tatcgctttt acaagaaata gaaaacacaa actttccatc ggagaaaaag ttttctatca 185640
aaaattcaaa atcggttatt attctagaaa agtattatca cgaagaagta gaaggatatt 185700
acattcatcc tgatatacta ccgcatattg taggatggtt atctcctaca ttcgctatta 185760
gtatgtctaa attcattaat gggtatatat ctaatagttt tacaattacc gaaaaagatg 185820
acaaaaaata caacacgtta ccaccatctt catcatacaa acaaggagat agaaattgtt 185880
tcatagatat gcttaacgaa atgacaaata aacatctcaa tgatataaca gaactaaaaa 185940
ctcattatag agagcagaaa agagaactaa aatatcaaaa taccgtactt agctcaaaaa 186000
taacagaatt aaagaacgtc aatgacgaat ttagatacag gataaaacat tttgatgata 186060
gtattaaaga aataaaagat gaaaataaca ctttaaaatc aaatatcaaa attacagaaa 186120
aacataacaa agaattacaa agagataaca atagattaaa gactttattg agagaactat 186180
acgaaaagaa tacttctttg caaaacaata taacagaact tagagaaaca atagccagag 186240
aaacaaaaga attacataat caagtaattg aactttccaa agacaagggg atagaaccta 186300
tagaagaata ccgcgttgac agatgctttg taaggaatag attacaccga tctaataaaa 186360
ataattatat aattatcttt caacataaaa aggacttgtt tactttcaaa tactttaaac 186420
tacatataag aaaagtatgc atagaactat ttaattatag agagagccat aatttatttt 186480
taattattta cgaacctact aataaatcta taatccgatt caagaatatg cttgaaaata 186540
acgaacatat agaactaaaa gataacaact ttaaaataac agatactaga tataccgtta 186600
taaatatatt aaaggatata aataaaatat tttcagataa ctaatataac ttttcgtacc 186660
gtgtaaattg cataattttt tatactataa atatggatgg taacaccaat aaccaacaga 186720
agaaagtccc tgacggggtg attccccagg gccaacaaaa gcttcctcca aaagcaccgc 186780
cgactaacgg cggtagtaca ggagatgtaa aaagtagtga tcaaaataca gaaccatcac 186840
agaaaagtgt ataatataaa attacgtctt atatcagtaa tactgatata agtgaagtta 186900
tgtgttttaa ggacgttagg accctttaca agaataaaag aagaaacaac tgtgaaatag 186960
tttataaatg taattcgtat gcagaaaacg ataatatatt ttggtatgag aaatctaaag 187020
gagacatagt ttgtatagac atgcgctctt ccgatgagat attcgatgct tttctaatgt 187080
atcatatagc tacaagatat gcctatcatg atgatgatat atatctacaa atagtgttat 187140
attattctaa taatcaaaat gttatatctt atattacgaa aaataaatac gttaagtata 187200
taagaaataa aactagagac gatattcata aagtaaaaat attagctcta gaagacttta 187260
caacggaaga aatatattgt tggattagta atatataaca gcgtagctgc acggttttga 187320
tcattttcca acaatataaa ccaatgaagg aggacgactc atcaaacata aataacattc 187380
acggaaaata ttcagtatca gatttatcac aagatgatta tgttattgaa tgtatagacg 187440
gatcttttga ttcgatcaag tatagagata taaaggttat aataatgaag aataacggtt 187500
```

-continued

```
acgttaattg tagtaaatta tgtaaaatgc ggaataaata cttttctaga tggttgcgtc 187560
tttctacttc taaagcatta ttagacattt acaataataa gtcagtagat aatgctattg 187620
ttaaagtcta tggtaaaggt aagaaactta ttataacagg attttatctc aaacaaaata 187680
tgatacgtta tgttattgag tggatagggg atgattttac aaacgatata tacaaaatga 187740
ttaatttcta taatgcgtta ttcggtaacg atgaattaaa aatagtatcc tgtgaaaaca 187800
ctctatgccc gtttatagaa cttggtagat gctattatgg taaaaaatgt aagtatatac 187860
acggagatca atgtgatatc tgtggtctat atatactaca ccctaccgat attaaccaac 187920
gagtttctca caagaaaact tgtttagtag atagagattc tttgattgtg tttaaaagaa 187980
gtaccagtaa aaagtgtggc atatgcatag aagaaataaa caaaaaacat atttccgaac 188040
agtattttgg aattctccca agttgtaaac atatttttg cctatcatgt ataagacgtt 188100
gggcagatac taccagaaat acagatactg aaaatacgtg tcctgaatgt agaatagttt 188160
ttcctttcat aatacccagt aggtattgga tagataataa atatgataaa aaaatattat 188220
ataatagata taagaaaatg atttttacaa aaatacctat aagaacaata aaaatataat 188280
tacatttacg gaaaatagct ggttttagtt taccaactta gagtaattat catattgaat 188340
ctatattgtt ttttagttat ataaaaacat gattagcccc caatcggatg aaaatataaa 188400
agatgttgag aatttcgaat acaacaaaaa gaggaatcgt acgttgtcca tatccaaaca 188460
tataaataaa aattcaaaag tagtattata ctggatgttt agagatcaac gtgtacaaga 188520
taattgggct ttaatttacg cacaacgatt agcgttaaaa ctcaaaatac ctctaagaat 188580
atgcttttgt gtcgtgccaa aatttcacac tactacttct agacacttta tgtttttaat 188640
atccggtctt aaagaagtcg cggaagaatg taaaagacta tgtatagggt tttcattgat 188700
atatggcgta ccaaaagtaa taattccgtg tatagtaaaa aaatacagag tcggagtaat 188760
cataacggat ttctttccat tacgtgttcc cgaaagatta atgaaacaga ctgtaatatc 188820
tcttccagat aacatacctt ttatacaagt agacgctcat aatatagtac cttgttggga 188880
agcttctgat aaagaagaat acggtgcacg aactttaaga aaaaagatat ttgataaatt 188940
atatgaatat atgacagaat ttcctgttgt tcgtaaacat ccatacggtc cattttctat 189000
atctattgca aaacccaaaa atatatcatt agacaagacg gtattacccg taaaatgggc 189060
aacgcctgga acaaaagctg gaataattgt tttaaaagaa tttataaaaa acagattacc 189120
gtcatacgac gcggatcata acaatcctac gtgtgacgct ttgagtaact tatctccgtg 189180
gctacatttt ggtcatgtat ccgcacaacg tgttgcctta gaagtattaa aatgtatacg 189240
agaaagcaaa aaaaacgttg aaacgtttat agatgaaata attgtaagaa gagaactatc 189300
ggataatttt tgttactata acaaacatta tgatagtatc cagtctactc attcatgggc 189360
cagaaaaaca ttagaagatc acattaatga tcctagaaag tatatatatt ccattaaaca 189420
actcgaaaaa gcggaaactc atgatcctct atggaacgcg tcacaaatgc agatggtgag 189480
agaaggaaaa atgcatagtt ttttacgaat gtattgggct aagaagatac ttgaatggac 189540
tagaacacct gaagacgctt tgagttatag tatctatttg aacaacaagt acgaactaga 189600
cggcacggat cctaacggat acgtaggttg tatgtggtct atttgcggat tacacgatag 189660
agcgtggaaa gaaagaccga tatttggaaa gataagatat atgaattatg agagttctaa 189720
gaagaaattt gatgttgctg tatttataca gaaatacaat taagataaat aatatacagc 189780
attgtaacca tcgtcatccg ttatacgggg aataatatta ccatacagta ttattaaatt 189840
ttcttacgaa gaatatagat cggtatttat cgttagttta ttttacattt attaattaaa 189900
```

-continued

```
catgtctact attacctgtt atggaaatga caaatttagt tatataattt atgataaaat 189960
taagataata ataatgaaat caaataatta tgtaaatgct actagattat gtgaattacg 190020
aggaagaaag tttacgaact ggaaaaaatt aagtgaatct aaaatattag tcgataatgt 190080
aaaaaaaata aatgataaaa ctaaccagtt aaaaacggat atgattatat acgttaagga 190140
tattgatcat aaaggaagag atacttgcgg ttactatgta caccaagatc tggtatcttc 190200
tatatcaaat tggatatctc cgttattcgc cgttaaggta aataaaatta ttaactatta 190260
tatatgtaat gaatatgata tacgacttag cgaaatggaa tctgatatga cagaagtaat 190320
agatgtagtt gataaattag taggaggata caatgatgaa atagcagaaa taatatattt 190380
gtttaataaa tttatagaaa aatatattgc taacatatcg ttatcaactg aattatctag 190440
tatattaaat aattttataa attttaataa aaaatacaat aacgacataa aagatattaa 190500
atctttaatt cttgatctga aaaacacatc tataaaacta gataaaaagt tattcgataa 190560
agataataat gaatcgaacg atgaaaaatt ggaaacagaa gttgataagc taattttttt 190620
catctaaata gtattatttt attgaagtac gaagttttac gttagataaa taataaaggt 190680
cgatttttac tttgttaaat atcaaatatg tcattatctg ataaagatac aaaaacacac 190740
ggtgattatc aaccatctaa cgaacagata ttacaaaaaa tacgtcggac tatggaaaac 190800
gaagctgata gcctcaatag aagaagcatt aaagaaattg ttgtagatgt tatgaagaat 190860
tgggatcatc ctctcaacga agaaatagat aaagttctaa actggaaaaa tgatacatta 190920
aacgatttag atcatctaaa tacagatgat aatattaagg aaatcataca atgtctgatt 190980
agagaatttg cgtttaaaaa gatcaattct attatgtata gttatgctat ggtaaaactc 191040
aattcagata acgaaacatt gaaagataaa attaaggatt attttataga aactattctt 191100
aaagacaaac gtggttataa acaaaagcca ttacccggat tggaaactaa aatactagat 191160
agtattataa gattttaaaa acataaaatt aataggtttt tatagattga cttattatat 191220
acaatatgga taaaagatat atatcaacta gaaagttgaa tgacggattc ttaattttat 191280
attatgattc aatagaaatt attgtcatgt cgtgtaatca ttttataaat atatcagcgt 191340
tactagctaa gaaaaacaag gactttaatg aatggctaaa gatagaatca tttagagaaa 191400
taatagatac tttagataaa attaattacg atctaggaca acgatattgt gaagaacctt 191460
acggcgcatc acattccagt gtaattattg aggtcaaagc tagtaactta atagatgaca 191520
ggacagctgg attttatgta cataaagatt tgatacctta tatactgaca tgcatatcta 191580
tacctttag tcttaaagtt gtccgtgtat tagatactta tataggtgaa aaactagaaa 191640
acagaattaa gctaagtcag agtatggatt tggaaacgaa caattcatac aacatgtaga 191700
aaagaaaaaa taatgttctt ataataatac tataactcca tattgttatg taaacctagt 191760
agtaacagct atgagagaga ttctaattat attaatgcta aaaaatatgt agtatcatcg 191820
ataataaaaa atttataaat ggcatagatt agaatattct aaagaactaa tagcttacaa 191880
tagatacgat cgttaataca aaaaatctaa gataaaaata agtagtacca taattaatag 191940
tgctcctagt aatatagata tactaggtta ttacgtccat ccgctgctag tacctcatac 192000
catataccat cttggaggtc agcggaataa gaattaaaaa tttcaaagat agtaaaggtt 192060
atctattcta agatgtatca taacaatgga aaaatctaaa aattaaaaaa acaactaata 192120
taattataac tataatgcat gattatatat aacagaatgg taataacagt aagatatacc 192180
atttttaaca atataaagtt atttgtaatt actataggat tgttatgtag tgtattatta 192240
ttacgtaata tagtgtactt gtacaataga atattacagt taataattga ttaaataaaa 192300
```

-continued

```
gaaattacca tgattttaaa tgtataagtt ctaaacatat taatagtaaa ttctgttata 192360
tacagcataa ttatttagaa ctaataaaga tgagagataa ttcttttata aatgccatac 192420
atttatgttt atcaggagga aaggattttt ctacgtggtt atcattatat acacctaggt 192480
gtctactaga tacgttagct aaaacaatct tcaatggaac gtcgatgttg actagtcaga 192540
aggaataatt aaagaaaagt cttatgatac tgatgaagag tataaatgtt actatattct 192600
cactatgacc atatagccgt gggtatttag ttattttgct gtaaacttat acgagctcgt 192660
tagtaacatc tatatcatat gcaaaaacag atgacatgtt ttaaactata ttttgcgttc 192720
atattagact acaaacctaa tgataataac aaaaatcatt tatattttac aagttttaac 192780
aatattgaac gcgtaattag ataaaccaaa atggttttat attagtgtaa atataatatc 192840
gagttcatgt aattaaatat catggttata gtgtaataaa gttaaggata attatgctaa 192900
atagcccgta ttataataca cgataaatta ataaattgaa gctatttata tcacaaggag 192960
atataatacc gtcgtaaagt aaatataaaa tattatcaga atacacgtat ttatctaaaa 193020
tcattaaatg gacttgtatg ataataattg aaaaacaatt atctcaatac atttgaatgg 193080
tgatatattg taacctacat acagtaatta tgaatatatt ctataacaat attcatcgat 193140
gttttaaaga cacaccttta cataaagccg taatgttacc tgatgcggta gaaagaataa 193200
gaatgtttgt atctaaaggc gcggacataa acgtaatatc agattttaaa aagacggcat 193260
tgcattatgc ggcaaagaaa ttggctactc cagaagtact taaaacactc atatatttag 193320
gtactaacgt aaacgtcacc gacatgtttg aatcaactcc tttgcattac gccgtacaag 193380
aaaatggatt agaagcaaca aaaaagttat tagacctagg tgcagatccc aacaccaaat 193440
acatgaacgg tcagactccg ttacattgcg cagcgatggt tatacccgat ggtcctgaac 193500
tggtaagaat tctggtcgag tacggtgcta atgttaatgc gctagacaat aaacataata 193560
caccgctagc tctagccgca gaattatcta atacaaacaa aacaatagaa acgcttatcg 193620
agctcggcgc ggacgtaaaa ataaaaaata atgacggtat aacaccctta catttagccg 193680
ctaaatcatc gtctgattcc aaaacagtgg aaacacttat ccttcacgga gctgatgtca 193740
acgctacatg ctcggaaggg aacacgcctt tacatgatgc ggctacttca tacgagttat 193800
ctaatacaat agaaatgctg atagaatacg gagctgaagt aaacgccgcg aattcggtag 193860
gtgatacacc tttacattgc gctgctcgtt ctcgtaatcc tgttcataag ctgaaaacac 193920
tcatagcaca cggttctaac gtaaacgctg ttaacgggat atcggtaact cctttacatc 193980
ttgcgactta ttcagataat gcaacggaag cattaaaggt attaatagag cacggcgctg 194040
aagtaaactc cgtagatatc tacggaagaa cacccatgca ttatatctct aggtcttatt 194100
cttcacaatc attaaaaacc gctgttgagt tactggtaga acacggtgcc gatatagaag 194160
ctaaaaatgt aataggtggt acacctttat ccagcgcgtg taataatata gagtatgatc 194220
taagacttat agaatgtttt atagaatacg gagcggatat aaatactaga gatatacgtg 194280
atgaaacacc tttatattcg gcaataaagt atccggagat agttaattta ttaatgaatt 194340
atagcgctag tacaaacata acaaataaaa gtaatattac tcctctggaa tcagctatcg 194400
ccaattgtat aggttctgca gaaattatag taactcaaat tatattagac gcgtttagat 194460
ttcctgatat aaaaaatgat gcgatattta tcagaaacat gaaaaccata gaagaatgta 194520
ccatgcttat cgatgtaaaa gaatcctgtg aatatgacat aaataaaatg cgatctatta 194580
aatttaataa tatgtacgga ctggatatat tcattcgctc aaataatata aatttgttgt 194640
caagtttggt atctaatgta gaagatatat acttagaacc aggttgtttt ttagtatatg 194700
```

-continued gaaataaatt aagaaaatct gtatatgccg ctaggaagcg attatcgtta ctaaaaaact 194760
ctatatctat tctgagtaat atcactacag atggttactg gaatgcttta cctatagaac 194820
ttaaatataa tatattagct atgttaggag ataatgattt gtttaatatt gtaagaaact 194880
gttcgtaaag aacgtgataa gatacagcca cgtttactag cgggacttat aagtgaaatc 194940
attttattgt tctatattag attacgtaaa tgtagatttt tttcattatg ttggaaggaa 195000
atattataat attttaatgg cttgttaata gttattatct taaaaacata catcatataa 195060
ataaactcag ttaaaaagtt aaaaataatc tcatagtttc gagtaaagac tattacaatc 195120
atgaatacct taccgtatat tattcaggat attgattcgc atttctgtta tataaaatac 195180
gatggaatta cacttactat gatgaaagac aacggctaca taaatgctac acaactgtgt 195240
atgcttggaa ataaagactt taaagaatgg ataaagttag atcacagtat agaactaata 195300
aaagaaatag aaaaaaatat caataaagaa actaccaaat atgtaaaagc tgttatatca 195360
gttagatcag attattataa ttcagagacc tccaatgaca taaaaggatt ttatatacac 195420
ggtaatataa tgccacatat ctgtgcctgg atatcatcta agtttgctat aaaagtatct 195480
aatattgttc ataactatct aaacgataga tatgtacaaa atgataaaga ggaaatacac 195540
caagaacccg ataaggatat taaatatata aagaaacaat gtaagttaat gcgagaaata 195600
agaattctat ttaaaaaaaa ctatactcgc gagttagacg aactcaaaaa agtaagggag 195660
ctttattacg aaaaaaataa aggacttgaa gaatatattg ataaattaga atatagttac 195720
actcagagaa tgaaagaatt aaccctatct atagatgaat taaaaaatag taacaagcaa 195780
ttaaagaaca agttagaaaa tatagagaaa cgtataaaat gtattaatcc acctactgaa 195840
agtagtaaaa atgtgatcta tgataggttc aaaaagttat atcacattct aacattcaga 195900
aaatctaaat aatcaattaa ttattataac cattaatagc tattattttg aatatattca 195960
aaaacagaca tacatcatgt aatataacac tatataatac ctttacacca cgcaactaca 196020
tatattgctt tgtatatgtt gtatgaaagg taattacgta aacataatag gtcgccttac 196080
taacgatcct aaaagaagtt atagcttcac atgatataga tataaaacta ggtaatctat 196140
acacactaaa aagtttttat acattacgat agatattatg gataaaagta gagaaactcg 196200
catttgcgat tatgcttcta ggactatact gtaaagtgtc tcgatcttag catatagata 196260
aatgtttgaa ctaatatcct aaaggctgta tgtaacagtt ggtgactatt gaaagatact 196320
gattatcaag gagaagaata atataaatcg taaaaataat acttattata taatataatg 196380
tataataata tacaaaaaca gccatgatac gtattataat attatcgtta ttatttatta 196440
acgtaacaac agatagtcaa gaatcttcaa aaaatataca aaatgtattg cacgttacag 196500
aatatagtag aactggtgta acagcttgct cgttacattg ttttgatcgt tccaaaggtt 196560
tagatcaacc aaaaaacattt atcctgcctg gtaaatatag caataacagt ataaaactag 196620
aagtagctat tgatacatat aaaaaagata gcgacttcag ttattctcac ccatgtcaaa 196680
tattccagtt ctgtgtgtct ggtaatttta gtggtaaacg gttcgatcat tatctatatg 196740
ggtatacaat ttccggattt atagatattg ctccaaaata ttatagcggt atgtctataa 196800
gtactattac tgttatgcca ttacaagaag gatcattaaa gcatgatgat gccgatgact 196860
atgactacga tgatgattgt gttccttata aagaaaccca gcctcgacat atgccagaat 196920
cggtaataaa agaaggatgt aaacccattc cactaccaag gtatgatgaa aatgacgatc 196980
ctacttgtat tatgtattgg gatcactcgt gggataatta ctgtaatgtt ggattttta 197040 attctctaca gagtgatcac aatcctctgg tttttccgtt aacaagttat tctgatataa 197100

-continued

```
acaatgcatt tcatgctttt caatcatctt attgtagatc actaggcttt aaccaatcat 197160
acagtgtatg cgtatctata ggtgatacac catttgaggt tacgtatcat agttatgaaa 197220
gtgttactgt tgatcagtta ttacaagaaa ttaaaacact atatggagaa gatgctgtat 197280
atggattacc gtttagaaat ataactataa tggcgcgtac acggattcaa agtttacctc 197340
ttactaacaa tacctgtatc cctaaacaag acgatgctga tgatgttgac gatgctgatg 197400
atgttgacga tgctgatgat gctgacgatg atgatgatta cgagttatat gtagaaacta 197460
caccaagagt gccaacagcg agaaaaaaac ccgttacaga agaatataat gatatattta 197520
gtagttttga taattttgac atgaaaaaga aataagacat attttattaa atcaaaaagt 197580
ctgtcgaact tttagtgttt aacctatatc gatttatgat tttccatgat gatccaggct 197640
atgactgact atggcaaatg tataaaaagc agtaatctgt atacgactta atagattcta 197700
aaaatcaaga aaaccttaat ttctatctca cgttcttgag aatttttgat gtatagttga 197760
ctacgaccta gtagaaagat tttgaaaaga agtttctatg tttttcaaat aggtatagaa 197820
aaataatcat tctgaagcac gtgctccaat aaaatgaaac tatttttgct actgaggtag 197880
acttttaatg taataacaat aagcatgact acctattatc tgctttaaaa tatactatgt 197940
tgatgtgata gatccttggt tattatattc cttatactag tagaatagtt acttagttaa 198000
tgatgtaatt ctaacaagaa atctgtgata cgtgattatg atgattcata aaaaagaata 198060
atatatagcg ttatttagaa aatgtatcta aaataatcat atcatctggc tctgttattg 198120
tacccgatat aacggtaata ctaatttatc taaatatgat gtataagagt tagataatgg 198180
tttaattcct tagtatcata ttctccagag actgtaagat tgttaccaga ttattgttct 198240
aatactaccg ttatagataa actagacttc actttttatg gaattataac attagtagag 198300
gtgaaatatt atagacgata tagaacatta tactatctga agaatatata ataactgata 198360
tagtattatc agctatatca tacaaggatt gttatatatt ttctaaaaat gtatacctat 198420
acacaataat tgatacatta aaagaaacaa cgaataacta tgaattaaca ttagctaact 198480
cattgattat taataagaac acagagcgat aaaagtaata gaaaacacta taccatgtct 198540
accgataata tgaagattat attcataaag tcgtagataa ttaaagagaa gtttaaattt 198600
attataaatt atcctacgtt actacacttc taaagaacat gttgtaaaac cataatctac 198660
aaatacgtat tcgtgtccgt aatcgtatac agatgtatta attttttttct ttttcatgta 198720
atctagaaag ttttcccata ctagttgatt actattgttc ttcgtgtagt ttttaaccgt 198780
ttggggttta aggttattcg ttacagatgt aagactaaat attttatcca aaaaaaacga 198840
ataattaata gttttcgaag gggtattttc ttgacagaaa aatactaagt gtttaaaaat 198900
ttctataact tcgtttattt tacttgtatc taaatttaat ttttcttctt ttatatgatt 198960
tattatttcg aatactagtt tataatcttt tttatttatt ttttcattcg cttttaaaaa 199020
cgatgataca aaattagcgt ctatatctgt agaagatata ttattttttg tcattacaga 199080
ctttaattcg acaatgacgt ctgaagaaca ttgattagaa agtaatctac gtagaacgtt 199140
tctcaagtgt atcaatttat tagatacatg aaaatttgat tttttagata ctttgttaga 199200
aagttggaat atagattgac agaaaataca gaattcatga ttagattctg ttatcaatcc 199260
gttatgctta caattactac aatgttttag attactcatg ttaaaactct tcttatttcc 199320
ggatctagta ttttagttaa cagagtttta tttctactaa atattagaaa ttgttttaat 199380
atatttttct tatattcgtt attatttaac attaatttta tcaattgtct atctgatttt 199440
agatattcaa ctaaattatt actacagtta ctacacctaa ctggaggatc tatactatat 199500
```

-continued

```
ttatactccg acatttactt tacgtaaatt aaacaaatat ttctgttatg cttttagttg 199560
ctaagtaagg tagatagtct tgagcataca ctaaaataca acaatttcta gaaataaggt 199620
tcatagcttc ttcgtgggac aataaatcat cttcaaacat aacagtatga tgcatcagtt 199680
gctgttgctt tatatcgcat agtttcttag tggattcttc tttcaaccaa tcgtagaaca 199740
ttccgtcgtc atttccatgt tctttataat attgattctt catcactctc attaatcttg 199800
actctcttga ctgtttgcta taaatagata gaggatcgta catccaagga cccatttccg 199860
tgaatagaat agtatagtat cctttgagaa atacatctcc gccgtcgcaa cttccggaca 199920
tggtagataa caaatcgtgt gtcttgtaac aaactgctga ttttagtaga tatgtaatac 199980
cgttgatatt tagttcatta gctatatcca ttggacgatc gttaattact gatctaaagc 200040
ctgtaaaaca ctcacctgat actatatttt tattttgtcg acgttctatg tagtagataa 200100
gagtcccgtt tactattact ggggaattta taatcctatc atgagaaata gaattcaata 200160
caggtagagc gtctacagtc ctacaagaaa tagtaccttg gtatctcata ttagcaggca 200220
tgaacattac tctacccgta gtattatcga aacttagaga ataaattgaa ttagagttaa 200280
tggatatagg attgtttata gtggtaatca tttttgaagg gcttacaact atataagata 200340
cgggtttaag aactacgtta agcggttggt aaggatctgt gatagatact agcgccggtc 200400
tgaatcctac aatagataga atcgaagcta gcatttgttc ttcgtcggcc atcatctgag 200460
agctgtttat gtgaataatc ttcataagat ggttgtcgac aagatcacaa tccttgctgt 200520
agaatatacc taatctcaaa ttcaatattg tttttctcag catagtatga atactggctc 200580
tatgtatttc actagataca gaatcattaa tacccgtaaa gataatagga gaatcttcag 200640
taagcctatt aatcaacaac atatagtttt ctggctttac tttcttcgag ttatacaatt 200700
gtttcataag actataacta tcacctaata ccatagcgtt ttctagagcc ggtagcttaa 200760
cgccgaataa agcaactaat ataggatgaa cgtagcctat ggaatcctgg tctttgaatc 200820
taaataacat atcactagat gttgacatgt caacaaagtt tgttgattga aacctagtcg 200880
tatctatcaa cgcttgatat ctggatggat catatgtatt ttctagtagt tttaactgtt 200940
ctcctatctt attatctgag tgcgaataaa taaccattag aggatgactc gtttttaccg 201000
aaacgctatt actagaaagt gatcctttga catgagatag taactcgaat aactcttgtc 201060
tttcatttct aataatattt aattccctca taacgcgaat aaggtcttgt atcgtaaagt 201120
tatttatatc acattttcta tccatgagat atcttactat agcatctgcg tcttttctaa 201180
gattatattg ccagtcatga gtagatgtaa tttcatctat gttgataatt gtgttttttt 201240
gttttacaga atctgaaact cctttacata tatcaggttt tggtttacta cgaagacgca 201300
taggtcgttg ttgtttagca cctgctgata taacatcttc ttcagtaatt ttattcaaga 201360
catcacatac gttacataaa ttatttttat ccggtttatg taaatgagat cctattactt 201420
ctaggttatt atagtaaaca ggttctaata aaatattagg atatttaact tcttcaatcg 201480
ctatattaga atcagattcc atttatattt gatagttttt tacttgtaac gtatcaaaat 201540
aagtacctaa agagacgtaa ctagttaagg aataatagca tctctgagtt ctcttatatc 201600
atctggtaac ataataccct tttcctgaag atatatattt atccacgtaa taacttcatc 201660
aaaaaacatt tgtttatcta tcttattgct attagataat ggtactttaa taggtggtag 201720
gatatcaata tatttatcat gcagatttct tatccaaagt ggagtactac taggcaatgt 201780
taatacttgt gactgctgaa tattagaaga cggtactaaa gtactactac tgctagatga 201840
agaaggtgtt tgagggccaa aactactacc actagatgag gttgtttgag gtccaaaact 201900
```

-continued actattgcta gacaatgacg atggtccttg taaaccaata ttgctagaca atgacgatag 201960
tccttgtggg gctaatccac taacggaaga cgaagttcct tgtggggcta atccactaac 202020
ggaagacgaa gttccttgtg gggctaatcc actaacggaa gacgaagttc cttgtggggc 202080
taatccacta acggaagacg aagttccttg attgccgcta gtcgagggta gagtagtact 202140
tgaattatag gaaggaggtc ctaaattttg tggataaggc aaattactgc tttgttgatt 202200
gttaaatcta ttaagaaaac tggtaaaaat accagcagta tcgttactac gtaatataga 202260
tatcattcta tcctgaatag acctactatc gtctgtattg tattcgtcta ctatagattc 202320
cttctcattt ctactatcat cttcatctag cttttctgaa aatatctctg gattattact 202380
aacattacgt ttgattctag aaataaaatc tttgtggaag ttctcagcca tttagtatcc 202440
taaaattgaa ttgtaattat cgataataaa tggacaattc tatggatatt aacgatatac 202500
tactgtcaga tgataacgat tataagagtt acgatgaaga tgatgactct atatccgata 202560
taggagaaac aagtgatgat tgttgtacga ctaaacaatc ggattccagg atagaatctt 202620
tcaagttcga tgaaactact caatcacctc atccaaaaca attgagcgaa aggataaagg 202680
ctataaaaca acgatacact agacgtataa gcctatttga aataactgga attttatccg 202740
aaagttataa tttattacaa cgtggaagaa ttccattact taatgacctg acagaagaaa 202800
cgtttaaaga ttcaattatt aatattatgt ttaaagaaat agaacaagga aattgtccta 202860
tagttataca aaagaatgga gaacttttat ccttaaccga ctttgataaa aaaggagtac 202920
agtatcatct ggactacatt aaaactatat ggcgtaacca acgtaaatta taatttagat 202980
atataatgtt cttgaataaa atcgaatatg aattctatat ctacagcatt ttctttatag 203040
ttaatgttgt aattatcggt tatacattga acaattgata taagtgttgt tttgtgcttt 203100
tcatattctt ccacaaatat gtttttatac atttcacggt tatttgatat ctcacttatc 203160
aatccctgaa tgttattaac ctttcttttc tttaaatctt ctacggaaac tttagtctta 203220
aatgatgcca ttatttcact aaaaagaacg tgtaagcgtt cgttagtaag tatttcagaa 203280
tacactatac tagagagttt agaaaatatg ttaacaaatt gtgttgtttt gacacagcta 203340
gtttgaaata aaataatatt aggtaatacc tttttaaaga agcttacgta tttattattt 203400
atctggtcta taccgtctat cgttatatcg cagaaacact taataccaaa tattacgttt 203460
tctttagaga aagaaaatac atctttatat tcttcaagtt ttatcttatc agatactaca 203520
tctgtattaa aaagtgcaat tatctttatg atataattgc tatccgctag gactttattt 203580
attgttctga taatgaaact attgttttcc attaatattt tgtaagcttg atgttcgtta 203640
ttagcacttt taattaacga cacaattcct agtatctttt ttaaatcctg cactatttca 203700
tttgtatctt ttttcatatt agagtacata ttgtttatag atgtaataac ttttgcatat 203760
actaacatat ctttaaatat tctgataaac tgttcttttg tttctttatc tgttattttg 203820
ttgagcatag attttacgtt tgccgctgat cgcatatacc aaaatgtaaa catcttgaat 203880
tctacttgct gcatggctag aataacagtc tcgtcagaca ttgcgcagtt aatatcaccg 203940
cctatcttac tttctagaat aggaaaaacc gttaaaaatg aatcgatatc attatcataa 204000
tttacttcat acactttttg acctgtacta ttctctaaat acttcttact taattcataa 204060
aattcaataa atgcattcct gaacttttcc atgatttata gcttgtagta tttttctaat 204120
attgatttga tttgtatatg tgtataatct ttaccgatac ctaatttaag catagtatta 204180
ataacccaag tttttataaa tatttctttg ttatcggtta ccacatattt aaatactgaa 204240
ttaaagtatt taactatagg attattctga gtagatatat tatccataaa tacagaccgt 204300

-continued

```
tttgtagata gaggttctgt aaataattca ccgtcgacat aaaaaccatc cgttgttagt 204360
ttgagtccat tttgttcttt tatatcaacc gttttaactt tataaggaaa catatccctc 204420
agtttgttgg tacgtagttc ttcaaaatat atcatatctt tatcttcttc ctttttagct 204480
atgactattt catgtactat ttcttgaact agtatgtata ttttattatt aatggatgag 204540
tatttcatag gaaagtaaac gatatcatta gctatgagag ttacattttc cgtgttaaca 204600
aactggataa tatcattttt agttcgtata cgtttcaatg tataataacg gcaattatgt 204660
agacaactcc tgattacatg atatcctttc gtacttttta accgcttatt atccgactcc 204720
aatgaaatgc ttaaatcgct gttaaagaaa tcattaaata tgggaggtag aaatgctatt 204780
ttagaatctg taactacttt gccataattt agtatatacg gactaattat attcttgtcc 204840
gtttgcttat tatgaacaca cgccataaaa gtatccgtat gactttggtt ctttagaaaa 204900
cagcacggta tacatatctt ttgtaattta tagaatatag caagaaaccc tatattatta 204960
tattttccgg tcttatcatc acaagtaaac attacctcgt tattattgac gaatacttct 205020
ttggtaggag atttataaaa gttatcgctt acttttaaca tatcaggttc tagggaagat 205080
attattacgg gtttcctatt tttatctttc gtgttttgac aaatacgtga ccaatagata 205140
gtttctatct tagtaaaatc catagactgt tttaccgtat taaacaggcg gtttataaaa 205200
acaactaaga aagtaaagta tttttctata ttgggtatgt gatttttaac ctttatagag 205260
atatggttct tcgctaaaat gattgatatt tttttatcta cggaaagcaa tatattgttg 205320
gtagctgttt caataaatat aaaactagtt tcaatatcta attttacttt tgatgtaatc 205380
ggagtagata gtttcacctt atacgtaata tcacttttga tacgttccat ctgtacgttg 205440
ttattcggta tcatatctgt aaaaagtttt acattattaa cagtaatagt atttccgtcg 205500
ctggatatag ctagagaacc atcatcgtcc catatagaca aattaagaga ttcgtcgtta 205560
ataacaaaat ggtttcctga taaattgata aaatactcat cagatttgat aaatagtatc 205620
ttcttatcgg tattactgag aactatattc tttaatccgg tcattttgag attagtccta 205680
aaaacgttat taaattttga ttctaccgtg aagtctaaat caagatcagg aaacatttct 205740
ataagacgag attcaaattt aaggacatta gcatctactt cttcgtaaga tcctaattct 205800
tttaccatag tatcggctgc ttttgctacc catatcacta aaaagttaca cgcgtccaca 205860
tagacattgt ataagaaact ttttgactta agtaacgttt ttcgttgtgt catagtgaat 205920
ggattaaaag tagtattatc tacatagcta tattccaaat tatttttgtg ggaatatata 205980
attatttcct catcgatatt cagaagatcg catatataac cctttacctg ggatatcttc 206040
aaggttagta ttatatgctt ttttagaacc cttactctat ccataggaac tctcaagtga 206100
ttctttatga agtaatacat agaagatctt tcatctattc catcgtatag cgtaagatat 206160
agaacgtcca atatttcctg atctttatca accaatacaa ctaactgagg atttactacg 206220
tacatttata gataataact atagagtaaa cgtaaaaaat aattagtata taaaatttta 206280
cgaatacaat atgtacgaga tagtaccaga tttagacact agtatgagcc tcgaactagg 206340
agactttaaa ctatctacaa ctcgtacaaa acctagagaa gaagacaacc aatattacct 206400
ttcgaagaac agacgtatgt acgtatgcag ttctaaagga agcgaaagag ctaaaagcct 206460
aggattcttc ttatccaaaa tccctttcct caattacaaa gaaaaaaact acatgtttca 206520
gaagatggat aatatcaata atattcaact aaccaagaaa aataacgtta tatcagctcc 206580
gtatgttata ctgattaatc tttcagcgaa tggttttaaa ttcacagaaa gttttctaga 206640
gatatacttt cctgagattt ataaggaaag cagtaagaag tttaaattta atactcaaat 206700
```

-continued

```
tcaattgata caggaaaaat taggatatga acattctagt tattataata tagaatttga 206760
acactattat actaccgtat gtttgatact acaaagtaaa agaaacatgg aaaaggaaga 206820
tcctgaacta tttgacatac gagaaatgtc tcctatacta aaatcattgt ctgagattac 206880
ttataagctg tatgttttat atataaaatc taaatttgtt caatggagta taagttcttc 206940
agcagttgta actcaattag ttaatactgt attgattacc gtatataatc ttgttactaa 207000
atttataact gagaataaga ccttcaaatg caaactagct cataataacg aactacctat 207060
agatatgtta gtatcctatt acgaagaatt ttctgaaatt ataacaaatt tgatgaaact 207120
taatagatat aggataaata aacacataca agaaacttta ctcagcttct gtaccatttt 207180
tggcgaggta gaataagcct agacctatca tgaagtagat taccatagtt attaaaattt 207240
taagtatgac aaacgctagc gtgttacaac gtattcgtgt ttcacaaaaa tgcattatac 207300
aatgcctcac tagttctatt acattgctag ctacttgtag gaatgctaaa gtacttatag 207360
aatttagtat agaactgtaa cacgacattt attcgttatc aaaaaccaca gcattggcat 207420
cttcgggatt cattattctt ttaatgtttt caaaatagga tttagtcatt tcagtataat 207480
agttagttag tttcaaaatt tttggtctgg cgatattata agctttctgg atatcctcct 207540
gtgtgatagg attatcatct atattcctcc cggttctatg aactatactg agaacggatt 207600
taatttggtc tatacctatc aagtccttat acagcgattt agataattct ataaaatctc 207660
gatatttctc taatatagat atttttacat cgtctgaaat cttagctttg aaataccttt 207720
ctgtaaaata gatatgcata gcaagttctt taaacatcat agtaccgtga caagttatct 207780
tcttgatacc atccatttgc ttttcagaaa tctgtgtgat cgaatttaga atattcgtgg 207840
ctataaagtt ggaatctttc atgttcctat ctttaagagc attagtaatt aattctatta 207900
cttcgttagt agcgttttca tcaggtactc tttcatccag attttcaagt agttctccta 207960
ccgatacacc tcccgccgat actattaaac gatctattgt gttgagagga attatatgcg 208020
ctattgattt tccatcgata gtatcttctt ttaaaagttg tttaagattt tctttaaaat 208080
ttgcattttc tgggagaaac acatctgtat ccataatttc atttaacgca ttagcagata 208140
gtattccttt aacattaatt cgatctaata tgtttacggg tgaaataaat tgtactaatg 208200
tagcgtcttc ttcagacgct gattctttaa aaccaccgaa gaaggaccta ttaatacgtc 208260
gataactatc cctattactg ctattattga cggataacat aaaacttact agatcatgcg 208320
cagatgataa gagtttttca gcttcagatt gagaacacga cgccttttgt aacatatttg 208380
ttagatacct tttgcttact ctgggactaa cgtagtaaga tgtataacta tgactagata 208440
tggtagtcct attaacacgt acgttaaacc ccattgcttt aaaaagcata aagatgaaag 208500
tcctataact ttcaggtgta atatagtatg gcgaaccctt gtcatcaatc ttaataccgg 208560
tatacgccat aagaatttct tttacagcaa tatggggttc tttattttcc attaatctca 208620
agaactgaaa gaacaacata aatccagcat ctgaaaggcc tatatgtttg acatcatggg 208680
tatcgtattt tggaaaatct cttactgata tattgtttat attttctaat atctcgcgta 208740
tcaaagtcgg aatagtttta cctttaagaa ttctcgggaa cacgcatata cgaataggtg 208800
tttcttctgc tctcaataca tcgtttaaca tagaacaata tgttatccca tttttattat 208860
acaaagcgaa tagataacag gtagtcccta gaaacatcat atctataaat ttcatattct 208920
tatactcatc gtacgacata ccatcccaga aaagagatat ttctttagga acattacgat 208980
gtcttactaa actcttagat acaatgttca ataaattaat gatataaggt ctgttggacg 209040
tcatatttaa gatacgtatt cctaattgct gagcggttac tgtaatattt aagttgctat 209100
```

-continued

```
tatctggcct aaatacaaac tgatcaatat agtctaacga aaataacttg ttatcttcta 209160
tatactttat ctctttacta aaataaattg atacaacata agacgctaac atagaattat 209220
caacacgtat tcgtactcct cccaaatata tatcccttaa cgtaaaacca gaaaaatgct 209280
ggaaatacat aactagatac tttagtgtct gcatcgttat aagatccgtg tctatattag 209340
gattttgtac aagtacaatg ttattagcgt tacaatgaaa ttgtatttta aatatagcgt 209400
cgaatatagc tctagacata ggttctaata gcgctcttac attcaacaga ttagctaaat 209460
ccttcttttc cataatacca ttaatcaaca atggtctgta agtagaataa tcagctcttc 209520
cctctatata tggataagta agactatgta tgtaagaatt tgcaaaactg atattaggat 209580
ttatttttgg ggatagaata ttaggcgacg aaggatgttc tacgtatcca ccgaagtatc 209640
tagcgtgagc ctcacaaccc atggttctta tctgtatcaa tatttttgta aatggaggaa 209700
gatcgttgaa agatatagta catggtatag gattcgtata cccaccggta tttttattcc 209760
acgtagatac tatttctccg ttttctctga tatttatagg aaaataaata cctaaatcat 209820
tttttctgga aagaatgtaa ttaataccca gtgtatctaa ctgttgtgat ctttcaccgt 209880
ctgtaagtat actaattaat tctggactgt atatagtatc taacgcatgt acgtatccat 209940
tcgctagttt tggatctatt ttgtaatcta gacataacga aggtaaaaca ctagaaatca 210000
atttatagag ataatctgaa gattctaact gatctagagt tacaatattc tttattaaca 210060
tcatttatta tatgataata aatgactgga ttgatggtaa cagatataac aaatatagcc 210120
aaagaatata acttaacagc cttttcagaa gacgtatatc cgtgtaataa aaactatgaa 210180
cttactaacg gacagttatc agcactcaag actataaatg ttgtattaac aaccaggtca 210240
gataattatg agaaggatgt aacttataat gacgacgatg atcatgatcg ttgcatagta 210300
tctgaaatag gtagccatca ttcattcaac gatgaaaaag ataattatat tcaaagtaac 210360
aatatacaac agactccttc tttatcagct gtatttgatg ataataaacg ggttcattta 210420
ctcgaacaag aaattgccga acttcgtaaa aagaaaacta aaagcaaaaa cttgttagat 210480
tttacaaaca cccttttttaa taagaaccct cttagaatcg gaattctcaa taaacgcgct 210540
ataatactaa actatgcatc tatgaacaat tctccgctga cgatggaaga tctcgaagct 210600
tgcgaagacg aagagataga aaatatgtat atttctataa aacaatatca cgaagttcat 210660
aaaaaaaagt taatcgttac taatatcatt tctattttga tttctgtgat agaacaatta 210720
ttggtaagaa ttggatttga tgaaataaaa ggattaagca aagaagtaac gtctaccata 210780
attgatttag aaataggcga agattgtgaa caattggcta ctaaaatggg tgtagcaaat 210840
aatccagtta tcaatatttc gttatttata ctaaaaatat ttattaggcg cataaacata 210900
ctctaattat gccatgccac cgtctattga attatcatta ctcatacgtt ttttacggga 210960
agttcttttt gttctagttt ttctaccacc gttaactata tcaagatcta tacccaaaag 211020
atcttcattt acttcaccga cgtgtccctt tacctccagt tgaccatctc ccgtaattac 211080
accgtatact atctttccag aattagtgac agcttgaact tcttgttcgt tagaagccat 211140
tgctcctcct ctacgtctag aacatggttt tctagtactt gtagttcctg tacaacggga 211200
tgatttacga ggagcaccag ctgttacatc ttttggcgtt gggctattgt tgctagcagg 211260
tggcgtagat ggcaaggaac cttcagaaaa attaggaggt gtatttgccg taatagcatt 211320
aatatgattt agcagcgact ttaactgcgg gttaagtttg tgcatagctt caacatattc 211380
gttaaagctg ctatgttgtt gagatcctct ttttcccgtc atttaaaata cagaaaatga 211440
gtattataat cattattttc tttgtactta tatgttattt tgctttgttt ttctatacat 211500
```

-continued

```
catccggcgt gatattcgga cccgattata aacgctataa agacggtgat ataatagctg 211560
acagaattaa tgaagagaaa gttaaaataa aaaagattgc gaaaaatata gacgttgtta 211620
accgtgaatt acttaaatac tagaagtaac caagcgatga agagctttta cctgatcagg 211680
agtaagagtt tgattgaata aagtatcgtc gttcaaagta ctttttagta ccttatctct 211740
gtcatcagga gaaggtatac acttgtatct tttatacgca gcgtatatta acaaacagaa 211800
tattattact gttaccgctg taataacaaa agtatctata attcccattt attgataatt 211860
aacttttgac aatatttata atagtttaac tagtaatctt taaaaaatag taatttactg 211920
tatttcagtt ccaggtgatg tagcgtatct agattcatct actacgttgc ctgtacagta 211980
tctgttatat ccagagaata atataatacc aagaagtagt aatatcgcta gtataaaaga 212040
tataatacta atggatctca atgcgctatc tgcaggtttc cctgatttgc tcagttctat 212100
gtaagcacag atacatgcta ctattagcaa tattataccg aatactacta cgtaagatgg 212160
tctgtttctg aaaaagccga gaggatccat ttagatacct gaaaaactac aataccgaat 212220
ataaaaagtg gaatagaaac cacataaaaa tcgcagaatg tataaagaat ataatactaa 212280
actttgctct agtagacata ctgatattca ttatacacga taatatgaat atagtgacta 212340
ttataatggg ttcatagttt gaaatcattt atcataataa gattatacgt taaatagtaa 212400
ataaaaatta ccgccccact tataattttt taaaaaatta aatactttaa ttatatcatg 212460
attgcgcgga ttaacaagat ataggttttt gaaagatcta aaatacatat gtatgttatc 212520
tatataagat atttgaacat tttccttttt actaggtatt aaggaatatc tagagcatac 212580
acatataggt ttattatcat gtatagtaaa caactgaggt gttatagaat tagtttctgg 212640
aataattaaa accaatgaat tattttcgat atacatttat tgtgttagaa tttattactt 212700
tagcatcata tatcctaagg aaataaaata acacgaatag acataagaga actatacata 212760
ccggtattat agaaaaaaat gaaggtaatt tagcttcttt attataagaa tcatctccta 212820
gtacagtatc ttcagctata cttcctccac atttagctat caattctgct actgaatttc 212880
ttagtcttaa agtatctacg ttaatattac atcctatata tttacaattg gttctttgaa 212940
catcttggtc gaaaagtagg tattttctat cttttgattt atccgtacac tcgtgtagcc 213000
agcatacttt aggaccaaga gctaactcca aactaaaaag cttatcgttt ttgggtgttg 213060
taacacacca acaatttggg ttattcctgt gcttagaaca gtaagataat atagcggcgt 213120
ctgaatatcc aaagttatca ggtctagtgt aatctacaaa atcagaacag taattggcat 213180
ctaaatgatc actacaaact ttcatgtacg tatcaaaagc tacttctctt ttcttctcta 213240
gccattctct acaaggtaaa gacccgggag tctgtaagca tatagatgac ataatggtat 213300
cacaatgatc cgtttcataa ttattagaaa atatttccgg acagtcttta tcggattctt 213360
tattgcaaca tcttttaata tcaggatctg tatataagta gtctatatta ataaatctac 213420
atctagttcc gtctaaaaca taactttctg taccataggg tatcttttgt aaatcaagaa 213480
tagaacccgg tctaaacgat aatgatttgc aaggttctcc tggtactatt acgaattttt 213540
ttttagcttc gggtgataga aaagacgcac attgttttac cgtggtatct ctagttagac 213600
aaaaaggtgg ggatatttca ctaccgatat cacctgagtg tatgttttct gcttcgaaaa 213660
atctaatata ttcatcatca taaccaccag tatattctac tcttaaatat ttagtttctg 213720
gtgcttgggg agtagctatt accgttatgt tactgacgtg ttgacccatt tattttatat 213780
caaatcagta atttgaatgt gtctgaaacg cattaagatt ttctaacgaa gaaggcccac 213840
tcatctgcct gcaatatcta cgagaaggta tagatatttg cctatctata ccgtatattt 213900
```

-continued

```
ttactatata aaatccaaga attacaagta gtactacatc tatagccctt ttaaatcctt 213960
tagaaatctt agaagtactc gtcagataaa tcgtaactgc ggacgccagc attaagagta 214020
tagagattcc tacgtgcgtg gcatccgatc cattctttaa gtgcaaagct atacagtaag 214080
ctattattaa tgccggtacc ggtacaaaaa ttgcagaaag aataataaat atcaatgcca 214140
ccaaagagtt tgtattaata gcgaatacca acataataag cgccaacaaa gattttatat 214200
cattgttgtt aattatattc gagtatagtc gttctactcc atcaaatcct ccattaccga 214260
gtcctttctt tggtaaaaac gataattgtt gttcttctgt gaaaagttcc ttttctttga 214320
taccagctcc cgcgtcgaac tcttcgaaaa cattatagta atttaaataa ttgttatcca 214380
tttatataga taaaaatgtc gtatattacg gttatagatg ataaactata ttcttccttg 214440
aggaagttag taggttattc acctttatac ttgtttaacg ataaaggcga ttttgttgaa 214500
gtaatgaaga attctgaatt tagattcttg ataccatcag gttacttttc aaatagtaac 214560
gtaccgttat acggattgac gtttcttat ggaagaaact ggatgaaaga tagacaaaaa 214620
attattcttc cggaattata tcccatacag cgtagagtta tagaagaaat tatattacag 214680
ttttctagaa agtgtaaaga aaaaaggcct ttgtatacaa cgctgcattt agcgtgtggg 214740
tttggaaaaa cagtaaccgc tagctatcta ataggtactc ataaaaagaa cgccgtagtt 214800
agtgtaccaa ataaacttat attaaaacaa tgggaaaact caatatcatc attaaaagtg 214860
agctactacg tatcttatga aggtgtttct aaactttga aagtactaac ttctaaaagt 214920
tttagtatat tagttgtagt tgataaacat ttttcgaata aagagttctg tgaattagta 214980
tacgaaaact acgatgtctt tatactcgat gaagcccata tatataatct tatgaacgaa 215040
tctattatga caagttttct atgttactac ccccctagaa tatgttactt tctaacggcg 215100
actcctagac aacaaaatgc agtttattgt aactctataa taaactttat aaagttttca 215160
ccgttacaaa aaatccttta cgtaataaga gaattgtaca atgaatatac aaaccctagt 215220
atacgagcac acgtatctca gttacaaaca actgctaata agtatcatct ttatacagaa 215280
aaggcattag cagaggatat tcataggaat aaaactatag tagataagat aatagaaaca 215340
tttaaaacta atcaaggtaa tagaatctta gttataacaa aactacgcaa tcacatgata 215400
ataatatata atgatttaag aaaagtatta tccgataagg tttacttagg tgatgcacag 215460
aaaaaatcta ctaccgacat gattaaagaa ttaaggacga tagataattt tatattagta 215520
tctactttac attacgcggg tacaggatta gatatcccaa acttagatag cctgttcata 215580
tgtaatactg ttatgaacag tatgcagagt gaacaagtaa tgggtaggat atgtagagac 215640
actggttcaa gtcctactag atcaatatat ttatttatta atacatcgat aaaggaaata 215700
aaatcattgg taggtgtatt tactcaacgt tttgcacaac aggctacaaa gttaggattt 215760
agagaggtct ctcaaatggc ataatgaaga tccgcacgct ttacatcgga tattgctatt 215820
agtgaatact tttcctgtat ttagataatc gcttaattta tatttactaa ccccagaaaa 215880
cataaccaac tttgactggc atatagaaca cgttgtacat tcatcttctg gtataacggt 215940
aggcggttct ttacgtgtgg atgtagcgga tgtagatctt ttcttcctct tcttagcacc 216000
tgctgtagag tctgccattt aagagctata aaaataattc tgtatacgct ctttcgcata 216060
tgttgcgatg tttgataaat ttagaagcat catcacaagt aactgctatt aatgaattta 216120
tattttttat atcattgcat atcgctggca ttttcgtatt tttatttact aaataatttg 216180
cttttacacc aaatggtgta aagctataat ttatcaagtt atctcctata caccgaaatt 216240
tgtttccgta tatttgcctg tacttagtaa atgcctcatg ttctaatctt aatttatctg 216300
```

-continued

```
ctattttagg aactattata ttaaaaatga gaataaaata acaaactatt aaaaatagga 216360
cgaacatgtc aaagtctaaa gatctagata aactaagaga attattaaag ttaaaaaaga 216420
atatacattt attgggtaaa aataataccg taagatacaa cgaattgtta gattggacta 216480
ccaaaagtta ttggtctgta ggatctatac atatagaaga acatgtatgt gtcgacgaat 216540
actatcagag tataaaaaat aattcgtatc tattacaggg aaggtattat tttttgcata 216600
aatatttcgg tacaaaatat gtttatcttc atgaatcttt ttacgaactg tcgggtggta 216660
ctacagaagc aactattgaa aaaagcttaa aggataaaat taaactagta actaataaat 216720
atcctgatat acgatttata ctattcgtag aatataaaaa tacattcgct atagaagata 216780
tagtatcaaa agataactac aagctatacg atattttaaa attttctaag tcagtaggat 216840
taaaagttaa cggctgtttg tcattacaaa tagataaaaa aacacaattc accaaagaat 216900
attatgagtt aattcataca aatatcgaaa agataaaagg attttatata aacggtttaa 216960
tatgtattag agaagatacg ttagtaagag aggtatctga tgcaaaatct aacgagtttt 217020
gttgtgttca atctataaaa ctagaaaaga tagatgataa cttgtggtta ccgtacgcga 217080
ttacttttaa taaccaagta ttaaaaatat caggatttaa gagtttagtt agagctagac 217140
tctatgtagg atcttttgta tccgttataa aatatagaaa cattttgtta ttgccggata 217200
gtacggttcc ggataaacag attccaaaaa acgaatatat tagaaaaatc ttagagtatt 217260
ttaataatga atatttttca ataggtaact atatggtaaa aactggaact atagaaataa 217320
acaaaatagg caattcagta actggtatat tattaccctt cagtaattca gaggaattaa 217380
aacaaaaact agaagacgtt gagtttgtga ataaactgaa gtctagatcg ttattcgatc 217440
tatcgtgtga ttatttctta caggataggg aaaaagtaat aaagttaata aatgaaatgg 217500
attttaaatt agacgataat aataaaatag tagaatttga tcttaattca gaatctgtta 217560
ttaaagggga tagaatttta gaagacatat atatgaaatt tcaccagttt gttattgtgt 217620
ttaattcttt atcgacggct aagtctatgt tacccgataa ccaataatga ttatatgctc 217680
cgtagatata ggtattaaaa atcccgccta tgccatattt aattacgata acactagtaa 217740
tactattaaa ctaatagcca ttgaaaaatc tgattggacc aagaactggg agcgtagtgt 217800
agcgagagat cttactagat ataatccaga cgtggttatc ttagagaaac aggggttcaa 217860
atctccaaac tcaaaaataa tatattttat caaaggtttt ttttataata gtaatacgaa 217920
ggtgatcgtg agaaatccta cttttaaagg gggtagttac agaaacagaa aaaaacaatc 217980
tattgacgta tttatacaga aaatttctga atatacagat tataaaaatg atatattaaa 218040
caagtataca aaattagacg atattgcaga cagttttaat ttaggattat cttacatgga 218100
atcattacta aaaaagtgta aaataagtaa agattgatag gagtaagatg tatgaattgt 218160
tttcatacct tcacgaaata gaagatgaat atataaggac aatatttaac ttccatatta 218220
agaaatgtga cgaaatatct aatatatata atataataat gacaaaaata aaggatgcaa 218280
aaaactttaa tgatgttatc gatgaaagat ttaacaaaac tatcaaaaaa ttaatttatt 218340
gtgatataaa aacaacaaaa cacatcataa accaatcatg ttatccgaca aagaacaaac 218400
agataaaaaa gataagtaag ataaatcaat actttgatat aaatattata tcagatacac 218460
ctgcatctaa acgcacaaag gaaatatttc tttctgatag atcgtctttg gtttcctata 218520
ttaagactag caacaaaaaa tgtaagatag attacggtga attaaagaaa acgataaatt 218580
ctcataatag atctatatat tattctggaa gaagatccga cgaatacatg tctacagaag 218640
ttcataaaga tcaaaagaat ccgtggatta aatctatctc caagaaactg actcttgata 218700
```

-continued tagaaaatca atctattaca actagaggaa aaagttctat attgcagacg attgaaataa 218760
tttatgttaa tcgtacgtgc ataaaaatat ttaaagattc tactattcat gttattctat 218820
caaaggataa gtcagaaaca aattgtgtag atacaataaa taaactattt gatacatata 218880
gcatactctt cgatcttata acagatatta caggtaatga aaaattttta gaatataaag 218940
cggttgcctc tgatatagta tctacagata actttaatga aaaaattcta attataaaaa 219000
aacatcctaa tatgtatggt atacataatt ttaaaatagg tatgtttaat attacgtaca 219060
agttatctat agatatgatt atatttcctt cattaatgga attcaacagt aaaattaaat 219120
tctttaaagg taaaaaacta aatatagtcg cgttaagttc attgcaagat tgcattaaat 219180
acgttaaaga ggcaaaagga atattgtgta tgatgaaaaa aaaatctgaa gaattagaag 219240
aaatagatat aattacagca tccgtggata gactaaaaaa cgtaattata aatatctaaa 219300
atagaaaaat taatacatat ctaaaatgga tcagaaacta ggaaacaagt ttttggaacc 219360
tgatcctaag cagaatgttt tttataggcc gctacatttc caatatgtct cctatgaaaa 219420
tttcatttct tacagactta aagaaatttt gtctgtgaat agaacgttgt tatcttttaa 219480
gaatgataca gaaaagatag ttctaagaat taataatatt aaaattatac ctcctgatta 219540
ctctcctatt attgcaagca ttaaaggaaa aagttacgac gccttagtga cttttacggt 219600
agatattaga aaagaggtaa tgactaaaga tggactccat gtaagcacga ttagtagcta 219660
cgaaggaaat gattcccagt tgataaagat acctcttctt ataggttacg gaaataaaaa 219720
ccctcttgat aattctaaat ttgtatctcc taatattata ggaggagtct ttattaataa 219780
gcaatctatc gagaaagtag gtattaatat agtagagaaa acaactactt ggccgaaatt 219840
taaaattgtt aaacccaatg cttatacttt ttccttttca tctatttcac ccgttaatat 219900
attacctaca aagtatagac attataaaat tacaatggat ttatcacagt tagaaaactg 219960
ttatatatcc tcggcgaaga ctttcattac cgttaacgtt atcgttctta ttaaattctt 220020
gattaatcag gacttgaatt atatcaagaa taacttgact tatggcatgc ccttggaaac 220080
gatttatctt attaacgcta ttatagaaag ttctaaaaca atattagaag cagaagattt 220140
caacatcaat gattatatag agagtttaat agaatcagaa tttcagaaac aacgctctat 220200
aacgtctata gacgatttta gatacgatct tatgtataat tttttaccac atatggtcaa 220260
tagttctgat cagctaaaag gattctatct attaggatta ttaagaaaat tcatatattg 220320
tatctatcat actagtaggt atccagacag agattctatg gtatgtcaca gagtattaac 220380
atacgggagg tattttgaaa tactggccaa tgatgaatta gaaaattata taactaatat 220440
taaaaatgat ataactaaca gtcacaaaaa caaaggcgtc tgcaacgtta gtatccatgt 220500
acttactact cctggattca accatgcgtt ctcgggactt ctaagtggaa agtttaaaaa 220560
gacggatggg agttatagaa ctcatcctca ttattcttgg atgcagaata tatccattcc 220620
aaggagtgta ggttattatc cggaccaggt aaaaatatca aaaatgtttt ctgtaagaaa 220680
ataccatccg agccaatatg ctttcttctg tccttccgac gtacctgaaa gaggtcccca 220740
agtaggtctt atttcacaac tctctgttct aacatccgtt tctaatatca gaacaacaga 220800
gtatatagat ctgaagaatg ctattatgaa atatatatat acttacgata aaaacgatat 220860
tagttatttt caaacaggac atattattac catagagaat gacttagtcg cggctattaa 220920
tccggaatta gtagataaat ttgtagatga ttttaaattc agaaaacgag taaactattt 220980
tgataaccta gaaataggta tttcaaacgt taaagatcac atgaatgaaa tacgtattaa 221040
cataggaagc ggtagattga tacgaccttt cctcgtggtt tataaaggag aattagtgat 221100

-continued

```
ggataccata ggtgaagaat tagaaaagcg tatagatact attacgttct cagacatcca 221160
aaaagagtat ccacacgtta tagaaatgtt ggatctggaa cagtttgttt ttagcaacgt 221220
atgtgaatcc gttagtaagt tcagagaatt aagcgatgaa gataaaaaac tatacgatta 221280
ttgtgatttt ccaaacgagt ttagagacgg atacgtagca tctacattag taggtattaa 221340
tcataattct ggacctagag ccatattggg ctgcgcgcaa gccaaacaag ccatatcttg 221400
tttgagttca gatcttagaa ataaaataga caacggaata cacctgctat atccggaacg 221460
ccctattgta ttaagtaagg ccactgaaac atccaaaata gctattaatt gcttcggaca 221520
gcacgtctta gttgctctca tgtcctataa aggaatgaat caagaagatg gtatagtagt 221580
caagagagaa tttatagaac gcggtggact ggatattgta acggctaaaa aacatcaagt 221640
agaaattcct atagaaaatt ttaaaaatag agaacgtata aactctaccg cttattcaaa 221700
actcgatatc aacgggttag tgagattgaa tgcattctta gaacccggag atgccatcgc 221760
taaaaacatt tcatctagaa cgctagacga tgatttcgtg gcagataatc aaattagttt 221820
tgacatatct gaaaagtaca ccgatatgta tatgtctaga gtagaacgag tacaagtaga 221880
tttaacagac aaagtaaaag taagagttct aaccatgaaa gaaaggcgtc ctattatggg 221940
agataaattc actagtagaa ctagccaaaa aggtaccatt gcctatatag cctcagaatc 222000
tgaactacct tatgataaga atggagtaac accggatata atcataaact ctacatcaat 222060
atattctaga aaaactatct cgatgttgat agagatgatt ctgacatcag cttattctgt 222120
aaaaccgtat aataataacg gtaaaaaccg tcctatatgt tttcctagta gcaacgaaac 222180
agatatcgaa tactacattg aatttgctag aaaatgttac cagtctgcta tacctgatct 222240
agataaagat gaattggaaa acgaagtata ttgcgaaagt attttatacg atccagaaac 222300
tgataaacca tataaaacaa aagtgtttat gggacctctc tactatctta ggcttagaca 222360
tcttactcaa gacaaagcta ctgttagatg ccgtggtaag aaaactaaac ttattcgtca 222420
agctaatgaa ggtagaaaga gaggaggtgg tatcaaattt ggtgagatgg aaagagattg 222480
tcttatcgct catggggctg caaatacgat tacagaaatc cttaaagatt ctgaagagga 222540
ttaccaagat gtttatgtct gtgaaaactg tggcgatata gctactaaaa agaacaataa 222600
tgtttattgt attagatgta ccaaattaaa tttgtataca gttctgacaa aaattgatac 222660
tactcatgta tctaaagtgt tccttaccca aatgaatgct agaggaataa aaatcaattt 222720
aacttttaac gaacaaaatc ctttattcta taaaccgatg aagcaaatcg atctctcacc 222780
aacaatatta aaaaaccatg atctgtcata atcacgatcg gattgattat ctagtttctt 222840
cggtaattct atagcgtgtt tacgcaagtg atcataatct tcctcaagtc gttccatttt 222900
tgatttaatt ttgcgataac tatctccgaa gctatcagct tctaatttac gcattgctct 222960
atcgacatca ttaagtctat cttcatcaga cttgtctttt tctctgggat attctctatc 223020
tttatccgga tgaggcctgt atacatcttt ttcaacgccc aagttgcgat gccctctatc 223080
gtaataatac ctatcttcgt cttttagaag atacccattc ctacgatttc tcaaagactt 223140
gggtgtataa tcatcgttat gtatggcatc catcatttca tcttcgaagt ctttggcact 223200
ttcaagattg ttggctctct taggaacaat gtgttcatca tctgaattac cacgatcatc 223260
atattttttg tgtttataat tatagtcatc gtagatatcg tatttgtttc tacgatgatg 223320
gcgtttatta tatacatctt ccatactatt atgcctcctt agtataggag cttcatcctt 223380
gattagatca tcttcgttgt tattattata atcgtcgtag tcttcttctc gaggaaactc 223440
gtcctcatta cgatttaggg taccgtttgt actaggacag ttctttctac gatcacattc 223500
```

-continued

```
aaaattgtct atataatatt cttgataatc tttaggccta cgttctctat cgttactata 223560
atcataggaa ggatatttat catcatctag ataccatttc catcttctac aatcatcagg 223620
gaaaaatagc atatgtctat tttgatagaa atcgttatct ttgtccttga agatacgaat 223680
agcgctacaa tcgtgaatac aattaggact aaaagacatc tttgtagtcg gaaattcgtc 223740
ggtcaatcta atatattcat aactatcacc aatatggcat ttagtatata gctgtacaaa 223800
atcataatga ttcttcttaa tggtaacttc atcggtaaaa caataacata gaccatccat 223860
gacctgttcg gaaatggaat agtcagtctc aaaaggaata ccacagagag atatctttag 223920
ccctttagtc tttgcttttt tggatgccat aatgaagtta agaaaatctt ggtatgcgca 223980
catttccttt atatggatag tagtatttct ttcgtattct tcaggaccag tacgcggctt 224040
tctgcctacc gattccatag ccgtgataat atcgtctggt gacataagat gaatatagta 224100
aacgggtaac cctataaaca tgcatttgca tttaaatcta taatggacgc tagacactaa 224160
tcttagataa tctgtaacga tactagaaac ttttttagat actgtacgtc cggaatctga 224220
atagctaaat ttggtatcat tatttcccat gtacagtaga tacattacga aataaagcac 224280
atatctacct ttggtagaaa tatcaggcat acgatcgtta gacatatcga ttttattata 224340
tagtttttttg atgccattat tattatattt tataaattct cctaggaaat aattttctaa 224400
gtttttagga tacaacagtt gtgcttgtac tccatggata cggtcattat cacaactata 224460
atgaataaaa cacctaaaga tgttacgaac gacttttcta tcccttctag ttaggaaact 224520
tctttcgttc aaatcatgat cccaagttct tacaattaga gtttcgaact tccttatgca 224580
cttttcgata ccacatttgt cccaacccat ttatatattg aaataattat ggaatataat 224640
gtaaattatt ccatgtatag atggccatat cctgtctggt aatctatctt cttagcgaga 224700
tttaccatag agtgtctcag agtatcagcg tggcgttcta gacggtctat agcttccgct 224760
acgatgctgc aggatttagc tacttctacg tgatcttgtt ctattctacc caaccttctt 224820
tctagtcttc tgagtgcttt ttgtttaagg gagcccaaat caccccgctt tttattttca 224880
tcgtatatat caaccttccc attttcagga atatttttat ctattctatc atcatcatca 224940
tcatcatcgt catcatcatc gtcatcaatc ggatcttcat ctataagtaa gccatcagaa 225000
gctttaccgt cctcgggagg aacaagatca tctgaatcta atttaacacc accagcggat 225060
ttaacttcgc ctattgtata gaatggatgt tcgtaagtag ttatcagatc gtctggccta 225120
ttaccttctt cttcaggatt tccgatagaa atagcaaatg tatcaaattt cacgcttact 225180
ggggatggga acttaacttg gggagttctc gtattaacct catgatatac atattttttg 225240
ctgtctggca agaatcttag atagaatctt accttatcat tcgtttccgt ggctattaga 225300
tcgtcgtgcc tataacacaa tcctttcaat acgtattccg gtacagaatt attaaaatac 225360
caagtactag cggtagtagc caacataaca actttcctat taccgggatt tctaacatta 225420
tttttgagat attctatata ttttttatgc ataatcatat acggtctcga gaacatgtta 225480
ctaccccatt ctagaatttc tccaaaagcc gaatcatctg gaaacagata acacggaata 225540
cctataaaca tagatttaca tctgaatctc atatggatac tagcgattct attaaagtag 225600
cgatgtctta tacggcgtat agtttcgtaa attttatccg tttcgtcttg cgttaagctg 225660
atacgttctt tggcggtggt tataaaaaac attactataa aagcaatata cttgcctact 225720
gtgtctaccg agttaaaact atgaatttgt tgcaacattt ctgcgaactc tccgtgattg 225780
tatgacatta gactagtata ggctcttcct ttaatcaacg tttcataatt gagtattttg 225840
ccataaaatt cggaaactga tatatgatct ttgaaactct ccatatgata acgtattata 225900
```

-continued

```
tttcttatac agtttgcata gtaatagttg atatacgtat cttgccttaa ttgcgtattc 225960
catgattctt ttactatact cacgaataat gtaactggat cgttagtgga tacgggttta 226020
ggtattacta catcatcttc ttcttcaccg gctccaggaa caacatccat ttatagatgt 226080
gattttaaag tgctgcactc tgcagaccct tctccgtatt cagcacaagg attccatatg 226140
gtacctattt ctcctcgagt ataattatag tacacacaat cttccaggtt agtaaaaagt 226200
acaggatttc tacttgatgt agctaaatat ccaaattttg atgcagatgc gtattggtta 226260
ttattataat tcacgcatct ccatttagct ttaggatcgg tttccgagtc attaggatca 226320
aatacccttt tgtcgatgta taaacctcca ggagatctag aatattctaa cccgccatat 226380
ttttcattaa attctattat gttatgatag ttatcgtata tggtataggc ttgaaaaaga 226440
aaaagacaaa ttaccgcggt tgctaatata attatgaata cgaagagagc atccattgat 226500
ttataccaaa ttaattaata gctttatata tttcacttat agttttgtta acagctttgt 226560
gaaaagtttt cgtgttaatg gatgaaatat tgaacttatg atacgtacct aattggcatt 226620
cacatccgaa gaagttaata atgcacatag tcgttatatc gttaacaaat acgatgttag 226680
acttaggatc gtacgctgat gatgttggtg tatctttttc catatctagt tttgttatat 226740
taaattccgc tatttgatcc gatataactt cttttagata agataacatg cttttaaagt 226800
atacagaaga attaaaccac gtatattttt ccatgaatat acttatatta ccttcgggtg 226860
caataatgct aaaaggaaaa tatgtttcat aattttgtga gtgaattatt ttaacgtttt 226920
tatattctct attaaataat tcggtatcta aaaatgataa tctgtttact aactcgtcat 226980
taattttagt tccgctacta aaagcggcta attctatagt tttagtattt gttgctctat 227040
attcggagaa tgaatgtaat aacgtttctt ttaattcttt tatgggatct aattttatta 227100
cctcttctgg tttgataata tagtagtcta tatctgccaa agaaatataa ctgtcgtttt 227160
ctttctgtgt tttcttcaag tgaatacaaa agttacattg catagcaata atatcgtata 227220
cataatcata aaatatttta tgcgttggta acgattctat ggatgttagc cattcttcgt 227280
taatagcggt agtagtattt atcataacaa ctcctacgtt gagtctagga attactagat 227340
gcttcttaca catatgcttt ataaaggtcg caatactggg attagcgcta acatcaatac 227400
gatactcttg acgatgcatt gttcatgcta ttaatatttc tattgttctt tttatatttt 227460
ttatctattt ctattatcct agaatttatt attttaagaa cttcttgcat taatgagata 227520
gtagcagaga attcaggatc tctaacattt gctaaagttg acagcatgtg gtttatactg 227580
tcttcattta tatcatctat ataatctata tcatccattc ctactattaa actagtatat 227640
aaaaagggaa aaaaaataaa aagtgtttaa tcacaacttc tgatagattg ccgagtattt 227700
atatactgtt tttaatattc gtgatatagt agatatatat ataagtttag tgtatatagt 227760
taatagattt acaatctgat aatacattta ataaagatgg aaatctttga actaatatcc 227820
gaaaacgaaa agtattttaa tggaataccc ataatattac caaagaagaa aaaaacatac 227880
gtttacaaaa atattacatt tatattttat ataccttctg ataacaagat agaacaatat 227940
atacaacgaa gtgaattaca ctattcagat tttatagttt atggaaaggt tataatagac 228000
gatgttgaaa tgcttcttct ttatgtaaac tttgaatatt atggtatatc tatagatggt 228060
aaaacaaaat acttaggaaa aagtataaaa gacctaaaga taagaggaac taagcggtgg 228120
aaagacttta ctcattaaat ggatatacta acgatcatga aaagaattaa aagcggtaaa 228180
gatattactc cttccatggt tactaggttc gtagaattgg taggtaataa agaattattt 228240
tatgatccac taccgataaa actgagttct agcactctaa caggaagaaa tattaattat 228300
```

-continued

```
tcagaagaac acgttaaaag tatgatcgtc attatctatg gttatttacc cagtataata 228360
aagaaaaaga tttttgttaa caagataagt aaattattat ctatacctcc cgacgatgca 228420
ttaaaaagaa tatttgggga cacatcagaa ataggtgtta atacatttat taagaaattc 228480
cttgctgagt taacaagcta attcttgtaa agattcttgc ttagaatagc ttttaagtag 228540
tttcatatta ctagacgctt ctttttcggg tgaatatata caatcttttt tatcacgatc 228600
atcatttata gaatttagct tactaagatc tttaaaataa tctgtatcct tgttatcatc 228660
gcttaatatg gtatgaagct gatctttcat atgagagaat tggcttaaca atatagcggt 228720
atcaggtttt tgttcgataa cggatttatc tgctgtatca tagcatatac gtatatcctt 228780
atttgcaaat acagtatttt ctataatata gacctttta cctctagatg cagcacgcat 228840
gacagatagt gcttttatta tctgcttagt agcgaccagt gacatagacc tagtaatatt 228900
ttcgatatcg gcatcagata cattgcaaca acatagatgt gtaatgcttg atctacaatt 228960
agacggtacg tgtctatatg tttgacataa cataacaata gacatcctta tgtgtctacc 229020
cgtgtttacc aaccaagata atatcttaga ttttaactgc atatcaccta aatcatctaa 229080
tattaccaaa aatttgtgat taatagaacc gcgttttcca agatttacta aatcttgttt 229140
catttttgat agtgaatatt ctaactcctc ggcagtagtt attttatata tatggtcggg 229200
ccatacataa taattatacg atggattgag tataggagta aacaagaaaa tatgtttata 229260
tttcgttata aatgttttaa ataaagatag gagaaatgtt gttttacctg atccgctacc 229320
tcctaatata accattctaa aataatcatt caacaagcta ttcctattaa acttaacttc 229380
ccttacgata tccatttaag ttgtttgtga tatttatata tctccgaaat tgattataac 229440
tatagtgctt cagtatgaaa gattatttgt attaaaatat atatatatgg aataaaatgt 229500
atctatatat ctatttcgat atctatgtcg tgtaataggt tatttattaa cgacatatgt 229560
cttagtgttt acgtatctta aatatgaata gacaaagcag tgagaaacta aaaaaaacat 229620
gcgcttggtt tatacattta atagcttcaa tgtgcggaac tggattattg ggactatttg 229680
ttacaaacgt tacgttatac agacagataa aaatatgtgg gaatagagaa ggcatgtcag 229740
gatgggtaca gattaataac aactgctata ctatggtaga aaatataaca tttgatgaac 229800
ttatagggca ttgtacaaaa cacgattcaa taattcccaa tgctttagac caaagcgaag 229860
tattaatcgt ttcttctgta ttgggtgtta aagaccattg gatgccgttt accaagaaaa 229920
gtagaaactg gtttcacgga aagttacctg tgaacattaa aggagatggt gataaacgtg 229980
aagagttagg aaaacctaga aaacctgata aatcagaaaa atgtactata tactatgata 230040
acggtatcat agaagaaaac tgtaacaaaa agcatacggg aatttgcttt agtccatttt 230100
tctaaaaagt tataattggt aattttttaa aataaatata tttacaataa atatacaaga 230160
tgcatatcag tagcttttac atattatcta ttatttgttg tactagtagc gctaatatca 230220
tagcagatat cggatcttct gtagtagtag attgcaaaat acccaacaat tatagcgtag 230280
ataccgttat attaaagcaa acttccagcg gtaagacaaa taaaataacc gtacctaacg 230340
aatacataac tggaaataca tgcaatacgg gatatagaac atacggattt actattaata 230400
atgtgactaa aaatgatgaa ggtagatata gatgtagttt ttatctaagt agcgtacaga 230460
tatacgaaac aaaactgact atgtatgtta ttcctgctat cgacgcgtat actctagatg 230520
ctagggataa taaaatgatg tacgcgtgta atagatcaag atctcgatta tatgatgacg 230580
atattaacat ggatattata ataggaggag tatatatatc tggtgaagaa aatgtacata 230640
cttttgatac ggatcacagt ttacatatat atacatttgg agataagaat tatcctgata 230700
```

-continued

```
tatcaaaaca aatgacatgt ttactaacgt ttaaaggagt aaaaaaaact aaacgtataa 230760
cgatttacga ctactcgtgg gaatctctaa taaatgataa tgaaatatac gtcgtctaaa 230820
ttcatatttt ctcttcttaa aatacactat aacatgaaat tcataattat actattatct 230880
attttacaat acgtctattc taaagacgat tattacgatg tggtatctca cgtaggagat 230940
tccgtaatcc taaattgtaa tgattatcca aatactagta atgtagattc ggttatttgg 231000
tttaaatatt ctgatcctgt taataaatac ttaagtatat ctactattaa cggaacacaa 231060
tactataaaa acgatcacaa gatatttaca agaacatcag tagacctaaa attaagttct 231120
ttaactatta ctagcgcatc tatagaaaat catggatgtt acggttgtaa atttaaatca 231180
ggaatttgta atagggaacg taagacgtgt ctaggtatac tagattcagt gtacctttcg 231240
tggatatctt tcatgtatac tactagggta agatgttata tagtatctgc aaaaaaagat 231300
ttgagcatta actggatggt aaacggtgtt attactgaag ggatgtcatt taatgaaatt 231360
agttatgacg atagttattt gtccgggtgt tttatgatag agttaaagat aattaatagc 231420
tttagtgata aggtaatttc tcctatatgt agggttaatt tcggctctaa aggatacaaa 231480
gaatatagaa taaatctaac aaatacactt cctgatacct tatacgataa atattctaat 231540
cctataagat attataatcc atcgaattca cgtattacaa aaatgaaata ataaaactag 231600
tttgtaatgt gatggcaacg gttgctagaa tgtataaaac tataaatacc accggtatat 231660
catgcgtctt gaaaagtttg ataccagata gctataatga agaatacaac atagatgacc 231720
tagatctatt aaagataaaa gagtttatag agatatccat gcaaagatgc ttttctataa 231780
aatccgtcac agattccaca gtattataca tagagaacag gactaacaga tattctatat 231840
ctactagtca cgataagaat gaaccgtatg aagaaaatgg tattataatg aacaatatag 231900
agtgttattt tgttgcgtgt ctagaaggat cgtgtacagt aaatgtaaat cttggagaca 231960
gacaaatatc agacaatata tctgaatcat caggattcct aatggatgta aacaccgatc 232020
acgttataga tacaaaatat gtaggattat ttattacaaa aatcaaagta gatgcgcatg 232080
tattttacgg gcaaaatgtg ataatgtttc cagaaaaaaa cttgttttct caaactaatg 232140
gtcctaattt cattttatat gatataacag ttcaagatcg taatgtactt ttgcttataa 232200
cgagcaagta tatttacaat ttgtgcgacg ataaatacta cgatattttc gaattaaaat 232260
atctagttga taactgtaaa ctacctatgc ctcttattcc actatcgaag tacgatttta 232320
catttactga tttgagtgtt atcaaatcag agaatgttaa aacggtactc tctaaagttc 232380
atacgagtat gaaatcgtac tacaacaatg atacgtctct tcctgtcgcc gttaaggtga 232440
tttacggaac agtaacaata taaaaagtgt ggagggagct ccggggggaa tagcgctggc 232500
tcgctaactg ccatattagc ttctgtaatc atgcttgctt gccttagccg ccattgtact 232560
tgatatattt cgctgatatc atttctcgga atcggcatca agagcaggct cataaaccat 232620
aaaaggaaat gtttgttgaa ggcaagcatc agaccacttg cacactaggt ggggcagcag 232680
gggtccggac tgaatcgtcg tagttcggta caacagtatt attgtataat attatatttt 232740
gtaatatata aaaaaataga aaataaataa tatattattt ttataatgga tattataact 232800
aatacaacta tgtttgatat acaatttaac gatataccga atatacccta tgtagatata 232860
gaaaagccct tattggtata ttcgtgtgat tcttataggt tatataacgc taaatatgac 232920
aacaatcccg tcagtttgaa gacttttaca tgcccatcta aaaatagtat aagacagttc 232980
ataaaagaac tagatctgtt acgttctcta caatcttctg aacacgttat taaactttac 233040
gggtacatat tggatatatc cgttccttta tgtagcctgg tggttgaaaa taactacctt 233100
```

-continued

```
acgttaagaa actttttaga tatggaaaaa gatatagatt acgccaagaa aacaagaatt 233160
atcatagatg ccgcaaaagg tctaaatgct atgcatacta gctactcgac tcccatacta 233220
cataaaaatt taaccagtga atctttttac atgactaata atggtgtttt aaaaataggt 233280
agcggggcat attataatat atacaaaaga gtaaatttta tggcatattt tgattatgac 233340
atgttaaaag atatcttttc aaattatact ataaaatccg aaatttatag attcggtatt 233400
gttatatggg aaattattac ccgtaaaata ccttttgaaa atatggacta ccaaggaata 233460
tacaatatgc taataaagga aaataaaggc gaatatatgc ctctagactg tcctctggaa 233520
ttacagtgta ttgttatcgc gtgtagaaat acaaattcta tatttagacc ttctataagt 233580
gcaataattg attttctgga aactttttat tctaatataa ttaaaaacag aaacttaaaa 233640
tagactaagt agagtatata cacatattac acggtaacat gtttgctatt tcagtgttaa 233700
aggaattata tgattccgga gagcctttat tattttcacc tagagggcta cataaaatat 233760
tatgtaatat caggcacggg tgcaacggaa atactaaaaa tcaattagat aatttattag 233820
aagaaaccat atatgattac ggagaagacc aggcgcttaa acatataata actaacattt 233880
ctgttctact aataaaaaga tgttataata taaacgagaa atttattaaa gatagtaata 233940
cgatatataa taccgatgta ttagaatttt ataatgtaag acaaatacct agaataatga 234000
ataaatggat tagatcaaga tctaataata aaataacaga tataggatgt catatctacg 234060
ataatactaa gtctataata gccgaagcaa tgttttttac tatgaaacac gaatctatat 234120
tcggttcaac aagaaaagat actataacct tctataagta cgatggaact tcgttacccg 234180
tagaagctat tcacgcggat ccatactact atccttatag atattttgat gatataaagt 234240
gtagcgtatt gcaattatgg aaactaggat acgcttttaa catgtttatt atattaccag 234300
atgatgaaaa aggtttagat aacttagtag ataatattac tggagatgta ttcagtaaaa 234360
tcatgaccga acaaatggat tataagagat tagaattacg gatgccagta tttagtatta 234420
gtcaagagac taacttttgt atgcctatat ttaatctggg atgccatagc atgtttatag 234480
acggagattt tagtggaata tctgaagtgt cagatttcca actttcaggc ataattcaga 234540
aaaatatcat agaagtacag tatgacaagg ttaaaacaac taaaccttta aatgtaagat 234600
gttcaagctt ttatgttaat aaacctttta tatttatagt tactgatgta ggcaattacg 234660
atactatccc tatactgtta ggtatatacc agggaagtag taaatagttt taattatcgt 234720
ctgattcgta ttcgctttcg tctatatggg taattaaggg ttctctatct ggatgaacgt 234780
taatcaatat aaacttttct gaattactaa tagtttttat ttttttattg atatatttgt 234840
gtttgtatga aatataacat actattataa ttattataac aacacatata ctacttaaaa 234900
ctagcgtata tagctgataa ttattcaaga aatgtactaa cacaatgttt gttgtattgt 234960
tgtaaagttc cgtagagtta tagttatcgc gtcttgttat atagctatcg tctacgaata 235020
tactttctat aacagaaccc atacatttct tctttattcc tatggataca tggtatacat 235080
cacccgtact ccatcttttc agtgtaattt tgtctaacgt taggttagat aagtagttag 235140
gttcttttat gtgataagag tcgggaaaaa ccattatacc taaggtttta taaatctgac 235200
ttttaggttc cttcttttct acatacatcc atttaacgca ttttatagaa gtagacgggc 235260
ataatattat attagcctct gactgttcta tagatacgct tcttttacac ggatatacat 235320
gaacaacgtt agataaaatt actaatatcc taataacacg attcatgttt aaatatatag 235380
tgatttatag tatattataa tattattata taagaaaatg taatataaat aatatacatg 235440
atacataaaa ttgaaattta attaagacta gcttacaaag atgaatttca caggtgattg 235500
```

-continued

```
tcttttatac gcaggatatg aaaaattgtc actatctttg gccgttgtta ctatactcat 235560
attttcttca agcttgatat taaatatatc ggcattagtg attggatttt atactacagc 235620
gcctgggcct atgaagatgt atcttattaa cttgatagtc tctgatatac tattcacagt 235680
aactttgcct cttaaaatag attattacta ctatttcttc aattggagat ggggagaaat 235740
ggcgtgtaga ataatgtcat tcttgtctta catcaataca tacgtaagta tcaatttcat 235800
gacgtggatc agcgtaaaca ggtactacgc ggtaactagg ccccataagt acaattcgcg 235860
tgacaatatc atgagaacaa agattgcatg cgcgtgcact tgggtgatta tattagtccc 235920
tatgtcatcc atacttttcg ttagtacaac gagttcggat cacgaaacta agattagatg 235980
tatggaatac aataaagtag gagattctat gtatttacct ccgtgggtaa ctatcgttat 236040
gtgctttata ggatttgtaa taccgtttgc tatgatggct ataagctatt cagctgtatg 236100
ttataccgtg ttatctggta tatctaaatc tactagatct tatagaacct gtaaactggt 236160
agcttgtata ctaacagaat ttgtcatttg ttttttacct tatcacgcat ctgttatatc 236220
ttatatgatt catataataa cttcaaaaac agtattatgt gaaaatgtat cttactacca 236280
aatgttacta catgccacac agtgtttgat gaagctgaat tgttgtatgg atcctataat 236340
atacttattt gtatctagtt ataaatctaa agctaaaagt aattctataa aattgatgtt 236400
taagtagatt tttgaaatga tatctttacc atcatcctgt caaaatatta tcaacactgt 236460
cataaacgga aagtgcttct ttggtagatg ttctaataaa cgattaaaaa tgactgttcc 236520
tatgacgtct tcggaactag cctacataca agaatggatg ttagaaaaac atgatttatt 236580
tatagaattt ccaatagatt tgattaccgt ggaacatata atgatgcatt tggctgttga 236640
cgttactact attaaaagaa aaaaaagtga tattactgcg tatagaactc gattgaaaga 236700
tgtacccgaa gccgagtaat ctattcttaa tgtttatttc aatataaatt actattctgg 236760
cgatacatca ggattttatg taccctgttt ttatatctct atttatagca taacactata 236820
aatgaggatc ccaagtactt acttaatgaa atgtagatgg taaagtggtt gtttttagta 236880
gatccctcga ataaaagaag ttatagaagt gacaaactta acggattcgg ccccatttgt 236940
atatctgtca ctaactggaa actgatacac atattatttc tagacaagat cctttatcgt 237000
cgatgctgtt aggttctgtt aaaacgtaac agtttacaag caatgtgtta aagaaaataa 237060
gccgttggga tataacaata gctctaaatt cttgggtaca gacaatcatc ttgttatgta 237120
atgtagtact tataaagacg taggaaacta tggtataaca tctttaaagg tatactctgg 237180
ttgtagttaa gtggtaaaag aaaaatatca agtaatagag ctaatattat agggaataaa 237240
caataactag agaaatttac atatagttat ttttgattct tataataatc taaatacttg 237300
attataactt ccagacatag ttccatttat tgtatattct agtttatgct ttctatcatc 237360
ctgtatcaac accttatttg tacattcaaa actattattg gttttagata taatcaaata 237420
tcttatatat ttgtttaacc tatattttta ttgtagtttt catctagata ttttaagagt 237480
catggtgttt atttttaata catattataa tataatgaaa tatataactt aacacatgaa 237540
agaccgcaat aaaaaactaa aaagtttact tctttagaaa atatgatata acctattcca 237600
attaatgaaa aggagtatca aaagtcctga tttcataata tggataaacg gacaaagaaa 237660
tatagttaat acgcttagat tcgaggaacc aaatgtatgt ataaaaaata ctttacagct 237720
tgtttcttca agattttata aaaatatcag ataccgcacg atggggagat gttttaccca 237780
aatatttaca tattcaaatc ttccatgaat gaaataactc ttacagaaag aattattata 237840
taaccgtagt tctgttctac ggaattaaca actcgtgaat ataaagatac aacattcagt 237900
```

-continued

```
ataagaaaat aagaagcaca gttatatcat tgcgtagcaa caggcaagta gtaatgtaat 237960
acagattttg gttgcttact tgcagttcct ttctaaaggt tattacagtt acaccggaat 238020
actaaaatta gaatagacga ttcatattac acacctgttt gtagatttac aatttaaaca 238080
taatacttta gttttttgta ttttctaatc actaaacttc taatttcttt tggattcata 238140
gtttttatag gcattatctt aatcataaat atattatcga tattatacga attaaatccg 238200
tgtacgtaat ctacttctct aatataacat tcaaaaatgt aactttttcc agacgaataa 238260
gtacctactt ggaatcgttg atctgggcta caaaacctat gctttgtaat tctatgaaat 238320
tctgaaaata cacgttttaa atcctccttt tcgtttataa aaaacgtttt tatagtgtcg 238380
agtcctctgt gtttccagaa gaactcctct ttcgaaatat tttctgatag aaatctaccc 238440
gtgatatcat ctttggtaga cgccatgata ttaccgctat ttactttaaa cgtatatatt 238500
taatttcatt ttaaacatat attcatagat atgtaatgta atggtataca gacaataata 238560
taaatatttc aaaacctctt ttactaataa tatatcatca tattttatta gaatctaaag 238620
ttattcgttg gtctaagtat tctagaaata taattaatat aaaaaccata ggtaggtatt 238680
gtgggatact ctagttgtaa ttgtaacaat aataggcgta aagaatcaca ttcgttccta 238740
aagataacac cctatataaa acctgtaatg aattattata tgaacataag atgattatct 238800
tgaggatgtg agggagttgt agtaagtagt ttctttctag aaagagatat acatcctttt 238860
aaaaaaatgt atatatacac cagtaattat ttcaaaagat atattaatca ctatacacta 238920
attcaaatat tacacatact acggtaatca atagtcatag gagacgtgta tgtatacact 238980
aaataaatcg aaaaatacaa taaaagaata taaaatgtca ccatcggttt acattgatat 239040
gttatatcta aaaatacatt taaactataa taatacaaca acacaaagta ctcttaaaaa 239100
tatacaagat gaaagaacca ttaatagaag taaagagaga atacaactta ataaaaacat 239160
taacgggtaa gaagtttgtt gtttctactt ccatcgtagt agtattgtta ataattaata 239220
tgatatttta tggtattaga atacacgaac tagctgttat aagaagaaac tctgaaactc 239280
atatttcttc ttttaactat aaaggacaag cacaagcaca aaataaacgc gtgaaaaata 239340
ctagattatt tgaaaaatgt aaaagtaaat ttaataactt ttgtatctat ggtgaatgta 239400
tgaatattat taatttagat aaaaaatttt gtatttgtaa taaaggttac accggtaata 239460
ggtgcgacat agtaagtata cgttaacaat gccccaaaac aaggttttat catttcctct 239520
tcctgaaggt actttactag aagatataac aaaaaataaa tggatactag gaaagcaatt 239580
aggttctgga ggatttggat tagtatatca agtttcttgt aagagtaaag aaatagattg 239640
tgtagctaaa atagaattaa aagagagtgg tgggttgttt tgtgaaatta atttctataa 239700
tagagttatg aagaataaaa catctcttga tacatggatg aaggaacaaa aaatagatta 239760
tataggtata ccttctttcc atggatttgg tattactatc tacaagaacg tagaatatag 239820
atttgcgata atacaaagac tgggtagaga tctggaaaat atactctcag aaaaagaaaa 239880
atttaatatt actgttatta aaaaattagc tattaagata ctggatatat taaaatttat 239940
acatagtaaa gagttttctc acggtgatat taaagctgga aacatactat tcggtaagga 240000
tgatgacaaa gtatacttag tagactacgg attagcgacg aaatattcat cgaatggtaa 240060
acacaaagaa tatactatta atcccaaaaa cagacataac ggtactatgg ctttcacaag 240120
tatagacgct cataaaggag ttacggtatc taggagaggc gatttagaat ctcttggatt 240180
ttgtatgcta aaatggtact ctgggaaatt accgtgggag aaatacgaaa aagaacctga 240240
aaatgttcaa ggcatgaaag aagcatttgt caataatata tctaaaaaaa ctataccctt 240300
```

-continued caaaaacgcg ggtataattt acaattatat aaaggtagtc actaagttag aatacgaaga 240360
agcccctaac tacgaatcac tgaaacaaat gtttttataa gataaatata ttaatgaaaa 240420
aacaagctca tagtaacaga ggtttacacc atggaacgag taaaaaaatg ttttagtaat 240480
ataatattct tttctaaaga tgtagatact agtatgtttt ctccaaacat agtttatagc 240540
ggattattag atagttacaa ttttagcttt gtagatgcat tattggcggt taatctgtct 240600
ataggtatag tacgtcgtag agagacttta tgcagcaaat gtactaatat atgtattttg 240660
aataatcaag taaaactatt attagaattc ggatatagag acgataagga tataattaaa 240720
aaaggtagtg tatcaatagg tcttttaaac atggattcta gagtaaacat aactactcta 240780
tttccaccct gttgtaattt tatggatgct aaagtactaa atttcaatct attattccca 240840
gaatgtgatt gtttcttcgt cgatgtaaag atgaatatag ctgaagaaag taactttata 240900
cccaggtact tgtttgtatc tcctttacag gatagctaat ttaaataatg acatatagtt 240960
atatttttct cgtgttcatt ataaacataa atatgaagat actttacatt gattatgtac 241020
ttttgatata acatgtgtaa tgctattaga atacggtgaa aaacggctaa ctaatgctat 241080
cgtatcgata agtatctgag atagtaatgc cgctatgtgg taaatttatc ccacgaaata 241140
gaaattatat ttgtctatgt agataagaat ctctaatgtc aaatgatagg ctctaactaa 241200
ccttctaata tttaccgctg tagcattgaa acagtattga aaaaataact tattacgatg 241260
aagacgaggg tacaataatg ttgtatatat atattatatc aacatctata ctattagtaa 241320
aaggatacgt gatagaaaat aataattgcg gatgcggtaa tatcacggct tccaaagatg 241380
taactacttc taattccaca tttgatagat tattgtgtac tgtatacatg agttctgaag 241440
atggttacat ttattggata ggccctaata gtacttttat agaaaattta gaaggagcta 241500
atgaaggttc tgacaatact tttgaggtag gtaatgaatg ttacaaacat actagagaac 241560
ttaatataac atctagggat tatgtaggca agaactttac gtgtacgtct atgacagagt 241620
acggaaccac attcttcaat gtaatactgt aggtatacta taaaaaaagt ataaacgtag 241680
tatttgtata tttctttata tgtataaaaa cttccattct aaatatagtt actatgttgt 241740
tagtattaaa acacatatag taacatgcaa ttctttactc ctatacttat gctagttact 241800
tcgctagcga taattacggc tgtaactatg atatcgttgt tgataacggc tactataata 241860
ttacccatat ctttgatatt accatctact agctcatcta cgtttttggt aacggtaata 241920
tcacttatct cttctgtatc tatagtcgct atagctataa atacagttat gataatacga 241980
tctcattaat ccgtatgtaa aaaaaataat actaaatgaa aatataataa aatcggttac 242040
ttacgaattt agacttctat atagaaaaat attatggtag aagtctatct ataaacaaga 242100
agatgtgact tattatacgc gtacataact tcatgatatc ttttaatatg aattacttca 242160
ctttatcttt cttacctgat tattgtttaa agattaaaag tgaaatatat tggaaggtaa 242220
tattacttaa ctactttaca gcgttaggtg ttatagtctt aatatttgta gtacctatat 242280
tactataatt gtttaaatag attaactatt gttacgggta tatgatatat ctactataat 242340
tagtatgtta taaaaaataa aaacaagtac aagtaaaagc aatatgagca ttactagtat 242400
aataaacaac ctaatagata tcataacgct atatattagg attttttatg taatatacta 242460
tattgctata aaatctaaaa atcagatatg tatagcgaat atactttata catccataaa 242520
attttattat acagacatta tagatgccgt gcttaaaaga ggtatcgacc ctaatattcc 242580
atttcctttg tcagaaaata gctatgtgaa tcctcttata tacgcgatag aatgtgataa 242640
tcatgacgca atattatctt taatacgata cggcgctgat gtaaatacat atagtaatta 242700

-continued tctagtgata acgccattat atatctctgt attacacggg tgccctaaat gtgtagaaat 242760
attactatat tatggtgcta atattaatat agttacctat aaaatggtaa ctcctataga 242820
actagcctct agaatatgtt acaataactt agcatttatg gtttgcgata gaactataac 242880
taacataccg aagaagataa cctataattt tgaaataatg aaaatactgg tatctcattt 242940
tatactacaa gcatcgaatg atagattaaa caatcgtcac aataaatatt tttcagaggg 243000
ctataataaa aataagatgc tagtatctac gtctattatt ttgacttatt tcaaaaaaca 243060
gtgtatagaa gatatagata tcatgaaaaa tataaaactg ggagatgatt catttttaga 243120
tatcttagta gaaagaaata ctatgaaact atctacatat atatctaatc aagacatatt 243180
ggatattcca aaaactgtaa aagtatacaa cacgagaata aatatgttac tagatgaagc 243240
tataatatat aataatataa atataaatatt ataaataata aaagcattta tcaggatggg 243300
agagtatagc aattccagat aaaaagttat gttcgataat attattttaa tagaatgaaa 243360
tagttatggc gtgcccattt ttgtagacac taatagtaga aaagaaatta cattaatcat 243420
ttatctgtaa cattctgatc agaagtatat tctataaaac ctgccgtcgt tactgtaaat 243480
aatataagca cacatgtgtc agaactgtta agcagcgtgc ctctgtagtt tattctgtta 243540
cggttgacat agatgagcgc ttatacagag atattttcat atgaagttaa tacttacttc 243600
aaaatatcat acgttaatga tatgtatgaa gagaaatacg tattccgtta tagataataa 243660
gaaaaaatga atacttaata gactatataa attaatacag ttatgaagtt agtttacgta 243720
tggtatcacg atagcgtgtt tgtaccagat agtttatatt atccatttct cagtaatttt 243780
agatttaatt ccaagtatag atcttgtcat gtttttttact atataaacaa tacagataac 243840
ttacgtatac cggaaaatga atataatcaa gattttatcg attttaaaac tgtatttcca 243900
gaagatatgg ccacactaac ggttttgcca aataaagcgc aaaagataga ctttatgaaa 243960
ctatctattt tgtttaaagg acaccgcata ctaaatacta aaagcgatat cttgttatta 244020
gattttgact gtcacataaa aactataggt aagatgatat acaacgtaga acctttttac 244080
tgtaaaaaaa ctaaatactt atatgttgga ggacagaatg atgaacaaga ttcatatata 244140
gaaaattatg ctactagaat cgacgaagtc ggttctagaa gactttacga tatatttact 244200
cgtttagatt ttcatccagg aaaatctaaa actaattctt acgtatatat gatttatgtt 244260
tctatgatca tagagtactt taaagtatat cataactaca tatttcctac actttgtgag 244320
aacgtgtatt tagaatctag cgtagatatg tcttactcta gaggatctac ttggaagata 244380
gatatttcaa atttagatga cgattcatta tggattataa agtacagtaa accgtttaat 244440
aaagctatta aagatgaaat acaggattgt atacacaaca aaaacttttc tgtgttttat 244500
accatcgtgt taaaagaact taatcttcct tttgataaag acatattttg gttaaacgat 244560
aaacaacgaa atggtacttt gaaagaatac gttcatgaaa acataaaaga tagtagtggt 244620
aatacattca ttagtatcat agatagagct atcaatttcc agaaatctta cataaaatac 244680
caaatataat aaaatttaaa aacaatattt ttttaaatat tattaacaat gctatcacta 244740
tattacgcca tcaactataa aaatagaaaa atggtagaaa ggttacttag agaaggagtc 244800
catcctgata gcactattaa aggattttac agaccgcttg taaaatcaat actcttaaga 244860
gacgtagacc tggtaagtat attattacaa aacggtgcaa atcctaataa tattaacgat 244920
gaaacggtta gtccgctggc tatagcgatt aaagtcaatt ctcctacaat agtgtctctc 244980
ttactggatt ataatgccga tacttcctta tttccattat acgttagttt tccgattata 245040
aaagtattgg tatatcatgg tatagatgta aacgttatag acagagaatc tagatctttt 245100

-continued ttacattacg cggctaaaaa cgatgatgtt gatacagtga tatcattaat attacacggt 245160
gctaatgtta acgtacaaga ttctaaagga ttatcccctt tacatcatgc cgttagtaag 245220
aaaacaacat taacagctaa gatactatta gaaaacggtg ccagagtaaa tattagagat 245280
tcgttaggta ggcttccttt acacttagga gctaatacat atgaaatggt aaaactgtta 245340
atagattacg ggagtcctat agatattaaa gatgttaacg gttctacgcc tctacattac 245400
gctatatgga aagttcgtt agatacaata cgattactag taaacgtgtc tactattaac 245460
gcattagata ataactgtaa tagtccgtta cattatatta tattatcaga aacagaaatc 245520
ctagtagaac ttttattaag aggagcggat atcactatca aggatatatg tggtaataca 245580
ccattagata ttctttgtaa attaagaata aaaaaactag ataatattaa agcgataaata 245640
tctaatgcgt ttcttatgcg agaagtagtt cctgacttat taaagctatg cggatttgaa 245700
agcaatagaa aaattatctc taatattagc gatttaaaac agcacgaggt tagttgtatt 245760
aaagaaatac atttaatgaa agagcatagt tttagaaaaa acggcccaac tatattagac 245820
gtatgtacag ataaagtaca ttttcttcat cgattagtta atgctcgtga taacgtacag 245880
tataaagatt ttcctatata ctgtaaatat ataaaattta gaatagagaa agcgatatac 245940
aaaaaaacaa ttatcgagaa aactatatta ctgttagacg atatattaat taaacacgaa 246000
tatacttctt ggcatgattt accatatgaa ttaaaacact atataataga atatataaac 246060
atagaattta ttaaatcgct gctagaacat acaaatctga aaaataaaga ataactgaaa 246120
tatgtgattg tacgaatatc aaaatgaaat taatcgaggc aatcgataat aataatctta 246180
aagaagttat aaggataatc agatcagaca atataaacct agaatctata aacgatgaag 246240
atgatctatc tccgttacat cacgctgttt cacgtggtta taaagaaata gttatttcta 246300
tgttagagca tggagctgat gtaaatctat gtaacgatga agtatgtagt cctttgcaca 246360
tagctataaa aaatgataac gtcgaaatgg tacaattact aatagataac ggcgcggaca 246420
cagactgttg taacaatact atacacggaa ctcctttaca atgtgctata ctaaacgaga 246480
attataggat tacagatgct ctactcgaat cgggagctga tacacatgaa atttatacta 246540
aaaaccaccc cattatcgag gctattaaac tagataacct accgctagtt agattattac 246600
taagacatgg cgcggatgta aatacatttg atcctttata cggatatcct attcatttag 246660
caataagata tggaaatata gatatcatca aagaactgct atatcacggt gttattgaat 246720
cgtattcttt gtatccttct cttttgcatc aatctataat gtgtaataat aaagaagttg 246780
tcttattatt gatatctatg ggttttgatg ttaatgctaa agataacgag ggaaatacac 246840
ctatgcattt agccgtacag aaaaatttag taggtatagt aaaaatatta ttagataaag 246900
gtgccgatac cagtatcatt aataatttat cagttacatg cttaaggagt tgttatgttt 246960
atggtaataa ttctacagaa atactccagc tgctaatatc tagaatagtt atcaacaaat 247020
acgctaatat accgtgtaga agtatagcag gtatgaatta taattggagt ttaatagaat 247080
caaatcagaa aaccaatagc tataaattag aatgtgagaa agaaatatta aaaatgctag 247140
atgtaaaaat aggaagtagg agtctattcg atatatatct aaataaaatt gaatcaaata 247200
tgttacttag attatacaac aaagtaacgt taccagaatt tatcatatac aaggatataa 247260
taataaatgc tgtatacacg gcaaaggaaa gagaaagctt aatttctaaa tcatttaccg 247320
ttttagaaga tactatttct aatgatacta tagataattt atggaaaaat atacctatag 247380
aagtaaaata catgattcta agatatttgg gtaaagatga cttgtataat atagtgaact 247440
cggtataaat catattgtta ttgcttgtaa aatatcatta taaaaataat cgttacttcc 247500

-continued

```
tcgaagttgg cgttccaatg tttgtaagaa taaatacggt tcgtatgttc ttctaatttt 247560
aaattcattt acgatggtat ctataatctc tttctttatg taataattta cagaattata 247620
ttttttatc aatatatcat tgttatccat aacagtcttt aacttattag atatactaaa 247680
attatcacga actgttctag gaaaaatatt gtgataattt ttagcatctt ctagagtttt 247740
ttttgctagc tctctatata tagattctat atcgcttctt tcagaaatac atttcaaaaa 247800
catgttgggc tcatagtccc atttgttata taaccaatga cccatacaat ctatcatcac 247860
tactttacca ttatcgctta gataatcaaa aactctcatc aagtaattat gatgtttgcg 247920
tataaagcta gtaatgcgct ttttagaata aatcatacta agtctatttt ttttgcttcc 247980
gtgtgtatta ttattaccca tttattaagt acttgttctt tatatagtat tgttataata 248040
aatgaataat aatacaaatg agataaatata ttaaactata caatcaaaat gggtattagt 248100
gataaagtta ataaactttt caactttatt tgtaaaaacg atgtagtttc tgtaagaaaa 248160
tacctagaaa agggaattaa tcctaatgaa aaaaacaagg ataattgtac gatgttgtat 248220
acagcagtag aacacagata tatagacata ataaaattac ttttggatca tggagcggat 248280
cctaacatct atagcagcga ccatatgaca ccgttacatt ctgtatcagt tatcatacct 248340
ataagaaaga tatcgaaact aataactaaa tacggcaatt tggtaacttt agctaattac 248400
cgtaatacat ttttcgttta taacgaaaac agaaatttag aaattgccaa aatgttaata 248460
caaaacggag ctttagtgaa catgaacaat atgaaaaata taacaccgtt acatatagct 248520
tccagttctg gaagctacaa aatggtagaa ctattattat tacacggagc taacaccaat 248580
gcgttaacta gttatggaga aacatcttta cattattctg tttccagcaa tgacttaaat 248640
atttcagagc tattaataga aaatggtaca aacgtaaacg tggctaacaa agatagcata 248700
acagcgttga ttatagcagt agaaataatg tcaatagatt tagtaagatt attattggat 248760
aaaggagccg atactaacgc tataggacta gaaaggttca agctatatgt gacagaaacc 248820
aaacaaaata ataatatctt gaaatacctt aatacaaata acgttaatac taatgtaaca 248880
atgataaacg aatatatagc gagcgaatta tacgactgga atagaaattc ggccacttca 248940
aagcttatgt ttcgatcttg ttttgaaccg tgtacagtac cagttactct agccacgagg 249000
aaaggatcta aagaactatt agaaatccta ttagaatacg gatgtaatcc tgatatttgt 249060
gaaaaaacta ctagtactta tgcgatgcac tatgctgtaa tacgaaaaca ttatgaaatg 249120
ttgaatatac taatacgtta cgacgcgtat acagatgtta aagatagaca acaaaatact 249180
cccgcgcatt atgcggtcaa attacctata tctgaatcat gtaagtatct gaaattatta 249240
aaattagcag gcgcatcttt caatctaaca aatagaaaag gtagaactcc tttacatacc 249300
gcgtgtaagt ataataatac ggaagctgtt aaatatttga tcgaaagcgg ttgtgacacc 249360
aatatcgtag atgtaatgtc ctttacacct cttaattacg ctgtttacta tgaaagggaa 249420
gatactgtaa aaatattatt agaaagcgga tgtgtggatc caaacttatg cgactataaa 249480
gaggtatctc ctattattca agcaattaag cgtaataata agaatattat taagatgctt 249540
ttaaacgcgg gtattgatat aaaacctata aacgaatgtt atggtttaca catgcttgcc 249600
gcactacata ataaagatct attaaaatgg ttgttgtgta ctatttctga attagaagta 249660
aatggtgtag atgatcatta cgttccatta gcttcttatg tagcagagct atcagatatt 249720
aggattatgg aaattctcat agaaaagggt ttagatctta acaaggtgac gggtccagac 249780
gaaaccatgt ttacaatgat cttttcggct acttcagact taaggaaatc tatcatagat 249840
ttattgatat ctcagatagc tgcggatgaa gaattctcag aaggctttaa gataaacaaa 249900
```

-continued aatatgatac aaacagataa atatttatta cgtgtgtatc atgaatgtaa aaatcaggtt 249960
tctaaaatgg gagaaatcaa attaggagat gggtttacta tgatagatat atacaaaaat 250020
aggagatcca tacatgtaaa ctttctagct aggtacgcaa tgcagctttc aactatagat 250080
ctacgcgaag taccaatata cagaaagtac ttagaaatac ttattaatcc agctattaaa 250140
agacataaaa tattaaatgc tgctaaagac actatgaata atatattgca caggaaagaa 250200
aaattttatt ggaatctatt accggtagaa ataaaattta atattttaga atacttgaat 250260
tctaaagacc tgatttcatt aatacacagt aataccgtaa atgaaataga tttatctcat 250320
atttttattt gatattatat ataaaacata aattaaataa cgtgtatata ataagctaat 250380
tacaatacaa tatgtaccca agggggtttt agtaaatgtg aatactgtta tcgctttcgg 250440
ctataaggaa atagtaaata ttctgttaga aagaggccaa gatgttaact ttatagacga 250500
tgttggttta gcgccggtat actatgctac gatatttgaa cggatgaatg tattaaagct 250560
gctatgtaaa taccatgtag atataaatat tagctctcat agttctggac gtacatctct 250620
acattatgcc gtattgttta atcataaaag agcattaagt tttctgttag ctagaggtgc 250680
tgacgtgttt aaaaaggatg cgtgtatgtg cacgcctcta tactacgcta tgttatctga 250740
ccaaagagat atggtaacga tgttattaca ctctaagaag tatatagtta aattcagaaa 250800
taagctagac ttacacaatg ctatagaaac cggtaatata aaggtaataa aaactttatt 250860
agataacgga gtaaatgaga atagtgttga caaagatgga cttactccat tacattatgc 250920
cgtaaaatat ggtaatatta gcatagtaaa gatgtttgtt attagatagt ggaatgaaca 250980
taaacgctac tgataattcg ttatctacac ctctacatca cgctataaac ttacttaaaa 251040
ccgatatagt ttcccttcta atgcaataca aagccgatgc ctctatacgt gacagtaaag 251100
gaattactcc attctgttat gccatgtatc taggatatta cggcgttaat aaggatattc 251160
ttaatattat aacacggtat aattctatta acggaactac tagagatatt aacgatgtat 251220
ataccatact actaaataat aaaaagaaga attatgtatt cgtaaaccta cacgatgccg 251280
ctagactagg atatgtatat attttaaaaa agataatata taatggtaag aacataaacc 251340
gcattgatga atattactat tctgcgttac actatgctgt caaatccagt aatttgaaag 251400
cagttaattt ttgatacaaa aaggtataga tataaagtta aaagatagta atatagaacc 251460
gcgctacatt acgcggttaa attgggtaac ttagatataa ttaacagtat tatagaaagt 251520
ggtgctgaca ttactaccag agatatattt aaccaatctc ctcttaccat agctttacaa 251580
gaaatagata acatatattt tttacgataa agtattttac aaaataaatg ataaccaaaa 251640
aactaagata gctaatgtat taatttcgaa tttagttacc tctgaaatta aaaaaatgaa 251700
acaattacgt ataaagaact atgcaatata ttaggtgata agacctatat aactatattt 251760
gtgagtaatt gctttaggga aatacataaa atgaagtatg ttaattttat aaatgcgtat 251820
agtgtctatg atatttatat aaataaaaac aagatagata taaatatacc attacatatt 251880
aactatgacc taaaatacaa agaaattaaa aatgaatttc ctatttacag agatatgata 251940
gaaaagaaaa tacgatatat actagataaa cctaatctag tatataaagt tattaattgt 252000
atgtccgaat atatggattc tacttattgg atgtttctac ccacagaaat aaaatttaag 252060
gtgttaagtt acttaagtag caaagattta tattttataa tataaacatg gaaggaatac 252120
cactcataga tatatatggt aaacaatgga aaatagataa acttatagga tgtggtggat 252180
ttgggtgtgt atactctact caatgtgcta gtaatacaag gcaagccgtg attaaagtag 252240
agagcctaaa taacactacc atggtatcag aagtattagt ttataacaac atatatgata 252300

```
aaaatagaat agcgttatgg aaaaactaca agaacataga tcatttagga atacctatgt 252360
actacgggtg tggaagtttc aaacgcaata ccatgtatta cagatttatt ttattagaga 252420
gattagtaga aaatactaaa gagttattaa agagagtaaa aaaacctaaa ccgttaataa 252480
aaaatataat gaaagatatg ttatatacct tagaatatat acatgagcat ggaatttcac 252540
acggggatat aaaaccagaa aacataatgg tagatggaag atacagatcg tacctaatag 252600
attatggtat agtatcctat ttcattgtta atggaaagca tgtaaaatac tacaaagaat 252660
ctaagaactg gcacagggga acattgtatt acgctagtct agatgcgcat aacggcacgt 252720
gcgttactag aagaggagac ttagaatcat tgggatattg tatgttaaaa tgggcgggta 252780
taccactacc gtggaaggta tttggaaata atgggaatat ggtacatgtg gcgaaatgtg 252840
attttataaa acgggtacat aaaaataaag ttaatattaa gtcagcgaat aaaggcatat 252900
atgattatat taagtgtgtt acaaaactat cgtacgaaga aaaacctgat tatgatctat 252960
taaggcaatt agttaatagc ttataaatta ttttcagaac ataaataaaa tataacatat 253020
ttgtacaagc ctgttatcat gtcggataat acattattac tgcacactat aatgatacta 253080
gatctagaac ctaactacaa cgaatgcaga tattgtgtta gaatgctgtt taatgctgta 253140
aaatttaaca acataaggtt agttatgcat ctactacgta acggagtaga tcctaacttt 253200
tacgatgaat acatgaggtc tcctattcat tatgctgtag aaaaaggtaa tacagaaatg 253260
gtaaaggcct tattggaaca taaggcagat cctaatatat tcgatgataa cttcgactat 253320
ccgattacaa attctataat agaaaacaaa gtagaaatcg taaagatact tttacaatat 253380
ggagctgaca aaacaatgat taacgaattt gatttattac acgacgctat caaaaataag 253440
catatagata tggctaaaat cctaatagat aatggaatta gtttaaccat gaaagacaca 253500
gatgactata cgcctttaca ttatgctatg ttagacaatg atacatctgt gatatataat 253560
ctattagact atatatttaa agtaaaagga tacgatgtat taggcaatat tgtgcatgat 253620
atattgtgta actatgattt atataaggaa acgacgttag aattattaat ctcttattac 253680
ataattatat cctacctcta tagaggtata gacctttcag atatttacaa tagtaatata 253740
gaaatattac ttaattctaa acatctttct gatattaaag agaaatgtga aaacgaaata 253800
gatgttatga agaacgctgt aatatgcgac ggtatagcca tcatagattt gtgtacaggc 253860
tacgatgcaa attctatagc tagaaattcc gttaatttga aaagattctc agatactaaa 253920
ctaaagatct acagatatta tatagaaccg attgtagaaa taggaaagta tagacgcgag 253980
ctattgtata atgcgattaa ttctatgaat gaatattgta aatccgaaag taacgatata 254040
gcaaattggt cttgtctacc attcgaaata aaatacaaaa tacttgaaaa tataaaagat 254100
gacgaaactt taagaaaaat ataagtattt acaatagtaa gtaataacaa ggttttgagt 254160
gtatggcttt taatcataat ttttatttaa aaatagaata gtgaaaataa aatatgttaa 254220
taatgagtag tataaaagaa ctatatcatg cggtttctat caatgatagg tttagtgtag 254280
ttaatattct agagaaaaaa aatattccta tagattatat aaattttcat cctgataacc 254340
cgttattaga agccgtaaag ttaactaaca ctgatatgat aaaaacattg ctagattatg 254400
gtatttgtat aaatactaga gatattttag gaaatacggc tttacacttg atagctatgg 254460
attattacgt tccacataac gatataaaac acggccatca caacgactat gtatttaaaa 254520
tggtgcctat aattaatctt tttttaagaa agaaagctaa cataaatgcg tgtaataatc 254580
taaatcaaac acccttgcat ttggctgccg aaagcaataa tacaacatta ttaaaaatat 254640
tattatataa taacgcaaag gtaaatattc tagatattta cggaaatact tgtctgcact 254700
```

-continued

```
atgcggttag aggaaggaac atagaatcta taaaactatt actatcctat aatgtcgatg 254760
ttaatataag aaattttact tattggtatt ctgctttgca cgaagcagta cagataggcg 254820
attcaaaaat atctagatgt attgtatcat tattactttg taataaggct aacgttaata 254880
ctagatgtag acttaataca acacccatat tttacgctat aaactgtata gacactctga 254940
aactattatt agaaaatggt gcggatataa acgcgacctc ggataatgat aatgccgtaa 255000
tacatctagc tactgaaaat agacgttatg atataataaa aacgttattg gattatggcg 255060
cggatgtgaa catgatagga tatagaggta agacaccatt atattatgct acagaaaatt 255120
atagttacag aaatatgaaa ttattactag accatggaag taatcctaat atagcagatc 255180
atattatgaa tacgccttta tttatttcta taaagtgcac gtgcatcgaa aacactaaga 255240
tgttactaga tagcggtgcc gatattaacc acgtaaacga taatggcgaa acacctattt 255300
cttacctagc tcctaattta atcccaaccc ccgttgctat attagtaata tctcatatag 255360
ttcttttaaa aaccaaatat aatcatataa agtacttacc cggttttata aaaaatattt 255420
ctgttataca gaattttact aaattcaata acataaaaaa ggtgtgtgaa gacgaattta 255480
gatttatgag atccgtatca ttatcggcta atcataattt atcgtcttat atatgtaatg 255540
ataacttgca tactttagta aggttcataa aaaatccaaa aatatattat tcgataaata 255600
aaatacgtat ttataggaac cgattatatt ctataataga aagattatta aatagaaaaa 255660
aattacatga tttagtttta gaattaatta aagatatagg cgtatttaat aaactaccgt 255720
tagatattat atcaatgata ttagattttt tatcggatga cgacttggcg cttatggcta 255780
tatttaattg atttatagtc ctaactaccg tatatcaata aatatataat gaaagtaaaa 255840
ggtgattcat cgaatactga ttactaaact atcagaagcc gaacaaggat gcaacttctt 255900
caactagtta ttctccataa aagaaatata atattattga gattatatta aattagggta 255960
tggatattga cgcgctttac tattatggtt ctgtactact ggtgggtaca acgagtgaat 256020
agaaactata aacatcataa taaaacacgg agctatatta acatattaga ttaacaagga 256080
ttcaccgagt tgtatagaac ttctatagag aatcttccta aagttataga attttgttag 256140
taaacggtgc taacccgaat atcaataacg agctagtatg cacgtcgtta tattatagaa 256200
gaaacttaat aatgttgaat tattgttaag atatggtatt aatattaacg ctatagatct 256260
taacagacac tcctttatct tttatccagg ccgatgatcg tgaaccacct acattacttg 256320
tggctcatat aacttttaac caattatgct gatgataggt cctatctaga aaggttatca 256380
ttctaacatg tctatgatat attatagtaa aaatctaaat agttttaagt tagaacgtga 256440
aaaagaatct ctatgctgaa atctataata atatgtagag aaatttcttt atttatgtca 256500
acaaccctga agaattttag aaaatctttt gactcgaagt gttaatgaca tacatatata 256560
ctttaatgcg ttaatacaaa taatatctta agtaaatata gacacgttaa ataaagaagc 256620
tttacaacat attgataaaa tgtttttaga ttgagattat taaccacagg tgagttaaaa 256680
atctattaga aatatgttaa tacaaaactt atttaccatc taatccataa caaccatgta 256740
ttattatata caaaatattt attttagtag atgaaaaaat ccattgttat acatcagata 256800
cagaggtata aaattcctta tttggtgtta tatcgaacta gtgagttcag gaatcttatc 256860
taatagaata ctattaaatt agagaagaaa gactttatga gtaagtatta aacaaaatat 256920
atactcacat ttataatata gtatgtaatt tatcatatat tttatcatat attttctttt 256980
ctgtaactga ttatttcttt taatagagat ttcgtttttt ctcttagaga tatatcgctg 257040
tcttgttctg ctaacatttt taaaaacaaa taagatctat aatcaccttt ttttttaaac 257100
```

-continued

```
tggttagctt tgtattctaa tttatcctcc tgaatttcat tattacaaaa atctgttatt 257160
tctttttcta cgatagatat tttatcttgt atattcttaa aaccatctag tattacagga 257220
tactcgtcga tttctttatt tctattttca tacactattt tagtggtgtc taccagtcta 257280
tctttaaccc gtttagtcat atcaatatct tgtaaagaag ataaaaataa ttgaagttca 257340
taattccatg atttaagaag atgaacagcc gctgcatcta tcatgtctat ttttccatca 257400
tctgacataa cagaaaacac atctaataac gtattatcac tagaactatt aagtttatga 257460
taaggattgt tattcacagt atgtatcata gaactagcat ttcccatgtt aatacaaacg 257520
accttattta tttttataat tagtaaattt attttaatgt agatattaaa attgatataa 257580
atgaaatata aaactattga cgataatagg aatactatta tttccttatt atagtactat 257640
ggaaaatgaa ttaaaattat actatgctgt aagctcccaa aatgaaaact tggtaataca 257700
gttactaaac aaaggttaca accccaatgc tataaacagg tttaagtata tgataccgtt 257760
acacaaagct gtagaatgca ggaacgtaga tataactaaa catttattat ctaacggcgc 257820
agacgctaac gttagggact ttctaggatt aggtgtattt cacatactga gcatgttttc 257880
tagtttacca gaactaaaag atatattaca taatacagaa ggcacttttg tcttgtgcaa 257940
atataattac gctcctttag aagaagacta tgaagttaaa acactagaga tagctagaat 258000
gctttttata agtaaagcta atattaatat gacgagcaaa cttggtagta cacctcttca 258060
tatagctagt aaatacaata ataaaacgat ggtgaaattc tttttggaaa gaggagccga 258120
tatcaatatt ctggattcta acaataatac tcctctcatc tatgcggtat gttcggtaat 258180
acgactatat ctaaaatgtt attagactac ggagcaagaa tagattctcg taataaagag 258240
gaatgtttgc ctttaaatca tgcgatagct acaaataaca aagagcttac gagtctattt 258300
cttgcaagag gagccgatac taatatcgta gataaatata atagatcggt tctacataaa 258360
gctataggta ataataatat aacgtcggta aaattattat taaatcacgg tattgattac 258420
aatttacgag ataatcacgg gtatacggca ctgcactacg ctataacatt acaaaataga 258480
gagattacag acatgttatt atcttcggga gccgacccta atataatgaa taatgaaaaa 258540
catactcctc tatatcacgc tctattgtat agatcgtcta acgttgaatc gctgatatta 258600
cacggagcgg atataaatat tgtagatgat acagggaaaa caccattatc taatacgtat 258660
atagatataa tagataataa aaatatcgaa gtcatagtat ctcaattcac tattttggaa 258720
tatatagcac cagatgatat aaaaaatcaa ttaggttaca aaataaatac tgacctaata 258780
aacaacaata aaagatattc tactataaaa cagaaatgtg ttcatgaaat aaatctatta 258840
aaagcaatta aatttcattc cggatattca gcggaaatat ttctaattaa aagcaaatcg 258900
aatatctttc ataattcaca gggtatccaa atattataaa tataattgaa acaagatttc 258960
ccatatatta ctcgttgata aaaaaatcta tagacatagg taattataga agaaagttac 259020
ttgacggtgc tgtaaatact attagtgaaa tccgactgtt aaacgtatta cctataaaca 259080
taaaatatgt tatattggag atgctagata ataaagatct aataacattg aataataata 259140
cataattgaa aatgtatata atactatttt tatagatata tagcacatca taatatatta 259200
taaaaatgtt aaaactctat atatcgatgt ttttagatag tacagaacat atattgaaag 259260
aaattaacag actacaacat aaagagcaac gcaccaacgg tatatcttgt atacctctta 259320
ttcctttaca ccaagctgta gaagctagaa atctagaagt agtagaagct ttactagaaa 259380
gaggccacaa tgtaaacgaa acagaccata gatatctaac acctttacat attatatgtt 259440
cacatcctaa taagattggg atgaaggaag taatcgcgga aaaaacaaaa agagatttat 259500
```

-continued

```
catcttacga agaaagagct atatcagaag cgtgttacaa taatgatata aatatcttta 259560
aaatgttatt acttaatgat ggtaatagaa cgattgatga cgtccaacta tgtacgatag 259620
attatgatga ttccatagat acaaaaataa taaaactgtt actggcgtat ggggcagata 259680
caaaaataaa aacagaagat aagttaaaaa cagctttaca ttatgcttct acaaataaaa 259740
attataaatt agctgaatat ttgttgatat acggagcgga agtaaattcc ccagatatag 259800
gtaataattc tcccatgcat gaagctgtac gacatagaaa cgaagatgta gtaaaaattc 259860
tattacaata tggatctaat actgatcaca tgaattcatg cggtactact ccattgcata 259920
tttctgtagg aagggtactt aatagaaata attattctat attaaagata ttactagaac 259980
acggtacgtc tgtgaatata cagagcagta tactaggttt taccgctttg catctatcta 260040
ttcatagtga agataaactt aatctattat tagaatacgg tgcagatcct aatattctca 260100
attttgagaa agaaacgcct ttaagtatgg ctgtaaaagt aactaggtat gatataaata 260160
tttataatcg tcttatatat aatatatgct tgagagcgtt taagtatcct ttcataaaaa 260220
ctacagaagg ttatattaag aacatgacgt gcataaacgg ttatcctaaa tgtaaatcca 260280
taaaagatgc atgtgaatac gagattaaaa acttggaatc tataaaatta agtcctagat 260340
tttctatggc cgatttccta aaagacgata actcgctaat gatggataaa ataataaata 260400
acgaccttat agattattat tactcgttta tggattcgtt tcccatatac ggaaatatag 260460
ttaagaaaag tatagacaca gcaaaagaca ggtatttatt aattcaggga gctatacgca 260520
gtatggataa tataactttt ccttcacaac gtgtatcttg gtataatatg cctttagaga 260580
taaaacatga tataatgtac ttattagatg ataaaagtct gtgtaattta atagtagccg 260640
aatatgatag ttaaataact gaaacaaaaa ttttattttt attagtatat gaaataatgc 260700
aaggtaatgt tatacacgta gacaagttat ataaaatgat gtacacggat aactacgaaa 260760
ctataaaaaa atatttagaa tatactgtca tagataaaac agaaaattat agtactagtg 260820
ctaatttaat accctttata cctctacatc aagcgataga agcaagaaac atagatatta 260880
taaaatcaat aataacggta gataacgtta atcaaccggg gcacgatgat acatatccta 260940
tacatatcat atgtaaggaa cccaatatgc tagcaatatc ttatatgcta agatctataa 261000
atcagtgcag cgtgtttaac acgcttgtaa aaattaaaga tatgtttaat tacagaaacg 261060
tagaaatagc taaaataatt ttgacaaata gatacaaaaa tatacaggat atagatttaa 261120
agtatataga taagaaaagt aaggacgata ttatagaaat aaccaaattg ttattttctt 261180
acggtgctga tattaatatg gtagacagac acggaaattc tcctctacat tacgctactg 261240
aaaatccaga tcagagatta acccgattat tgcttagtaa aggagctaac ccaaatatat 261300
taaataaaac taataagtca cctctctatt attctataga atccgacaat ccagatataa 261360
ctatgttgct aatagataaa ttcatattta ataatacgga tccaatatta tcacacgcta 261420
ttaaacacta ccgtaaacct atattacacg cgttaataga aaatggtgct tctattaacg 261480
cacgagacaa atacggtaat acaccgttac actacgcggt aagttactgt aaagatatag 261540
atgtgataaa attactttta gaaagaggtg tagatgttaa cgcaaaatct tatattagga 261600
atttaactcc tctgcatagt tcatatctta aatcgcctcg tgttctaaaa ctacttttac 261660
aatacggtgc tgatattaat agtttagatt catatagttt gactccttta acgtccgtag 261720
tacttcagta cttgtgtata gaatgtggga gaatagtagt ttcgcatatc tgctgcttaa 261780
agcgtattaa accagatatc gaaaattctt tgggttttat agataatata gatgctatta 261840
ctagtaataa aaggcttaat caaatacgtt taaaatgtga ggatgaattg aatagaatgg 261900
```

-continued

```
caagtattaa aattactaat acatattctt tcgatgtatt tgtcctttgc gataatatta 261960
ctttattatg taaactggta aataatagta ttatagacga tatattaatt aatagtttta 262020
acatatataa aggcatcatt ttaaagaata tatacagatc tagaaaacga ctttatctaa 262080
tagaaaatac attatacgtt ttaaataata cttttaaacc taattatatg tggaataggt 262140
tacctgtaga gttacaaaat tatataatgg agtacataga tgatgcatca ttaaaggtaa 262200
tgcacgaata cgaaaaacat aaattaaagt attaagtgat tacaggtttg attttaatcg 262260
gtataatgca ggtacgtaat aaagatgata tactaatatg cgaagccata gaaaattatg 262320
atagcgaatc tttacgcaat attcttgaaa atggagcaga tcctaatgtt agagtacctt 262380
atcagtacag ccatttgcat aacgctatag aaaagaagaa tggaagtgca gtatctcttc 262440
tactaaagca tggagcggat cctaacattt ctgggttctt tacaccacca ttacataagg 262500
ctataaaaaa aggttgtgta gatatagcta gatcgctatt agaatacgga gctattgtta 262560
atttagaaca ttattgtttg aaacctatac atatagctgc taatagaaca gaaagtaaaa 262620
tagtaaaatt gcttatagaa tacggcgctg acattaattc agaagacggc gcgaatggta 262680
aataccctat acattacgct atgaaagtat acgatccgtt tagattaaaa ataataaaag 262740
tattattaga ccacggcgcc gatattaaca aacaaagcgt tttaactaat acatccccct 262800
tatacgaaac taggtttatt accgacgacc tattagatta catcatatct agaggagcta 262860
atataaatat aaaaggaaga atgggtagaa atatattaca cgaaataata ttaagaaacg 262920
gatataatga ttttagtaat atattggtat taatagacca cggtgctgat ataaacgctt 262980
tagatgatga ggggaataca ccttttatgt tacatactat taacaataat gctattattc 263040
ttgctaacta tatagtatca ttgtattact tatcttacaa agctagaatt tctaacggaa 263100
tggaaaagaa tatgaaaata attaataagt gtgaatactt aagttcctgc ataaatatta 263160
taaaagaaga aatagaacgt atgaaaacgt tcaagatata cgacggaaat tcttttcaag 263220
atttaagtct tttcgattta ttatctaacg aagataacat cgctatagtg tatagactgt 263280
ccgatacatt attagaaaaa atgaatataa tcaaaacaat atttcccaac tgttttcgta 263340
taatacaaaa tatattaaaa atgttgacaa aaagatatga aatgttatta gagataaaca 263400
atataatgaa tgcaaaccta gtaaatacaa aatggtatac tttacccata gaaattagat 263460
ggatgatact gacaaaatta gatgacatga tcttacgaaa tctactacta caaaatgaga 263520
caaataatat taaaaattgt aaaaaacagt aatataaata tgataagaaa atgtgtaaaa 263580
aagctaggaa acgcggtcta ttaacgatag ctttcactat attgttattt gttattattt 263640
tagtagatat agacagagat agatatttag taaggtgtgg taaagactgg ttagaattcg 263700
ataatttatg ttattttatt tccgaaaata agttaagttg ggatgatagc atgatggtat 263760
gtgataatct tggcggtggg aataatatta acataaatac gaatagtggc ttattaaata 263820
catctaagga ctattggata aaaatagtag acgaactaga ttgtacaaat attaatatgt 263880
gtaatttctt atatagtaat atagtaggat gtgatatatg caccatagaa aaattttata 263940
tttgtataaa accgataaat aaaataaact tatttagtta ctttgtagag tatactaaat 264000
aataatgaaa tttaaggaag ttagaaatac tatcaagaag atgaatataa cagatataaa 264060
aatatgcggc attaatgagt attttatgtc tatgaaatta ttagatgtag aagtagtaat 264120
tatgagaagt aacgggttcg taaatattac tagattatgc aacttagaag gcaaagattt 264180
taatgattgg aagcaattag aatcgtctag gagattgctc aatacattaa aagataacaa 264240
caagttacac gatccgataa taaatattag gcatactaga ataaaaataa acggagaata 264300
```

-continued

```
cgtttcacaa ttactactgg actatgtaat tccatggatt tctccatatg tagcgactag 264360
agtatctatt ctcatgagat actatagacg atgcgtagcg ctaaacatag aaactgaaaa 264420
agatatagac catagccaag aactacagaa tcagatttcc aaaatagacg aagtttatga 264480
tagatctata aaggatataa gtaatcgctt taaagaaata gaaacatctt attacagtaa 264540
attgagtact tatttactaa caaaagctga aagagtatta gaaaaagact attctatgga 264600
acaggatata gataataacg aagatatccg tacagatgaa atgatagctg ctatagaagc 264660
tgaaattgaa gaaaataatc gtcgctattt gtcaataatt agcggcataa gaaaacaaca 264720
cgcagaagat cgtattaata tatctaaaat tatgcttagt ggtgattcat ttaatgaaat 264780
aatagtaaaa ataagagact atatagaaac aacggcaaaa ccagcggtag cgaataatta 264840
cgaatagtaa cggttttaaa taatattata taaaaaacat aaaaataaat ataatatact 264900
tacgaaggcc caaggcttta tataatacaa atcaaaatgg aatctgttat tcgcaaaatg 264960
gatacttgat tctgataaac tatcatcttc caagactttc ggtgttatta tcaccatctt 265020
aatagttata tctgtatttg catattttaa actgctcatg tatacctatg atcaaagtat 265080
acaagacatc ttgcaatatc atacttttgg ttataattat gcatatcaat ttccattttt 265140
tcataaaaat attatacatt attagctagc atttctataa aagtattatt ctgcatatcc 265200
acttcttcgg taaaaaacaa aatgacgaca ttatagatct atcgcttaaa tatgcacaat 265260
cacctattcc tttgatagga actatattat cataagatga cccatcttct aatttccaag 265320
ttccattaaa atcaactttt tctattccaa tccagtgatt tcccggacct ttgtatctta 265380
ggataaattt aaattcttct ttgctagaaa ttgaagtcag atgcccgtcc atatccttac 265440
atctttctac agctaatgat ttattatttt tttcctcaga gaaaaaatag cagtttttat 265500
tatatcctac ccatccttct ttacagtaaa gtattttaat atctggaggt acaggaggtc 265560
ttgtggataa aataatcaca aatacagata gcacgataat aatacttccg catggaatca 265620
acatccataa tactgcgcta ctacgtcgcg gtttaccctc ctccattttt taaatatact 265680
ttatcaagat ttattaaact taaaaatgca ttcaaactac ttataataaa attgaaaaaa 265740
caaataatga tatatcgaga ggtgttgaac acctatatta tacaatggat cgtgtagaac 265800
tttgcaatgc tattctcttt ggagaactgg atgtggctag acgcctgttg gattcttaca 265860
tcaatccgaa ttttactatc aacggatact cgcctataaa gatggccgtc agacttagag 265920
atgttgaaat gattaaatta ctgatgagtt acaacactta tcccgattat aactatccgg 265980
atatagaatc tgaattgcat gaggccgtgg aagaaggaga cgttgttaaa gtggaagaat 266040
tattagattc tggaaagttc ataaatgatg ttatctacaa gaaaggaaac actcccttac 266100
atttggcaac aattagtaaa aatcttgaca tgatgaggct ccttatagct agaggagccg 266160
acactgatgt gcccaacact gatcgtttta cgcctctcca tttagctgtt atgtcaaaag 266220
atattaaagg tatagaattg ctattagatc acagagcctg taccaacata gaagattgct 266280
acggatgtac tccccttatc atcgccatga gcaaaggaga cacagaagta tgcaggatgt 266340
tgctagattc cggagcaaac attgactatt tcagcaaaag gccctgtgtg acagcgatgt 266400
gctacgctat acaaaacaac aaaatagata tggtaagcat gtttctcaag agaggcgctg 266460
atagtaacat tgtgtttacc gtgatgaatg aagaacacac aactttagag atgatctgta 266520
atatggatac aaatccagaa tctgaatccg tggatatgct gatagcggac atagcattaa 266580
gacaatatac aaatacaata tcatcggata aaggattttc cagaaacatg acagtcatta 266640
acagcaaaag tcgtttaaaa gatgtatttg aaaaatgtaa aattgaatta aggagaataa 266700
```

-continued acagcgaaag catcagaacc tacaacattc tggacctgtg tttaaaacca tccaaaaatc 266760
ttgatgagaa catattggca agacattcta gaaaaatatt aggtctgtat gataatgcca 266820
tattctacaa atatctatta aaagaattgg cagacacggc atcgcaaaga gcggaagcta 266880
ttgaatcagc gatgcgagtt atagatgaaa aaattactgg tgatgaaaca aaatggaatt 266940
ggttacccca cgaaataaaa tacaacatac ttgaatatat aggcaataaa gagcttgaca 267000
tcgcatctat gaaataaaat acaacatact tgaatatata ggcaataaag agcttgacat 267060
cacatctatg aaataaaatt atttttataa ctaaatatat attttgatat agaaaaatct 267120
agtcatgaat atggtacaaa cagaaatatt gaaggtgata agtcttatat agcaatatag 267180
aagtaaacat aggcaaaaca agtattctaa tagatatttt gctaactatg tagtacaata 267240
taagtatatt aattttgtta ccgtgtcgtc ttaatcaata aaacgtaaaa gccgttatta 267300
aacatatata aatatcctga ttatcgtgat atatgataaa tattgcctta tgatgtaaag 267360
aaagatagag cgtgtactaa aaaaataaac aaataagtga ctaaattata atataatggg 267420
caattctaca tctttatttc aacgactagt aaatactttt atcatagcga tgcaagaacc 267480
caacaaatta actaaagaaa ccatgctaaa aatcgccatt gacaaacaat atgttaatgt 267540
agtagaatac ttgatacgta aaagagtgaa tatagtaaat tgtagaaatt cctataatcc 267600
tttaatttct gctatagaaa cagagaatga agaaatagta aacctactta tacttaacgg 267660
cgcttctgtt aacgaacttt ctcacacaaa taatacaccg ttacatgttg ctgtagacaa 267720
gaatataaag ccttaatacc aaatgtttca gaaagcgacg aaggaaaata tcgttgtaaa 267780
ttttcattga acgggccgac tactcagaga agataagata tagacttacg acttactcgt 267840
catgcctaga gtatacatac ctactatgac ataaacaata atacaattac gtgtgtaata 267900
gaactaaatc tatagatgaa agaaatgcaa agttatatgc taaattaggc ggtgtaaaag 267960
ttaccaaaaa ctaagactgt ttcgtatatt ccataaaatt ggaatttata ttaatagtga 268020
tatcatataa cggacgtacg gaagaacgcg gtatgaatat attacagtat aaagactgta 268080
tacaaaaaat gatattatag atcgtaagat aattggtaca atgatatcat tcaataacaa 268140
ctacagaaaa ttgcgtaaag ctataataaa cgaagatata gaagaaataa aatatattat 268200
agaaaaagat cctaatatga tagttaaagt agataacaac aaccacacac ttctacacat 268260
agccataatg tataggaaag ttaacgccgt taaagtacta ttagataaag gagataatct 268320
agtatacgtt attaattctt ttcctatatt accacctctg tattgtgcta taattggatt 268380
ttgtaaatta actagaagaa ataaaattag taatgcatta gaaaaaataa ataatcataa 268440
aaaaatcata gaagctctag tagataaagg tgtggaactg acgggattgg aaatagcatt 268500
atcctgtaag aatatatggc ttataaaatt tcttatagaa aagggaattt cagtagagta 268560
taccggtttc tttcctgtgg gtgttaatta taatacaata gatatagata tttgtaaggt 268620
tctattagaa aataaaatag acattaacaa acctgtttgt ggagaaactt tagtccgata 268680
cgctataaga tccagcgact tgaatctctt aaaatactta atcagtaaag gtgctgatat 268740
agaaaaaagg aacaagtatg aacaagatcc taatataata gaagctgtag aaaaaggaaa 268800
tttaggtatt gtagaatact taatagataa tggtataagt atcgatacgg tttccatata 268860
taatcataaa cccgctatat actacgctat actagcgggt cattacaata tggtagatct 268920
actattaaga agaggagcga atccctttat aacatgcgag ggtaatacat ctttaattag 268980
cgtggctaca caagccaaaa gaaatagatt aaaattaatt aatttgcttt tgaaatacgg 269040
agtaagactg cccggagatc atgattatta tattcaacct attttattag attattcata 269100

-continued

```
tgaaacgtat aatatcatac acatattgct agaacacggt ttgcgaatta ctagtaatac 269160
tactttagtt agtacgtttc taattatacg agtttaagaa tttttaagaa gttattacct 269220
catataagcg atattaatat taataatcct ttacatttct ctgctatgtt cgatagaaca 269280
tggcatattt ccagattctt attagaatac ggagcagatg ttaatattaa aaataggtat 269340
ggtagtacac cactttttga agcaatatgt aattgctctt gtaaaaacgt aaaactattt 269400
ttggaaaaca atgcagacat aaatgaggtt gacttagatg gagatgctac gttgatgaaa 269460
atatttaatt acaactgtag gatacattct ggattgaata gtgtccattt acgtatagct 269520
agaatagtta taccttacct aaaggttata ggattaaaga ataaacatgt taaaaatgta 269580
cacgcgtata aacaaaacat taatttcttt aattcggtaa aacaactacg cttgataagc 269640
gacgaaagcg atagagaaat caatagaatg aaaaatacga tattaagaaa aaataaattt 269700
ggaaatgata taactatgta cgatatatta ttagaaaaaa atatgaatca actagtacaa 269760
ataataaaaa atccattaat taagaaaagg tgttcagaac taatactgtt taaacgtata 269820
gtaaaaaaca atattatata tatagaaaat agatatcaaa agattcatgg tgctaatacg 269880
gttatagaat tttatcaata cgagtataca gataagtgga tgattctacc ccaagaaata 269940
aaaattaata tattgtgtta tctagacaac aaggaactcg attatatata cgagtcatcg 270000
ttagaaaaca ataaaaataa taccagtgat aaaaagtacg atgtgtgttg ttaggttgcg 270060
agagtgtatt tctagaaaat ggtactaata ttaataatac tgatacaaac taccctgttg 270120
tattatccgt ttaacgacaa atggcaaaac tattgttaaa gtacggagtt gatgttagac 270180
aagaatattc ctagattttt aaataaactg taaataactg ataaatctac ttaattatat 270240
attgtaacct atcatgtata cgtgatattt acaactatta tgtattttta ttccgctaga 270300
actatagatg ctaatgtaga aacaaagaag gattaaaaat agattgtatg ctagaaagtg 270360
gaacacttgc cgatgattat tattttattc tgttaaagat gaataagaca cttattagta 270420
acatatctat aatccgaaaa attatacttg ttattgtgga atcctgataa gtattaacgg 270480
ttggttatat ctaagaacac atctagacaa gatgaaggat ttcacttatc aacaaatttt 270540
atcgatgatt atatgaagat aaagatatgt caaattcaat aatgtgataa caaatctcaa 270600
ttacagtaaa cgttataaag aagcaactat gggaagatat agccaagaat gtaagaaaat 270660
gtttactagt ggtagtggat gatcgaatgg aaacaactac cagaaacaaa gttatgatca 270720
tatgttattg gtatttatgg actaccggga actacttggt ctatgggagg gacttaaagg 270780
agctaataaa tacacgggta agcggacgga tatacggcga tataagtgta ttggaagctc 270840
tataataata gataaaaacg actaatcttc tgtatctgcg ccttactgta ctaattgaat 270900
gaaatgaaaa tacgcaagaa tatctcatag atatgataca acacaacact acaaattata 270960
tgagttaaaa aatatagaat atctaataaa taatttatgt aatactagct agtgtttatt 271020
tatgaaatgt ggcccgatga tttgtatagg atcatgtgtc gtggaaatta tatagaaatc 271080
ttatctgcaa taacgaatta caatcttcat aagcatggcg ctaatcaatg tgaaaacgag 271140
agtattcctt tcacggctat tcatcaagct ctacagctta gacaaataga tatagtaaaa 271200
gagctgatac aacaaaatcc gaaattgata tacgtgacgg atcacagacg taattccact 271260
ttacatacta tatgtataac ccctaatgtt atggatatag ttatatcatt aaccgtagac 271320
tgtgatatta tactagatat taagtacgct tccatcattc taaataaaca taaattaggc 271380
gaagcgtgta tacacgttct caaagaaggg atatccggta atgaaatatc ttataacaaa 271440
ataaataaat ctatagaata tatgaaattg attaaagaaa gaatacagca agatgagcta 271500
```

-continued

```
cttatagcag aaatgttatt gaagaaagga atagatgtca acgctaaaga cgtatattgt 271560
agaacaccta ttcattatgc cgctgaaagg ggtaatacta aaatggttaa tttattattg 271620
agttatggag ccgatgttaa tattataacg ttagatgacc taagtgttct agaatatgcg 271680
gttgactcta agaatataga tactattaaa gctattatag ataacagaag taacatcaat 271740
aaaaacgatc tatctttact taaagctatt cgtaatacag atttagaaac atcgttgtta 271800
ctttatgatt ctggatttag cgtgaattct atagatgttt ataagaatac tcctttgcat 271860
tacgcggtac aagcaccttc gttaagtaga ctagtaccca agttattgga aagaggaata 271920
gatgttaacg ctaaaaacat taaaggagaa actcctctgt atctcatggc taagaatgga 271980
tacgatacag aaaacattag aactttaata atgcggggtg cagatgttaa cgccgctgat 272040
agtctgtata tcactccatt acatcaagcc tctactctag atagatataa agatacagtt 272100
ataacgttgt tagaattggg agcgaacgta aatgctagag attattgtga caagacgcct 272160
attcattatg ccgctgtaag aaacaatgta gttatcataa acactctttt agattacggg 272220
gccgatatag aagcgttatc gcagaagata ggaacggttt tacattttgc cttatatgga 272280
acaaatccgt atatgagtgt aaaaacgctc atagatagag gagctaatgt taattctaaa 272340
aacaaatact tatctactcc gttgcattat gcgtgtaaaa agaattgtaa accagaagtt 272400
ataaaaatgt tattagataa cggagcggat gtaaatgcta ttaacataag gaatcaatat 272460
cctttattaa tagcattaga atatcatggt atagtaaata tattattaca ttatggtgct 272520
gaacttagag atagtagggt actgcataag agccttaaca gtaatatgtt ttcttttaga 272580
tatatcatag cacatatatg tatacaagat tttatacgtc acgatatcag aagtgaagta 272640
aaccccttga gagaaattat tcaaagcgat gatacgttta aaagtatttg gttgagttgt 272700
aaggaagaac taaaagatat atctaaaatt cgtattaata tgttttactc tttagatata 272760
ttcgttatta gtaaaaacat gaacctgtta catcacttag taaataatcc tataataaag 272820
gaaattaata cttactattt ctataattac ggagatcgtc ttaaaacttc catatcctta 272880
gccagtaata gacataaaat attagaaaaa agtagatcaa aattagatga aatattagat 272940
tctagcggtt ggtctaaact tcctccggat atcaaactct caatattaga gtttatagga 273000
aatactgagc tacgtaagat atgtaaccgc taataatttc gttatttttt ataccgatta 273060
tgtatgcaag agcccatttc ttttaatata ttaccatatt catataggca tcttacgaga 273120
tacatagaat atataggaaa ttcattaata tctatagttt ttaacatacg agtactatta 273180
tcatcaagac aacgcaaata gtctttaata ctatccttat taccgtcata tttgtgttta 273240
taccttatca tgtatacgtc aaacatacta tagtcaccga cacatttagt tttcttcatt 273300
tttttaattt cttcattaca ttcgtacaca aagtttgaaa acacggtatt gtcttttatt 273360
tctttgtgtt ctaagatagt agtatctttt aatttaccga cctcgttaat taacacggcg 273420
tttgcgagaa gttcttttat aacgctatct ctgttaatat acttaaacgc ggtatcgata 273480
ggattgcgtc cgttattatc ttttatagat atatcggcgt tgttatatag tagtatatct 273540
ataaatatcta tactacacgg aggttgcaaa gcataatgta gtggagtata tccgtctaca 273600
tccgtatcat taatagatcg attgttaatc agtaattcta cggcagatct attatatagt 273660
atagcgttat gtaacggtgt aacaccgttg ttgcacttat tgcttatgtt attagtatgg 273720
tctaaaacta atttaataca agcataatcg ccatatttag ccgcgttatg taacggagaa 273780
ttaccataat tgtcttttac gtttgcataa gcaccttttt ctaatagtaa ttttatgatt 273840
tcatatgaat tactcctagt agctatgtga ataggataac atccgttatc atcttttata 273900
```

-continued

```
ttaacatcag ctccatactc aaaaagcatt ttgataacct ctaagtcatt attcttaatc 273960
gcgtaatgca agaaagtttt agatttagca ttttttgtgt ttactttcac accactatct 274020
aatatagttt ttatcatttc tttatttatg caggggactg gcaaaataga agtatcaact 274080
ccgttaatca acagcagttt tactatatcg tgtgatccta ttttgatagc tgttaacaag 274140
ggattaggaa ttttagtatt tacatgatta acttgcgctc cgtgcttgat aaatagttct 274200
actattttgg catttccggt tcttatagcg tctattaacg gagttgttgt ttcctctaca 274260
gatatattga tgcaattacc tttattcttt ataagttttt ctactaggga tatatcaccc 274320
gaatagattt ctgtacgcca atcaacagac atttttgcaa agctcgatat atcataaaat 274380
ctttaattat tatttatatt ttattagcga tataaatcta tcaaagaacc ttatgatgtt 274440
tatgtagata gatatattcc ttccctctta ttagacgaac atggatacta gtaaccagat 274500
gtaaaaaata tggaaaatag aagatgccga tagtatcaga tcttataatg aatggtacat 274560
acaataagtt tttaagccac ggaagaaggt aaatttcatg aatagtattt ctaccaacta 274620
tcggcgatga atattgaatt caagattttt ataaaaatga aaagataaac tagattatga 274680
gcacaccagt attttgtaga tcgtttagcg cttgatttac tgctgtttca aacatgggtc 274740
tatacaagct atatcgtagt atctatatag actcggatga agaatctttg tctgctataa 274800
aagattttga aatgctagaa ggatatgatc cttatacacg agatagaatc gaggaaataa 274860
ttgaactaaa taggattata gaattggacg atgatgatgt aatatatgac cagatttact 274920
ttccttacaa tccgttacat caagttatag aggctagaag agcaaacctg gtagagatta 274980
ttttggatca aggaaaatac acggttaatt ccgtaaacga tgactttatt ttctaccctt 275040
tacacgtatt aacatgcgtt ccagaaacaa gtgatgtact tacttatctt aatgaaattg 275100
aggaatttac tttagtaaaa gatttagaac tcagagcttg taaaatgaat ttatcaaaat 275160
ctatatctat agctatcata aagcaagtat taaaaggtat aagagaattt acagataatg 275220
atttgcggaa attagataat caaataagag aagatgagtt aaagatcgcg caattactaa 275280
tttccagggg tgcaaaattg gatatcaaaa atgaatatgg ttatacacct ttgagaaaca 275340
ccgttataaa tgggaatttc gcactaacaa agttgctttt ggataacggc gccgacgcgt 275400
ctataaaatg caacggaatg acaatttttg aaatatcaac tttatcacag aatgttgata 275460
tgattaaaga aataataaag aggtgtggat ataatcacga tagcaagatt ctatgtaggg 275520
tagcgagtaa aggttatatt aacgtaatac atttcttgtt agatatcggg tttaacgtca 275580
attcctttga cagctttgga gaaacgccct tacatgccgc taccagatcc ggatccgttg 275640
aaactgttaa tgcgttaatt tcatacggtt ctaccgtgga tataaaagac aacataggga 275700
gcactccttt aatgcacgcg tgtggaaaca aggatattag caaattactg atagagaaag 275760
gagcagatcc taatatctct aatatccacg gatatacgcc tttacataat gcggcggcat 275820
acggttccgt cgatgtcgta aatctgcttc tttcttacgg agtatctatt gatgcaaagg 275880
acaagataat aggaagtact cccttagatc acggagtaca tcatccggaa atagttaaat 275940
tattattaga gaaaggcgct aatcctaata ccattaattt atacggttat acaccgctga 276000
agaacgctat cttaaagtct aggttatcag ccgaatacat aattccttac gtagtgttac 276060
aagattttag tatattagat ggtagaaata tgccaggctc cgggattaat atggaattaa 276120
taagaaacga taagttgcta caaaacatta aaacatcatg tgaaatagaa ctgaaaagga 276180
tgaaagaaat acgaattagt aataggtatt cattggatat atttataact acaagtaata 276240
taaaattcct atcaaggtta gtaacaaatg acaaattcag ttctattaat atttcgtctt 276300
```

-continued

```
tccctattta caaatcgtta ttgcaaaatg ctataaattc agcaatagaa ttaagaaaat 276360
gtttagatgt cgctctttat acaattaact caaggctgga aaatacttta tgggatatgt 276420
tgcccataga gataaagaac caaatagtat tacttttaga taacacagat cttagtataa 276480
tcagcaattc catacaacat tcacaaaatt gaaaacagaa ctaaatgcct agcgaggctg 276540
acctgaatct tacatatatc cattatggtg ctggatttta aagtaagata catagtcaa 276600
gagtcgatga aaagtattct ggcatccgct ttagatcctt tgaattctca aaacggccgt 276660
acagaggatg gttgttttac attacagatc ataaaaaata taaactttac cgctcctaaa 276720
cagctctgtg ctgtagaagg ggatactgta aaaatctact tttttgaagg gaaaggtgga 276780
ttgatatttt ctgtaaaaga tgtaatgtcc gaatcttcgg aagaagaaag cggttatgtt 276840
gtggaaggtg attatgttga attcgaggcc agatttactt gctttataac acttgcttgt 276900
accgatccca aaaataccat aatctattgt ctggaataat aatgtaaata gtttttgtat 276960
gtggttttta tagagaaata caaatattta ggttattaac aaattatgaa aattaagtat 277020
ttgtattcca gcttataaca attattcaat atggaaatca aagtagaatc gatcaataat 277080
aacttttgta agctaagtta cgaagatata gaaattatta tgatgaaaga aaatgaatac 277140
ataaatgcta caaggttatg tagttctaga ggaagagata tattagattg gatgagtaag 277200
gagtcctccg tagaattaat aaatgaatta gacaggataa atagatcatg caatgactac 277260
tacgattata ggggaatagt attaaatgtg gtatcggaca gcgaaacaag tgaattgtac 277320
gtccaccgcg accttatatt acatatttca cattggattt ctcctctatt ttctttgaag 277380
gtagtaaagt ttataaatag ttacatacaa gattcttatc aattagaata tgagctaata 277440
cataaaaaaa gtttaatgga tcagttaaaa gaaataatac tgttaaacga tgataacaat 277500
atgtagttac atgagatagc taataaacca taaagttacg tatagatgag ctagcaatat 277560
aaacgaaaat ggtaaaaatg ctattatcac taggtacaat atacatgttt tagatcatat 277620
agaaagctat acttaatgat atcttctggt agagcttaaa actccattgt tttaatatta 277680
tatactatca acacaataat cgggtgtgaa taaagattct aaatctacgc acgtaataaa 277740
ccaaatatac taaaatataa aattatgccg cgggatgata agatacttca gatgatcgtg 277800
atgaactata tttattaatt ggcaatactt aaaaataatg tttataacat atgtaaatat 277860
aataaacaat aatttagatt tttaaaatga taatacgtag gaataataaa gctcttggaa 277920
gtgtaatgag tgatttcata aaaacaataa atgaagaata tgatagtaac ataaaagaaa 277980
taaaatcaga aattgatata aagtgtaata gtattctaaa agaactcgat gaaaaatatc 278040
gccaagagat aaaagaatta tgtatgatag tagatcaact taagaaccaa tataaaatta 278100
tagataatat ttatagtagg tatataaccg aaattagaat acaactttta gctctcaaag 278160
aggaaaataa atgtttaaaa gaagagttaa caaaattaaa gtaataattt tacggatgaa 278220
aatctgagag gaagatgttt ttatgaatat atattcgtgg gtatgactaa cttaataata 278280
gagataaaag tagtttaata gattactaaa gtaaataacc gcggcggata cagaagctac 278340
tccgctattc tctagcgtat cgattttaat ccaaataaaa aaatacataa gcgtacacgg 278400
acatacgtat tttgctacct tatattatat acctaaattg atacatgttt attctccaaa 278460
gaatctagaa tggcctcaaa atctttttgt gaattatcta taagctgcct ggctttttcc 278520
cttatcttca ttatatactc atccttatcc ctatcctctt cgggaagagg ttttatatcc 278580
tctctacaat gataaacttc atttcctaga ttaataagtc ctatttcaga gaactcttcc 278640
atagtatccg ctactttgta tagagcttca tcgtcgtaca cataaatctt accatcttcc 278700
```

-continued

```
gacattagaa tgatgagatt ttcattccaa gaaatatcgc tatcattcat aacaccgatt 278760
atatccattc tcgtcggctg gggtaaataa agaacttcgc aacattcttt tatatattta 278820
agctcttctt cgggtaaatt aatgtttcta tccattttaa ttaagtatct aaggtgtata 278880
tctatatgtc tattttattt cctaataaac gtaaattaag agaactatat ttctttacga 278940
tataagttta tatactaaac aaataaaaag atgttaaaac taatatgttt acgtaatttt 279000
aatacttttt ctattttagg agtagttgat tctctcaata acggtaagaa tatcaataaa 279060
ataatatcta aaaaagatat gactttgaaa gaaatagttc tttatttacc taaattcgaa 279120
ttagaagatg acgtagactt gaaagacgcg ctaatccata tgggatgtaa tgatctattc 279180
aagtcaggtg aattagtagg tatatccgat acaaaaactt tgaggatagg taatatcagg 279240
caaaaatctg tgataaaagt agatgaatac ggaactgaag cagctagtgt taccgaatca 279300
tgcactacag acggaataaa gaaaattcct atcgtaaaag cgaacgtacc tttcatgttc 279360
ctagtagccg acgtacaaac aaaaattccg ctatttttag gaatattcca gggatagtta 279420
cttaaacaaa gacattatac gtagacttat gcgcgtaaaa agcgattaac taaattatat 279480
agaattgtat gtataccgat acctccgagt aaatagttaa ctcttaaaag aggaacgtgg 279540
tagtattatt ttattttttt tccttagagc tttgtaaatt ggaggaaagt cgcgttagta 279600
gataactata ttcacatatc taaatacgaa aatcacaata tctcgcagat gcgggcatac 279660
ctctttgtac ggaagtgtta agatcggtta gtatataatt actatataat gttaaagtaa 279720
gcagataact tataatataa tcacgtaatt taactaacat atacatctaa gaaaaatatt 279780
ttcgggaata taaatctgat ttagacatta cgtcctattt cttcattaaa agaaataata 279840
ccttatacac ttattgattt acgttttatc aaaacatatt atttttatgt actcgagagg 279900
tatataaata tacagatgtg ctattattat gttgttatac gactactaat aacctttaa 279960
tcccgtgata tatcgttagc acaccttaaa gattagaaga aatacaggtt agtgtaataa 280020
taacgtatta ttatctagca caaaaatgtt tcaaagggcg tgttattaga tttaaacgaa 280080
gatagcgagt actactgtgc tgaaataata acaacgaatc aataatttta cttcgtttaa 280140
ctttgtagtg gttgtataga ctacggtata ataaaatagc aaagtatcat ctcagggaat 280200
gcaaatgacg tacgttgaga atttaatatc tagaatctgc gtttatacgt gacatcgaga 280260
tattcgttat tactttgatt aaaaatataa actatacgga ttttctgttt acaagaacgt 280320
acaaaatact attgtataaa aaagaggtag taaatctaac gcatgtattc ggtataccaa 280380
tgggtgtatc tatcttcttt aacacatatc gttctttcgt gaaatataca agacatttcg 280440
ataatgttac tcgtgtcaaa taatagacaa atatcattaa cgccttgttc ataatatagt 280500
gagaaattaa tacccggaat ttttctattt tgatttatgt ctatccagta actaccctta 280560
ccgtatcgcg acacgaaatt tagagtttct atgttatcga accttatcaa tgaagaatcc 280620
ataacatcgc atagtttttt gctatcattc caattagttt cattgatagt aaagtagtag 280680
catttactat tatatcctat ccactcatca ggacatacct tgctaaagta cggaaacgcg 280740
taataccatt tgcatgttac gactactagt atcgtaaata atattaagca tagtattcct 280800
agtaccgtta tcgcgtaaca agatacttcc gatacctgtt tttttaacaa tataggcatt 280860
gcggtcgtat attgccagaa tcatttctgt tttattattt ttccgtattt tgtatatacg 280920
cgtaaaaaca ctgtatagca tctatataaa aaacctaaga aaatagttat tcgtaatata 280980
taaaatcagt ctgttgtttg ttatacgtag aaataaagtt taagagatat tttcatgtag 281040
attttaatcc gttaacacgc gcagattttt tggaaataga cgtccgttgt atactttaaa 281100
```

-continued

```
cacgatttat cagcgcacta aataaaatac aaattttctt atgtataata agtagagcag 281160
atgtataata ttatactacg atcaaagtct ttcgaaagat gtaacgtatt aataaatata 281220
tccttacctc atgttacagc ataatttcga ttgtagaact aacagtaaag gtattatttt 281280
gctaaaacta ttacttcagt cgcttgtaaa caatacttga gattagtttt tagaaaagta 281340
ttaccattaa tgttaatcac agccatattc attgtcttct tcaagagcta tattacctct 281400
tactatatta aataactctt cgtaagacat attacctagg atagtttgtt taacttctat 281460
aggcagagta taccagtcgg gtgtacccac tgacttagta tcataatcga tagaattaat 281520
cacctcgtgt attaaatctg tttttgtagg taagtcgaaa tagtacttag ataccgaaca 281580
acaaatatac tccgttctgc tattacaaaa ccctctcaaa tctttgtatt ctttatgctc 281640
tttagaagaa atagctttta acttttcgta aagtacagga tctataggta taaaagacgt 281700
tcctgttttt ttatcaatag tagaccatat aatatgtttc ttatcaccag tccaaatttc 281760
atccacttca ttcatgttat atatacatag agcatcgaaa gatccatatt cttctttacg 281820
gtatctaaca atactaccgt tatgatgaga ttttatacat ctacctgatc tatcagatat 281880
cattcctagg ctatattctt tatcttctgt cattctttct attaccatat cacaataaca 281940
caactgaaga tcattttctc tgtcatataa atttattttt ttacctaagt attctatgct 282000
acctattacg tttgttgacg cggataactt tttttctagt aagacatcga ataacgccac 282060
gcattttcta ccgctttcaa cggtaatact ttcatgttct atagttttat caaatagatg 282120
atctgttttt aatttcactg acgtattatt atcgatatat ataaccgttt cacctcccgt 282180
ttctggttgt tccaaatata gaagcaggtg aacgcatatt atgtttttag aaaagacggt 282240
actaaaatct ctatgcctgg caaagtaatc tcctttttca tacataatca atgtaacggt 282300
attctctacg gtaacggaat ctactaccgt acttaattca tcatagatca aggcgtgtaa 282360
ttttttaagc aagtcatcgt ttagggagtt ttcgaaaact atttgtttag atttacgatc 282420
tttaatactt aagagctccg ttctcttttc cggaaagaat attttagaat cctcgcatat 282480
gtttttttata tcatttaagt cacttattcc taaattaact aaaagttctt ttttgaaaga 282540
tgtaaaacgc gtttctgtaa atctgtgaac ggccaactgg ttattagttc ccgtacaact 282600
gaactccatc gcgtaaattt gttaaatgac cgccgtagca tcataataaa tacgatttag 282660
tttttatatt ttttatatat gaataacgct tataaaacta gaatatattt aacaactgaa 282720
aagataatta attattattt taacgtttat ttctattatc tattataata acgtaacacg 282780
cgcataaaaa cgtcatcaga tattttatta tttgaacggc atctacctaa cgtatatcag 282840
aagagataaa ataattctat ataaggatat tgagtacata taaattaatt ttttaaaact 282900
gaaaatataa tcaatttatt accgagggcg tcctcgacta tacgtcagcc atggctttaa 282960
atctccgcgt tcgtccagta gaacaagagt cgggtataaa ggtcttggca gccgcgtcgg 283020
atcccttgaa ttatgaaaat gatcacacgg gcgacggagg cttcgtcgcg cgagctatca 283080
ggaatatgga attctgtagg gccagatacc tatgcgccgc tgccggcgat acagtgaaaa 283140
tctacttttt ggaaggagaa ggagaactta tctactcggt gagccgagtg ggatctccca 283200
cagcggatag tggatacgtg acgaggggca actgcgtaga gtttgaaacc gattcttcgt 283260
gttttataac actgatgtgc actagttcct ataacacggt ggtttattgg atggaataaa 283320
aggatacccg tcttccctct cctccttccc ccctccccac gaacatattt tttattttta 283380
caataaaaca aagtaaatat cgtgtcatta ttcatgatac tttagtaaaa ataaaatttc 283440
ttaatctttt ataacgtaat tatcgtctta cgaaaagtaa aagctgtttt ggtatataac 283500
```

-continued

```
cgtcgtcaga acttaaagaa gaattaataa aactaacgag gtaacgtcgt cgacagagaa 283560
tcacatggta actcctctag atttttatta tgtataattg aaaattaatc gcgtaactat 283620
tggtggggta tatctctata gactattaaa attgatccgt gtatcaaaat gaaatcatta 283680
atcttgatag cgatgttgtt aatgttggat tgcgctaact ctctaaattg cagaggaccg 283740
tacacctctt acaacaataa gtgtatctgg gtaaaccgat tagataaaat gcatcacaaa 283800
aaaacttaca gcgaagcgtc gactacgtgt ttgataacgt ttcccatggg tacgttagct 283860
agacgtagtc taatagacaa tgaaaaagac atgaaattca taagcaaatt cggtatggga 283920
cagagtttgt ggataaggga tgacaagaaa ccagaagtgg gtaagtgtgc ctatacggac 283980
gggaaaacgt tcggattctc cccgtgtaac gcgacgtacg gtttcgtatg catagattaa 284040
taatattcaa aacccgataa cttttaattt attaacgata gatttttttt tagcattagt 284100
ttttagtagg acgaacagcg actttcttca tgagatatag aaaagcgaac ctccaaaaat 284160
ttttcctcgc gtaataaaac gggactatat ccctaacgat aggaagccta taggtcacca 284220
gtctgtgaaa gagcatgaga gcggctttag cgtaaagttt ttctccgata gttttgataa 284280
aggtccttaa gaatcttaac ctatccctta ctctgatgaa aaagattgcg gtagacgccg 284340
ttttagaaat cgtattacgt agaatcgaca gtttgttttt atcttgtatt tccttactcg 284400
cgttctcttt atcatcttcg aggcacgacg acgagcgcga ttcgtaataa tacgagcgta 284460
tacctttgg cgtccaatct ctttcatcta cacgtcgcga tgcttcacga cgaaaagacc 284520
tttctcgata gcggagaagg ttcctcgggc attctcggcg atcctgcggg ggcgatgaac 284580
cagtagaaaa ttttttagt gaaggtgtcg cacatcgtgc gaatacatct cttgacgtaa 284640
caacacggag accatatcca tacgcagaga tcttcgcacc agtcgttgac ccaggttccc 284700
cgtctggcgg gatctcttga atctctaaac gctcccggtt ctcttactcc ggtcagtctg 284760
cctctatgca ttcttctcaa catcatgcaa ggaaagagga gacacctcaa gaaaacctcg 284820
caagggcaac agaaacaacg acaccaagat ttagctaacg ggcagatggt tcttttacag 284880
aatcttctgg tgagaacgca cggtagccta atacagtcgc aagtcgcttt tagagtaggt 284940
aatatcacgc gtctccagaa ctctctgata atcaatagag gaagcacgca acagtaacaa 285000
caactgtgtt ccagagagtc taacgtctcg ctcatgcatt cgcaacatac ttcgaaggga 285060
tacaagagac agtggacgca tttgcaagtg gcgggcctta ccgagttaca gaggaaacat 285120
cgtagaaggc atagcggata caataaccac gctgctattt tctctacgat catatcggcg 285180
tctcgattta acttcaaata aaaatgcgcg agtttatacg agcgtccgtg cgcattttgt 285240
attctagagc cccggcgagt atcaagtttc gttagtaact gacgcgggtg agtaggggtg 285300
tcgtcggtgc gcgcgcgaag gaaaatgtaa atcttactct taatattaat aacagattgt 285360
ataaaaccat tcggaagtaa gtatttactc ctacacggtt ataatatcgt ttgattttca 285420
agcgttagtt ctgtaaggca cgtcatatgg tatcgaaaga acacaactag tatcctagag 285480
ccttaaatcc gataccgtga acaccaacca cgcccggtaa acgctaatat cttcgatagt 285540
gtacgtagta tcgataatag attttgttcg gccgaagaaa taaagaggaa tgagacgact 285600
ccgtcttgtt ataccactgc atctctaagt cttaacttat tatatacgcg tgaaccgggg 285660
gcaacagcga ccgttattcg catccgcgat caccgaacat aggaaaacca aattctatga 285720
tataaagaat ggtcaaaaac tactaattga cgtaacggtc ctggtttcac atgtatagcg 285780
tatgctaaaa atatctctca acttcaaatc atacctatgc gcagagacta catcataata 285840
ggcattaatt gatgaattca tatgattata ttttagcacg tattatgtag atactgtcta 285900
```

-continued acaaagttat tcaagatatt aataaacgat caaacggtta acttttaccc gatatccgat 285960
gacaattata tcttttattt atgcatatct gcttaataag taagatctat ttcttttggt 286020
aaataaataa tacataaata taactagcat gaaaatgaat tatccaatag aatattacaa 286080
agaaaaaatg aagttcctgc gcgataatag cgaaaggtat attttaccaa ttacttgtct 286140
gtgtttaact agcgtagtga taacgtcctg tctgttcgcg gctctcttcg tcgcagtacg 286200
cgattgcaaa cgggattctt ttctggaaga taccactaca gctatcacta cgtcctcctc 286260
tattgcgact acatatagag ataatctggt tattcattgt cctcgtgact ggataagtca 286320
taacggaatc tgcctcttat cgaccggtga aaaagtggga ttcagacaag gcatccagaa 286380
gtgtgagaag ttaggctctg acatgatagg taagtcagaa gaagaaatga aagcccttaa 286440
aaatatttgg acgggaaacg atcactcacg tttctgggtg gacaaccgcg cggccgcttc 286500
gacttttgat cccgtgaacg agtgtgctta cggaactaga agtagcgtgt ctgaagtgcc 286560
aaaagtatta acgtctccgt gctcggtaag aagatatctg gtatgtaaaa aaaccgataa 286620
tagttatcct accacgcaaa gttcttttta taatcaatac gaataaaaat atttttattt 286680
tattatacca acgaagattt taatctcgtg ataaaagttt ttctataact cgagctctcg 286740
ataaaaaagt tttctataa ctcgagctct cgataaaaaa gtttttctat aactcgagct 286800
ctcgataaaa aagtttttct ataactcgag ctctcgataa aaaagttttt ctataactcg 286860
agctctcgat aaaaaagttt ttctataact cgagctctcg ataaaaaagt ttttctataa 286920
ctcgagctct cgataaaaaa gtttttctat aactcgagct ctcgataaaa aagtttttct 286980
ataactcgag ctctcgataa aaaagctttt cgaaatctcg ataaaaactt tttctataac 287040
tcgagctctc gataaaaaag tttttctata actcgagctc tcgataaaaa agtttttcta 287100
taactcgagc tctcgataaa aaagtttttc gaaatctcga taaaaacttt ttctataact 287160
cgagctctcg ataaaaaact ttttctataa ctcgagctct cgataaaaaa gcttttcgaa 287220
atctcgataa aaactttttc tataactcga gctctcgata aaaaagcttt tcgaaatctc 287280
gataaaaact ttttctataa ctcgagctct cgataaaaaa gtttttctaa cattcgagct 287340
ctcgataaaa aagtttttct ataactcgag ctctcgataa aaaagttttt ctataactcg 287400
agctctcgat aaaaaagttt ttctataact cgagctctcg ataaaaaagc ttttcgaaat 287460
ctcgataaaa actttttcta taactcgagc tctcgataaa aaagtttttc tataactcga 287520
gctctcgata aaaaagtttt tctataactc gagctctcga taaaaaagtt tttcgaaatc 287580
tcgataaaaa ctttttctat aactcgagct ctcgataaaa aactttttct ataactcgag 287640
ctctcgataa aaaagctttt cgaaatctcg ataaaaactt tttctataac tcgagctctc 287700
gataaaaaag tttttctata actcgagctc tcgataaaaa gtttttctat aactcgagct 287760
ctcgataaaa aagcttttcg aaatctcgag ctctcgataa aaagtttttc tataactcga 287820
gctctcgata aaaaagtttt tctataactc gagctctcga taaaaaagct tttcgaaatc 287880
tcgataaaaa ctttttctat aactcgagct ctcgataaaa aagtttttct ataactcgag 287940
ctctcgataa aaagtttttc tataactcga gctctcgata aaaaagcttt tcgaaatctc 288000
gataaaaact ttttctataa ctcgagctct cgataaaaaa gtttttctat aactcgagct 288060
ctcgataaaa aagtttttct ataactcgag ctctcgataa aaaagttttt ctataactcg 288120
agctctcgat aaaaaagctt ttcgaaatct cgataaaaaa gtttttctat aactcgagct 288180
ctcgataaaa aagtttttct ataactcgag ctctcgataa aaaagctttt cgaaatctcg 288240
ataaaaactt tttctataac tcgagctctc gataaaaaag tttttctata actcgagctc 288300

-continued

```
tcgataaaaa gtttttctat aactcgagct ctcgataaaa aagcttttcg aaatctcgat 288360

aaaaactttt tctataactc gagctctcga taaaaaagtt tttcgctaac gttgggtagc 288420

tttataaaat attttccgga aggaaattag atatagtatt attttatgta aaaccgtatg 288480

gttttttttt attaaaacaa taatatatat tttaataggg ggtattttac accttaaca  288539
```

INSERTION SITES IN FOWLPOX VECTORS

CROSS-REFERENCE TO RELATED APPLICATIONS

This application is a 371 National Phase Entry Application of co-pending International Application PCT/US2004/005077, filed 20 Feb. 2004, which designated the U.S. and which claims the benefit under 35 U.S.C. § 119(e) of U.S. Provisional Application 60/448,591, filed 20 Feb. 2003.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 375,958 Byte ANSI (Text) file named "701315 ReplacementSeqListing_ST25.txt," created on Jul. 31, 2009.

FIELD OF THE INVENTION

The present invention relates generally to improved pox vectors utilizing novel insertion sites, and their use as an immune stimulating agent, such as a vaccine. The improved poxviruses can be used for example for parenteral immunization, as a vector system, or in the active or inactivated form as an adjuvant or as a regulator of the unspecific components of the immune system.

BACKGROUND OF THE INVENTION

In recent years, attention has been given to the development of recombinant poxvirus technology. Such poxvirus-based vectors are useful for a range of uses, for example generating immune responses such as vaccines, for the development of new vaccines, for delivery of desired proteins and for gene therapy. The advantages of these vectors include: (i) ease of generation and production; (ii) the large size of the genome permitting insertion of multiple genes, (iii) efficient delivery of genes to multiple cell types, including antigen-presenting cells; (iv) high levels of protein expression; (v) optimal presentation of antigens to the immune system; and (vi) the ability to elicit cell-mediated immune responses as well as antibody responses; and (vii) the long-term experience gained with using this vector in humans as a small pox vaccine.

Poxviruses can be genetically engineered to contain and express foreign DNA with or without impairing the ability of the virus to replicate. Such foreign DNA can encode a wide range of proteins, such as antigens that induce protection against one or more infectious agents, immune modulating proteins such as co-stimulatory molecules, or enzymatic proteins. For example, recombinant vaccinia viruses have been engineered to express immunizing antigens of herpesvirus, hepatitis B, rabies, influenza, human immunodeficiency virus (HIV), and other viruses (Kieny et al., *Nature* 312:163-6 (1984); Smith et al., *Nature* 302: 490-5 (1983); Smith et al., *Proc. Natl. Acad. Sci. USA* 80:7155-9 (1983); Zagury et al., *Nature* 326:249-50 (1987); Cooney et al., *Lancet* 337:567-72 (1991); Graham et al., *J. Infect. Dis.* 166:244-52 (1992), and have been shown to elicit immune responses against influenza virus, dengue virus, respiratory syncytial virus, and human immunodeficiency virus.

Poxviruses have also been used to generate immune reactions against tumor-associated antigens such as CEA, PSA and MUC.

Poxviruses are also attractive candidates for use in gene therapy for the delivery of genetic material into cells for therapeutic use. See U.S. Pat. No. 5,656,465. Compared to other systems such as retrovirus vectors (including lentiviral vectors), adenoviral vectors, and adeno-associated virus vectors, the large genome of poxviruses enables large genes to be inserted into pox-based vectors. Yet, because of the cytoplasmic nature of the virus integration of foreign DNA into a host cell's chromosomes will not occur.

Historically, poxviruses were used as a vaccine for protection against smallpox. Variola virus is the etiological agent of smallpox. During the smallpox era, overall mortality rates were approximately 30%. Vaccinia virus is a highly effective immunizing agent that enabled the global eradication of smallpox. The last naturally occurring case of smallpox occurred in Somalia in 1977. In May 1980, the World Health Assembly certified that the world was free of naturally occurring smallpox. As a result, smallpox vaccination was halted in the US, except for military personnel and laboratory workers. However, recent world events have resulted in a renewed interest in smallpox vaccination as a response to potential bioterrorism.

Vaccinia virus is the prototype of the genus Orthopoxvirus. It is a double-stranded DNA (deoxyribonucleic acid) virus that has a broad host range under experimental conditions but is rarely isolated from animals outside the laboratory (Fenner et al. *Orthopoxviruses*. San Diego, Calif.: Academic Press, Inc., 1989; Damaso et al., *Virology* 277:439-49 (2000)). Multiple strains of vaccinia virus exist that have different levels of virulence for humans and animals. For example, the Temple of Heaven and Copenhagen vaccinia strains are highly pathogenic among animals, whereas the NYCBOH strain, from which the Wyeth vaccine strain was derived, had relatively low pathogenicity (Fenner et al. *Smallpox and its eradication*. Geneva, Switzerland: World Health Organization, 1988). Dryvax,® the vaccinia (smallpox) vaccine currently licensed in the United States, is a lyophilized, live-virus preparation of infectious vaccinia virus (Wyeth Laboratories, Inc., Marietta, Pa.). However, Dryvax® is associated with adverse effects due to local or generalized vaccinia virus replication in children, the elderly and the immunosuppressed.

Attention has focused on attenuated orthopox such as NYVAC (U.S. Pat. No. 5,364,773) and modified vaccinia Ankara (MVA). MVA was derived from the Ankara vaccinia strain CVA,[1] which was used in the 1950s as a smallpox vaccine. In 1958, attenuation experiments were initiated in the laboratory of Dr. Anton Mayr (University of Munich) comprising terminal dilution of CVA in chicken embryo fibroblast (CEF) cells that ultimately resulted in over 500 passages. The resulting MVA is an attenuated, replication-defective virus, which is restricted to replication primarily in avian cells.[2] Comparison of the MVA genome to its parent, CVA, revealed 6 major deletions of genomic DNA (deletion I, II, III, IV, V, and VI), totaling 31,000 basepairs. (Meyer et al., J. Gen. Virol. 72:1031-8 (1991)). MVA has been administered to numerous animal species, including monkeys, mice, swine, sheep, cattle, horses and elephants with no local or systemic adverse effects.[1,3,4] Over 120,000 humans have been safely vaccinated with MVA by intradermal, subcutaneous or intramuscular injections.[3] MVA has also been reported to be avirulent among normal and immunosuppressed animals (Mayr et al., *Zentralb. Bakteriol.* 167:375-90 (1978). Accordingly, in addition to utility as a smallpox vaccine, these more attenuated strains are particularly attractive poxviruses for use as vectors for immune modulation and gene therapy.

One of the main advantages of poxviruses as vectors is the large size of their genomes, which permits the insertion of a wide range of genetic material including multiple genes (i.e., as a multivalent vector). However, the genetic material must be inserted at an appropriate site within the pox genome for the recombinant virus to remain viable. Thus, the genetic material must be inserted at a site in the viral DNA which is non-essential.

Accordingly, it is desirable to identify specific sites within a poxvirus genome that can accommodate insertion of foreign DNA, while retaining the ability to infect foreign cells and express that DNA, while maintaining the desired immunogenicity and diminished virulence. Certain insertion sites are known in different poxviruses. For example, as described above, MVA contains 6 natural deletion sites, which have been demonstrated to serve as insertion sites. See e.g. U.S. Pat. No. 5,185,146, and U.S. Pat. No. 6,440,422. However, these insertion sites are only found in one specific strain of vaccinia, MVA. It would be desirable to identify insertion sites which are more broadly represented, i.e. are present in other attenuated strains, other vaccinia strains such as CVA, Wyeth and other vaccinia strains in addition to MVA, as well as present in other poxvirus genomes.

Accordingly, there remains a need in the art for improved pox vectors containing novel insertion sites, for use for example for parenteral immunization, as a vector system, or in the active or inactivated form as an adjuvant or as a regulator of the unspecific components of the immune system.

SUMMARY OF THE INVENTION

Figure 1:
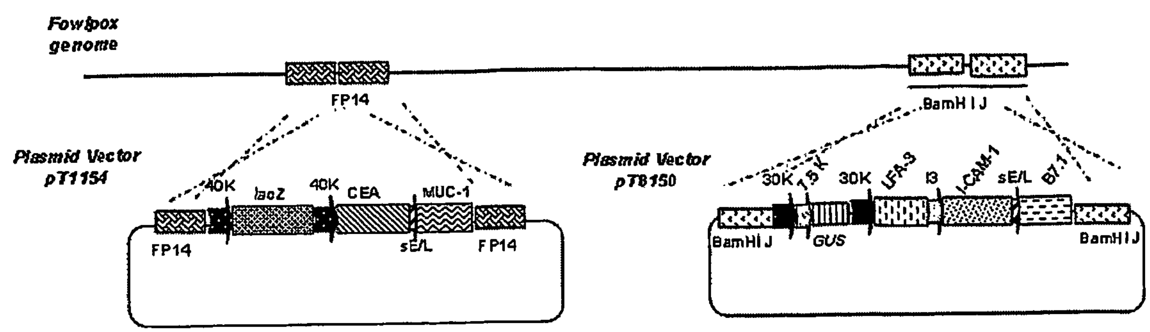
FIG. 1 shows the PANVAC-F recombinant vector schematic. To generate PANVAC-F, two plasmid vectors were used. The first plasmid, designated pT1154, directs insertion of the wCEA(6D) and wMUC-1(6) coding sequences into the FP14 region of the fowlpox virus genome. The second plasmid, designated pT8150, directs insertion of the LFA-3, ICAM-1, and B7.1 coding sequences (collectively known as TRICOM) into the BamHIJ region of the fowlpox virus genome. The wCEA(6D) gene is under the transcriptional control of the vaccinia 40K promoter. The wMUC-1(6) gene is under the transcriptional control of the synthetic early/late (sE/L) promoter. The LFA-3 gene is under the transcriptional control of the vaccinia 30K promoter, the ICAM-1 gene is under the transcriptional control of the vaccinia I3 promoter, and the B7.1 gene is under the transcriptional control of the synthetic early/late (sE/L) promoter. In addition, pT1154 contains the *E. coli* lacZ gene, under the control of the vaccinia 40K promoter, which is included as a screen for recombinant progeny, and pT8150 contains the GUS gene, under the control of the 7.5 promoter, for use in screening for recombinant progeny.

The present invention provides improved pox vectors containing novel insertion sites. The improved poxviruses can be used for example for parenteral immunization, as a vector system, or in the active or inactivated form as an adjuvant or as a regulator of the unspecific components of the immune system.

DETAILED DESCRIPTION

We have now discovered improved pox vectors containing novel insertion sites, for inserting foreign nucleic acid. The improved poxviruses can be used for example for parenteral immunization, as a vector system, or in the active or inactivated form as an adjuvant or as a regulator of the unspecific components of the immune system. Preferred pox include orthopoxviruses such as vaccinia virus, avipox such as fowl pox and canary pox, and swine pox. One preferred type of vaccinia is an attenuated vaccinia such as Modified Vaccinia Ankara (MVA) or NYVAC. MVA is preferred. These vectors can be used in virtually any setting.

Poxviruses are well known cytoplasmic viruses. Thus, genetic material expressed by such viral vectors typically remains in the cytoplasm and does not have the potential for inadvertent integration of the genetic material into host cell genes, unless specific steps are taken. As a result of the non-integrative, cytoplasmic nature of the poxvirus, the poxvirus vector system will not result in having term persistance in other cells. Thus, the vector and the transformed cells will not adversely affect cells in the host animal at locations distant from the target cell. Preferably, the pox used is attenuated relative to a vaccinia such as vaccinia Copenhagen in a mammalian cell. This includes both replicative or replication impaired pox relative to the target cell. For example, an avipox in a mammalian cell, a suipox in a human cell, etc.

The recombinant poxviruses having utility in the present invention have a number of attributes, including (i) efficient delivery of genes to multiple cell types, including APC and tumor cells; (ii) high levels of protein expression; (iii) large genomes, allowing delivery of a wide range of genetic material including multiple genes (i.e., as a multivalent vector), (iv) optimal presentation of antigens to the immune system; (v) the ability to elicit cell-mediated immune responses as well as antibody responses; (vi) transient, rather than permanent, genetic modification of cells, and (vii) the ability to use combinations of poxviruses from different genera, as they are not immunologically cross-reactive.

One preferred poxvirus of the present invention is vaccinia virus, including highly attenuated vaccinia viruses such a Modified Vaccinia Ankara (MVA), NYVAC, a derivative of the Wyeth strain, vTBC33, which lacks a functional K1L gene, and the like. A particularly preferred vaccinia virus is an attenuated vaccinia, including NYVAC and MVA. More preferably, MVA.

Another preferred poxvirus of the present invention is an avipox, including but not limited to fowlpox, and canary pox, including ALVAC. Preferably fowlpox.

Insertion Sites

The novel insertion sites of the present invention are located in intragenic regions between known genes, also referred to herein as open reading frames or simply ORFs, and allow the introduction of foreign DNA at the insertion sites.

The present invention provides methods for identifying novel insertion sites in poxviruses. Novel insertion sites can be identified by analyzing the a poxvirus genome to identify sequences with the following characteristics. First, the insertion site should lie in an intergenic space, preferably between non-essential genes. Second, the insertion of foreign DNA at the insertion site should not disrupt any cryptic ORFs in the region, or promoters of adjacent genes or other regulatory elements.

Any putative insertion site identified using the method of the present invention can be tested by construction of a recombinant poxvirus with foreign DNA (e.g. a marker) inserted at the putative site to allow testing of the recombinant poxvirus, to ensure that any essential genes, non-essential genes, and cryptic ORFs have not been affected.

For example, the method for identifying novel insertion sites can be used to identify novel insertion sites in vaccinia. In one embodiment, novel insertion sites can be identified by analyzing the MVA genome (see Antoine et al., 1998) to identify sequences with the characteristics described above—namely, the site should lie in an intergenic space, preferably between non-essential genes, and the insertion of foreign DNA at that site should not disrupt any cryptic ORFs. In addition, assessment of the essential nature of the MVA genes can be determined by comparing the MVA with its vaccinia homologue. Furthermore, there should be essential genes between the native sites of the 40K, 7.5K, and I3 promoters and the insertion site, and T5NT sequences of surrounding genes should be left intact.

Three particularly preferred insertion sites of the present invention in vaccinia are designated insertion site 44/45, insertion site 49/50, and insertion site 124/125, with the numbers designating the ORFs lying on either side of the insertion site. Particularly preferred vaccinia viruses include attenuated vaccinia viruses such as MVA, NYVAC (attenuated), and Wyeth strain, as well as non-attenuated strains such as TROYVAC.

In one preferred embodiment, the novel insertion site in vaccinia is designated insertion site 44/45. In MVA, insertion site 44/45 lies between ORFs 044L and 045L, and the insertion site is between positions 37346-37357 in the MVA genomic sequence (Genbank Accession # U94848). This region is 5' of the translational start codon of MVA 044L and 3' of the translational stop codon of MVA 045L. In vaccinia Copenhagen, for insertion site 44/45 the corresponding ORFs are F14L (homologous to MVA 044L) and F15L (MVA 045L), and the insertion site is 5' of the translational start codon of vaccinia F14L and 3' of the translations stop codon of vaccinia F15L. Vaccinia Copenhagen, which contains this region and has its sequence available as Genbank Accession number M35027, is a preferred vaccinia. Similarly, insertion site 44/45 can also be used in other vaccinia strains including NYVAC (where the insertion site is not known to be modified) and TROYVAC. In this embodiment, the DNA sequence at the specified insertion site, i.e. between the nucleotides, contains defined inserts representing a sequence of interest; the flanking nucleotides on both sides remain unchanged.

In another preferred embodiment, the novel insertion site in vaccinia is designated insertion site 49/50. In MVA, insertion site 49/50 lies between ORFs 049L and 050L, and the insertion site is between positions 42687-42690 in the MVA genomic sequence (Genbank Accession # U94848). This region is 5' of the translational start codon of MVA 049L and 3' of the translational stop codon of MVA 050L. In vaccinia Copenhagen, for insertion site 49/50 the corresponding ORFs are E2L (homologous to MVA 049L) and E3L (MVA 050L), and the insertion site is 5' of the translational start codon of vaccinia E2L and 3' of the translations stop codon of vaccinia E3L. Vaccinia Copenhagen is a prototypical vaccinia. Similarly, insertion site 49/50 can also be used in other vaccinia strains including NYVAC (where the insertion site is not known to be modified) and TROYVAC. In this embodiment, the DNA sequence at the specified insertion site, i.e. between the nucleotides, is deleted in the recombinant virus and replaced with defined inserts representing a sequence of interest.

In yet another preferred embodiment, the novel insertion site in vaccinia is designated insertion site 124/125. In MVA, insertion site 124/125 lies between ORFs 124L and 125L, and the insertion site is between positions 118481-118482 in the MVA genomic sequence (Genbank Accession # U94848). This region is 5' of the translational start codon of MVA 124L and 3' of the translational stop codon of MVA 125L. In vaccinia Copenhagen, for insertion site 124/125 the corresponding ORFs are A13L (homologous to MVA 124L) and A14L (MVA 125L), and the insertion site is 5' of the translational start codon of vaccinia A13L and 3' of the translations stop codon of vaccinia A14L. Similarly, insertion site 124/125 can also be used in other vaccinia strains including NYVAC (where the insertion site is not known to be modified) and TROYVAC. In this embodiment, the DNA sequence at the specified insertion site, i.e. between the nucleotides, is deleted in the recombinant virus and replaced with defined inserts representing a sequence of interest.

Another preferred poxvirus of the present invention is an avipox, including but not limited to fowlpox, and canary pox, including ALVAC.

A particularly preferred avipoxvirus is fowlpox.

Particularly preferred fowlpox insertion sites of the present invention are designated the LUS insertion site, the FP14 insertion site, and the 43K insertion site. These sites are also referred to sometimes as FPV006/FPV007 (LUS insertion site), FPV254/FPV255 (LUS insertion site), FPV060/FPV061 (FP14 insertion site), and FPV107/FPV108 (43K insertion site).

In one preferred embodiment, the novel insertion site in fowlpox is designated the LUS insertion site. In fowlpox, there are two long unique sequences (LUS) at each end of the viral genome (Genbank Accession # AF198100), and thus two LUS insertion sites in each genome. The LUS insertion site at the left end of the genome is between positions 7470-7475 in the fowlpox genomic sequence, and lies 3' of FPV006 and 5' of FPV007 125L. The LUS insertion site at the right end of the genome is between positions 281065 and 281070 in the fowlpox genomic sequence, and lies 5' of FPV254 and 3' of FPV255. In this embodiment, an insert representing a sequence of interest can be inserted at any position within the specified insertion site.

In another preferred embodiment, the novel insertion site in fowlpox is designated the FP14 insertion site. This site is between positions 67080-67097 in the fowlpox genomic sequence, and lies 5' of FPV060 and 3' of FPV061. In this embodiment, the DNA sequence at the specified insertion site, i.e. between the nucleotides, is deleted in the recombinant virus and replaced with defined inserts representing a sequence of interest.

In yet another preferred embodiment, the novel insertion site in fowlpox is designated the 43K insertion site. This site is at position 128178 of the fowlpox genomic sequence, and lies 5' of FPV107 and 5' of FPV108. These genes are divergently transcribed, and the insertion site lies between the two promoter elements for the two ORFs. In this embodiment, an insert representing a sequence of interest can be inserted at this position within the fowlpox genome.

Poxviruses

Poxviruses having utility in the present invention include replicating and non-replicating vectors. Such poxviruses include but are not limited to orthopox such as vaccinia, raccoon pox, rabbit pox and the like, avipox (e.g. fowl pox, canary pox), suipox (e.g. swine pox), capripox (e.g. sheep pox), leporipox, and iridoviruses. Other DNA viruses include iridoviruses and the like. Poxviruses may be selected from the group consisting of vaccinia-MVA strain, vaccinia-Copenhagen, vaccinia-Wyeth strain, NYVAC, TROVAC; avipox such as fowl pox or canarypox such as ALVAC; suipox such as swinepox, and the like. In one embodiment, the recombinant vector is a vaccinia virus. Preferably, an attenuated vaccinia such as MVA or NYVAC. Other preferred vectors include an avipox such as fowl pox or canary pox.

Parental poxviruses useful in the method of the present invention include but are not limited to orthopoxvirus such as highly attenuated vaccinia viruses such as modified vaccinia Ankara (MVA) (Sutter and Moss, *Proc. Nat'l Acad. Sci. U.S.A.,* 89:10847-10851; Sutter et al *Virology* 1994), replicating vaccinia virus (Perkus et al *Science* 229:981-984, 1985; Kaufman et al *Int. J. Cancer* 48:900-907, 1991, Moss *Science* 252:1662, 1991), Wyeth; avipoxviruses such as fowlpoxvirus, canary poxviruses, such as ALVAC and the like (Baxby and Paoletti, *Vaccine* 10:8-9, 1992; Rinns, M. M. et al (Eds) *Recombinant Poxviruses* CRC Press, Inc, Boca. Raton 1992-Paoletti, E. *Proc. Nat'l Acad. Sci. USA* 93:113491-11353, 1996), and suipoxvirus, capripoxvirus and the like.

In one preferred embodiment, the vaccinia virus is a Wyeth strain or derivative thereof. A derivative of the Wyeth strain includes but is not limited to vTBC33 which lacks a functional K1L gene and the like. In yet another embodiment, the virus is Dry-Vax available as a smallpox vaccine from the Centers for Disease Control, Atlanta, Ga. In another embodiment, the parental poxvirus is a strain of fowlpox, for example POXVAC-TC (Schering-Plough Corporation), and the like.

In another preferred embodiment, the vaccinia virus is a modified vaccinia virus Ankara (MVA) or derivative thereof. MVA has been generated by long-term serial passages of the Ankara strain of vaccinia virus (CVA) on chicken embryo fibroblasts (for review see Mayr, A., et al., Infection, 3:6-14 (1975). The MVA virus itself may be obtained from a number of public repository sources. For example, MVA was deposited in compliance with the requirements of the Budapest Treaty at CNCM (Institut Pasteur, Collection Nationale de Cultures Microorganisms, 25, rue du Docteur Roux, 75724 Paris Cedex 15) on Dec. 15, 1987 under Depositary No. I-721 (U.S. Pat. No. 5,185,146); MVA virus was deposited in compliance with the Budapest Treaty at the European Collection of Cell Cultures (ECACC) (CAMR, Porton Down, Salisbury, SP4 OJG, UK) on Jan. 27, 1994, under Depository No. V94012707) (U.S. Pat. No. 6,440,422 and United States patent publication number 20030013190). Also, United States patent publication number 0030013190 further discloses particular MVA strains deposited at the ECACC under Depository No. 99101431, and ECACC provisional accession number 01021411. All of the above documents are herein incorporated by reference in their entirety. Therion Biologics brand MVA products, identified by the tradenames Therion-MVA(™), Therion Prifree(™) Vectors and Therion M-Series Vectors(™), are products of Therion Biologics Corporation, Cambridge, Mass., United States.

The poxvirus of the present invention is able to infect, transfect or transduce host cells in a host. The host includes but is not limited to mammals, including humans, birds, fish and the like. The host cells are any cell amenable to infection, transfection or transduction by the poxvirus and capable of expressing the poxvirus; including any foreign genes inserted therein, at functional levels.

The poxviruses of the present invention are sometimes referred to herein as a viral vector or a vector system or simply a vector.

The poxvirus of the present invention preferably has a low replicative efficiency in the target cell. This preferably means that no more than about 1 progeny per cell are produced, still more preferably, no more than 0.1 progeny per cell. Replication efficiency can readily be determined empirically by determining the virus titer after infection of the target cell.

As a result of the low replication efficiency and the non-integrative, cytoplasmic nature of the vector, the vector system will not result in sustained replication and infection of other cells. Thus, the pox vector and transformed cells will not adversely affect cells in the host animal at locations distant from where the target cell is.

The poxvirus gene delivery system described herein can be used for any host. Preferably, the host will be a mammal. Preferred mammals include primates such as humans and chimpanzees, domestic animals such as horses, cows, pigs, etc. and pets such as dogs and cats. More preferably, the host animal is a primate or domestic animal. Still more preferably the host animal is a primate such as a human.

In order to further ensure that the poxvirus vector used for a particular host animal is avirulent in that animal, in addition to the above criteria, one can readily screen for a viral vector by looking at the virus's host range and tissue specificity. For example, one method is looking at a virus' natural host range. Preferably, the virus vector selected would be from a virus whose primary range of infection is for a different host animal than the animal that the gene delivery system is to be used in. For example, swinepox can be used as a viral vector when the host is a primate such as a human. However, for veterinary purposes where the host is a pig it would not be preferable. Certain highly attenuated or modified strains such as modified orthopoxvirus (e.g., the MVA or NYVAC strain of vaccinia or strains genetically modified or selected to be non-virulent in their normal host range or in a desired host cell) that are not virulent in their normal host range can, however, be used. Tissue specificity also can be used to preliminarily screen for infectivity and replication efficiency.

Where the host is human, preferred vectors include pox vectors, for example, suipox, such as swinepox, avipox such as fowlpox, canary pox, or pigeon pox, and capripoxvirus. In addition, iridoviruses such as frog virus, and African swine fever virus are also preferred. Preferred viral vectors for use with human cells are non-lytic, avirulent poxviruses such as avipox [Taylor, et al., Vaccine, 6:497-503 (1985) and Jenkins, et al., AIDS Research And Human Retroviruses 7:991-998 (1991)] and suipox [Feller, et al., Virology 183:578-585 (1991)].

Genes for Insertion into Poxvirus

Any DNA of interest can be inserted into the poxvirus vector of the present invention.

Because poxviruses have a large genome, they can readily be used to deliver a wide range of genetic material including multiple genes (i.e., act as a multivalent vector). The sizes of the poxvirus genomes ranges between about 130-300 kbp with up to 300 genes, depending on the strain of the virus. Therefore, it is possible to insert large fragments of foreign DNA into these viruses and yet maintain stability of the viral genome.

In one embodiment, at least one nucleic acid fragment encoding a gene is inserted into a poxvirus vector. In another embodiment at least two and up to about ten different nucleic acids encoding different genes are inserted into the poxvirus vector.

In one embodiment of the present invention, the recombinant poxvirus has the DNA encoding a disease-related antigen of interest, such as an antigen(s) from a disease causing agent or an antigen associate with a disease state, inserted at its novel insertion site, and expresses that antigen(s).

In another embodiment of the present invention, the recombinant poxvirus has the DNA encoding a co-stimulatory molecule(s) inserted at its novel insertion site, and expresses the co-stimulatory molecule(s).

The, recombinant vectors of the present invention are particularly useful to generate cell-mediated immune reactions.

Cell-mediated immunity is crucial to cancer and diseases such as those caused by pathogenic microorganisms, particularly viruses and other intracellular microorganisms. Accordingly, the present invention provides a composition that has at least a first recombinant virus which has incorporated into its genome or portion thereof a gene encoding an antigen from cells of a disease state. The first recombinant poxvirus may also comprise one or more genes encoding one or more immunostimulatory molecules or genes. In one preferred embodiment, the co-stimulatory molecule is a combination of nucleic acids encoding B7 (e.g. B7-1), ICAM-1, and LFA-3, also known as TRICOM, which include activation of both CD4 and cd8 activators. Another embodiment provides a composition that has a second recombinant virus that comprises one or more genes encoding one or more immunostimulatory molecules or genes. A host cell infected with both recombinant viruses expresses both the antigen(s) from a disease causing agent and expresses the immunostimulatory molecule(s). The antigen may be expressed at the cell surface of the infected host cell. The immunostimulatory molecule may be expressed at the cell surface or may be actively secreted by the host cell. The expression of both the antigen and the immunostimulatory molecule provides the necessary MHC restricted peptide to specific T cells and the appropriate signal to the T cell to aid in antigen recognition and proliferation or clonal expansion of antigen specific T cells. The overall result is an upregulation of the immune system. In a preferred embodiment the upregulation of the immune response is an increase in antigen specific T-helper lymphocytes and/or cytotoxic lymphocytes, which are able to kill or inhibit the growth of a disease causing agent or a cell infected with a disease causing agent.

The disease-related antigen of interest can be an antigen from a pathogenic microorganism or a tumor associated antigen. The genes can be derived from any organism, including bacteria, parasites, normal or transformed cells, viruses or other microorganisms. Preferred genes are derived from transformed cells. For example, any gene for which a poxvirus-based live vaccine is desired.

Such disease causing agents include but are not limited to cancer and pathogenic microorganisms.

Cancers which may be treated using the recombinant poxvirus of the present invention include but are not limited to primary or metastatic melanoma, thymoma, lymphoma, sarcoma, lung cancer, bladder cancer, colon cancer, liver cancer, non-Hodgkins lymphoma, Hodgkins lymphoma, leukemias, uterine cancer, and adenocarcinomas such as breast cancer, prostate cancer, ovarian cancer, pancreatic cancer and the like.

The aforementioned cancers can be assessed or treated by methods described in the present application. In the case of cancer, a gene encoding an antigen associated with the cancer is incorporated into the recombinant poxvirus genome or portion thereof along with a gene encoding one or more immunostimulatory molecules. Alternatively, the gene encoding an antigen associated with the cancer and the gene encoding one or more immunostimulatory molecules are incorporated into separate recombinant poxviruses. The antigen associated with the cancer may be expressed on the surface of a cancer cell or may be an internal antigen. In one embodiment the antigen associated with the cancer is a tumor associated antigen (TAA) or portion thereof. Examples of TAA that may be used in the present invention include but are not limited to melanoma TAAs which include but are not limited to MART-1 (Kawakami et al. J. Exp. Med. 180:347-352, 1994), MAGE-1, MAGE-3, GP-100, (Kawakami et al. Proc. Nat'l. Acad. Sci. U.S.A. 91:6458-6462, 1994), CEA and tyrosinase (Brichard et al. J. Exp. Med. 178:489, 1993). In another embodiment the TAAs are MUC-1, MUC-2, the point mutated ras oncogene and the point mutated p53 oncogenes (pancreatic cancer), CA-125 (ovarian cancer), PSA (prostate cancer), c-erb/B2 (breast cancer) and the like (Boon et al., Ann. Rev. Immunol. 12:337, 1994). Other antigens associated with cancer include MN antigen, Jade, and BZLF-1. The present invention is in no way limited to the genes encoding the above listed TAAs. Other TAAs may be identified, isolated and cloned by methods known in the art such as those disclosed in U.S. Pat. No. 4,514,506.

In another preferred embodiment, the target antigen is a tumor associated antigen, a tumor specific antigens, and/or a tissue-specific antigens. In this embodiment, at least one epitope of an antigen is selected from the group consisting of IL-1, IL-2, IL-3, IL-4, IL-5, IL-6, IL-7, IL-8, IL-9, IL-10, IL-11, IL-12, IFN-.alpha., IFN-.beta., IFN-.beta 17 mutants, IFN-65, CD2, CD3, CD4, CD5, CD8, CD11a, CD11b, CD11c, CD16, CD18, CD21, CD28, CD32, CD34, CD35, CD40, CD44, CD45, CD54, CD56, OX40L, 4-1BBL, K2, K1, P.beta., O.alpha., M.alpha., M.beta.2, M.beta.1, Hepsin, Pim-1, LMP1, TAP2, LMP7, TAP1, TRP, O.beta., IA.beta., IA.alpha., IE.beta., IE.beta.2, IE.alpha., CYP21, C4B, CYP21P, C4A, Bf, C2, HSP, G7a/b, TNF-.alpha., TNF-.beta., D, L, Qa, T1a, COL11A2, DP.beta.2, DP.alpha.2, DP.beta.1, DP.alpha.1, DN.alpha., DM.alpha., DM.beta., LMP2, TAPi1, LMP7, DO.beta., DQ.beta.2, DQ.alpha.2, DQ.beta.3, DQ.beta.1, DQ.alpha.1, DR.beta., DR.alpha., G250, HSP-70, HLA-B, HLA-C, HLA-X, HLA-E, HLA-J, HLA-A, HLA-H, HLA-G, HLA-F, nerve growth factor, somatotropin, somatomedins, parathormone, FSH, LH, EGF, TSH THS-releasing factor, HGH, GRHR, PDGF, IGF-I, IGF-II, TGF-.beta., GM-CSF, M-CSF, G-CSF1, erythropoietin, .beta.-HCG, 4-N-acetylgalactosaminyltransferase, GM2, GD2, GD3, JADE, MART, BAGE, GAGE, MAGE-1, MAGE-2, MAGE-3, XAGE, MUC-1, MUC-2, MUC-3, MUC-4, MUC-18, ICAM-1, C-CAM, V-CAM, ELAM, NM23, EGFR, E-cadherin, N-CAM, LFA-3 (CD58), EpCAM, B7.1, CEA, DCC, PSA, Her2-neu, UTAA, melanoma antigen p75, K19, HKer 8, pMel 17, TP10, tyrosinase related proteins 1 and 2, p97, p53, RB, APC, DCC, NF-1, NF-2, WT-1, MEN-I, MEN-II, BRCA1, VHL, FCC and MCC, ras, myc, neu, raf, erb, src, fms, jun, trk, ret, gsp, hst, bcl and abil, C1q, C1r, C1s, C4, C2, Factor D, Factor B, properdin, C3, C5, C6, C7, C8, C9, C1Inh, Factor H, C4b-binding protein, DAF, membrane cofactor protein, anaphylatoxin inactivator S protein, HRF, MIRL, CR1, CR2, CR3, CR4, C3a/C4a receptor, C5a receptor, Epstein-Barr Virus antigens (EBNA), BZLF-1, BXLF-1, and Nuclear Matrix Proteins, modified TAAs, splice variants of TAAs, functional epitopes, epitope agonists, and degenerate nucleic acid variations thereof.

Genes encoding an antigen of a disease causing agent in which the agent is a pathogenic microorganism include viruses such as HIV (GP-120, p17, GP-160, gag, po1, qp41, gp120, vif, tat, rev, nef, vpr, vpu, vpx antigens), smallpox, influenza (NP, hemagluttinin (HA antigen), neuraminidase, PB1, PB2, PA, NP, M.sub.1, M.sub.2, NS.sub.1, NS.sub.2)), papillomaviruses (E1, E2, E3, E4, E5a, E5b, E6, E7, E8, L1, L2), adenovirus (E1A, E1B, E2, E3, E4, E5, L1, L2, L3, L4, L5), HSV (ribonucleotide reductase, .alpha.-TIF, ICP4, ICP8, 1CP35, LAT-related proteins, gB, gC, gD, gE, gH, gI, gJ, and dD antigens), human papilloma virus, equine encephalitis virus, hepatitis (Hep B Surface Antigen (gp27.sup.S, gp36.sup.S, gp42.sup.S, p22.sup.c, pol, x)) and the like. Pathogenic bacteria include but are not limited to anthrax, *Chlamydia, Mycobacteria, Legioniella* and the like. Pathogenic protozoans include but are not limited to malaria, Babesia, Schistosomiasis and the like. Pathogenic yeast include *Aspergillus*, invasive *Candida*, and the like. In a preferred. embodiment the pathogenic microorganism is an intracellular organism.

For purposes of a vaccine, genes of interest are those which encode immunogenic proteins of a pathogenic organism. In many cases, these are protein components of surface structures such as the bacterial cell wall or viral envelope. In appropriate instances, immunogenic fragments or subunits of the proteins may be used.

One preferred group of nucleic acids for insertion into the poxvirus include co-stimulatory molecules, accessory molecules, and/or genes encoding a cytokine and/or growth factor. Examples of costimulatory molecules include but are not limited to B7-1, B7-2, ICAM-1, CD40, CD40L, LFA-3, CD72, OX40L (with or without OX40), and the like.

Examples of cytokines and growth factors encompassed by the present invention include but are not limited to: granulocyte macrophage-colony stimulating factor (GM-CSF), granulocyte-colony stimulating factor (G-CSF), macrophage-colony stimulating factor (M-CSF), tumor necrosis factors (TNF.alpha. and TNF.beta.), transforming growth factors (TGF.alpha. and TGF.beta.), epidermal growth factors (EGF), stem cell factor (SCF), platelet-derived growth factors (PDGF), platelet-derived endothelial cell growth factor, nerve growth factor (NGF), fibroblast growth factors (FGF), insulin-like growth factors (IGF-I and IGF-II), growth hormone, interleukins 1 to 15 (IL-1 to IL-15), interferons .alpha., .beta. and gamma. (IFN-.alpha., IFN-.beta. and IFN-.gamma.), brain-derived neurotrophic factor, neurotrophins 3 and 4, hepatocyte growth factor, erythropoictin, EGF-like mitogens, TGF-like growth factors, PDGF-like growth factors, melanocyte growth factor, mammary-derived growth factor 1, prostate growth factors, cartilage-derived growth factor, chondrocyte growth factor, bone-derived growth factor, osteosarcoma-derived growth factor, glial growth-promoting factor, colostrum basic growth factor, endothelial cell growth factor, tumor angiogenesis factor, hematopoietic stem cell growth factor, B-cell stimulating factor 2, B-cell differentiation factor, leukemia-derived growth factor, myelomonocytic growth factor, macrophage-derived growth factor, macrophage-activating factor, erythroid-potentiating activity, keratinocyte growth factor, ciliary neurotrophic growth factor, Schwann cell-derived growth factor, vaccinia virus growth factor, bombyxin, neu differentiation factor, v-Sis, glial growth factor/acetylcholine receptor-inducing activity, transferrin, bombesin and bombesin-like peptides, angiotensin II, endothelin, atrial natriuretic factor (ANF) and ANF-like peptides, vasoactive intestinal peptide, Bradykinin and related growth factors. Preferred cytokines and growth factors include but are not limited to IL-2, GM-CSF, TNF.alpha., IFN.gamnma., IL-12, RANTES, and the like.

One does not have to use a gene encoding an entire protein, but rather only the domain desired. For example, if an immune reaction is desired, only the fragment necessary to stimulate the immune reaction needs to be encoded. The co-stimulatory molecules, accessory molecules, and cytokines of the present invention are useful as biologic adjuvants, which can be administered systemically to the host via inserting nucleic acids encoding such into the same or different recombinant poxvirus vectors. In one preferred embodiment, one administers a poxvirus vector containing B7, LFA-3 and ICAM-1 in conjunction with the tumor associated antigen. In a further preferred embodiment, the poxvirus also contains OX40L. In another embodiment, the poxvirus contains OX40L alone. In yet another embodiment, the poxvirus encodes both OX40L or OX40 intrabody and OX40.

Poxviruses expressing B7-1, ICAM-1, and LFA-3, also known as TRICOM™, induce activation of both CD4+ and CD8+T cells. (U.S. Pat. No. 6,045,802; Hodge et al., J. Natl. Cancer Inst. 92: 1228-39 (2000); Hodge et al., Cancer Research 59: 5800-07 (1999)). OX40 is a primary co-stimulator of T cells that have encountered antigen, rather than naïve T cells, and promotes T-cell expansion after T cell tolerance is induced. (Bansal-Pakal et al., Nature Med. 7: 907-12 (2001)). OX40L plays a role during T cell activation by a) sustaining the long-term proliferation of CD4+ and CD8+T cells, b) enhancing the production of Th1 cytokines such as IL-2, IGN-g, and TNF-a from both CD4+ and CD8+T cells without changing IL-4 expression, c) protecting T cells from apoptosis. The combination of B7-1, ICAM-1, LFA-3, and OX40L enhances initial activation and then further potentiates sustained activation of naïve and effector T cells.

Another preferred group of nucleic acids for insertion into the poxvirus encode antibodies. Antibodies have long been used in biomedical science as in vitro tools for the identification, purification and functional manipulation of target antigens. Antibodies have been exploited in vivo for both diagnostic and therapeutic applications. Recent advances in antibody engineering have now allowed the gene encoding antibodies to be manipulated so that the antigen biding domain can also be expressed intracellularly. The specific and high-affinity binding properties of antibodies, combined with the ability to create large human immunoglobulin libraries and their ability to be stably expressed in precise intracellular location inside mammalian cells, has provided a powerful new family of molecules for gene therapy applications such as the one including a poxvirus vector in the present application. These intracellular antibodies are called "intrabodies". (Marasco et al. Gene Therapy, 4:11-15, 1997; U.S. Pat. Nos. 5,965,371; 5,851,829; 6,329,173; and 6,072,036). Preferably nucleic acids encoding angiogenesis modulating intrabodies encode a single chain antibody.

In another preferred embodiment, the poxvirus vectors of the present invention can be used to generate a pox-virus vaccine of use to the poultry industry. Examples of genes will be derived from pathogens which are important to the poultry industry and include those pathogens for which vaccines of variable efficacy already exist, namely; infectious bronchitis virus, infectious bursal disease virus, reovirus, Marek's disease virus, Newcastle disease virus, laryngo-tracheitis virus, and avian encephalomyelitis virus. The genes will also be derived from poultry pathogens for which no vaccines currently exist despite the need to control their spread. This list includes: *Eimeria* species which cause *coccidiosis salmonella gallinarum, Salmonella pullorum, Salmonella typhimurium, Staphylococcus auereus, Aspergillus flavus, Escherichia coli, Mycoplasma gallisepticum, Mycoplasma gallinarum, Mycoplasma synoviae*, RNA lymphoid leukosis virus, avian influenza, and hemorrhagic enteritis virus.

Methods for Inserting Genes into the Proxrivus Genome

Foreign genes for insertion into the genome of a poxvirus in expressible form can be obtained by any conventional technique for isolating a desired gene.

For organisms which contain a DNA genome, the genes encoding an antigen of interest are isolated from the genomic DNA; for organisms with RNA genomes, the desired gene may be isolated from cDNA copies of the genome. If restriction maps of the genome are available, strategies can be designed for cleaving genomic DNA by restriction endonuclease digestion to yield DNA fragments that contain the gene of interest. In some cases, desired genes may have been previously cloned and thus, the genes can be obtained from the available clones. Alternatively, if the DNA sequence of the gene is known, the gene can be synthesized by any of the conventional techniques for polymerase chain reaction or synthesis of deoxyribonucleic acids (e.g., the phosphate or phosphite triester techniques).

Genes encoding an antigen of interest can be amplified by cloning the gene into a bacterial host. For this purpose, various prokaryotic cloning vectors can be used. Examples are plasmids pBR322 and pEMBL.

The genes encoding the antigen of interest can be prepared for insertion into the poxvirus vectors by standard techniques. In general, the cloned genes can be excised from the prokaryotic cloning vector by restriction enzyme digestion. In most cases, the excised fragment will contain the entire coding region of the gene. The DNA fragment carrying the cloned gene can be modified as needed, for example, to make the ends of the fragment compatible with the insertion sites of the poxvirus vectors, then purified prior to insertion into these vectors at restriction endonuclease cleavage sites (cloning sites) as described below.

The basic techniques of inserting genes into viruses are known to the skilled artisan and involve, for example, recombination between the viral DNA sequences flanking a gene in a donor plasmid and homologous sequences present in the parental virus (Mackett, et al., Proc. Natl. Acad. Sci. USA 79:7415-7419 (1982)). For example, a recombinant virus such as a poxvirus for use in delivering the gene can be constructed in two steps known in the art and analogous to the methods for creating synthetic recombinants of the fowlpoxvirus described in U.S. Pat. No. 5,093,258, the disclosure of which is incorporated herein by reference. Other techniques include using a unique restriction endonuclease site that is naturally present or artificially inserted in the parental viral vector.

First, the DNA gene sequence to be inserted into the virus can be placed into a plasmid, e.g., an *E. coli* plasmid construct, into which DNA homologous to a section of DNA such as that of the poxvirus has been inserted. Separately, the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA which is the desired insertion region. The resulting plasmid construct is then amplified by growth within *E. coli* bacteria and isolated. Preferably, the plasmid also contains an origin of replication such as the *E. coli* origin of replication, and a marker such as an antibiotic resistance gene for selection and propagation in *E. coli*.

Second, the isolated plasmid containing the DNA gene sequence to be inserted is transfected into a cell culture, e.g., chick embryo fibroblasts, along with the poxvirus. Recombination between homologous pox DNA in the plasmid and the viral genome respectively results in a poxvirus modified by the presence of the promoter-gene construct in its genome, at a site which does not affect virus viability.

Where the embodiment of the present invention provides insertion of more than one nucleic acid (e.g. a tumor antigen and a costimulatory molecule), the first nucleic acid is inserted into the novel insertion sites of the present invention, as described above, and additional nucleic acid(s) can be inserted either into the novel insertion sites described here or other insertion sites.

The gene is preferably inserted into a site or region (insertion region) in the virus which does not affect virus viability of the resultant recombinant virus. The novel insertion sites are intragenic regions between known genes, preferably nonessential genes. The skilled artisan can readily identify such regions in a virus by, for example, randomly testing segments of virus DNA for regions that allow recombinant formation without seriously affecting virus viability of the recombinant. One region that can readily be used and is present in many viruses is the thymidine kinase gene. For example, it has been found in all poxvirus genomes examined [leporipoxvirus: Upton, et al., J. Virology, 60:920 (1986) (shope fibroma virus); capripoxvirus: Gershon, et al., J. Gen. Virol., 70:525 (1989) (Kenya sheep-1); orthopoxvirus: Weir, et al., J. Virol., 46:530 (1983) (vaccinia); Esposito, et al., Virology, 135:561 (1984) (monkeypox and variola virus); Hruby, et al., PNAS, 80:3411 (1983) (vaccinia); Kilpatrick, et al., Virology, 143: 399 (1985)(Yaba monkey tumor virus); avipoxvirus: Binns, et al., J. Gen. Virol. 69:1275 (1988) (fowlpox); Boyle, et al., Virology, 156:355 (1987) (fowlpox); Schnitzlein, et al., J. Virological Methods, 20:341 (1988) (fowlpox, quailpox); entomopox (Lytvyn, et al., J. Gen. Virol. 73:3235-3240 (1992)].

In fowlpox, in addition to the TK region, other insertion regions include, for example, BamHI J [Jenkins, et al., AIDS Research and Human-Retroviruses 7:991-998 (1991)] the EcoRI-HindIII fragment, BamHI fragment, EcoRV-HindHIII fragment, BamHI fragment and the HindIII fragment set forth in EPO Application No. 0 308 220 A1. [Calvert, et al., J. of Virol. 67:3069-3076 (1993); Taylor, et al., Vaccine 6:497-503 (1988); Spehner, et al., (1990) and Boursnell, et al., J. of Gen. Virol. 71:621-628 (1990)].

In addition to the requirement that the gene be inserted into an insertion site, successful expression of the inserted gene(s) by the modified poxvirus requires the presence of a promoter operably linked to the desired gene, i.e., in the proper relationship to the inserted gene. The promoter must be placed so that it is located upstream from the gene to be expressed. Promoters are well known in the art and can readily be selected depending on the host and the cell type one wishes to target. For example in poxviruses, poxviral promoters should be used, such as the vaccinia 7.5K, 40K, fowlpox. Enhancer elements can also be used in combination to increase the level of expression. Furthermore, the use of inducible promoters, which are also well known in the art, in some embodiments are preferred.

Promoters useful according to the present invention include poxvirus promoters such as, e.g., an entomopox promoter, an avipox promoter, or an orthopox promoter such as a vaccinia promoter, e.g., HH, 11K or Pi. For example, the Pi promoter, from the Ava I H region of vaccinia, is described in Wachsman et al., J. of Inf. Dis. 155, 1188-1197 (1987). More particularly, this promoter is derived from the Ava I H(Xho I G) fragment of the L-variant WR vaccinia strain, in which the promoter directs transcription from right to left. The map location of the promoter is approximately 1.3 Kbp (kilobase pair) from the 5' end of Ava IH, approximately 12.5 Kbp from the 5' end of the vaccinia genome, and about 8.5 Kbp 5' of the Hind III C/N junction. The Hind III H promoter (also "HH" and "H6" herein) sequence is an up-stream of open reading frame H6 by Rosel et al., J. Virol. 60, 436-449 (1986). The 11K promoter is as described by Wittek, J. Virol. 49, 371-378 (1984) and Bertholet, C. et al., Proc. Natl. Acad. Sci. USA 82, 2096-2100 (1985). One can take advantage of whether the promoter is an early or late promoter to time expression of particular genes. Additionally, as discussed below, one can use additional promoters.

Another preferred embodiment provides a poxvirus vector in which the promoter is modulated by an external factor or cue, allowing control of the level of polypeptide being produced by the vectors by activating that external factor or cue. For example, heat shock proteins are proteins encoded by genes in which the promoter is regulated by temperature. The promoter of the gene which encodes the metal-containing protein metallothionine is responsive to $Cd^{+}$ ions. Incorporation of this promoter or another promoter influenced by external cues also make it possible to regulate the production of the proteins.

In another preferred embodiment, the poxvirus genome is modified to carry a nucleic acid encoding at least one gene of interest which is operably linked to an "inducible" promoter. Such inducible systems allow careful regulation of gene expression. See, Miller and Whelan, Human Gene Therapy, 8:803-815 (1997). The phrase "inducible promoter" or "inducible system" as used herein includes systems wherein promoter activity can be regulated using an externally delivered agent. Such systems include, for example, systems using the lac repressor from *E. coli* as a transcription modulator to regulate transcription from lac operator-bearing mammalian cell promoters (Brown et al. Cell, 49:603-612, 1987); systems using the tetracycline repressor (tetR)(Gossen and Bujard, Proc. Natl. Acad. Sci. USA 89: 5547-5551, 1992; Yao et al., Human Gene Ther. 9:1939-1950, 1998; Shokelt et al., Proc. Natl. Acad. Sci. USA 92.6522-6526, 1995). Other such systems include FK506 dimer, VP16 or p65 using castradiol, RU486/mifepristone, diphenol muristerone or rapamycin (see, Miller and Whelan, supra, at FIG. 2). Yet another example is an ecdysone inducible system (see, e.g. Karns et al, MBC Biotechnology 1:11, 2001). Inducible systems are available, e.g., from Invitrogen, Clontech, and Ariad. Systems using a repressor with the operon are preferred. One would adapt these promoters by substituting portions of pox promoters for the mammalian promoter.

One embodiment of the present invention provides the use of a regulatory element such as a transcriptional regulatory element or an enhancer.

In one preferred embodiment of the present invention, a "transcriptional regulatory element" or "TRE" is introduced for regulation of the gene of interest. As used herein, a TRE is a polynucleotide sequence, preferably a DNA sequence, that regulates (i.e., controls) transcription of an operably-linked polynucleotide sequence by an RNA polymerase to form RNA. As used herein, a TRE increases transcription of an operably linked polynucleotide sequence in a host cell that allows the TRE to function. The TRE comprises an enhancer element and/or pox promoter element, which may or may not be derived from the same gene. The promoter and enhancer components of a TRE may be in any orientation and/or distance from the coding sequence of interest, and comprise multimers of the foregoing, as long as the desired, transcriptional activity is obtained. As discussed herein, a TRE may or may not lack a silencer element.

Another preferred embodiment of the present invention provides an. "enhancer" for regulation of the gene of interest. An enhancer is a term well understood in the art and is a polynucleotide sequence derived from a gene which increases transcription of a gene which is operably-linked to a promoter to an extent which is greater than the transcription activation effected by the promoter itself when operably-linked to the gene, i.e. it increases transcription from the promoter. Having "enhancer activity" is a term well understood in the art and means what has been stated, i.e., it increases transcription of a gene which is operably linked to a promoter to an extent which is greater than the increase in transcription effected by the promoter itself when operably linked to the gene, i.e., it increases, transcription from the promoter.

The activity of a regulatory element such as a TRE or an enhancer generally depends upon the presence of transcriptional regulatory factors and/or the absence of transcriptional regulatory inhibitors. Transcriptional activation can be measured in a number of ways known in the art (and described in more detail below), but is generally measured by detection and/or quantization of mRNA or the protein product of the coding sequence under control of (i.e., operatively linked to) the regulatory element. As discussed herein, the regulatory element can be of varying lengths, and of varying sequence composition. By transcriptional activation, it is intended that transcription will be increased above basal levels in the target cell by at least about 2-fold, preferably at least about 5-fold, preferably at least about 10-fold, more preferably at least about 20-fold. More preferably at least about 50-fold, more preferably at least about 100-fold, even more preferably at least about 200-fold, even more preferably at least about 400- to about 500-fold, even more preferably, at least about 1000-fold. Basal levels are generally the level of activity, if any, in a non-target cells, or the level of activity (if any) of a reporter construct lacking the TRE of interest as tested in a target cell type.

A "functionally-preserved" variant of a TRE is a TRE which differs from another TRE, but still retains ability to increase transcription of an operably linked polynucleotide, especially cell-specific transcription activity. The difference in a TRE can be due to differences in linear sequence, arising from, for example, single or multiple base mutation(s), addition(s), deletion(s), and/or modification(s) of the bases. The difference can also arise from changes in the sugar(s), and/or linkage(s) between the bases of a TRE.

Certain point mutations within sequences of TREs have been shown to decrease transcription factor binding and gene activation. One of skill in the art would recognize that some alterations of bases in and around known the transcription factor binding sites are more likely to negatively affect gene activation and cell-specificity, while alterations in bases which are not involved in transcription factor binding are not as likely to have such effects. Certain mutations are also capable of increasing TRE activity. Testing of the effects of altering bases may be performed in vitro or in vivo by any method known in the art, such as mobility shift assays, or transfecting vectors containing these alterations in TRE functional and TRE non-functional cells. Additionally, one of skill in the art would recognize that point mutations and deletions can be made to a TRE sequence without altering the ability of the sequence to regulate transcription.

In the present invention, the poxvirus vectors directed at specific target cells may also be generated with the use of TREs that are preferentially functional in the target tumor cells. Non-limiting examples of tumor cell-specific heterologous TREs, and non-limiting examples of respective potential target cells, include TREs from the following genes: .alpha.-fetoprotein (AFP) (liver cancer), mucin-like glycoprotein DF3 (MUC1) (breast carcinoma), carcinoembryonic antigen (CEA) (colorectal, gastric, pancreatic, breast, and lung cancers), plasminogen activator urokinase (uPA) and its receptor gene (breast, colon, and liver cancers), E2F1 (cell cycle S-phase specific promoter) (tumors with disrupted retinoblastoma gene function), HER-2/neu (c-erbB2/neu) (breast, ovarian, stomach, and lung cancers).

In the present invention, tumor-specific TREs may be used in conjunction with tissue-specific TREs from the following exemplary genes (tissue in which the TREs are specifically functional are in parentheses): hypoxia responsive element, vascular endothelial growth factor receptor (endothelium), albumin (liver), factor VII (liver), fatty acid synthase (liver), Von Willebrand factor (brain endothelium), alpha-actin and myosin heavy chain (both in smooth muscle), synthetast I (small intestine), Na—K—Cl transporter (kidney). Additional tissue specific TREs are known in the art.

Accordingly, in one embodiment, the cell specific, heterologous TRE is tumor cell specific. Preferably, both heterologous TREs are tumor cell specific and functional in the same cell. In another embodiment, one of the first heterologous TREs is tumor cell specific and the second heterologous TRE is tissue specific, whereby both TREs are function in the same cell.

Introduction of the viral vector carrying the gene to be delivered to the target host cell may be effected by any method known to those of skill in the art.

Administration of the recombinant poxvirus of the invention can be either "prophylactic" or "therapeutic" depending on the subject. When provided prophylactically, the recombinant poxvirus of the present invention is provided in advance of any symptom, but when one believes the subject is at risk. The prophylactic administration of the recombinant poxvirus serves to prevent or ameliorate any subsequent angiogenic-related condition. When provided therapeutically, the recombinant poxvirus is provided at or after the onset of a symptom of infection or disease. Thus the present invention may be provided to either prior the anticipated exposure to a disease-causing agent or disease state or after the initiation of the infection or disease.

The term "unit dose" as it pertains to the inoculum refers to physically discrete units suitable as unitary dosages for mammals, each unit containing a predetermined quantity of recombinant poxvirus calculated to produce the desired immunogenic effect in association with the required diluent. The specifications for the novel unit dose of an inoculum of this invention are dictated by and are dependent upon the unique characteristics of the recombinant virus and the particular immunologic effect to be achieved.

Administration

For administration to a subject, the poxvirus of the present invention is prepared as an inoculum. The inoculum is typically prepared as a solution in a tolerable (acceptable) diluent such as saline, phosphate-buffered saline or other physiologically tolerable diluent and the like to form an aqueous pharmaceutical composition.

The route of inoculation may be scarification, intravenous (I.V.), intramuscular (I.M.), subcutaneous (S.C.), intradermal (I.D.), intraperitoneal (I.P.), intratumor and the like, which results in eliciting a protective response against the disease causing agent. The dose is administered at least once. Subsequent doses may be administered as indicated.

In one embodiment, heterologous prime-boost regimens are employed. For example, the host can be immunized at least once with a first vector such as a nucleic acid-based vector. Subsequent immunizations are performed with a poxvirus vector. In another example, the host is first immunized with a first poxvirus vector and then with a second poxvirus vector of a different genus.

In providing a manual with the recombinant poxvirus of the present invention, preferably a human, the dosage of administered recombinant poxvirus will vary depending upon such factors as the mammal's age, weight, height, sex, general medical condition, previous medical history, disease progression, tumor burden and the like.

In general, it is desirable to provide the recipient with a dosage of recombinant virus in the range of about $10^5$ to about $10^{10}$ plaque forming units, although a lower or higher dose may be administered.

One would inject a sufficient amount of the viral vectors to obtain a serum concentration in the organ of interest of the protein ranging between about 1 pg/ml to 20 μg/ml. More preferably between about 0.1 μg/ml to 10 μg/ml. Still more preferably, between about 0.5 μg/ml to 10 μg/ml.

Examples of methods for administering the recombinant poxvirus into mammals include, but are not limited to, exposure of tumor cells to the recombinant virus ex vivo, or injection of the recombinant poxvirus into the affected host by intravenous, S.C., I.D. or I.M. administration of the virus. Alternatively the recombinant poxvirus or combination of recombinant vectors may be administered locally by direct injection into the cancerous lesion or tumor or topical application in a pharmaceutically acceptable carrier. The quantity of recombinant poxvirus carrying the nucleic acid sequence of one or more antigens in combination with nucleic acid sequences encoding multiple costimulatory molecules to be administered is based on the titer of virus particles. A preferred range of the immunogen to be administered is $10^5$ to $10^{10}$ virus particles per mammal, preferably a human. If the mammal to be immunized is already afflicted with cancer or metastatic cancer, the vaccine can be administered in conjunction with other therapeutic treatments.

The present invention also provides a pharmaceutical composition comprising a poxvirus, including a recombinant poxvirus, and a pharmaceutically acceptable carrier.

The effect of the genetic material delivered can be carefully monitored and regulated using this system. Preferred poxvirus vectors such as swinepox will only express the genetic material for about two weeks. Thus, if the condition being treated is alleviated within that time frame, since the vector system is self limiting, no unnecessary material will be produced after that time period. Where additional dosages will be needed, additional administration of the material can be accomplished by repeating the injection. In certain cases, the addition of a second, third, etc. material can also be added with these vectors.

A preferred embodiment of the present invention relates to a method of modulating immune responses to achieve a desired goal.

One embodiment of the present invention provides treating a subject in need, for example, a subject having cancer, with a poxvirus of the present invention in combination with a chemotherapeutic agent. Preferably, the poxvirus expresses a gene associated with a cancer. The chemotherapeutic agent can be any anti-cancer drug.

Examples of anti-cancer drugs that may be used in the various embodiments of the invention, including pharmaceutical compositions and dosage forms and kits of the invention, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; capsitabine; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleulin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine, mechlorethamine oxide hydrochloride rethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, improsulfan, benzodepa, carboquone, triethylenemelamrine, triethylenephosphoramide, triethylenethiophosphoramide, trimethylolomelainine, chlomaphazine, novembichin, phenesterine, trofosfamide, estermustine, chlorozotocin, gemzar, nimustine, ranimustine, dacarbazine, mannomustine, mitobronitol, aclacinomycins, actinomycin F(1), azaserine, bleomycin, carubicin, carzinophilin, chromomycin, daunorubicin, daunomycin, 6-diazo-5-oxo-1-norleucine, doxorubicin, olivomycin, plicamyciri, porfiromycin, puromycin, tubercidin, zorubicin, denopterin, pteropterin, 6-mercaptopurine, ancitabine, 6-azauridine, carmofur, cytarabine, dideoxyuridine, enocitabine, pulmozyme, aceglatone, aldophosphamide glycoside, bestrabucil, defofamide, demecolcine, elfornithine, elliptinium acetate, etoglucid, flutamide, hydroxyurea, lentinan, phenamet, podophyllinic acid, 2-ethylhydrazide, razoxane, spirogermanium, tamoxifen, taxotere, tenuazonic acid, triaziquone, 2,2',2"-trichlorotriethylamine, urethan, vinblastine, vincristine, vindesine and related agents. 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine, edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopraminde; MIF inhibitor; mifepristone; miltefosine; nirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; taxel; taxel analogues; taxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rheniuim Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division ibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil, leucovorin, capsitabine, cyclosphosphamide, and gemcitabine. The magnitude of a prophylactic or therapeutic dose of each active ingredient in the treatment of a patient with a solid tumor will typically vary with the specific active ingredients, the severity and type of tumor, and the route of administration. The dose and the dose frequency may vary according to age, body weight, response, and the past medical history of the patient; the likelihood of mestastic recurrence must also be considered. Suitable dosing regimens can be readily selected by those skilled in the art with due consideration of such factors by following, for example, dosages reported in the literature and recommended in the Physician's Desk Reference® (54th ed., 2000). Unless otherwise indicated, the magnitude of a prophylactic or therapeutic dose of each pharmaceutical used in an embodiment of the invention will be that which is known to those in the art to be safe and effective, or is regulatory approved.

In one embodiment, a treatment method in accordance with the present invention includes treating a subject in need, for example, a subject having cancer, for example breast cancer, ovarian cancer or prostate cancer, with a first poxvirus vector designed to elicit a cytotoxic T-cell response to a foreign gene. For a cancer patient, the gene can be a tumor associated antigen, such as PSA, PSAM, BRCA1, ras, CEA or MUC. One can also use a foreign gene encoding a viral antigen or antigens to treat an individual having or susceptible to an infectious disease, preferably a viral envelope protein. Cytotoxic T-cells specific for the desired cancer-associated antigen can be generated by administering between about $10^5$-$10^9$ pfu of a recombinant poxvirus carrying a sequence encoding a tumor-associated antigen to the individual affected with the tumor. For detailed construction of such vectors, see, e.g., U.S. Pat. No. 5,656,465. Preferably one would also use an immune modulator such as the use of cytokines, e.g., IL-2, or co-stimulatory molecules, e.g., B7.1 or B7.2, as biologic adjuvants, which can be administered systemically to the host via inserting nucleic acids encoding such into the same or different recombinant poxvirus vectors. In one preferred embodiment, one administers a poxvirus vector containing B7, LFA-3, ICAM-1 and Ok40L in conjunction with the foreign gene.

The invention will be further characterized by the following examples which are intended to be exemplary of the invention.

EXAMPLES

Example 1

Vaccinia Insertion Site Studies

The relative paucity of defined-insertion sites in MVA hastened the search for new sites in the MVA genome into which foreign genes can be inserted. Analysis of the published MVA sequence (Antoine et al., 1998) identified several other potential insertion sites hereafter referred to as MVA 44/45; MVA 49/50 and MVA 124/125. The numbers designate the ORF s lying on either side of the insertion site.

Selection of appropriate sites was determined following examination of the sequence to determine whether several criteria were met. First, the insertion site should lie in an intergenic space, preferably between non-essential genes. Assessment of the essential nature of the MVA genes was determined after comparing the MVA gene with its' vaccinia homologue. Second, there' should be essential genes between the native sites of the 40K, 7.5K and I3 promoters and the insertion site. Third, the proposed insertion site should not disrupt cryptic ORFs in the region, or promoters of adjacent genes. Similarly T5NT sequences of surrounding genes should be left intact.

Regions corresponding to the 5' and 3' flankers of the new vectors were amplified from genomic DNA using Pfu polymerase. These fragments were inserted into plasmid vectors and sequenced. Following confirmation of sequence, the SHIV 89.6P env gene under 40K promoter, and the C1-lacZ cassette were inserted into these vectors to generate test plasmids for IVR: pT5158, pT5164, pT5172. The choice of antigen was dictated by available MVA reagent for comparative immunogenicity studies.

Site 44/45

Site 44/45 in MVA lies between ORFs 044L and 045L—the insertion site is between positions 37346-37357 in the MVA genomic sequence (Genbank Acc # U94848). DNA sequence between these nucleotides is deleted in recombinant virus and replaced with defined inserts. This region is 5' of the translational start codon of MVA 044L and 3' of the translational stop codon of MVA 045L. This region is present in the vaccinia Copenhagen sequence (Genbank Accession number M35027). The corresponding vaccina ORFs are F14L (homologous to MVA 044L) and F15L (MVA 045L). Although the DNA sequence of NYVAC is not available in Genbank, there is nothing in the literature to indicate that this region has been modified in the NYVAC genome.

Site 49/50

Site 49/50 in MVA lies between ORFs 049L and 050L—the insertion site is between positions 42687 and 42690 in the MVA genomic sequence. This region is 5' of the translational'start codon of MVA 049L and 3' of the translational stop codon of 050L. This region is present in the Copenhagen sequence—the homologues are E2L (MVA 049L) and E3L (MVA 050L). This region has not been modified in the NYVAC genome.

Site 124/125

Site 124/125 in MVA lies between ORFs 124L and 125L—the insertion site is at positions 118481-118482 in the MVA genomic sequence. This lies 5' of the translational start codon of MVA 124L and 3' of the translational stop codon of 125L. This region is present in the Copenhagen sequence—the homologues are A13L (MVA 124L) and A14L (MVA 125L). According to the literature, this region has not been modified in the NYVAC genome.

Example 2

FowlPox Insertion Site Studies

Generation of recombinant fowlpox generally involves inserting foreign genes and a lac Z promoter-gene cassette at the unique regions of the fowlpox genome. Recombinant viruses are selected on the basis of colorimetric screening with bluo-gal. Identification of alternative insertion sites in the fowlpox genome is desirable to enable insertion of multiple gene-promoter cassettes into the virus.

Three potential new insertion sites were identified and designated: 43K, FP14 and the Long Unique Sequence (LUS). The 43K insertion site is the subject of another independent study based on plaque selection in a manner similar to that of vaccinia Δ37K.

The overall aim of this project is to identify insertion sites that are at least as stable as those with the foreign gene and lacZ inserted in the BamHI J region. Furthermore, the immunogenicity of recombinant viruses with insertions at these new sites should be equivalent to those with insertions at BamHI J. The organization of the new viruses and controls available for comparative studies are listed in Table 1.

TABLE 1

Structure of the viral recombinants designed to test alternative insertion sites in the fowlpox genome.

| Virus | Insertion site | gene 1 | gene 2 | |
|---|---|---|---|---|
| TBC-FPV | — | — | — | negative control |
| | 43K | 40K-BH10 env | C1-lacZ | new site |
| | FP14 | 40K-BH10 env | C1-lacZ | new site |
| | LUS | 40K-BH10 env | C1-lacZ | new site |
| vT155 | Bam J | 40K-BH10 env | C1-lacZ | positive control |

The 43K Insertion Site

The fowlpox 43K gene has homology to the vaccinia 37K major envelope antigen gene, F13L. Calvert et al (1992) demonstrated that this gene encodes a major membrane protein, which is critical for the generation of extracellular enveloped virions. As an alternative to the selecting recombinant plaques based on the expression of 43K, we have designed a vector which enables the region immediately 3' of the 43K coding region to be used as an insertion site in the fowlpox genome, where recombinant plaques can be screened for expression of lac Z using a colorimetric screen.

Examination of the available 43K gene sequence, Genbank Accession #M88587, revealed a short intergenic space between the 3' end of the 43K gene and the 5' end of the P74 gene. A plasmid was designed where the 5' flanker corresponded to nt 282-1753 in the 43K gene sequence. This sequence comprises 338 bp of 5' untranslated sequence and the entire coding region of the 43K gene. The last 12 codons in the 43K gene that are present in the 5' flanker were wobbled to minimize the possibility of recombination between these and the native sequences that are present in the 3' flanker as part of the promoter for the 74K gene. The 3' flanker extends from nt 1718-2233 in the 43K gene sequence and consists of the terminal 12 codons of the 43K coding region, the promoter for p74 and the first 442 bp of the p74 coding region. The terminal part of the 43K coding region includes some motifs that correspond to poxvirus transcriptional sequences, and might presumably be required for function of p74. The test vector—pT5104—was constructed by inserting the 40K-BH10 env and C1-lacZ promoter-gene cassettes between these flanker regions.

Fowlpox has now been completely sequenced, and its genomic sequence is available in Genbank, Acceession No. AF198100. Within this genomic sequence, the 43K insertion site is at position 128178 of the fowlfox genomic sequence, and lies 5' of FPV107 and 5' of FPV108. These genes are divergently transcribed, and the insertion site lies between the two promoter elements for the two ORFs.

The FP14 Insertion Site

This insertion site was identified from sequence generated by Tartaglia et al (1990) accession #X17202, corresponding to a 10.5 kb HindIII fragment which has some homologies with the HindIII D region of vaccinia virus. This region was mapped to approximately 70 kb from the left end of the viral genome. Part of this region was also sequenced by Binns et al. (1990), who generated some stable recombinant viruses by inserting lac Z into particular genes in this region. One particular area of the Tartaglia et al (1990) sequence satisfies many of the criteria previously identified as important for a new insertion site: intergenic space with good distance between genes; non-disruptive of promoter regions of adjacent genes and no crypic open reading frames (ORF) in the region.

The area of this new insertion site lies between the end of FP14 and the start of FP18. Each of these genes is transcribed towards the right side of the genome, and the intergenic space is 447 bp. The fowlpox homologues of the vaccinia D genes are located on either side of this region; these genes have been shown in vaccinia to be essential for viral replication. Detailed analysis of this intergenic space identified cryptic minor ORFs on both strands of the DNA, however a potential insertion site was identified 160 bp upstream of the FP18 translational start—this site is not part of any cryptic ORF. Flanker regions of a plasmid transfer vectors were generated by PCR from genomic DNA of TBC-FPV. The 5' flanker corresponds to sequence between nt 1344 and 1949 and the 3' flanker to sequence between nt 1964 to 2462 of the Tartaglia sequence. The test vector—pT5105—was constructed by inserting the 40K-BH10 env and C1-lacZ promoter-gene cassettes between these flanker regions.

Within the fowlpox genomic sequence deposited with Genbank, the FP14 insertion site is between positions 67080-67097 in the fowlfox genomic sequence, and lies 5' of FPV060 and 3' of FPV061.

The LUS Insertion Site

The Inverted Terminal Repeat (ITR) region of the poxvirus genome is an attractive option for the insertion of foreign genes. Recombination between the ends of the genome offers the possibility of duplicating the genes inserted at one end of the genome, and thus possibly increasing the level of expression of an inserted antigen and consequently the immunogenicity of the recombinant virus. There are two reports in the literature describing sequences in the fowlpox ITR region: Boursnell et al (1990) and Tomley et al (1988). The ITR region of the left end of the fowlpox genome is approximately 10 kb long and comprises two different types of sequence: ~4 kb of tandem repeat sequence and ~6 kb of Long Unique Sequence (LUS). Boursnell et al (1990) demonstrated that the fusion gene of Newcastle disease virus and the lacZ coding region could be inserted into genes of the LUS and generate a stable recombinant with a double copy of the inserted genes.

Examination of the Tomley et al sequence (Genbank Accession # D00295) reveals a large intergenic space of 410 bp between two identified ORFs. There are cryptic ORFs in this sequence, however a possible insertion site was identified between the promoters of these oppositely transcribed ORFs. Fragments of DNA corresponding to flanker regions were amplified by PCR from TBC-FPV, and a test vector was constructed by inserting the 40K-BH10 env and C1-lacZ cassettes between the flanker regions. The 5' and 3' flankers corresponds to nt 1322-1954 and 1961-2660 respectively in the Tomley sequence.

Within the fowlpox genomic sequence in Genbank, there are two long unique sequences (LUS) at each end of the viral genome, and thus two LUS insertion sites in each genome. The LUS insertion site at the left end of the genome is between positions 7470-7475 in the fowlpox genomic sequence, and lies 3' of FPV006 and 5' of FPV007 125L. The LUS insertion site at the right end of the genome is between positions 281065 and 281070 in the fowlpox genomic sequence, and lies 5' of FPV254 and 3' of FPV255.

Recombinant Selection and Analysis

IVRs will be performed in CEDs and 10 independent plaques will be carried for several rounds of purification. The isolates will be tested by interim back plaque analysis for BH10 env expression and 4 independent isolates will be selected and amplified into small Seed Stocks (2 to 3×15 cm plates for each). After titration they will be passaged twice at moi=0.1 in, CEDs (1×15 cm plate for each isolate and amplification) to observe their stability.

While the 3 independent IVRs may be done independently, the passages will be done in parallel and also include vT155. After the yield of these recombinants and their passage 1 (P1) and passage 2 (P2) is determined, the stability assessed by black plaques assay, the expression of the env assessed by ELISA, the best isolate for each insertion site will be selected for the immunogenicity study.

Immunogenicity Study

A small scale immunogenicity study will determine if the new insertion sites elicit an immune response against HIV-1 BH10 env as good as vT155 in which env is inserted in the BamHI J fragment of FPV. 5 groups of 5 mice each (corresponding to the 5 different viruses) will be injected with $10^6$ or $10^7$ pfu of virus 4 times at 3 weeks interval and bled prior to each injection. All blood sample will be tested for Abs against HIV-1 env by ELISA.

Example 3

Vaccinia and Fowlpox Recombinant Vectors Containing Insertions

MVA recombinant vectors containing a test antigen in the specified intergenic sites were successfully generated and evaluated, i.e. they were used and expressed the appropriate proteins. The DNA inserted into these vectors contained the following elements: the SHIV 89.6P env gene under the control of the 40K pox virus promoter, and the *E. coli* marker gene LacZ under the control of the C1 pox promoter. The SHIV 89.6 P envelope gene is a chimeric simian/human immunodeficienty virus type 1 isolate (Reimann, K. A. et al., 1996. *J. Virol.* 70:6922-6928; Yao Q. et al., AIDS Res Hum Retroviruses. 2000 Feb. 10; 16(3):227-36). The following schematic recombinant virus structures represent the insertion of this insert into a) MVA at MVA 44/45; b) MVA at MVA 49/50; and c) MVA at MVA 124/125:

a)—5' flanker 44/45-40K-SHIV 89.6P env-C1-LacZ-44/45 3' flanker— b)—5' flanker 49/50-40K-SHIV 89.6P env-C1-LacZ-49/50 3' flanker— c)—5' flanker 124/125-40K-SHIV 89.6P env-C1-LacZ-124/125 3' flanker—

Fowlpox recombinant vectors containing a test antigen were also successfully generated and evaluated. The inserted foreign DNA contained the following elements: the HIV BH-10 envelope gene under the control of the 40K pox virus promoter, and the *E. coli* marker gene LacZ under the control of the C1 pox promoter. The HIV BH-10 gene has been previously described (Muesing, M. A. et al., 1985 *Nature.* 313:450-8; Yao Q. et al., AIDS Res Hum Retroviruses. 2000 Feb. 10; 16(3):227-36). The following schematic recombinant virus structures represent the insertion of this insert into a) FPV at FPV 43K; b) FPV at FP14; and c) FPV at FP LUS:

a)—5' flanker 43K-40K-BH10 env-C1-7LacZ-43K 3' flanker— b)—5' flanker FP14-40K-BH10 env-C1-LacZ-FP14 3' flanker— c)—5' flanker LUS-40K-BH10 env-C1-LacZ-LUS 3' flanker—

Additional recombinant vectors have been generated to date using these insertion sites for MVA and FPV.

For example a further example of a recombinant vector with an insertion at the novel fowlpox insertion site, FP14, is the recombinant vaccine vector PANVAC-F. PANVAC-F was constructed using two plasmid vectors. A schematic depicting the construction of this vector is provided in FIG. 1. The first plasmid, designated pT1154, directs insertion of the wCEA (6D) and wMUC-1(6) coding sequences into the FP14 region of the fowlpox virus genome. The second plasmid, designated pT8150, directs insertion of the LFA-3, ICAM-1, and B7.1 coding sequences (collectively known as TRICOM) into the BamH I J region of the fowlpox virus genome. The wCEA (6D) gene is under the transcriptional control of the vaccinia 40K promoter. The wMUC-1(6) gene is under the transcriptional control of the synthetic early/late (sE/L) promoter. The LFA-3 gene is under the transcriptional control of the vaccinia 30K promoter, the ICAM-1 gene is under the transcriptional control of the vaccinia I3 promoter, and the B7.1 gene is under the transcriptional control of the synthetic early/late (sE/L) promoter. In addition, pT1154 contains the *E. coli* lacZ gene, under the control of the vaccinia 40K promoter, which is included as a screen for recombinant progeny, and pT8150 contains the GUS gene, under the control of the 7.5 promoter, for use in screening for recombinant progeny. A plaque-purified isolate from the POXVAC-TC vaccine strain of fowlpox virus was used as the parental virus for this recombinant vector. In vivo recombination between the plasmid vectors and the viral DNA resulted in the formation of a recombinant virus in which pT1154 was integrated at FP14, and pT8150 was integrated at the BamHI J region, as illustrated in FIG. 1.

A further example of a recombinant vector with an insertion at the novel fowlpox insertion site, FP14, is the recombinant fowlpox virus designated rF-OX40L. This vector was generated by insertion of the murine OX40L gene under the control of the 40k promoter into the genome of rF-CEA at the FP14 site in the genome. The OX40L cDNA was amplified from anti-CD40/anti-IgM-activated murine B cells by RT-PCR using primers specific for the 5'-(dGGTACCGGTACCATGGAAGGGGAAGGGGTTC) (SEQ ID NO:1) and the 3'-(dCTCGAGCTCGAGTCACAGTGGTACTTGGTTC) (SEQ ID NO:2) ends of the open reading frame. The cDNA was cloned into a poxvirus transfer vector. Sequence analysis confirmed that no mutations were introduced in the cloning process.

A further example of a recombinant vector with an insertion at the novel fowlpox insertion site, FP14, is the recombinant fowlpox virus designated rF-MUC-1-TRICOM/OX40L. This vector was generated by insertion of the murine OX40L gene under the control of the 40k promoter into the genome of rF-TRICOM at the FP14 site in the genome. Both recombinant fowlpox viruses expressing OX40L were generated by methods previously described (Gritz, L., Destree, A., Cormier, N., Day, E., Stallard, V., Caiazzo, T., Mazzara, G. and Panicali, D., *J Virol* 64, 5948-57, 1990). These viruses also express the human MUC-1 gene and the bacterial beta-galactosidase gene.

REFERENCES

1. Antoine, G., Scheiflinger, F., Dorner, F., and Faulkner F. G. (1998) The complete genomic sequence of the Modified Vaccinia Ankara Strain: Comparison with other poxviruses. Virology 244: 365-396.

2. Binns et al. (1990) J. Gen. Virol. 71:2873-81.

3. Boursnell et al. (1990) J. Gen. Virol. 71: 621-628.

4. Calvert et al. (1992) Virology 191: 783-792.

5. Tartaglia et al. (1990) J. Gen. Virol 71:1517-1524.

6. Tomley et al. (1988) J. Gen. Virol. 69:1025-1040.

All references cited herein are hereby incorporated by reference.

We claim:

1. A recombinant fowlpox virus containing and capable of expressing at least one foreign gene inserted at an insertion site within the fowlpox virus genome, wherein the insertion site is located (i) at a position corresponding to position 128178 of the fowlpox genomic sequence, (ii) at a position corresponding to a region between positions 67080 and 67097 in the fowlpox genomic sequence, (iii) at a position corresponding to a region between positions 7470 and 7475 in the fowlpox genomic sequence, or (iv) at a position corresponding to a region between positions 281065 and 281070 in the fowlpox genomic sequence wherein the fowlpox virus genome corresponds to SEQ ID NO:3.

2. The recombinant fowlpox virus of claim 1, wherein the foreign gene encodes a marker, a therapeutic agent, or an antigenic determinant.

3. The recombinant fowlpox virus of claim 2, wherein the foreign gene codes for an antigenic determinant selected from the group consisting of a pathogenic virus, a bacteria, other microorganism, a parasite, and a tumor cell.

4. The recombinant fowlpox virus of claim 2, wherein the foreign gene codes for an antigenic determinant expressed in a pathogen, wherein the pathogen is selected from the group consisting of *Plasmodium, Mycobacteriua*, Herpes virus, influenza virus, hepatitis, and HIV.

5. The recombinant fowlpox virus of claim 1, wherein the foreign gene is selected from the group of genes encoding hormones, growth factors, immunostimulatory molecules, enzymes, cytokines, receptors, and tumor suppressor genes.

6. A pharmaceutical composition, comprising the recombinant fowlpox virus of claim 1.

7. A method for inducing an immunological response against at least one antigen in a mammal, said method comprising inoculating the mammal with at least a first recombinant fowlpox virus containing and capable of expressing at least the gene encoding said antigen inserted at an insertion site within the fowlpox virus genome, wherein the insertion site is located (i) at a position corresponding to position 128178 of the fowlpox genomic sequence, (ii) at a position corresponding to a region between positions 67080 and 67097 in the fowlpox genomic sequence, (iii) at a position corresponding to a region between positions 7470 and 7475 in the fowlpox genomic sequence, or (iv) at a position corresponding to a region between positions 281065 and 281070 in the fowlpox genomic sequence wherein the fowlpox virus genome corresponds to SEQ ID NO:3.

8. The method of claim 7, wherein said recombinant fowlpox virus further contains a gene encoding at least one immunostimulatory molecule.

9. The method of claim 7, wherein said method further comprises inoculating the mammal with a second vector containing and capable of expression at least one additional gene.

10. The method of claim 9, wherein said second vector contains a gene encoding at least one immunostimulatory molecule.

11. The method of claim 9, wherein the second vector comprises an adenovirus vector.

12. The method of claim 9, wherein the second vector comprises a recombinant vaccinia virus vector.

13. The method of claim 9, wherein the second recombinant vector comprises a recombinant fowlpox virus vector.

* * * * *